(12) United States Patent
Pai et al.

(10) Patent No.: US 12,337,544 B2
(45) Date of Patent: Jun. 24, 2025

(54) METHODS OF DESIGNING AND FABRICATING CUSTOMIZED DENTAL CARE FOR PARTICULAR USERS

(71) Applicant: ZeroBrush, Inc., San Diego, CA (US)

(72) Inventors: Nidhi Pai, Del Mar, CA (US); Akash Pai, Del Mar, CA (US); William Anderson, Seattle, WA (US); Josaiah Clark, Kenmore, WA (US); Richard K. Taylor, Fall City, WA (US)

(73) Assignee: ZeroBrush, Inc., San Diego, CA (US)

( * ) Notice: Subject to any disclaimer, the term of this patent is extended or adjusted under 35 U.S.C. 154(b) by 103 days.

(21) Appl. No.: 17/865,363

(22) Filed: Jul. 14, 2022

(65) Prior Publication Data
US 2022/0347933 A1 Nov. 3, 2022

Related U.S. Application Data

(63) Continuation-in-part of application No. 17/355,084, filed on Jun. 22, 2021, which is a continuation-in-part
(Continued)

(51) Int. Cl.
*B29C 64/393* (2017.01)
*A46D 99/00* (2006.01)
(Continued)

(52) U.S. Cl.
CPC ........... *B29C 64/393* (2017.08); *A46D 99/00* (2013.01); *A61C 17/228* (2013.01);
(Continued)

(58) Field of Classification Search
CPC ............... B29C 64/393; B29C 64/386; B29C 64/165; B33Y 50/02; B33Y 40/20; B22F 10/80;
(Continued)

(56) References Cited

U.S. PATENT DOCUMENTS

| 803,475 A | 10/1905 | Dennis |
|---|---|---|
| D72,543 S | 5/1927 | Balmer |

(Continued)

FOREIGN PATENT DOCUMENTS

| CN | 106308962 A | 1/2017 |
|---|---|---|
| KR | 20100121923 A | 11/2010 |

(Continued)

OTHER PUBLICATIONS

Pai, Office Action, U.S. Appl. No. 14/939,909, Jan. 8, 2018, 14 pgs.
(Continued)

*Primary Examiner* — Yunju Kim

(74) *Attorney, Agent, or Firm* — Morgan, Lewis & Bockius LLP

(57) ABSTRACT

The various embodiments described herein include methods, devices, and systems for customizing dental care. In one aspect, personalized toothbrush devices are 3-D printed for a plurality of users. A 3-D dental model of a respective user's mouth is obtained, and a configuration for a mouthpiece of a respective personalized toothbrush device is determined. The respective personalized toothbrush device is 3-D printed, and includes a top cleaning tray, a bottom cleaning tray, and a set of cleaning elements, each customized based at least in part on the 3-D dental model of the respective user's mouth. Each personalized toothbrush device is 3-D printed for each respective user of the plurality of users, and is different from every other user's personalized toothbrush device.

27 Claims, 72 Drawing Sheets

Related U.S. Application Data of application No. 16/719,877, filed on Dec. 18, 2019, now Pat. No. 11,058,523, which is a continuation-in-part of application No. 15/910,940, filed on Mar. 2, 2018, now Pat. No. 10,869,541, and a continuation-in-part of application No. 15/910,950, filed on Mar. 2, 2018, now Pat. No. 10,888,201, said application No. 15/910,940 is a continuation-in-part of application No. 14/939,909, filed on Nov. 12, 2015, now Pat. No. 11,213,118, said application No. 15/910,950 is a continuation-in-part of application No. 14/939,909, filed on Nov. 12, 2015, now Pat. No. 11,213,118.

(60) Provisional application No. 63/222,921, filed on Jul. 16, 2021, provisional application No. 62/078,134, filed on Nov. 11, 2014, provisional application No. 62/486,698, filed on Apr. 18, 2017, provisional application No. 62/466,014, filed on Mar. 2, 2017, provisional application No. 62/466,010, filed on Mar. 2, 2017.

(51) Int. Cl.

| | | |
|---|---|---|
| *A61C 17/22* | (2006.01) | |
| *A61C 17/34* | (2006.01) | |
| *B29C 64/165* | (2017.01) | |
| *B33Y 10/00* | (2015.01) | |
| *B33Y 40/20* | (2020.01) | |
| *B33Y 50/02* | (2015.01) | |
| *B33Y 80/00* | (2015.01) | |
| *B29L 31/42* | (2006.01) | |

(52) U.S. Cl.
CPC ........ *A61C 17/3481* (2013.01); *B29C 64/165* (2017.08); *B33Y 10/00* (2014.12); *B33Y 40/20* (2020.01); *B33Y 50/02* (2014.12); *B33Y 80/00* (2014.12); *B29L 2031/425* (2013.01)

(58) Field of Classification Search
CPC ........ B22F 10/28; B22F 10/62; A61C 17/228; A61C 17/34; A61C 17/3481; A61C 7/08; A61C 13/0019
See application file for complete search history.

(56) References Cited

U.S. PATENT DOCUMENTS

| | | |
|---|---|---|
| 1,818,146 A | 8/1931 | Maker |
| 2,140,294 A | 12/1938 | Loeffler |
| 2,176,309 A | 10/1939 | Love et al. |
| 2,257,709 A | 9/1941 | Anderson |
| 2,415,447 A | 2/1947 | Stanton |
| D155,372 S | 9/1949 | Whitman |
| D175,924 S | 11/1955 | Aul |
| 2,783,490 A | 3/1957 | Kutik |
| D196,635 S | 10/1963 | Kinsella |
| 3,109,192 A | 11/1963 | Levenson |
| 3,163,874 A | 1/1965 | Bauer |
| 3,241,168 A | 3/1966 | McMaster et al. |
| D207,094 S | 3/1967 | Rakocy |
| D210,928 S | 5/1968 | Guth |
| 3,527,218 A | 9/1970 | Westine |
| D219,598 S | 12/1970 | Dieter et al. |
| D219,599 S | 12/1970 | Dieter et al. |
| D221,824 S | 9/1971 | Cook |
| D221,826 S | 9/1971 | Cook |
| 4,123,844 A | 11/1978 | Kurz |
| 4,224,710 A | 9/1980 | Solow |
| 4,346,493 A | 8/1982 | Goudsmit |
| 4,637,660 A | 1/1987 | Weihrauch |
| 4,691,405 A | 9/1987 | Reed |
| 4,876,157 A | 10/1989 | Barman |
| D312,546 S | 12/1990 | Goldenberg et al. |
| 5,030,098 A | 7/1991 | Branford |
| 5,104,315 A | 4/1992 | Mckinley |
| 5,137,039 A | 8/1992 | Klinkhammer |
| 5,148,567 A | 9/1992 | Daub |
| 5,158,342 A | 10/1992 | Pai |
| 5,171,066 A | 12/1992 | Klinkhammer |
| 5,175,901 A | 1/1993 | Rabinowitz |
| 5,177,827 A | 1/1993 | Ellison |
| 5,259,762 A | 11/1993 | Farrell |
| 5,305,491 A | 4/1994 | Hegemann |
| 5,316,027 A | 5/1994 | Klinkhammer |
| 5,337,436 A | 8/1994 | Saxer et al. |
| 5,365,624 A | 11/1994 | Berns |
| D355,804 S | 2/1995 | Crivelli |
| 5,443,386 A | 8/1995 | Viskup |
| 5,497,526 A | 3/1996 | Klinkhammer |
| 5,531,582 A | 7/1996 | Klinkhammer |
| 5,615,443 A | 4/1997 | Lai |
| 5,673,454 A | 10/1997 | Quintanilla et al. |
| 5,799,353 A | 9/1998 | Oishi |
| 6,223,376 B1 | 5/2001 | Lee |
| D476,182 S | 6/2003 | Hensel |
| 6,792,739 B1 | 9/2004 | McConnell et al. |
| 6,893,259 B1 | 5/2005 | Reizenson |
| D513,322 S | 12/2005 | Jackson, III et al. |
| 7,044,737 B2 | 5/2006 | Fu |
| 7,082,638 B2 | 8/2006 | Koh |
| 7,419,626 B2 | 9/2008 | Mark |
| 7,744,360 B2 | 6/2010 | Ebner et al. |
| 8,042,217 B2 | 10/2011 | Sorrentino |
| 8,359,692 B2 | 1/2013 | Brewer |
| 8,448,282 B2 | 5/2013 | Stapelbroek et al. |
| 8,617,090 B2 | 12/2013 | Fougere et al. |
| 8,631,531 B2 | 1/2014 | Garner et al. |
| 8,635,731 B2 | 1/2014 | Garner et al. |
| 8,677,541 B2 | 3/2014 | Meadows et al. |
| 8,684,956 B2 | 4/2014 | McDonough et al. |
| 8,745,802 B2 | 6/2014 | Steur |
| 8,856,997 B2 | 10/2014 | Moll |
| 8,863,346 B2 | 10/2014 | Headstrom et al. |
| 8,990,992 B2 | 3/2015 | Stapelbroek et al. |
| 9,173,476 B2 | 11/2015 | Miñano Fernandez |
| 9,198,505 B1 | 12/2015 | Brar |
| 9,277,980 B2 | 3/2016 | Leveling et al. |
| 9,486,061 B1 | 11/2016 | Rosenberg et al. |
| 9,636,197 B2 | 5/2017 | Khangura |
| 9,885,195 B1 | 2/2018 | Hayes et al. |
| D814,041 S | 3/2018 | Kile et al. |
| D830,571 S | 10/2018 | Ghahary et al. |
| 10,413,390 B2 | 9/2019 | Yao |
| 2003/0159224 A1 | 8/2003 | Fischer et al. |
| 2004/0103492 A1 | 6/2004 | Kwon et al. |
| 2004/0128777 A1 | 7/2004 | Koh |
| 2004/0191720 A1 | 9/2004 | Coopersmith |
| 2005/0037315 A1 | 2/2005 | Inoue et al. |
| 2005/0125918 A1 | 6/2005 | Brooks |
| 2006/0014121 A1 | 1/2006 | DelGrosso |
| 2008/0227046 A1 | 9/2008 | Lowe et al. |
| 2008/0227047 A1 | 9/2008 | Lowe et al. |
| 2008/0315668 A1 | 12/2008 | Huber et al. |
| 2009/0091178 A1 | 4/2009 | Waguespack et al. |
| 2009/0155740 A1 | 6/2009 | Jensen et al. |
| 2009/0249571 A1 | 10/2009 | Rohrig |
| 2009/0277461 A1 | 11/2009 | Gallagher, Jr. et al. |
| 2010/0055634 A1 | 3/2010 | Spaulding et al. |
| 2010/0062397 A1 | 3/2010 | Brewer |
| 2011/0027746 A1 | 2/2011 | McDonough et al. |
| 2011/0072605 A1 | 3/2011 | Steur |
| 2011/0132390 A1 | 6/2011 | Jacob |
| 2011/0154595 A1 | 6/2011 | Hill |
| 2011/0252590 A1 | 10/2011 | Steur |
| 2011/0289709 A1 | 12/2011 | Attaway |
| 2012/0077144 A1 | 3/2012 | Fougere et al. |
| 2012/0163902 A1 | 6/2012 | Jimenez et al. |
| 2012/0198640 A1 | 8/2012 | Jungnickel et al. |
| 2012/0260441 A1 | 10/2012 | Miller et al. |
| 2012/0295216 A1 | 11/2012 | Dykes et al. |
| 2012/0295218 A1 | 11/2012 | Moll |

(56) References Cited

U.S. PATENT DOCUMENTS

| | | |
|---|---|---|
| 2013/0014331 A1 | 1/2013 | Garner et al. |
| 2013/0014332 A1 | 1/2013 | Garner et al. |
| 2013/0055513 A1 | 3/2013 | Meadows et al. |
| 2013/0067665 A1 | 3/2013 | Sowinski |
| 2013/0220357 A1 | 8/2013 | Campbell |
| 2013/0260332 A1 | 10/2013 | Shapiro |
| 2013/0333133 A1 | 12/2013 | Miller |
| 2014/0011159 A1 | 1/2014 | Miller et al. |
| 2014/0093836 A1 | 4/2014 | Wolpo |
| 2014/0272761 A1* | 9/2014 | Lowe ................ A61C 17/3481 433/2 |
| 2014/0373290 A1 | 12/2014 | Leveling et al. |
| 2015/0020323 A1 | 1/2015 | Moll |
| 2015/0024340 A1 | 1/2015 | De Gentile |
| 2015/0282911 A1 | 10/2015 | Steiner et al. |
| 2015/0313697 A1 | 11/2015 | Prins et al. |
| 2016/0088920 A1 | 3/2016 | LaHood, Sr. et al. |
| 2016/0135581 A1 | 5/2016 | Pai |
| 2016/0206415 A1 | 7/2016 | Kraft et al. |
| 2016/0256240 A1* | 9/2016 | Shivapuja ......... A61C 13/0013 |
| 2017/0225395 A1 | 8/2017 | Boydston et al. |
| 2018/0153299 A1 | 6/2018 | Schiffer |
| 2018/0184795 A1 | 7/2018 | Pai et al. |
| 2018/0184857 A1 | 7/2018 | Pai |
| 2018/0328062 A1 | 11/2018 | Ortiz |
| 2018/0333239 A1 | 11/2018 | Wen |
| 2019/0000599 A1 | 1/2019 | Hanuschik |
| 2019/0000601 A1 | 1/2019 | Huang et al. |
| 2019/0014895 A1 | 1/2019 | De Bardonneche |
| 2019/0105142 A1 | 4/2019 | Koo et al. |
| 2019/0216583 A1 | 7/2019 | Zhuo et al. |
| 2019/0231499 A1 | 8/2019 | Laurent et al. |
| 2022/0313409 A1 | 10/2022 | Pai |

FOREIGN PATENT DOCUMENTS

| | | | |
|---|---|---|---|
| WO | WO2007/121760 A1 | 11/2007 | |
| WO | WO2008/016342 A1 | 2/2008 | |
| WO | WO2012/085799 A1 | 6/2012 | |
| WO | WO2015/070688 A1 | 5/2015 | |
| WO | WO2016/046701 A1 | 3/2016 | |
| WO | WO2018/087481 A1 | 5/2018 | |
| WO | WO2018/160986 A1 | 9/2018 | |
| WO | WO2019/224450 A1 | 11/2019 | |

OTHER PUBLICATIONS

Pai, Final Office Action, U.S. Appl. No. 14/939,909, Jul. 12, 2018, 16 pgs.

Pai, Office Action, U.S. Appl. No. 14/939,909, Dec. 3, 2018, 15 pgs.

Pai, Final Office Action, U.S. Appl. No. 14/939,909, Jul. 5, 2019, 15 pgs.

Pai, Notice of Allowane, U.S. Appl. No. 14/939,909, Aug. 26, 2021, 5 pgs.

Pai, Office Action, U.S. Appl. No. 15/910,950, Jan. 27, 2020, 8 pgs.

Pai, Notice of Allowance, U.S. Appl. No. 15/910,950, Aug. 25, 2020, 7 pgs.

Pai, Office Action, U.S. Appl. No. 15/910,940, Feb. 12, 2020, 11 pgs.

Pai, Notice of Allowance, U.S. Appl. No. 15/910,940, Aug. 26, 2020, 8 pgs.

Pai, Office Action, U.S. Appl. No. 16/601,387, Mar. 5, 2020, 17 pgs.

Pai, Final Office Action, U.S. Appl. No. 16/601,387, Sep. 28, 2020, 9 pgs.

Pai, Notice of Allowance, U.S. Appl. No. 16/601,387, Mar. 24, 2021, 8 pgs.

Pai, Office Action, U.S. Appl. No. 16/719,877, Apr. 6, 2020, 22 pgs.

Pai, Notice of Allowance, U.S. Appl. No. 16/719,877, Mar. 19, 2021, 10 pgs.

Pai, Office Action, U.S. Appl. No. 17/355,084, Mar. 16, 2023, 17 pgs.

Pai, Quayle Office Action, U.S. Appl. No. 17/355,084, Oct. 24, 2023, 6 pgs.

Pai, Notice of Allowance, U.S. Appl. No. 17/355,084, Nov. 13, 2023, 7 pgs.

www.blizzident.com/how-it-works.html, "How it Works," Blizzident, Published 2013, (Year: 2013), 4 pgs.

Zerobrush, Inc., Communication Pursuant to Rules 161(1) and 162, EP18711770.0, Oct. 18, 2019, 3 pgs.

Zerobrush, Inc., Communication Pursuant to Article 94(3) Epc, EP18711770.0, Oct. 16, 2020, 4 pgs.

Zerobrush, Inc., Communication Pursuant to Article 94(3) Epc, EP18711770.0, Apr. 20, 2023, 21 pgs.

Zerobrush, Inc., International Search Report and Written Opinion, PCT/US2018/020691, Jul. 18, 2018, 16 pgs.

Zerobrush, Inc., International Preliminary Report on Patentability, PCT/US2018/020691, Sep. 3, 2019, 11 pgs.

Zerobrush, Inc., International Search Report and Written Opinion, PCT/US2022/037493, Oct. 12, 2022, 10 pgs.

Zerobrush, Inc., International Preliminary Report on Patentability, PCT/US2022/037493, Jan. 16, 2024, 7 pgs.

Zerobrush, Inc., International Search Report and Written Opinion, PCT/US2021/020709, Jul. 6, 2021, 11 pgs.

Zerobrush, Inc., International Search Report and Written Opinion, PCT/US2024/014351, Jul. 31, 2024, 15 pgs.

* cited by examiner

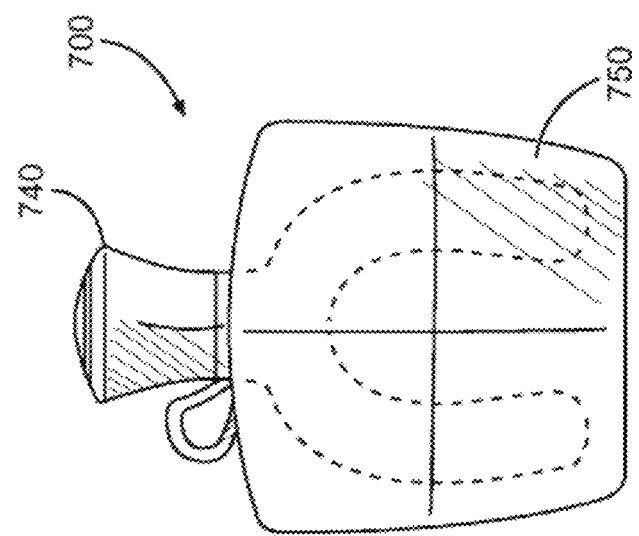
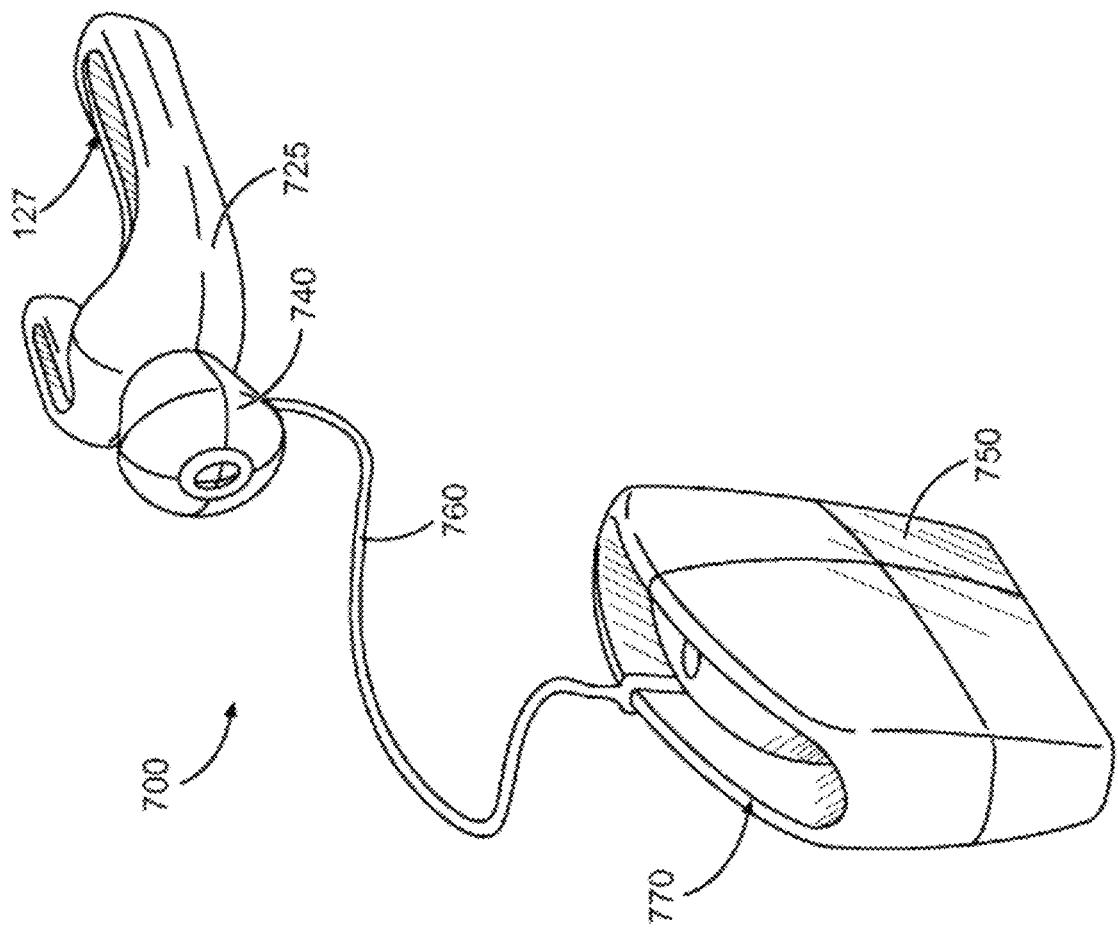
Figure 7B
Figure 7A

Representative Drive Profile 1048-1

Representative Drive Profile 1048-2

Example Frequency Modes

| Frequency (Hz) | Mode |
|---|---|
| 300 | Flap in phase |
| 400 | Flap out of phase |
| 500 | Sweep |
| 1100 | Twist |

Figure 13A

Possible Vibrational Modes

| Extreme 1 | Direction | Extreme 2 |
|---|---|---|
|  Mode 1 |  Mode 1 |  Mode 1 |
|  Mode 2 |  Mode 2 |  Mode 2 |
|  Mode 3 |  Mode 3 |  Mode 3 |
|  Mode 4 |  Mode 4 |  Mode 4 |
|  Mode 5 |  Mode 5 |  Mode 5 |

METHODS OF DESIGNING AND FABRICATING CUSTOMIZED DENTAL CARE FOR PARTICULAR USERS

RELATED APPLICATIONS

This application claims priority to U.S. Provisional Application No. 63/222,921, entitled "Methods of Designing and Fabricating Customized Dental Care for Particular Users," filed Jul. 16, 2021. This application is a continuation-in-part of U.S. application Ser. No. 17/355,084, filed Jun. 22, 2021. U.S. application Ser. No. 17/355,084 is a continuation-in-part of U.S. application Ser. No. 16/719,877, filed Dec. 18, 2019, entitled "Methods of Designing and Fabricating Customized Dental Care for Particular Users," now U.S. Pat. No. 11,058,523, which is a continuation-in-part of both (i) U.S. application Ser. No. 15/910,940, filed Mar. 2, 2018, entitled "Systems, Devices, and Methods for Customized Dental Care," now U.S. Pat. No. 10,869,541, and (ii) U.S. application Ser. No. 15/910,950, filed Mar. 2, 2018, entitled "Systems, Methods, and Devices for Providing Customized Oral Care Agents," now U.S. Pat. No. 10,888,201. U.S. application Ser. No. 15/910,940 and U.S. application Ser. No. 15/910,950 are both a continuation-in-part of U.S. application Ser. No. 14/939,909, filed Nov. 12, 2015, entitled "Methods and Devices for Personalized Dental Care," now U.S. Pat. No. 11,213,118, which claims priority to U.S. Provisional Application No. 62/078,134, filed Nov. 11, 2014, entitled "Methods and Devices for Personalized Dental Cleaning. U.S. application Ser. Nos. 15/910,940 and 15/910,950 each claim priority to: (i) U.S. Provisional Application No. 62/486,698, filed Apr. 18, 2017, entitled "Device for Cleaning Teeth," (ii) U.S. Provisional Application No. 62/466,014 filed Mar. 2, 2017, entitled "Device for Dispensing a Teeth Cleaning Agent such as Toothpaste;" and (iii) U.S. Provisional Application No. 62/466,010, filed Mar. 2, 2017, entitled "Device for Cleaning Teeth." Each of the aforementioned is hereby incorporated by reference in its entirety.

TECHNICAL FIELD

This disclosure relates generally to dental care, including but not limited to, 3-D printing devices and systems for customized dental care that are unique to each of multiple users.

BACKGROUND

Toothbrushes are typically used for conventional teeth cleaning. Such toothbrushes generally have clustered bristles on a brush head that are brought into contact with a user's teeth and gums and moved about the user's mouth by the user for sequential cleaning of different areas of the user's teeth. The effectiveness of using a toothbrush to clean teeth is highly dependent on the technique and duration of the brushing, which many users find difficult to master or apply consistently.

Moreover, most toothbrushes have bristles arranged on a toothbrush head that are arranged to engage with the user's teeth at an optimal angle. The Bass Technique, for example, describes an optimal brushing technique in which the toothbrush head is vibrated while in contact with the tooth at an angle of about 45°. In this approach, however, manual to and fro movement from the user may lead to gum and enamel attrition, and is therefore discouraged. It is difficult for many users, particularly for children and the elderly, to brush all teeth surfaces using the optimal technique.

As mentioned above, conventional toothbrushes are designed to clean one side of one or more adjacent teeth at any given time. For example, the brush head of a manual toothbrush or a powered toothbrush has a width on the order of the width of a single adult tooth. Therefore, it often takes a person using such a device many minutes to clean all of his/her teeth adequately. For example, the American Dental Association recommends brushing one's teeth for two to three minutes (e.g., thirty seconds per quadrant) using a manual toothbrush. Some toothbrushes even include a timer that generates an alert (e.g., a vibration pattern) to inform a user that it is time for him/her to move from brushing one quadrant of his/her mouth to brushing another quadrant.

Unfortunately, many people brush their teeth for significantly less than the recommended length of time. For example, without a timer, a user often overestimates the length of time that the user has been brushing his/her teeth. Or a user may be in a rush. And even if the user uses a timer (e.g., a toothbrush with a quadrant timer), the user still may not brush each tooth surface within a quadrant with uniformity relative to the other tooth surfaces within the quadrant.

Furthermore, people may underbrush or overbrush, and thus abrade their gums. For example, people may underbrush by not following the recommended brushing process or time spent per tooth, and people may overbrush by vigorously applying pressure or abrasive action to their gums.

Furthermore, it can be difficult for a user to clean certain regions of his/her teeth using a conventional toothbrush. For example, it can be difficult for a user to properly engage the brush head of a conventional manual or electric toothbrush with the backs of the molars on the same side as the hand in which the user is holding the toothbrush. Moreover, a user with a sensitive mouth/throat may avoid brushing the backs of his/her molars to avoid activating his/her gag reflex. Consequently, even people who brush their teeth regularly may not clean their teeth properly.

In addition, many users who clean their teeth use a manual or electric toothbrush with an oral care agent, such as toothpaste, applied to a brush head of the toothbrush. However, a need has arisen for an oral care agent (e.g., toothpaste) dispenser that is convenient to operate and that dispenses an oral care agent that is customized to each individual user.

Toothpaste is typically packaged within a flexible capped tube, and a user typically applies the toothpaste to a brush head of a toothbrush by uncapping the tube, squeezing the tube to dispense the toothpaste, and then recapping the tube. Unfortunately, dispensing toothpaste from a tube can be inconvenient, or otherwise problematic. For example, if a user does not tightly recap the tube, then the toothpaste can be exposed to agents such as pollutants and bacteria that can degrade one or more ingredients of the toothpaste. Furthermore, because it can be difficult to impossible for a user to squeeze all of the toothpaste from a tube, at least a portion of the toothpaste in the tube is often wasted; considering that millions of tubes of toothpaste are sold worldwide each year, the aggregate amount of toothpaste wasted in this manner can be significant.

Moreover, it can be difficult for a user to precisely control the amount of toothpaste the user squeezes onto a brush head of a toothbrush, e.g., if the user dispenses too little toothpaste, then the user may be unable to clean all of his/her teeth adequately no matter how "hard" or how long the user brushes; and if the user dispenses too much toothpaste, then the user may cause an excessive level of abrasion to his/her tooth enamel. In addition, it can become more difficult to squeeze toothpaste from the tube as the tube empties. Furthermore, because recapping a toothpaste tube typically requires two hands, a toothbrush (with toothpaste on the brush head) that a user places on a counter while the user recaps the tube can fall over and create a mess.

Another problem with using an off-the-shelf toothpaste, regardless of its packaging, is that the toothpaste typically is not customized or personalized to the preferences and clinical needs of a particular user (e.g., fluoride toothpaste with a prescribed amount of fluoride). For example, if a user prefers a flavor of one toothpaste brand, and the whitening ability of another toothpaste brand, his/her choices are limited to choosing one of the brands, or attempting to combine the toothpastes onto the brush head of his/her toothbrush, which may not result in the preferred flavor or characteristics.

Therefore, a need has arisen for an oral care agent dispenser that is configured to address the above-described drawbacks. For example, a need has arisen for an oral care agent dispenser that is configured to dispense a precise amount of customized oral care agent in a "hands-free" manner.

In addition, information about the user's brushing history and their dentition is not analyzed to predict oral care possibilities, such as problems with, and solutions for, the user's gum health and smile design.

SUMMARY

In light of these drawbacks, there is a need for a dental care system that accurately and precisely cleans and maintains a user's teeth and gums (i.e., dental health), without causing discomfort to the user, and without requiring complex or intricate dental cleaning regimes. Such systems optionally complement or replace conventional systems, devices, and methods for maintaining a user's dental health.

Accordingly, some embodiments described herein include a dental cleaning device with a customized shape with customized cleaning tips. For example, the length, shape, stiffness, and material of the cleaning tips (also sometimes called cleaning protuberances herein) is customized to the particular user's dentition (e.g., jaw, mouth, and teeth geometry). In accordance with some embodiments, the vibration cleaning pattern (also sometimes called a drive profile herein) is also customized for each user to produce superior cleaning of each tooth and tooth surface, hence superior whole-mouth cleaning. In some embodiments, the dental care device is customized for each user's jaw and teeth geometry. In some embodiments, the cleaning tips have customized shape and/or stiffness based in part on a vibration pattern for each user.

In some embodiments, the dental care device is configured to operate at a customizable range of vibration frequencies to ensure proper cleaning using multiple motors to create different kinds of motion, which, when put together in a sequence, ensures proper whole-mouth cleaning. In some embodiments, the vibration frequencies include one or more frequencies in the sonic range and/or one or more frequencies in the ultrasonic range.

In some embodiments, the dental care device is configured to gather personalized data to guide a personalized treatment plan. In some embodiments, the personalized treatment plan includes a plurality of different frequencies selected based on the user's dental information. In some embodiments, the dental care device is configured to utilize a personalized toothpaste selected in accordance with the user's dental information. In some embodiments, the dental care device is configured to send feedback to the user's dental health provider (e.g., to confirm that the user is complying with a prescribed treatment regime, or for use in future diagnoses, prescriptions, and/or procedures). In some embodiments, the information about the user's dentition along with usage and feedback information from the dental care device is automatically mined via AI (Artificial Intelligence) and ML (Machine Learning) to identify and/or predict dental issues and propose corresponding dental procedures. For example, identifying issues such as gum recession and propose procedures so as to improve in smile and/or overall smile and facial features.

Some embodiments include a dental cleaning device customized for a particular user. In some embodiments, the dental care device includes: (1) a support plate having: (a) a first portion configured to be inserted into a mouth; and (b) an attachment mechanism configured to attach the dental care device to a drive assembly; and (2) an elastomer (elastic polymer) portion enclosing the first portion of the plate, the elastomer portion including a plurality of cleaning tips and shaped in accordance with dental details of the particular user. For example, the elastomer portion is configured to match the teeth and jaw geometry of the particular user. In some embodiments, the elastomer portion is customized to the particular user based on the dental information of the particular user. In some embodiments, the elastomer is composed of biocompatible silicone. In some embodiments the elastomer portion is integrally formed. In some embodiments, there are sensors attached to the dental care device to detect various dental physiological parameters, such as breath analysis, bacteria detection, and the like.

Accordingly, some embodiments include a customized oral care agent dispenser in accordance with a user's dental information. In some embodiments, the customized oral care agent is based on one or more of: the user's age, periodontal condition, enamel health, sensitivity, health condition, and the like. In some embodiments, the user receives the paste via a subscription model. In some embodiments, the oral care agent is prescribed by a dentist. In some embodiments, the customized oral care agent is dispensed via an oral care agent dispenser device. In some embodiments, ingredients for the customized oral care agent are individually inserted within the dispenser device. In some embodiments, ingredients are contained within replaceable capsules. In some embodiments, the dispenser device is hands-free (e.g., uses a sensor to automatically dispense the oral care agent with a toothbrush is in position).

In some embodiments, the dispenser is configured to dispense the right quantity of oral care agent formulated according to the user's dental information, preventing an over- or under-supply of oral care agent (e.g., dentifrice) required to clean the user's teeth and gums.

In some embodiments, one or more characteristics of the customized oral care agent is customized to a particular user, such as flavor, color, fluoride content, tartar control ingredients, whitening agents, sensitivity reduction ingredients, stain removal ingredients, and mouthwash ingredients.

Some embodiments include an oral care agent dispenser device having: (1) multiple chambers each configured to receive a cartridge containing a different oral care ingredient of a plurality of oral care ingredients; (2) memory configured to store an oral care formulation that includes one or more of the plurality of oral care ingredients; and (3) a dispenser positioned above a dispensing region, the dispenser configured to dispense one or more of the plurality of oral care ingredients in accordance with the oral care formulation information. In some embodiments, the dispenser device dispenses prescription material by communicating with a HIPPA-compliant software module which authorizes the dispensing based on identification of the user (e.g., via a unique ID from the dental care device).

Some embodiments includes method of making a personalized toothbrush device. The method includes obtaining a model of a particular user's teeth and determining, based on the model of the particular user's teeth, a configuration for a set of cleaning elements for the toothbrush device. The method also includes integrally forming a cleaner body with a set of cleaning elements, whereby (i) the cleaner body includes upper and lower mouthpieces shaped for receiving the particular user's teeth, and (ii) the set of cleaning elements has the configuration determined based on the model of the particular user's teeth.

Some embodiments include methods of making a personalized toothbrush device that is customized for a particular user and no other user. The method includes, for each of a plurality of users, obtaining an electronic 3-D dental model of a respective user's mouth and determining a configuration for a mouthpiece of a personalized toothbrush device. The method includes 3-D printing the mouthpiece of the personalized toothbrush device, with a top cleaning tray, a bottom cleaning tray, and a set of cleaning elements, each customized based at least in part on the electronic 3-D dental model of the respective user's mouth. Each personalized toothbrush device that is 3-D printed for each respective user of the plurality of users is different from every other user's personalized toothbrush device.

Thus, devices and systems are provided with methods for customizing and improving dental health, thereby increasing the effectiveness, efficiency, and user satisfaction of such devices and systems.

BRIEF DESCRIPTION OF THE DRAWINGS

For a better understanding of the various described embodiments, reference should be made to the Detailed Description below, in conjunction with the following drawings in which like reference numerals refer to corresponding parts throughout the figures.

FIGS. 7A-7B are schematic three-dimensional views illustrating a representative dental care device according to some embodiments. FIG. 7A shows the dental care device in an operational mode, while FIG. 7B shows the dental care device in a stowed mode.

FIG. 8A shows the kit in a docked, charging mode; FIG. 8B shows, in isolation, a mouthpiece attachment forming part of the dental care kit.

FIG. 13A is table illustrating example frequencies for various representative modes of operation of the dental care device of FIG. 10A in accordance with some embodiments.

FIG. 27A shows a scan of a user's teeth before processing, while

Like reference numerals refer to corresponding parts throughout the several views of the drawings.

DETAILED DESCRIPTION

Figure 1A:
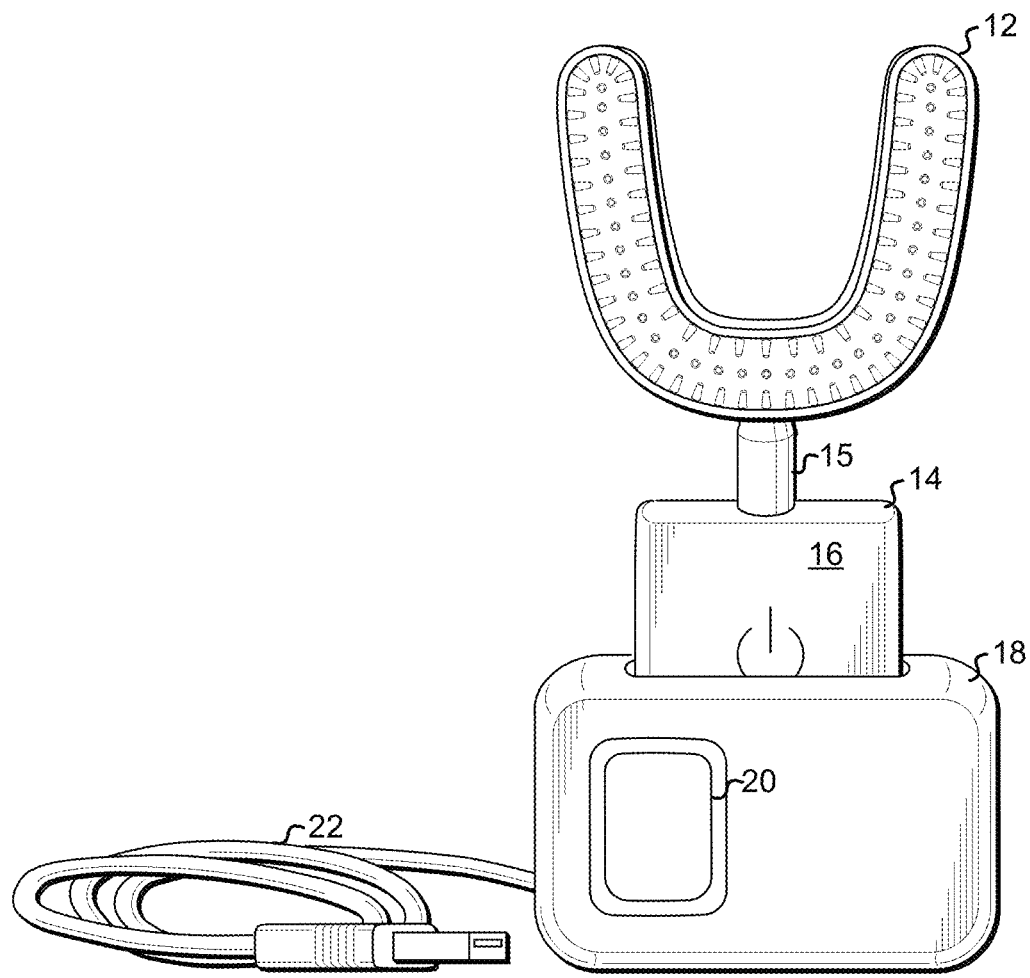
FIG. 1A is a schematic view illustrating a representative dental care device in accordance with some embodiments.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Many modifications and variations of this disclosure can be made without departing from its spirit and scope, as will be apparent to those skilled in the art. The specific embodiments described herein are offered by way of example only, and the disclosure is to be limited only by the terms of the appended claims, along with the full scope of equivalents to which such claims are entitled.

In the following description, "approximately," "about," and "substantially" mean that a quantity (e.g., a length) can vary from a given value (e.g., ten feet) by up to ±20% (e.g., ±two feet), and that a difference between two quantities or other items can vary by up to ±20% of the larger of the quantities.

The disclosed embodiments include a dental care device for use in personal dental care, the device including: (1) a cleaner body that defines a cleaning chamber shaped to the user's dentition and jaw geometry for receiving a group of teeth of a user; and (b) a powered driving mechanism that is mechanically coupled to the cleaner body and that is configured for imparting drive movement to the cleaner body during reception of the group of teeth in the cleaning chamber, to cause cleaning of the teeth.

Another aspect of the disclosure provides for a method of personal dental care that includes: (1) placing a group of teeth of a user in a cleaning chamber provided for the group of teeth by a cleaner body; and (2) while the group of teeth is received in the cleaning chamber, imparting movement to the cleaner body manually or by operation of a motorized mechanism, thereby to cause cleaning of the group of teeth housed in the cleaner body.

In some embodiments, the cleaner body is customized for the user. In some embodiments, the cleaning chamber is complementary in shape to teeth and jaw of a particular user only. Thus, the shape of the cleaning chamber is optionally unique.

In some embodiments, the cleaning chamber is shaped for receiving a set of teeth on a particular dental arch of the user. In some embodiments, the cleaning chamber is shaped for receiving all of the teeth on the user's upper jaw, or all of the teeth on the user's lower jaw. For ease of description, the complete set of teeth on any particular arch is referred to herein as a dental arch set.

In some embodiments, the cleaner body is an arch-shaped tray that is optionally formed based on a dental imprint or scan of the corresponding dental arch of the associated user. In some embodiments, the cleaner tray is a molded component of a polymeric plastics material. In some embodiments, a method of fabrication includes obtaining a tray mold having an imprint of the corresponding dental arch of the particular user, and forming the cleaner tray based on the tray mold.

In some embodiments, the device includes a complementary pair of cleaner trays (also sometimes called mouthpieces herein), each of which is configured for receiving a respective one of the dental arch sets of the user. Each cleaner tray may in such a case be an attachment configured for removable and replaceable connection to the driving mechanism, to allow for separate use of the cleaner trays on the respective dental arch sets. In other embodiments, the cleaner body may define oppositely outwardly facing cleaning chambers for both arches, so that both dental arches can simultaneously be cleaned by reception in the unified cleaner body.

The cleaning chamber is optionally shaped such that substantially each tooth received in the cleaning chamber is bilaterally enveloped by opposite sidewalls of the cleaning chamber, such that both an outer major face and an inner major face of each tooth is received in the cleaning chamber, and the sidewall of the cleaning chamber provided by the cleaner tray extends towards a base of the teeth for at least a majority of the tooth's height. In some embodiments, the sidewalls extend up to, or over a gumline of the user. In some embodiments, the cleaning chamber is shaped to match the user's jaw size both for maxilla and the mandible circumference and curvature angle.

In some embodiments, the device includes cleaning elements (e.g., cleaning tips) on the cleaner body and protruding into the cleaning chamber for contact engagement with the teeth, when the device is in use. In some embodiments, the cleaning elements comprise a plurality of filamentary elements, such as bristles or sponge-like filaments, projecting into the cleaning chamber from a chamber wall provided by the cleaner tray and defining the cleaning chamber. In some embodiments, the cleaning elements comprise protrusions or other irregularities on the chamber wall. Such protrusions are optionally integrally formed with the cleaner tray, so that the cleaner tray and the protrusions are provided by a single component of monolithic construction. In the description that follows, described variations of the arrangement of cleaning elements on the cleaner body will be understood as applying (instead, or in addition) analogously to the arrangement of protrusions on the chamber wall.

In some embodiments, the cleaning elements have a substantially regular arrangement in the cleaning chamber, so that the number of cleaning elements per unit of surface area on the chamber wall is substantially equal throughout. In some embodiments, however, the cleaning elements are arranged on the cleaner body to have a greater concentration (e.g., a greater number of cleaning elements per unit of surface area) in some areas of the chamber wall than in others. In some embodiments, greater concentrations of cleaning elements are provided in areas where more vigorous cleaning is desired. For example, the cleaning elements may be more densely concentrated towards the ends of the dental arch set, corresponding to areas of the mouth most prone to dental decay. In some embodiments, the cleaning elements are arranged to be more densely concentrated at embrasures between adjacent teeth and/or at the bottom of the teeth.

Instead, or in addition, the cleaning element arrangement is such that physical properties of the cleaning elements vary for different areas of the cleaning chamber. For example, softer or more flexible cleaning elements are optionally provided at positions on the chamber wall corresponding or adjacent to the gumline of the user, thereby lessening the likelihood of irritating the gums. Stiffer or less flexible bristles are optionally provided at positions corresponding to potential problem areas, such as towards the backmost teeth and/or corresponding to teeth embrasures.

In some embodiments, the arrangement of cleaning elements on the cleaner tray are customized. For example, the arrangement of cleaning elements (in positioning and/or in physical properties) are optionally specific and unique to the particular associated user. Some embodiments include: (1) performing or obtaining a dental scan of the respective dental arch sets of a particular user, (2) identifying potential problem areas based on the dental scan, and (3) arranging the bristles in the cleaning chamber based on the identified problem areas. In some embodiments, potential problem areas are provided with a greater concentration of cleaning elements, and/or with cleaning elements whose physical properties are selected to cause more effective dental cleaning due to powered contact engagement with the teeth.

In some embodiments, the driving mechanism includes a vibration mechanism for causing driven vibration and/or reciprocation of the cleaner tray. In some embodiments, the driving mechanism is configured for causing subsonic oscillation of the cleaner body, e.g., at a frequency lower than 20 Hertz (Hz).

The vibration speed of toothbrushes is often measured in movements per minute, where conventional electric toothbrushes vibrate at a speed of between a few thousand times a minute to approximately 10,000 to 12,000 times per minute. Sonic toothbrushes are so called because the speed or frequency of their vibration (as opposed to the sound of the motor) falls within the average range that is used by people in spoken communication. Voiced speech of a typical adult male will have a fundamental frequency from 85 to 180 Hz (10,200 to 21,000 movements per minute), and that of a typical adult female from 165 to 255 Hz (19,800 to 30,600 movements per minute).

In contrast, ultrasonic toothbrushes work by generating an ultrasonic wave, the frequency of which may begin at 20,000 Hz (2,400,000 movements per minute). The most common frequency for existing ultrasonic toothbrushes, however, is in the region of approximately 1.6 MHz, which translates to 96,000,000 waves or 192,000,000 movements per minute. As described below, the devices of this disclosure in some embodiments are configured primarily for sonic cleaning, in other embodiments are configured primarily for ultrasonic cleaning, and in yet further embodiments are configured for cleaning both by sonic and ultrasonic action.

In some embodiments, the vibration mechanism is configured for causing sonic vibration of the cleaner tray (or mouthpiece assembly 12). In some embodiments, cleaning by sonic vibration relies on sweeping cleaning element movement at a relatively high amplitude (relative to ultrasonic movement, which will be discussed below). In some embodiments, such sonic vibration is in a frequency range between 20 Hz and 20 kHz, corresponding to 12,000-24,000 oscillations or cycles per minute. In some embodiments, sonic cleaning relies on the sweeping motion of the cleaning elements to clean the teeth by scrubbing engagement. In some embodiments, the induced vibration of the cleaner body is similar or analogous to vibrations generated in conventional brush heads.

In some embodiments, instead, or in addition, the vibration mechanism is configured for causing ultrasonic vibration of the cleaner tray (or mouthpiece assembly 12). Ultrasonic motion is typically at a lower amplitude than is the case for sonic motion. In some embodiments, such ultrasonic vibration is in the frequency above 20 kHz (approximately 2.4 million movements per minute), for example being at about 1.6 MHz (approximately 192 million movements permit). In some embodiments, ultrasonic cleaning operates by the generation of ultrasonic waves that break bacterial chains making up dental plaque and moving or weakening their attachment to tooth enamel.

In some instances and embodiments, such induced vibration of the mouthpiece (e.g., cleaner tray 125, FIG. 1B) also agitates natural cleaning fluids (such as saliva) around the teeth. Because of the fast-moving vibration of the cleaner tray, minuscule bubbles are created that push out dental plaque that may be lying just underneath the gum line. These fluids not only push away the plaque, they also dilute and move bacteria-produced acids. In some instances and embodiments, this fluid movement and plaque removal occurs without the cleaning elements of the cleaner tray touching the enamel surface.

In some embodiments, the induced vibration of the cleaner body of the present disclosure is similar or analogous to ultrasonic vibrations generated by brush heads of existing toothbrushes available.

In some embodiments, induced vibration of the cleaner body is a combination of ultrasonic and sonic motion. In embodiments where the device is configured to induce a combination of ultrasonic and sonic oscillation or vibration in the cleaner body, sonic vibration is optionally provided to produce a sweeping action to remove particles and bacterial remnants previously broken up or weakened by ultrasonic wave action.

In some embodiments, the dental care device is configured for dental cleaning at least in part by operation of fluid dynamic interaction between the user's teeth and/or gums and liquids contained in the cleaning chamber. As discussed above, such high-speed brushing action in some instances creates pressure waves and shear forces in the liquids around the teeth, thereby causing or facilitating teeth cleaning (e.g., without physically contacting of the teeth with the cleaning elements of the device). In some instances and embodiments, such a fluid dynamic cleaning mechanism further operates through the generation of minute bubbles that forcefully impinge on the tooth surfaces, thereby to cause dislodgment of plaque and/or other undesired substances from tooth enamel.

In some embodiments, the device is configured for manual manipulation or agitation, thus operating without a motorized driving mechanism. In such embodiments, the device optionally comprises a handle connected to the cleaner tray and configured for manual control by the user, to insert the cleaner tray into the mouth and perform manual brushing.

FIG. 1A is a perspective view of a dental care device 10 in accordance with some embodiments. The device 10 includes a stand 18 (e.g., a computer-interface-and-battery-charging stand) and a teeth-cleaning device 14, which is configured to clean a user's teeth in a reduced amount of time as compared to conventional teeth-cleaning devices, without causing discomfort to the user.

In accordance with some embodiments, the stand 18 is configured for communicatively coupling to a computer (not shown), and/or for electrically coupling to an energy source, such as an electrical outlet (not shown), via connector 22 (e.g., a Universal Serial Bus (USB) port). In some embodiments, the stand 18 provides an interface through which one can use the computer to charge a battery of the cleaning device 14 and/or to configure the cleaning device. For example, one can upload software, firmware, or a combination of software and firmware, from the computer to the cleaning device 14, e.g., to select and to configure operational features of the cleaning device. As another example, one can couple the stand 18 to an AC adapter to charge the battery of the cleaning device 14 (e.g., without connecting to a computer). In some embodiments, the stand 18 includes a user interface 20 enabling a user to adjust one or more settings or preferences and/or enabling presentation of device data to the user.

In accordance with some embodiments, the cleaning device 14 includes an electronics enclosure 16, an optional coupling 15, and a mouthpiece assembly 12. In some embodiments, as described below in more detail, the electronics enclosure 16 houses electronic circuitry, one or more rechargeable batteries, and one or more actuators (e.g., motors) configured to drive the mouthpiece assembly 12. In some embodiments, the electronic circuitry is configured to charge the one or more batteries and when the cleaning device 14 is disposed in the stand 18. In some embodiments, the electronic circuitry is configured to manage power on the electronics enclosure 16, to control the operation of the one or more actuators, and/or to communicate with the stand 18. In some embodiments, the electronic circuitry is configured to communicate with a computer, a wireless router, or other device so that the electronic circuitry can send and receive information via the internet to/from one or more remote devices, such as cloud or other servers. In some embodiments, the electronic circuitry is configurable via software, firmware, or both software and firmware, and can communicate over a wired connection or a wireless link via any suitable communication protocol such as Bluetooth® or Wi-Fi®, and via any suitable circuitry or hardware such as an RFID tag or circuitry. In some embodiments, the cleaning device 14 includes a user interface (e.g., on the electronics enclosure 16). In some embodiments, the user interface includes a screen (e.g., a touch screen), one or more buttons or affordances, one or more microphones, and/or one or more speakers.

In some embodiments, the coupling 15 is configured to couple the mouthpiece assembly 12 to the electronics enclosure 16 such that one or more motors in the electronics enclosure drive motion of the mouthpiece assembly (e.g., excite the mouthpiece assembly). In some embodiments, the coupling is integral with either or both of the electronics enclosure 16 and the mouthpiece assembly 12. In some embodiments, the coupling 15 is formed from any suitable material, and can have any suitable shape and dimensions. In some embodiments, the coupling 15 is configured to allow removal and replacement of the mouthpiece assembly 12, e.g., such that multiple mouthpiece assemblies may be selectively used with the electronics enclosure 16.

In some embodiments, as described below in more detail, the mouthpiece assembly 12, which is optionally custom designed for a user, is configured to be inserted into the user's mouth to clean all of the user's teeth quickly and concurrently.

In operation, the one or more actuators within the electronics enclosure 16 drive the mouthpiece assembly 12 such that the mouthpiece assembly cleans all of the user's teeth equally well or better, and in significantly less time, than a conventional manual or electric toothbrush. For example, the actuators and mouthpiece assembly 12 are configured to clean a user's teeth fully, completely (e.g., to remove at least 99% of plaque buildup on the user's teeth), and uniformly within a time that ranges from approximately five seconds to approximately thirty seconds (e.g., within twenty seconds or less). Therefore, even at the high end (thirty seconds) of this time range, the teeth-cleaning device 14 not only cleans a user's teeth on par with, or significantly better than, conventional manual and electric toothbrushes, it also reduces the time for cleaning the user's teeth by approximately 75% as compared to the two-minute (or more) cleaning time recommended for conventional toothbrushes.

Figure 1B:
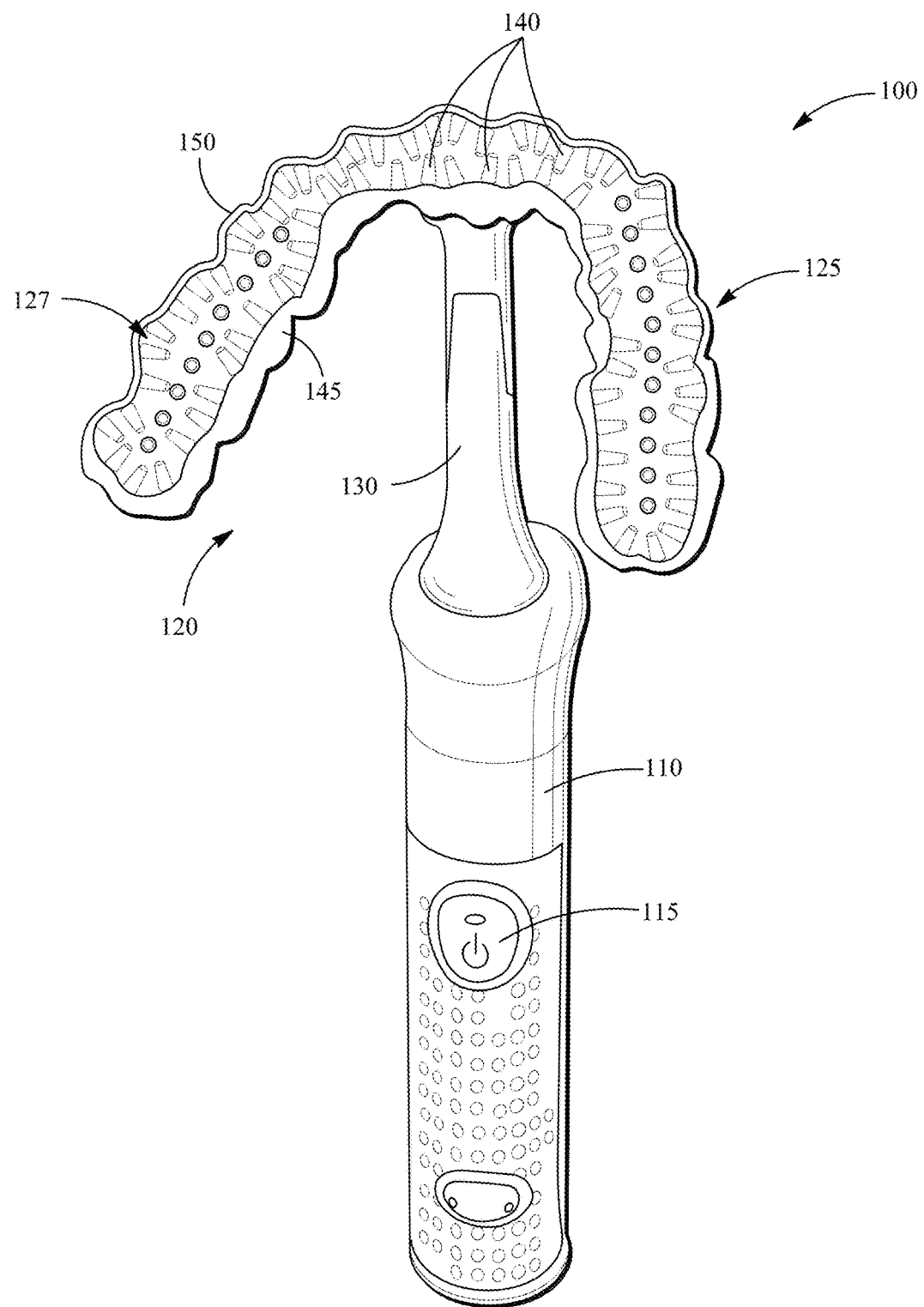
FIG. 1B is a schematic three-dimensional view illustrating a representative dental care device in accordance with some embodiments.

FIG. 1B is a schematic three-dimensional view of a dental care device in the example form of a whole-arch dental care device 100 in accordance with some embodiments. The dental care device 100 comprises a cleaner body in the example form of a cleaner tray 125 for receiving an upper arch set of teeth of a user (e.g., the whole set of teeth on the user's upper jaw), and a housing 110 to which the cleaner tray 125 is connected for driven movement of the cleaner tray 125 during use. As will be described in greater detail below, the housing 110 holds an electric motor and an onboard power source (in the example form of a rechargeable battery, such as a lithium-ion battery) for causing driven oscillation of the cleaner tray 125 when activated by a user-operable press button 115.

The cleaner tray 125 is a generally arch-shaped element defining a cleaning chamber 127 complementary to an upper dental arch set of a particular user. Within the cleaning chamber 127 is located an arrangement of cleaning elements for physical contact engagement with the user's teeth and/or gums when the set of teeth is inserted into the cleaning chamber 127. In the example of FIG. 1B, the cleaning elements comprise a plurality of cleaning tips 140.

The cleaning chamber 127 in FIG. 1B is generally U-shaped in plan view (corresponding to the U-shape of the corresponding dental arch), and is generally U-shaped in cross-section (corresponding more or less to a lateral width of corresponding teeth). The cleaning chamber 127 thus has an inner sidewall 145 for face-to-face location adjacent and substantially parallel to inwardly facing major faces of the corresponding teeth, and a substantially parallel, opposed outer sidewall 150 for face-to-face location adjacent and substantially parallel to outwardly facing major surfaces of the corresponding teeth. The height of the sidewalls 145, 150 from a base of the cleaning chamber 127 is in this example embodiment is somewhat greater than the height of the teeth, so that the sidewalls 145, 150 extend past the gum line of the user when in use.

In accordance with some embodiments, the cleaning chamber 127 is personalized, being customized for use by a specific associated user only, in that the cleaning chamber 127 has been formed based on a dental imprint of the particular user and is thus substantially complementary in shape to the corresponding arch of the particular user. Such customization of the shape of the cleaning chamber 127 promotes proper alignment of the cleaning tips 140 with the respective teeth of the corresponding set, while also ensuring a comfortable fit of the cleaner tray 125 in the user's mouth.

The cleaning tips 140 are arranged on the cleaner tray 125 to project cantilever-fashion into the cleaning chamber. In some embodiments, as will be discussed at greater length later, physical properties and/or distribution density of the cleaning tips 140 vary from one part of the cleaning chamber 127 to another. In some embodiments, the cleaning tips 140 (or corresponding cleaning elements) have a substantially regular distribution throughout the cleaning chamber 127.

In accordance with some embodiments, the cleaner tray 125 is rigidly connected to the housing 110 by an attachment stem 130; enabling transmission of vibratory or oscillating movement from the motor in the housing 110 to the cleaner tray 125. The housing 110 can thus function as a handle by which the dental care device 100 is held to insert the cleaner tray 125 into the mouth, and to hold the cleaner tray 125 in position during brushing.

The vibration mechanism incorporated in the housing 110 is configured, in some embodiments, to drive movement of the cleaner tray 125 so as to cause cleaning of the teeth at least in part by ultrasonic action. For example, the dental care device 100 is configured to generate ultrasound in order remove plaque and/or render plaque bacteria harmless. In this example, ultrasonic cleaning action comprises reciprocating or oscillating movement of the cleaner tray 125 at a frequency of about 1.6 MHz. In some embodiments, a movement cycle comprises a linear to and fro movement and/or a circular or elliptical movement.

In some embodiments, the dental care device 100 is, instead or in addition, configured for sonic cleaning, e.g., with the vibration mechanism being configured for producing at least some vibration of the cleaner tray in the audible range. In some embodiments, the frequency range of such driven movement is in the range of 200 to 400 Hz, translating to 12,000-24,000 movement cycles per minute.

In some embodiments, the dental care device 100 provides for user-controlled switching between sonic and ultrasonic cleaning, for example by operation of the press button 115. In some embodiments, control circuitry of the dental care device 100 is configured to allow cycling through different modes (e.g., based on repeated pressing of the button 115). In some embodiments, the different modes include an ultrasonic mode, a sonic mode, and a switched off mode. In some embodiments, the dental care device 100 is preprogrammed to automatically perform a cleaning cycle (e.g., a cleaning cycle that comprises both ultrasonic and sonic vibrations) with vibrations produced in a predefined sequence. In such a case, for example, a few seconds of ultrasonic vibration may serve to generate ultrasonic waves to break up bacterial chains that make up the dental plaque and remove or weaken their methods of attachment to the tooth surface.

Fluid dynamic action caused by impelled movement of the cleaner tray 125 disrupts plaque at traditionally hard-to-reach areas, such as between teeth and below the gum line. Cleaning by use of the dental care device 100 thus serves not only to clean the major outer faces of the teeth, but additionally effectively performs a flossing operation by causing removal of foreign material from spaces between adjacent teeth. In some embodiments, the fluid dynamic cleaning effects operate at a distance of up to 4 mm from the contact points between the cleaning tips 140 and the teeth. Thereafter, sonic vibration is optionally produced for physically cleaning and removing the weakened or loosened materials. The vibration mechanism is in some embodiments configured such that the amplitudes of the sonic movement will typically be larger than that of movements produced during ultrasonic cleaning.

In operation, the user may use the assembled dental care device 100 as illustrated in FIG. 1B to clean the teeth of the upper arch, and may thereafter (or before) use an analogous attachment 120B (FIG. 3) for cleaning the teeth of the lower arch. In some embodiments, each one of these operations comprises gripping the dental care device 100 by the housing 110; inserting the cleaner tray 125 into the mouth; biting down lightly on the cleaner tray 125, so that the teeth are snugly inserted in the cleaning chamber 127; and then activating the driven sonic and/or ultrasonic vibration of the cleaning chamber 127 by operation of the push button 115. It has been found that effective dental cleaning is achieved within a brushing period of as little as about 5 seconds for each arch.

In some embodiments, the user is directed to hold the cleaner tray 125 substantially stationary in the mouth during driven vibration thereof. In other embodiments, however, the cleaner tray 125 may be moved around in the mouth during vibration. In one example, the cleaning process for each arch comprises a five second sequence in which the user moves the cleaner tray 125: forward for one second, backward for one second, down for one second, up for one second, and side-to-side for one second. It has been found that such a scrubbing motion is highly effective, due partly to the high number of brush strokes per minute generated simultaneously across the entire dental arch.

In some embodiments, the dental care device 100 is configured for use without any toothpaste or specific oral care agent. In some embodiments, conventional toothpaste is applied to the teeth or to the cleaning chamber 127 prior to use. In some embodiments, the dental care device 100 is configured for use with a dental paste or oral care agent constituted specifically for use with the cleaner tray 125. In some embodiments, such an oral care agent is configured for promoting fluid dynamic cleaning actions, as described herein, when applied to the teeth or to the cleaning chamber 127 prior to reception of the teeth in the cleaner tray 125.

It will be appreciated that, due to the generally U-shaped cross-sectional profile of the cleaning chamber 127, the oral care agent will be retained within the cleaning chamber 127 during cleaning. The oral care agent is in some embodiments substantially free of abrasives to preserve tooth enamel. In some embodiments, the oral care agent has a viscosity a higher than that of conventional toothpastes. In some embodiments, the oral care agent is a very high viscosity fluid, the viscosity being selected to promote transmission and therefore effectiveness of sonic and/or ultrasonic waves induced by tray vibration. The oral care agent is in some embodiments an all-natural product.

Figure 2:
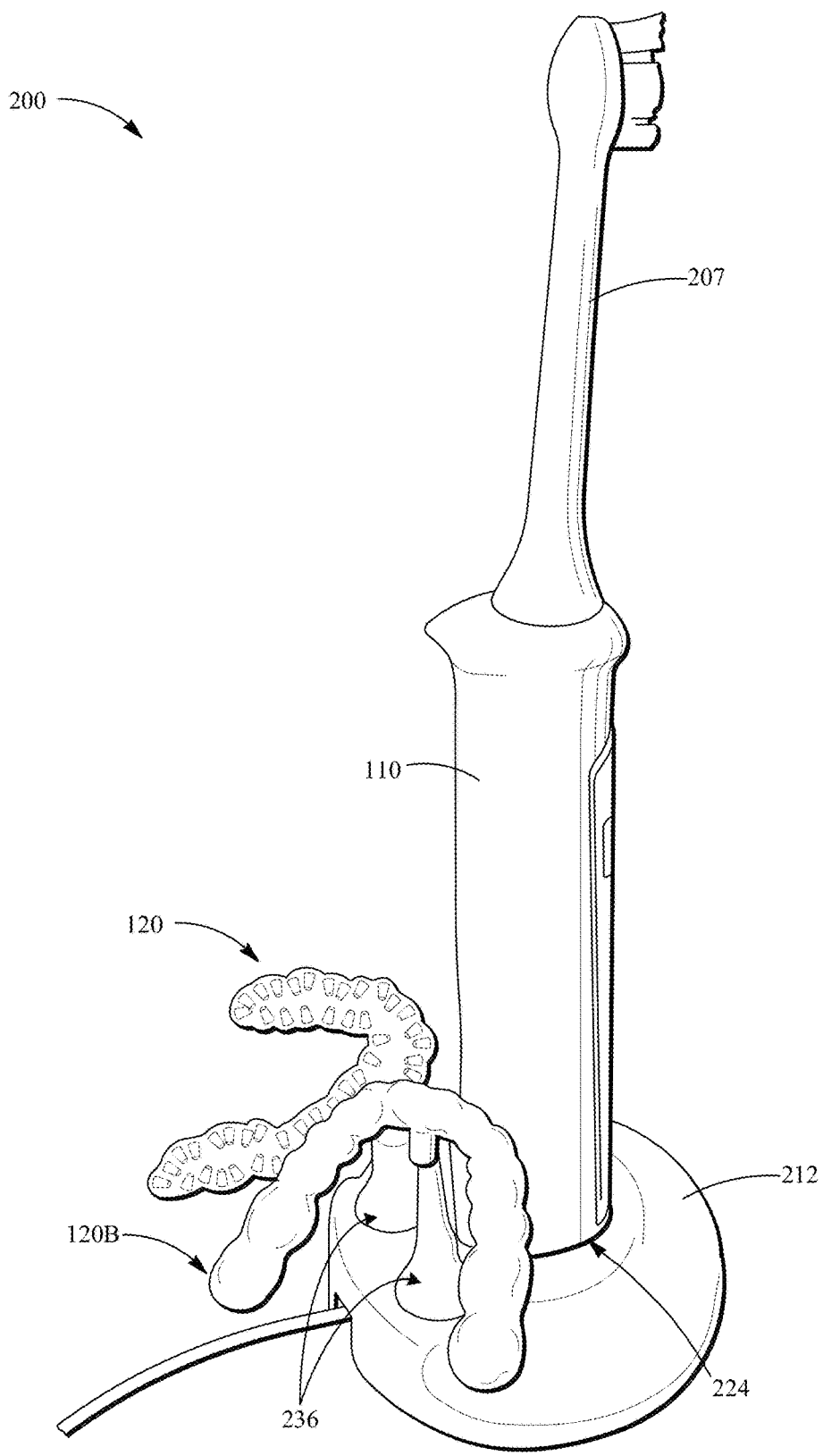
FIG. 2 is a schematic three-dimensional view illustrating a representative dental cleaning kit in accordance with some embodiments.

In FIG. 2, numeral 200 generally indicates a toothbrush kit 200 that includes the handle housing 110, a charging base or stand 212, and three attachments which are configured for removable and replaceable connection to the housing 110. The attachments in this example embodiment includes the upper arch attachment 120 described previously, a similar lower arch attachment 120B which is connected to its attachment stem 130 in an inverted orientation relative to the upper arch attachment 120, and a conventional toothbrush attachment 207, which is shown as being connected to the housing 110. Note that the attachments 120, 120 B, each comprises a respective cleaner tray 125 to which the corresponding attachment stem 130 is rigidly connected. Removability and replaceability of the attachments 120 are thus achieved by this engageable coupling between the stem 130 and the housing 110. In some embodiments, the stem 130 is rigidly connected to a rigid framework of the cleaner tray 120, the cleaner tray 120 being a molded component supported by its internal framework and through which vibratory movement is transferred from the stem 130.

In accordance with some embodiments, the stand provides a charging socket 224 for receiving and supporting the housing 110 in an upright orientation while electrically connecting the battery inside the housing 110 to a mains power supply for recharging the battery. The stand 212 further provides two separate seats 236 for holding the unused attachments 120 in an upright orientation in which the respective cleaner trays 125 are clear of a support surface.

Figure 3:
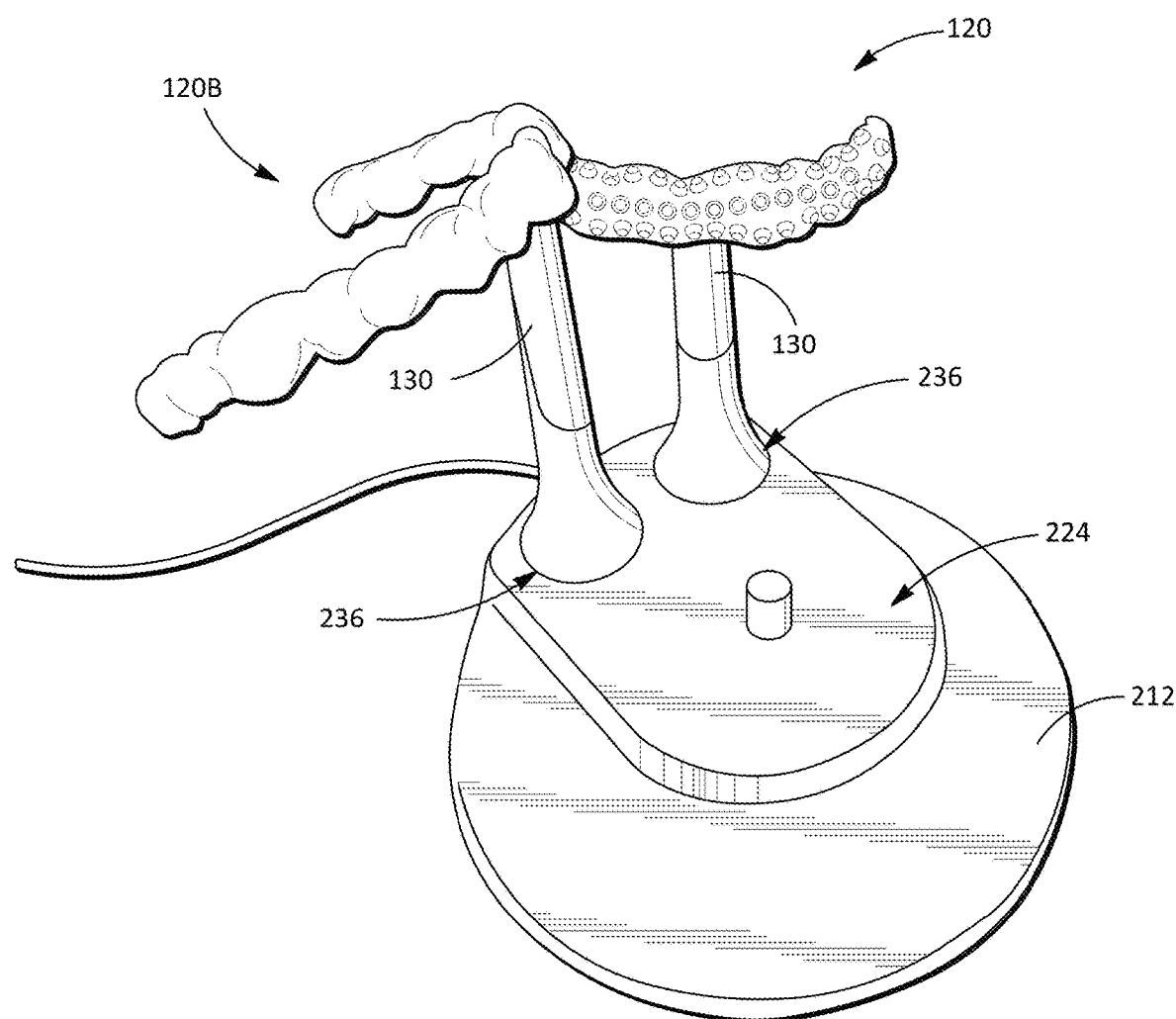
FIG. 3 is a schematic view illustrating part of the dental cleaning kit of FIG. 2 in accordance with some embodiments.

FIG. 3 shows another view of the stand 212 holding the upper arch attachment 120 and the lower arch attachment 120B in stored positions for selective use. Some embodiments of the kit 200 further include an accessory for cleaning the cleaner tray(s) 125 by removal of foreign material from the cleaning chamber 127. In some embodiments, the cleaning accessory is configured for ultrasonic cleaning of the trays.

Figure 4:
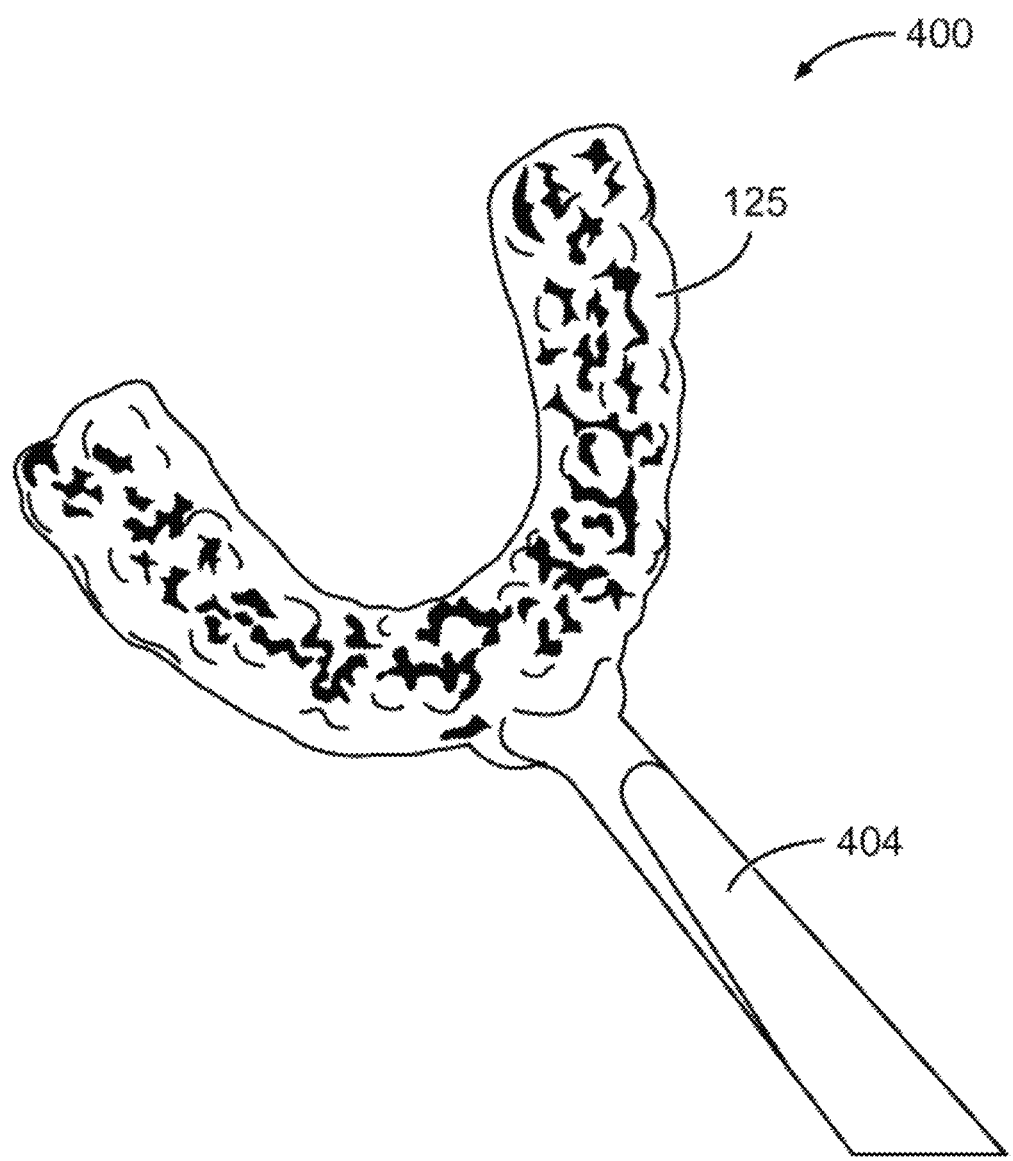
FIG. 4 is a partial three-dimensional view illustrating a representative customized dental care device in accordance with some embodiments.
Figure 5:
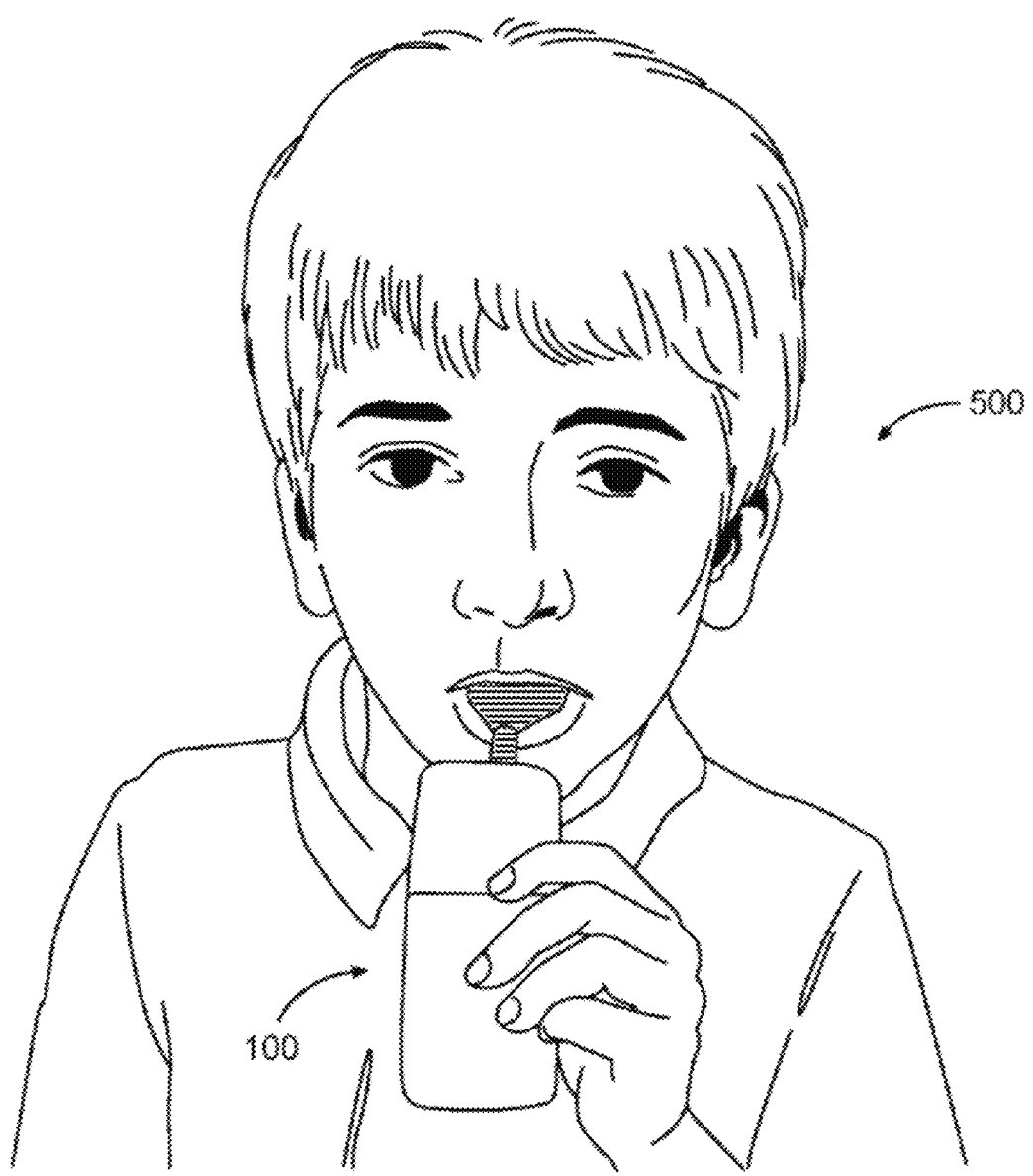
FIG. 5 is a schematic three-dimensional view illustrating use of a dental care device by a user for dental cleaning in accordance with some embodiments.

In some embodiments, a dental cleaning device in accordance with the disclosure is provided and used for dental cleaning without driven agitation of the cleaner tray 125. A partial view of such a manual toothbrush 400 is shown in FIG. 4 and comprises a cleaner tray 125 such as that described above attached to a rigid elongated handle 404, which functions analogously to conventional manual toothbrush handles. As can be noted in the foregoing drawings, as well as in FIG. 5 (which shows dental cleaning use of another embodiment of a dental care device 100 according to the disclosure by a user 500) the handle 404 of the manual toothbrush 400 is attached to the cleaner tray 125 at or adjacent the apex of the arch defined by the cleaner tray 125. The same applies to attachment of the respective attachment stems 130 to the cleaner trays 125 in some embodiments.

Such placement of the handle 404 (or, in other embodiments, the attachment stem 130) causes the toothbrush 400 to be aligned more or less with a midline of the user's face, when the cleaner tray 125 receives the corresponding set of teeth. In other embodiments, the handle 404 or attachment stem 130 is somewhat offset from the axis of symmetry of the cleaner tray 125.

For manual dental cleaning by use of the toothbrush 400, the cleaner tray 125 is inserted into the mouth, being manipulated via the handle 404, and the user bites down lightly on the cleaner tray 125 to ensure a complementary mating fit between the corresponding set of teeth and the cleaning chamber 127. Thereafter, the cleaner tray is moved backwards and forwards via the handle 404, to cause sweeping movements of the cleaning tips 140 over teeth and gums. Thereafter, the opposite set of teeth may be similarly cleaned using a separate device (or attachment 120) for that arch. Note that the pair of attachments shown in FIGS. 2 and 3 may be configured for either manual or automated use, so that the user can grip the respective attachments 120 by their respective attachment stem 130 to clean the respective arches.

In embodiments described above, each cleaner tray forms a distinct unit for cleaning a separate one of the user's opposite dental arches. In other embodiments, however, a unified cleaner body is provided that defines respective cleaning chambers 127 for both the upper and the lower arch (e.g., as shown in FIGS. 15A-15D). The user will in such embodiments simultaneously insert both the lower arch and the upper arch into the respective cleaning chambers provided by the single cleaner body, so that subsequent vibration, oscillation, or manual agitation of the cleaner body causes simultaneous cleaning action of both the upper arch and the lower arch.

This disclosure also extends to methods of facilitating personal dental health for a user by providing the user with a customized dental care device 100 as described above. In some embodiments, the customized cleaner tray 125 is formed based at least in part on a dental scan performed at a facility such as a dentist's office. In some embodiments, the dentist performs a 3-D scan, taking a digital impression of the teeth, embrasures (e.g., the space between teeth for flossing), and/or gums. These impressions are translated to customized and personalized brushing trays for both upper and lower arches (e.g., via a molding process and/or a 3-D printing process).

The 3-D scanning operation calculates each tooth's shape, curvature, and anatomy. In some embodiments, the 3-D scan also records the interdental spaces (e.g., the flossing areas or embrasure areas of the respective teeth). In some embodiments, the cleaning chamber 127 is then formed based on a somewhat enlarged model, or with an offset spacing relative to the original imprint, to provide space for cleaning elements between the chamber wall and the teeth. In some embodiments, the scanned imprint is enlarged by an offset of 1-3 mm, depending in part on the individual patient's preference.

In some embodiments, the offset spaces are then covered with cleaning tips, which may be angled to precisely clean each surface of the tooth. While, in some embodiments, the cleaning tips are arranged to universally project more or less perpendicularly from the chamber wall, the cleaning tips in other embodiments have varied angles of incidence relative to the chamber wall, with their angles being determined at least in part for optimal cleaning efficiency. In some embodiments, cleaning tip arrangement at respective embrasures is configured to promote cleaning tip access to the respective embrasures, for example, by providing cleaning tips angled for optimal or improved brushing action in the embrasures. As described elsewhere, the interdental areas may in some cases be cleaned via a wave action.

A customer service thus provided to facilitate customized dental care optionally includes providing the user with the option of choosing a particular cleaner tray 125 and cleaning tip arrangement from a plurality of different available options, based on user preference. For example, a user with a strong gag reflex may choose a smaller offset, so that the body of the cleaner tray can be smaller and fit more tightly on their teeth. Someone who, on the other hand, prefers greater leeway to move the brush within the mouth (e.g., to add mechanical brushing along with sonic and/or ultrasonic brushing) may select a larger offset. Fabrication of the cleaner trays in some embodiments comprises injection of prefabricated sheets of a polymeric plastics material into a mold shaped in accordance with the dental patient's jaw and teeth geometry.

Figure 6:
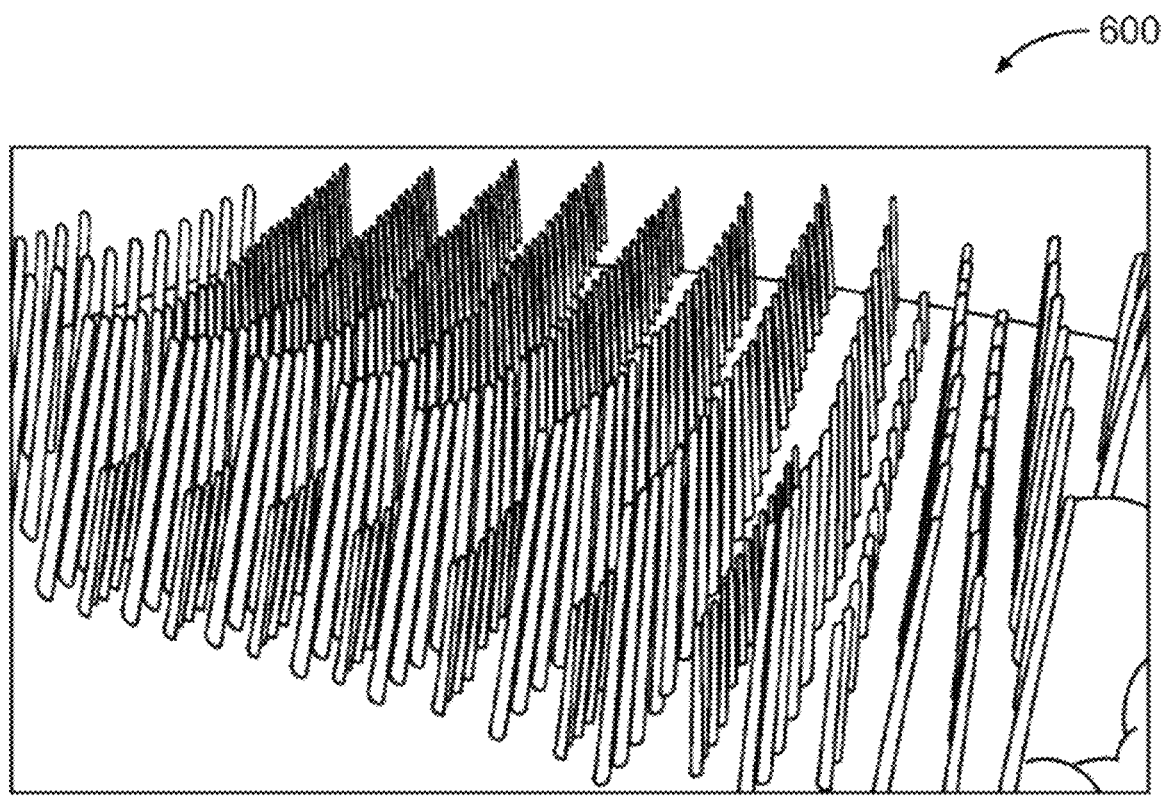
FIG. 6 is a schematic three-dimensional view illustrating a monolithically formed bristled sheet blank for use in forming a cleaner tray in accordance with some embodiments.

In some embodiments, the prefabricated sheets have bristle-like filaments injected into the sheet or integrally formed therewith, to provide the fibers or cleaning elements in the cleaning chamber 127. An example of the prefabricated bristled sheet 600 is illustrated in FIG. 6. In some embodiments, manufacture of the cleaner tray 125 comprises a 3-D printing operation to the prefabricated bristled sheets based on the above-described 3-D scan.

In some instances and embodiments, the cleaner tray 125 is formed based on a user-provided imprint. Users who, for example, do not have access to a dental scanning facility, or who wish to limit costs, may opt to form the dental imprint at home. Some embodiments include delivering, upon request, to the user a blank mold for use in forming of the cleaner tray 125, e.g., by mail or courier service. The user can then form a dental imprint in the mold by biting into it, whereafter the mold bearing the dental imprint is returned. The mold is then used at a central manufacturing facility to produce the customized cleaning tray(s) 125 in a manner similar or analogous to that described above with reference to the 3-D scan. The customized cleaner tray 125 is then returned to the user (e.g., by mail, courier service, or personal pick up) for personal use. In some embodiments, manufacture of the cleaner tray 125 includes a 3-D printing process.

Some embodiments include continually sending to the user, on a regular or periodic basis, replacement cleaner trays 125, based on the original mold or 3-D scan. A regular period for such cleaner tray replacement may be based on the rate of deterioration, in use, of the cleaner tray 125. In some embodiments, replacement cleaner trays 125 are, for example, automatically (e.g., without a specific user request) sent to the user at three-month intervals. Some embodiments include, on an ongoing basis, obtaining new dental imprints or 3-D scans for the user at spaced intervals, and producing subsequent cleaner trays 125 based on the most recent 3-D scan or dental imprint.

As mentioned previously with respect to FIGS. 1-3, the arrangement and/or configuration of cleaning elements 140 in the cleaner trays 125 can in some embodiments be varied for different positions in the cleaning chamber 127, e.g., by varied positioning and/or distribution density of the cleaning elements 140. In some embodiments, this variation is generic, applying to multiple (e.g., all) users. In some embodiments, the variation is customized based on individual user needs.

Generic variations optionally include providing higher cleaning tip densities or stiffness in areas that are universally or typically of concern. Thus, in some embodiments, the cleaning elements 140 are arranged in the cleaning chamber 127 such that the cleaning elements are arranged more densely and/or are individually stiffer towards the ends of the arch (corresponding to the back teeth), while softer and/or less dense arrangements are provided adjacent the gum line.

In some embodiments, individualized variations in cleaning element positioning and/or properties are based on identified areas of concern or weaknesses in the corresponding dental arch of the user. In some embodiments, areas of the particular user's teeth that are identified as actual or potential problem areas (e.g., suffering decay or early indicators of decay, or identified as particularly difficult to clean areas) have an increased cleaning element stiffness or concentration on the corresponding areas of the cleaning chamber 127.

In some embodiments, methods of facilitating personal dental cleaning include performing a dental scan of the user, identifying actual or potential problem areas based on the dental scan, and customizing the spatial arrangement and/or distribution of different types of cleaning elements (or cleaning elements with different physical properties) in the cleaning chamber 127 based on the identified problem areas.

In some embodiments, the cleaning elements are integrally formed with the material that provides a body of the cleaner tray 125. In some embodiments, the cleaner tray 125 is of monolithic construction, with the cleaning elements being provided by protrusions or other cleaning formations formed on the interior surface of the cleaning chamber 127. In some embodiments, manufacture of the cleaner tray 125 includes forming the cleaner tray in a molding operation from a single mold, without prior positioning of the cleaning elements in a mold chamber or afterwards attaching the cleaning elements to the molded body of the cleaner tray 125.

In some embodiments, the mold is formed with connection formations for connection of individual cleaning elements. In some embodiments, the body of the cleaner tray 125 is formed with an arrangement of connection sockets to which individual cleaning elements of polymeric plastics material are connectable by snap-fit engagement. In some embodiments, a set of relatively soft, sponge-like polymeric plastics cleaning elements are connected socket-spigot fashion to a molded base or body of a cleaner tray. In some embodiments, the cleaning elements are tightly packed together in a grid, so that closely spaced, slightly concave end faces of the cleaning elements together form an engagement surface for contact engagement with the teeth and for promoting fluid dynamic teeth cleaning action.

In some embodiments, the cleaning elements are arranged on the cleaner tray 125 such that they do not touch the tooth enamel during cleaning. It will be appreciated that such an arrangement may be provided for instances where the dental care device 100 is configured for ultrasonic cleaning, with the cleaning elements being configured for promoting ultrasonic fluid dynamic cleaning, without physical scrubbing of the teeth and/or gums.

Turning now to FIGS. 7A-7B, therein is shown a dental care device 700 in accordance with some embodiments. Functioning of a cleaner tray 725 forming part of the device 700 is substantially similar to that described previously with reference to FIGS. 1-3. In FIGS. 7A-7B, the vibration mechanism is enclosed in a knob-like handle 740 attached to the cleaner tray 725 at its apex, or in proximity to the apex (e.g., within 1 cm, 2 cm, or 5 cm) in accordance with some embodiments. In some embodiments, a power source for the vibration mechanism is carried in a base unit 750, the vibration mechanism being connected to the power source via an electrical power cord 760 connecting the handle 740 to the base unit 750.

In accordance with some embodiments, the base unit 750 further defines a complementary docking chamber 770 for the cleaner tray 725. In accordance with some embodiments, when the cleaner tray 725 is received in the docking chamber 770 (see FIG. 7B) the cleaning chamber 127 of the cleaner tray 725 is located wholly within the docking chamber 770, being hidden from view and from exposure to the atmosphere. The device 700 in such a stowed mode forms a compact portable unit in which the cleaning tray 725 is sealingly located within the base unit 750, with the handle 740 projecting upwards from the base unit 750 for easy access by the user.

In accordance with some embodiments, the base unit 750 is configured not merely for holding the cleaner tray 725 such that it is protected from exposure between brushings, but is additionally configured to actively sanitize the cleaner tray 725 during docking. In some embodiments, the base unit 750 is provided with an ultra-violet (UV) cleaning arrangement that irradiates the cleaner tray 725 in general, and the cleaning chamber 127 in particular, with sanitizing UV light when the cleaner tray 725 is inserted in the docking chamber 770. In some embodiments, the base unit 750 is configured to effect cleaning of the cleaner tray 725 during docking by causing exposure of the cleaning chamber 127 to a sanitizing liquid. In some embodiments, the cleaner tray 127 forms a liquid-tight seal with the base unit 750, to contain the sanitizing liquid safely and to permit use of the device 700 as a travel accessory.

FIGS. 8A-8D show a dental care kit 800 in accordance with some embodiments. In some embodiments, a dental care device 810 forming part of the kit 800 functions in a manner similar or analogous to that described with reference to FIGS. 1-3.

Figure 8B:
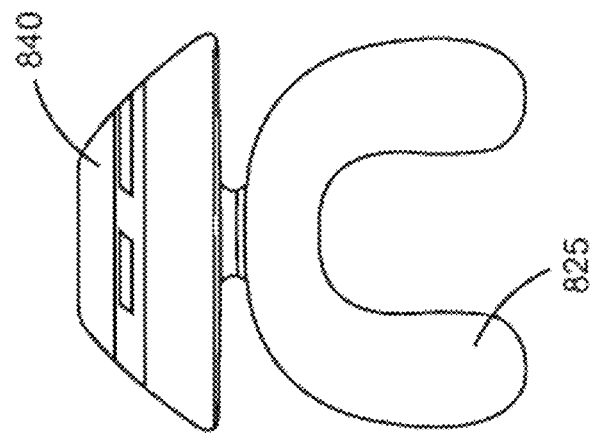
FIGS. 8A-8B are schematic elevational views of a representative dental care kit that includes a dental care device according to some embodiments.
Figure 8A:
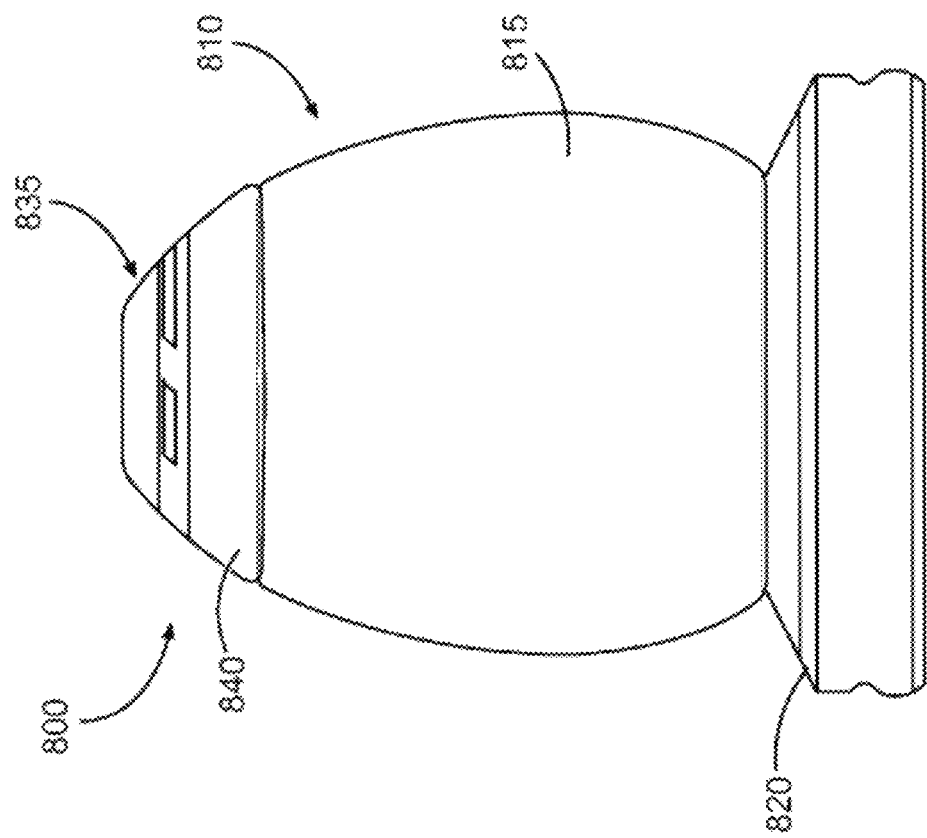

In accordance with some embodiments, the dental care device 810 has a housing 815 that houses a vibration mechanism in the form of an electric motor, together with a coupled rechargeable electric battery. As shown in FIG. 8A, the housing 815 has a base that is receivable in a complementary mating charging socket defined by a docking station 820. In some embodiments, when the dental care device 810 is docked on the docking station 820, an electrical connection is automatically formed between the rechargeable battery and mains power to which the docking station 820 is connected, thereby recharging the battery.

Figure 8D:
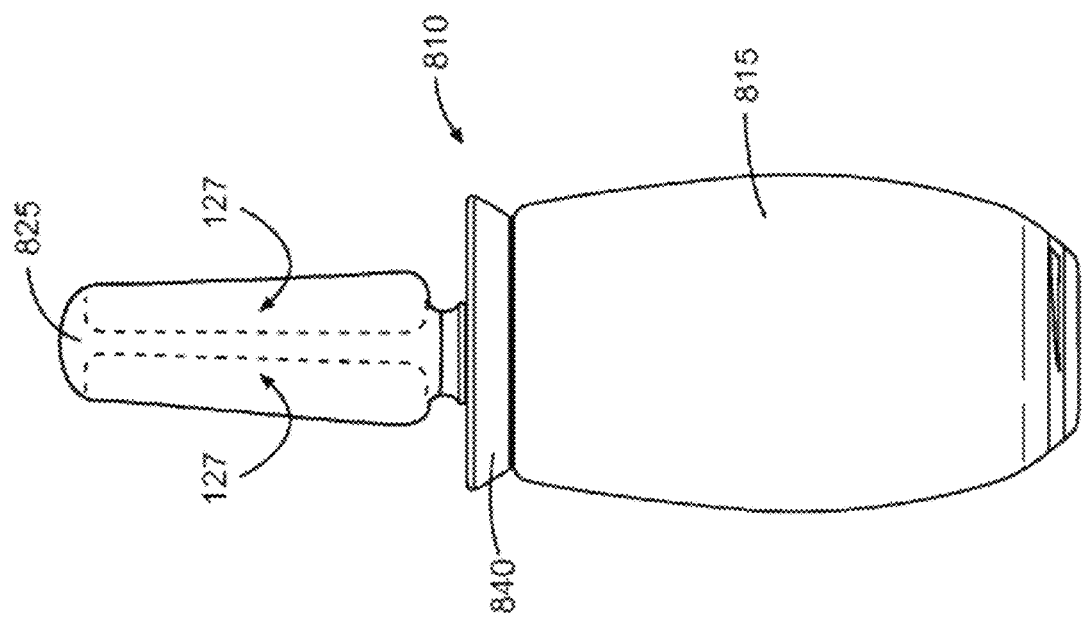
FIG. 8D shows the dental care device in side view.
Figure 8C:
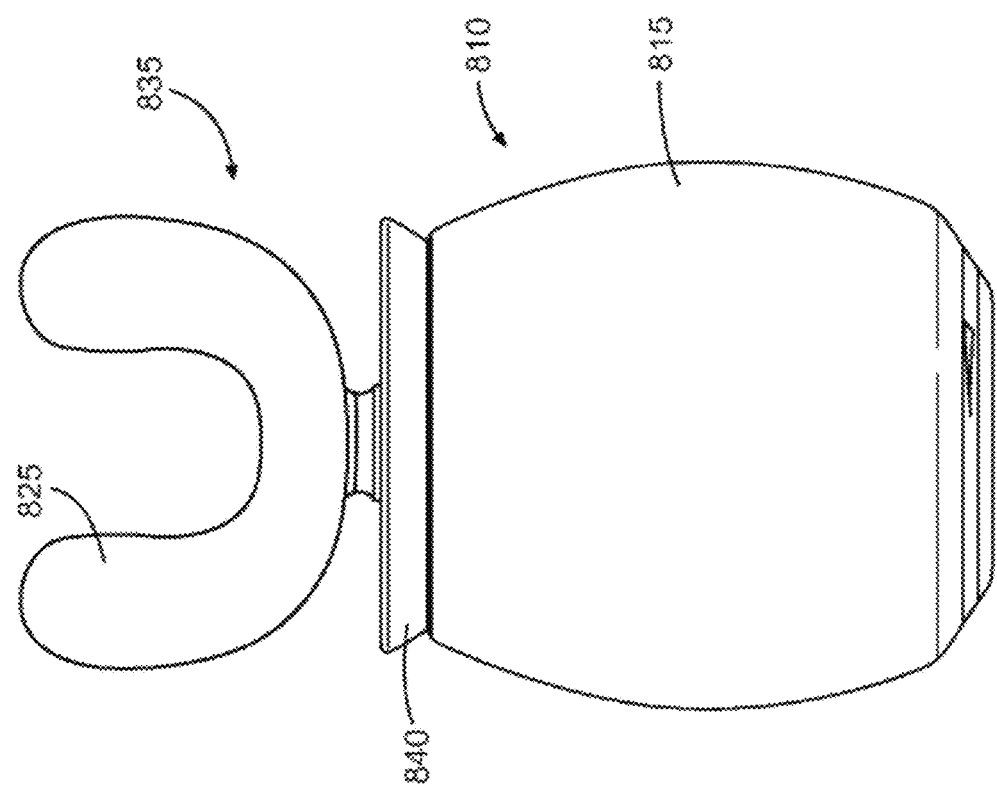
FIG. 8C shows the dental care device in front view.

In accordance with some embodiments, the dental care device 810 includes a reversible mouthpiece attachment 835 (see FIG. 8B) that is connectable to an upper end of the housing 810 in either a storage mode (FIG. 8A) or in an operational mode (FIGS. 8C-8D). In the storage mode shown in FIG. 8A, a cleaner body 825 forming part of the attachment 835 is located within the interior of the housing 810, so that the cleaner body 825 is hidden from view and is not exposed to the atmosphere.

In accordance with some embodiments, a handle 840 of the attachment 810 in this configuration serves as a lid for the housing 810. As was described with reference to FIG. 7, the housing 810 provides a sanitizing mechanism (e.g., a UV cleaning system) that serves to sanitize the cleaner body 825 when the device 810 is in the storage mode. In the storage mode, the dental care device 810 forms a self-contained, sealed unit suitable for use as a travel accessory.

In some embodiments, the cleaner body 825 is configured for simultaneously cleaning both dental arches of a user. As shown in broken lines in FIG. 8D, the cleaner body 825 thus defines a pair of oppositely outwardly facing cleaning chambers 127, each being complementary in shape to a respective dental arch of the specific user for which the device 800 is customized. In use, the user can therefore insert the cleaner body 825 between their dental arches, bite down onto the cleaner body 825 to receive each dental arch in its corresponding chamber 127, and can then clean both arches at the same time by activating the vibration mechanism. In accordance with some embodiments, the cleaning chambers 127 in FIGS. 8A-8D include no filamentary cleaning elements for contact engagement with the teeth, but are instead configured to effect dental cleaning primarily through operation of fluid dynamics. In some embodiments, the cleaner body 825 includes cleaning tips such as those shown in FIGS. 15A-15D.

In the operational mode (FIG. 8C), however, the orientation of the attachment 835 is reversed, so that the handle 840 is firmly connected to an upper end of the housing 810, the cleaner body 825 projecting away from the housing 810 in accordance with some embodiments. Note that the selectively detachable coupling of the attachment 835 to the housing 810 is such as to transfer operational or oscillatory forces from the motor in the housing 810 to the cleaner body 825.

It is a benefit of the described embodiments that it provides for personal dental cleaning that is both quicker and more effective than is the case with conventional toothbrushes. In some circumstances, the whole mouth can be cleaned in as little as 5-10 seconds, while achieving more consistent and thorough cleaning results than with conventional toothbrushes. This is in part because all surfaces of the teeth of the corresponding dental arch are brushed simultaneously, based on the vibratory or reciprocating movement that is imparted to the cleaner tray 125 and that all of the cleaning elements therefore have in common.

It is also beneficial that all parts of the dental arch can consistently be accessed with equal ease and effectiveness by the cleaner tray 125, independent of user skill or dexterity. Many users are not able, for example, to reach rearward facing surfaces behind the molars and areas where the tongue covers the teeth, or fail to do so consistently. These and other problems associated with user-controlled brushing patterns are exacerbated for children and the elderly, who often do not have sufficient manual dexterity for implementing correct brushing techniques using conventional toothbrushes. These problems are greatly reduced by the described methods and devices.

Yet a further benefit of some of the described embodiments is that flossing is effected simultaneously for all the embrasures in the relevant arch, and simultaneously with cleaning of other tooth and gum surfaces (e.g., by operation of fluid action induced by tray vibration within particular frequency ranges, as described), and without needing to pass a filament or other cleaning element sequentially through the embrasures of different teeth, as is the case with conventional flossing. Again, simultaneous whole-arch dental flossing without forceful insertion of dental floss or toothpicks into the embrasures promotes enamel and gum health by preventing abrasive contact with these surfaces.

A further benefit is that the arrangement of cleaning elements in the cleaning chamber 127 can be configured such as to avoid or prevent deleterious effect from bad brushing habits. Conventional tooth brushing can, for example, be detrimental to the health of enamel and gums, particularly by abrasion that can be caused by overly brushing. Most users are also not able to maintain the correct angle of conventional toothbrushes heads.

As mentioned, the cleaner tray 125 in some embodiments is formed such that there is no bristle contact with the gums during brushing. In some embodiments, as described previously, dental cleaning by use of the device is effected without abrasive contact with tooth enamel, thereby protecting enamel from wear caused by brushing and scraping.

Moreover, customization of the cleaner tray 125 provides for user-specific cleaning mechanics, providing the ability to accommodate dental conditions unique to any particular user.

One aspect the above-describe example embodiments includes a toothbrush (dental care) device which includes a cleaner body that defines a cleaning chamber shaped for receiving a group of teeth of a user. The device optionally includes a powered driving mechanism that is mechanically coupled to the cleaner body and that is configured for imparting driven movement to the cleaner body during reception of the group of teeth in the cleaning chamber, to cause cleaning of the group of teeth.

In some embodiments, the cleaner body is personalized for a specific user, the cleaning chamber corresponding substantially to a dental imprint of the corresponding group of teeth. In some embodiments, the cleaner body is configured for receiving a particular dental arch set of the user, being a set of teeth on a corresponding dental arch of the user. In some embodiments, the cleaner body defines a pair of oppositely outwardly facing cleaning chambers. In such cases, each of the cleaning chambers is optionally shaped and configured for receiving a respective dental arch set of the user, to allow simultaneous reception of all of the user's teeth by the cleaner body. In some embodiments, the cleaner body is removably and replaceably coupled to the powered driving mechanism.

In some embodiments, the cleaning chamber is shaped so as to substantially envelop, between opposing side walls of the cleaning chamber, each tooth received in the cleaning chamber. In some embodiments, the opposing side walls that define the cleaning chamber are shaped and configured such as to extend over respective gum lines of the group of teeth, when the group of teeth are fully received in the cleaning chamber.

In some embodiments, such a dental care device further includes cleaning elements carried by the cleaner body and protruding into the cleaning chamber for contact engagement with teeth received in the same chamber. In some embodiments, the cleaning elements include elongate filamentary elements protruding into the cleaning chamber. In some embodiments, the cleaning elements include protrusions on a chamber wall defining the cleaning chamber. In some embodiments, the protrusions are of monolithic construction with the cleaner body.

In some embodiments, arrangement and configuration of the cleaning elements are non-uniform for different areas of a chamber wall that defines the cleaning chamber. In some embodiments, the cleaning elements are arranged and configured for relatively more vigorous cleaning action in one or more focus areas. In some embodiments, the one or more focus areas include areas corresponding to embrasures between adjacent teeth. Instead, or in addition, the one or more focus areas optionally include areas corresponding to ends of a dental arch.

In some embodiments, variation in arrangement and configuration of the cleaning elements includes higher density concentration of the cleaning elements in the one or more focus areas. Instead, or in addition, variation in arrangement and configuration of the cleaning elements optionally includes differences between, on the one hand, one or more physical properties of individual cleaning elements in the one or more focus areas, and, on the other hand, corresponding physical properties of individual cleaning elements in other areas.

In some embodiments, the arrangement and configuration of the cleaning elements are customized for a specific user, such that at least one of the one or more focus areas corresponds in location to an identified dental problem area of the corresponding specific user.

In some embodiments, the powered driving mechanism includes a vibration mechanism for causing driven vibration of the cleaner body. In some embodiments, the vibration mechanism is configured for causing sonic and/or subsonic oscillation of the cleaner body. Instead, or in addition, the vibration mechanism is configured for causing ultrasonic vibration of the cleaner body. In some embodiments, the vibration mechanism is configured to enable dental cleaning via the cleaner body using both sonic and ultrasonic cleaning.

Figure 9:
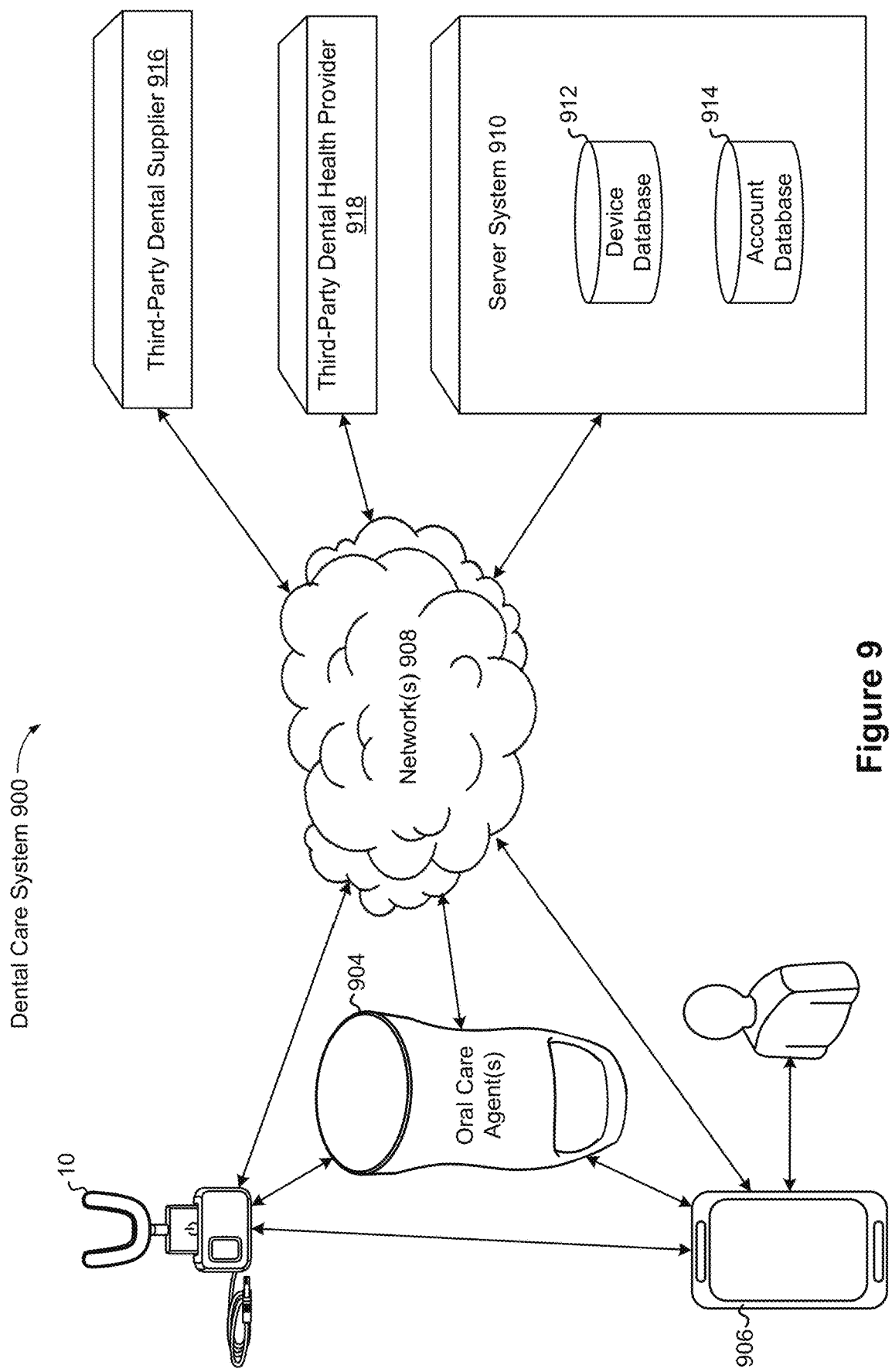
FIG. 9 is a schematic view illustrating a representative dental care system in accordance with some embodiments.

FIG. 9 is a schematic view illustrating a dental care system 900 in accordance with some embodiments. The dental care system 900 includes a dental care device 10, an oral care agent dispenser device 904, a user device 906 (e.g., a smart phone, tablet, personal computer, or the like), a server system 910, a third-party dental supplier 916, and a third-party dental health provider 918, communicatively coupled to one another via one or more networks 908 (e.g., one or more LANs, WANs, and/or the Internet). In some embodiments, the dental care device 10 is directly coupled to the dispenser device 904 and/or the user device 906 (e.g., via Bluetooth protocol). As will be discussed in greater detail below with respect to FIGS. 12A-12B, the server system 910 includes a device database 912 and an account database 914 in accordance with some embodiments.

Figure 10A:
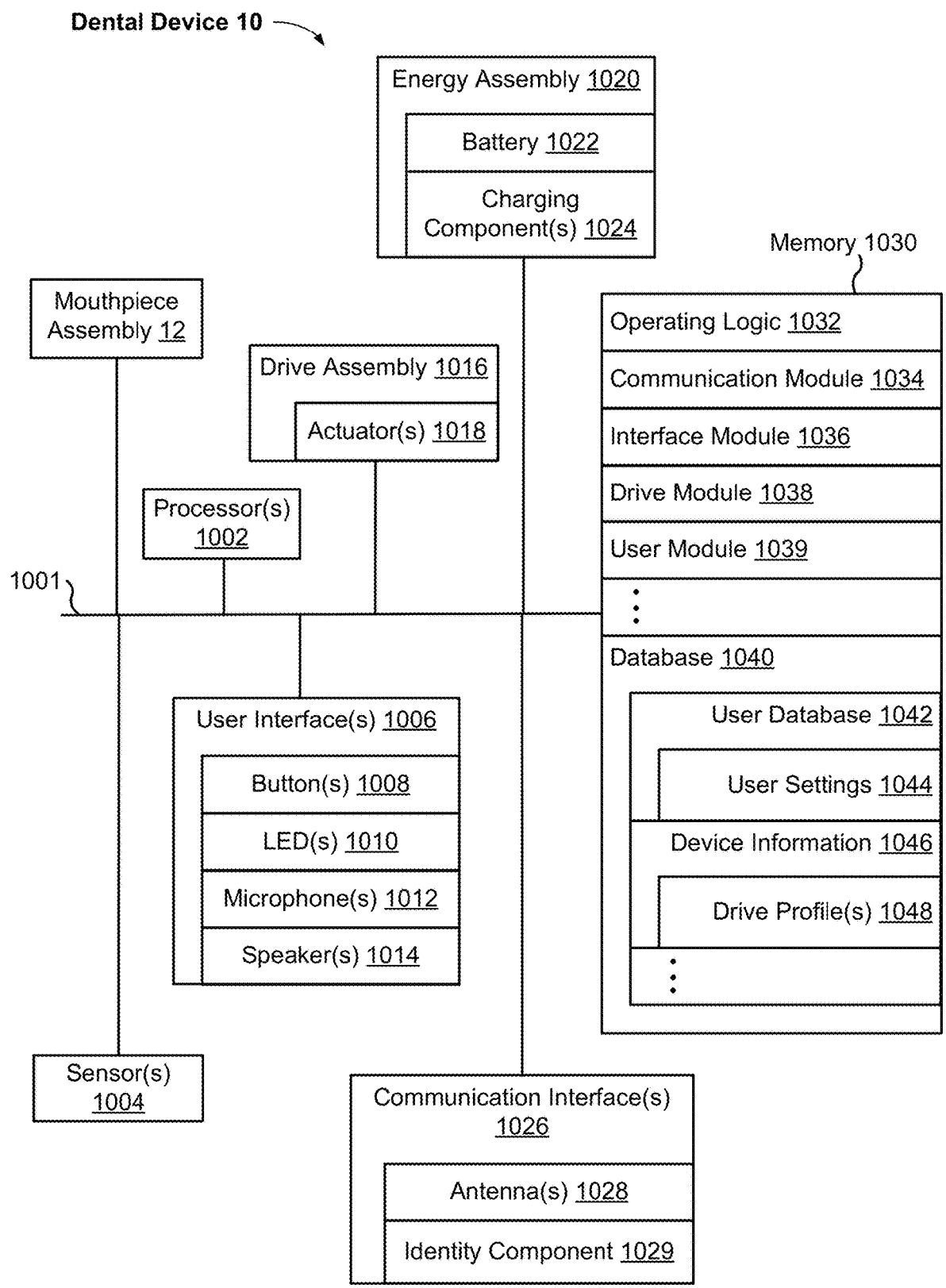
FIG. 10A is a block diagram illustrating a representative dental care device in accordance with some embodiments.

FIG. 10A is a block diagram illustrating a dental care device 10 in accordance with some embodiments. In some implementations, the dental care device 10 includes one or more processors (e.g., CPUs, ASICs, FPGAs, microprocessors, and the like) 1002, one or more communication interfaces 1026, memory 1030, mouthpiece assembly 12, energy assembly 1020, drive assembly 1016, user interface(s) 1006, sensor(s) 1004, and one or more communication buses 1001 for interconnecting these components (sometimes called a chipset). In some implementations, the user interface(s) 1006 includes one or more output devices that enable presentation of media content, including one or more LED(s) 1010, one or more speakers 1014, and/or one or more visual displays. In some implementations, the user interface(s) 1006 also includes one or more input devices, including user interface components that facilitate user input such as a voice-command input unit or microphone 1012, a touch screen display, a touch-sensitive input pad, a gesture capturing camera, or other input buttons or controls 1008. Optionally, the dental care device 10 includes a location detection component, such as a GPS (global positioning satellite) or other geo-location receiver, for determining the location of the dental care device 10.

The sensors 1004 include, for example, one or more breath sensors, thermal radiation sensors, bacteria detection sensors, ambient temperature sensors, humidity sensors, IR sensors, presence sensors (e.g., using RFID sensors), ambient light sensors, motion detectors, accelerometers, and/or gyroscopes.

The communication interface(s) 1026 enable the dental care device 10 to communicate with other devices. In some implementations, the communication interface(s) 1026 are capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, MiWi, etc.) custom or standard wired protocols (e.g., Ethernet, HomePlug, etc.), and/or any other suitable communication protocol, including communication protocols not yet developed as of the filing date of this document. In some embodiments, the communication interface(s) 1026 includes one or more antennas 1028 configured for data communications using any of a variety of custom or standard protocols (e.g., the protocols listed above). In some embodiments, the communication interface(s) 1026 includes an identity component 1029 configured to transmit (e.g., broadcast) an identifier for the dental care device 10 and/or an identifier for a user of the dental care device 10. In some embodiments, the identity component 1029 comprises circuitry, memory, and/or software configured for wireless communications (e.g., using Bluetooth or Internet of Things (IoT) protocols). In some embodiments, the identity component 1029 stores a unique identifier for the dental care device 10.

In accordance with some embodiments, the energy assembly 1020 includes one or more batteries 1022, and optionally, one or more charging components 1024. In some embodiments, the charging component(s) 1024 include one or more components to enable inductive charging.

In accordance with some embodiments, the drive assembly 1016 includes one or more actuators 1018. In some embodiments, the one or more actuators 1018 comprise one or more piezoelectric actuators and/or one or more electric motors (e.g., magnetic motors, offset weight motors). In some embodiments, the drive assembly 1016 is configured to generate vibrations in the mouthpiece component 12.

The memory 1030 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 1030, or alternatively the non-volatile memory within memory 1030, includes a non-transitory computer-readable storage medium. In some implementations, memory 1030, or the non-transitory computer-readable storage medium of the memory 1030, stores the following programs, modules, and data structures, or a subset or superset thereof:

- Operating logic 1032 including procedures for handling various basic system services and for performing hardware dependent tasks;
- Communication module 1034 for connecting to and communicating with other network devices (e.g., a router that provides Internet connectivity, networked storage devices, network routing devices, server system 910, dispenser device 904, etc.) connected to one or more networks 908 via one or more communication interfaces 1026 (wired or wireless);
- Interface module 1036 for detecting one or more user inputs or interactions and interpreting the detected inputs or interactions, and for providing and displaying a user interface in which settings, captured data, and/or other data can be configured and/or viewed;
- Drive module 1038 for operating the drive assembly 1016, e.g., in accordance with one or more drive profiles 1048;
- User module 1039 for managing user information, such as user preferences, user settings, user dental information, user identifiers, user drive profiles, user dispensing profiles, and the like (e.g., a HIPPA-compliant module); and
- Database 1040 storing data associated with the dental care device, including, but not limited to:
  - User database 1042 storing information related to user accounts for the dental care device, such as user settings 1044 (e.g., user interface settings and display preferences), user dental information, cached login credentials, device identifiers (e.g., MAC addresses and UUIDs), authentication tokens and tags, password keys, etc.; and
  - Device information 1046 storing information related to the dental care device 10 and, optionally, associated devices such as dispenser device 904 and user device 906, including one or more drive profiles 1048 associated with user(s) of the dental care device.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 1030, optionally, stores a subset of the modules and data structures identified above. Furthermore, the memory 1030, optionally, stores additional modules and data structures not described above, such as a charging module configured to operate the energy assembly 1020.

In some embodiments, one or more of the components shown in FIG. 10A are located within a stand (or mount) of the dental care device 10. For example, one or more of the components are arranged within the stand 18 (FIG. 1A). In some embodiments, one or more elements of the user interface(s) 1006 are positioned on the stand (e.g., user interface 20, FIG. 1A). In some embodiments, one or more of the components shown in FIG. 10A are located within a housing of the dental care device 10 (e.g., within the base unit 750 or the housing 815).

Figure 10B:
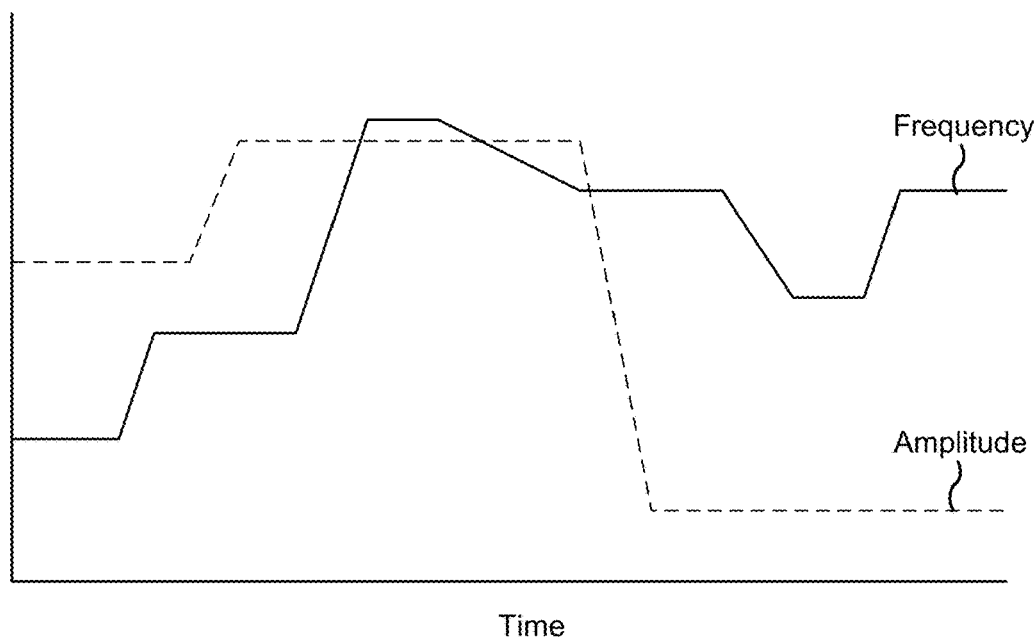
FIG. 10B is a graphical view illustrating representative drive profiles for use with the dental care device of FIG. 10A in accordance with some embodiments.
Figure 10B:
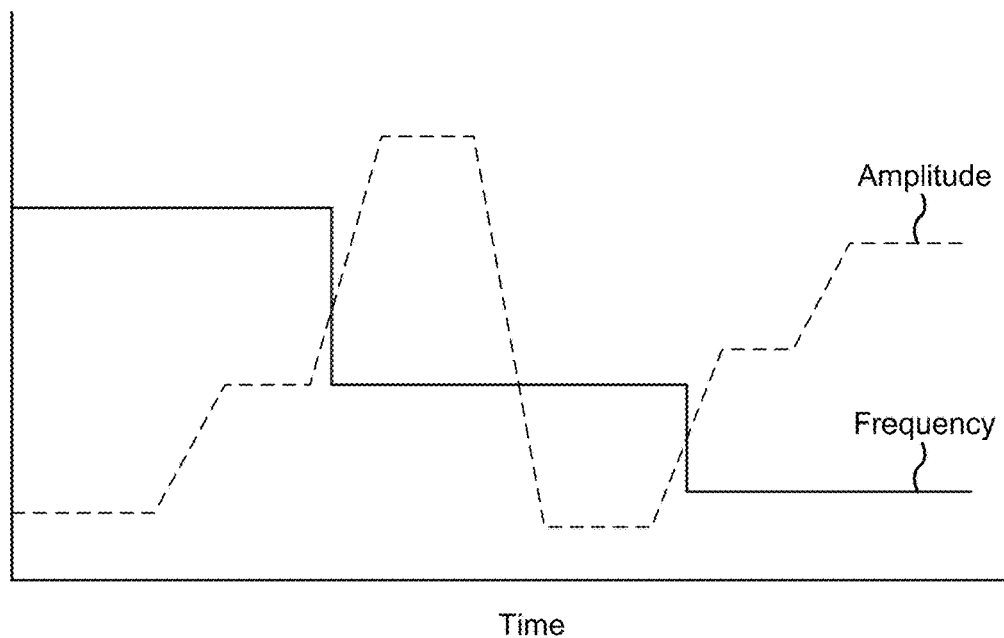

FIG. 10B is a graphical view illustrating example drive profiles 1048 for use with the dental care device of FIG. 10A in accordance with some embodiments. The drive profiles 1048-1 and 1048-2 illustrate two example profiles (e.g., constructed for two different people based each user's dental details). In some embodiments, the frequencies and timing for the drive profile 1048 are adjusted for each user based on the user's dental health, teeth geometry, age, and the like. In some embodiments, the frequencies include one or more sonic frequencies and/or one or more ultrasonic frequencies.

Figure 11:
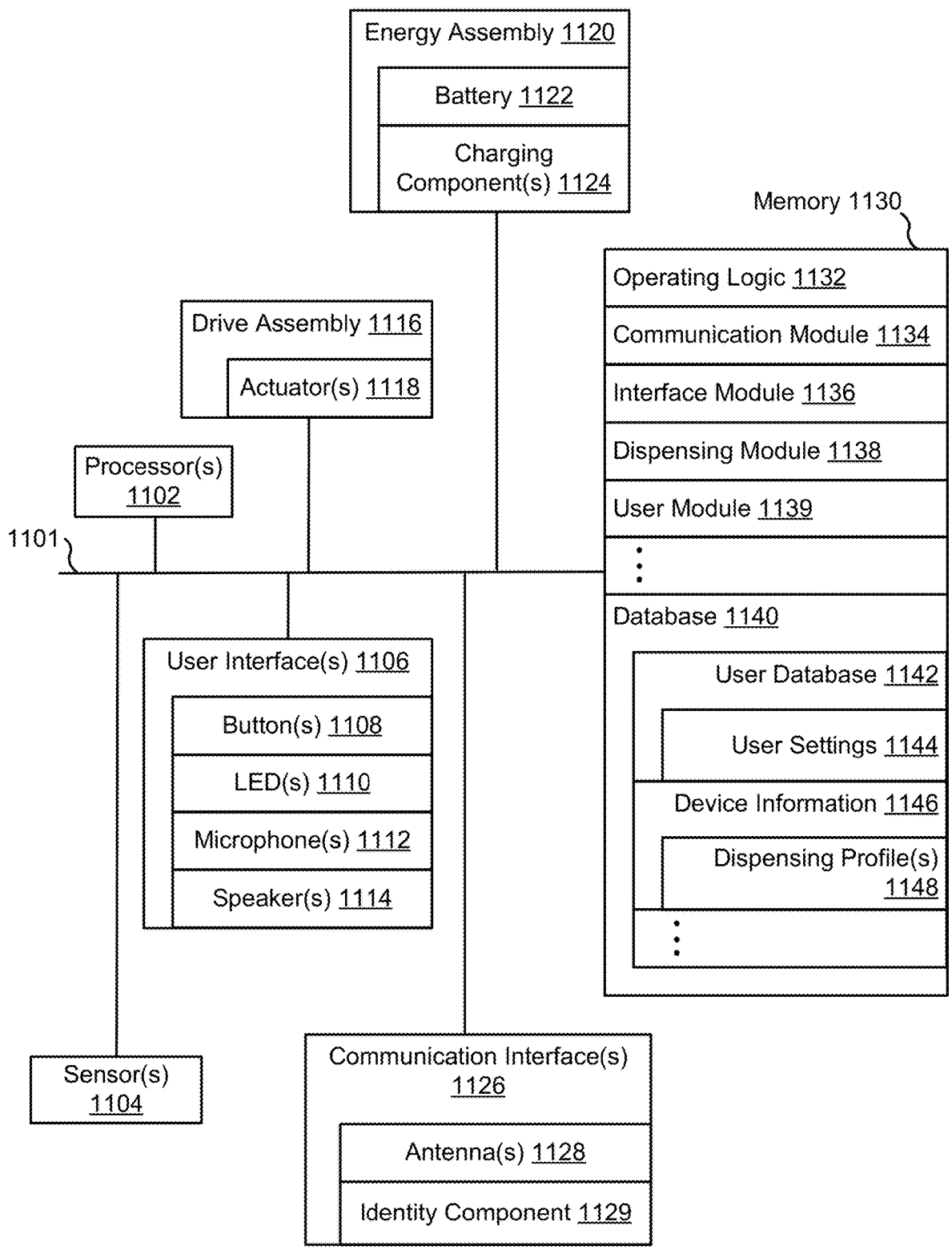
FIG. 11 is a block diagram illustrating a representative dispenser device in accordance with some embodiments.

FIG. 11 is a block diagram illustrating an oral care agent dispenser device 904 in accordance with some embodiments. In some implementations, the dispenser device 904 includes one or more processors (e.g., CPUs, ASICs, FPGAs, microprocessors, and the like) 1102, one or more communication interfaces 1126, memory 1130, energy assembly 1120, drive assembly 1116, user interface(s) 1106, sensor(s) 1104, and one or more communication buses 1101 for interconnecting these components (sometimes called a chipset). In some implementations, the user interface(s) 1106 includes one or more output devices that enable presentation of media content, including one or more LED(s) 1110, one or more speakers 1114, and/or one or more visual displays. In some implementations, the user interface(s) 1106 also includes one or more input devices, including user interface components that facilitate user input such as a voice-command input unit or microphone 1112, a touch screen display, a touch-sensitive input pad, a gesture capturing camera, or other input buttons or controls 1108. Optionally, the dispenser device 904 includes a location detection component, such as a GPS (global positioning satellite) or other geo-location receiver, for determining the location of the dispenser device 904 (e.g., for use with ordering oral care agent ingredients).

The sensors 1104 include, for example, thermal radiation sensors, ambient temperature sensors, humidity sensors, IR sensors, presence sensors (e.g., using RFID sensors, barcode readers, passive infrared (PIR) sensors), ambient light sensors, motion detectors, accelerometers, and/or gyroscopes.

The communication interface(s) 1126 enable the dispenser device 904 to communicate with other devices (e.g., dental care devices 10). In some implementations, the communication interface(s) 1126 are capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, MiWi, etc.) custom or standard wired protocols (e.g., Ethernet, HomePlug, etc.), and/or any other suitable communication protocol, including communication protocols not yet developed as of the filing date of this document. In some embodiments, the communication interface(s) 1126 includes one or more antennas 1128 configured for data communications using any of a variety of custom or standard protocols (e.g., the protocols listed above). In some embodiments, the communication interface(s) 1126 includes an identity component 1129 configured to transmit (e.g., broadcast) an identifier for the dispenser device 904 and/or an identifier for a user of the dispenser device. In some embodiments, the identity component 1129 comprises circuitry, memory, and/or software configured for wireless communications (e.g., using Bluetooth or Internet of Things (IoT) protocols). In some embodiments, the identity component 1129 stores a unique identifier for the dispenser device 904.

In accordance with some embodiments, the energy assembly 1120 optionally includes one or more batteries 1022, and one or more charging components 1024 (e.g., for coupling to an AC adapter). In some embodiments, the charging component(s) 1024 include one or more components to enable inductive charging for a dental care device.

In accordance with some embodiments, the drive assembly 1116 includes one or more actuators 1118. In some embodiments, the one or more actuators 1118 comprise one or more piezoelectric actuators and/or one or more electric motors. In some embodiments, the drive assembly 1116 is configured to combine and dispense toothpaste or oral care agent ingredients (e.g., in accordance with a dispensing profile 1148).

The memory 1130 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 1130, or alternatively the non-volatile memory within memory 1130, includes a non-transitory computer-readable storage medium. In some implementations, memory 1130, or the non-transitory computer-readable storage medium of the memory 1130, stores the following programs, modules, and data structures, or a subset or superset thereof:

- Operating logic 1132 including procedures for handling various basic system services and for performing hardware dependent tasks;
- Communication module 1134 for connecting to and communicating with other network devices (e.g., a router that provides Internet connectivity, networked storage devices, network routing devices, server system 910, dental care device 10, dental care device 100, etc.) connected to one or more networks 908 via communication interface(s) 1126 (wired or wireless);
- Interface module 1136 for detecting one or more user inputs or interactions and interpreting the detected inputs or interactions, and for providing and displaying a user interface in which settings, captured data, and/or other data can be configured and/or viewed;
- Dispensing module 1138 for operating the drive assembly 1116, e.g., in accordance with one or more dispensing profiles 1148;
- User module 1139 for managing user information, such as user preferences, user settings, user dental information, user identifiers, user drive profiles, user dispensing profiles, and the like (e.g., a HIPPA-compliant module); and
- Database 1140 storing data associated with the dental care device, including, but not limited to:
  - User database 1142 storing information related to user accounts for the dental care device, such as user settings 1144 (e.g., user interface settings and display preferences), user dental information, cached login credentials, device identifiers (e.g., MAC addresses and UUIDs), authentication tokens and tags, password keys, etc.; and
  - Device information 1146 storing information related to the dispenser device 904 and, optionally, associated devices such as dental care device 10, dental care device 100, and user device 906, including one or more dispensing profiles 1148 associated with user(s) of the dispenser device.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 1130, optionally, stores a subset of the modules and data structures identified above. Furthermore, the memory 1130, optionally, stores additional modules and data structures not described above, such as a charging module configured to operate the energy assembly 1120.

Figure 12A:
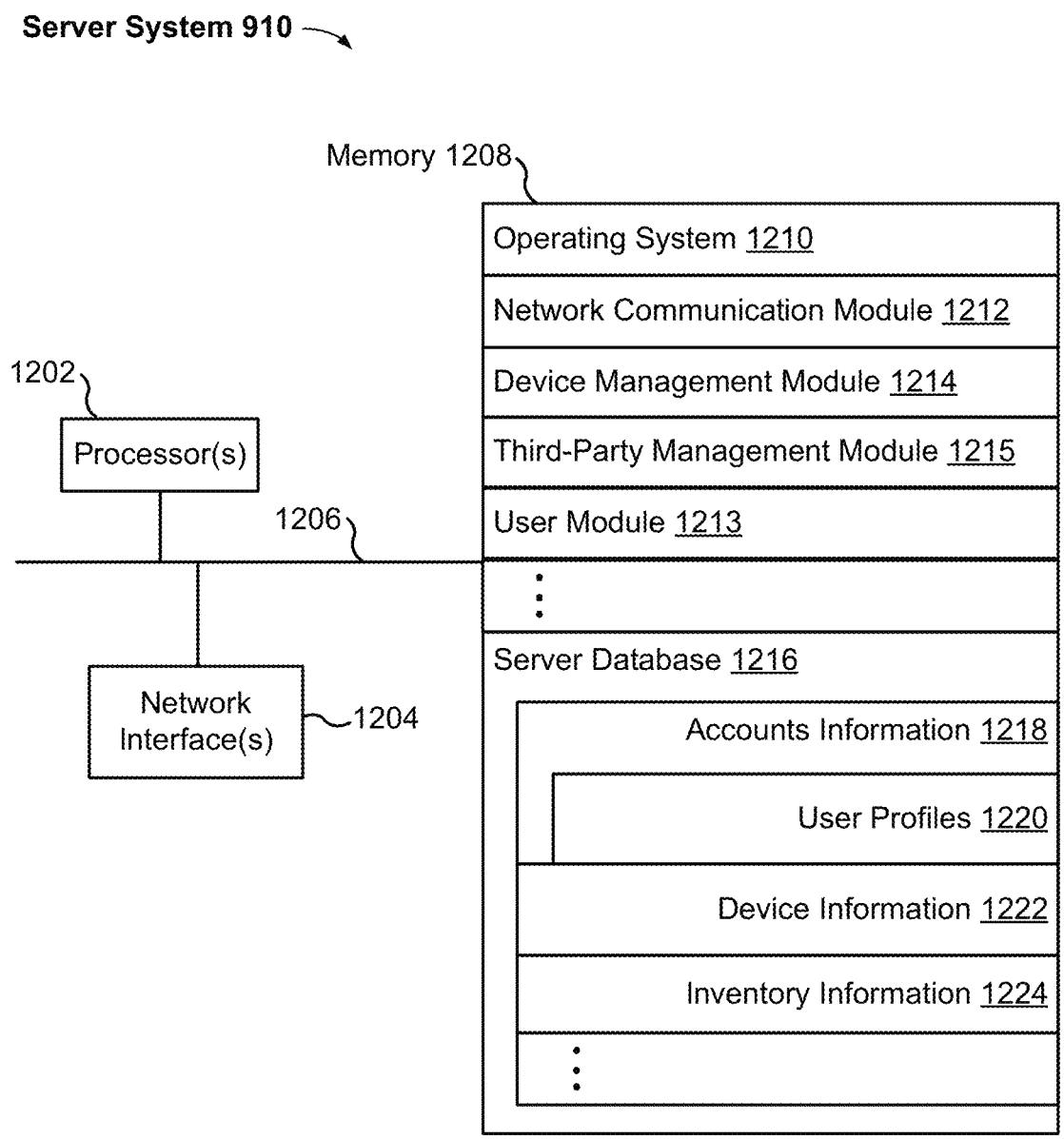
FIGS. 12A-12B are block diagrams illustrating a representative server system in accordance with some embodiments.
Figure 12B:
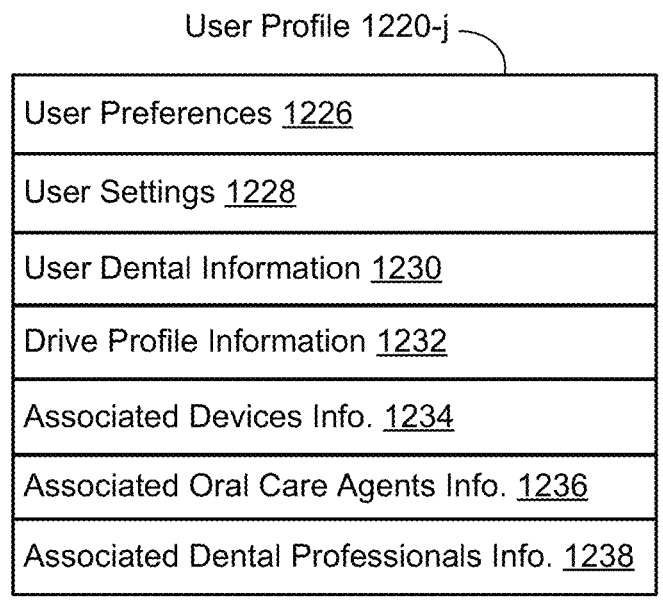
Figure 12B:
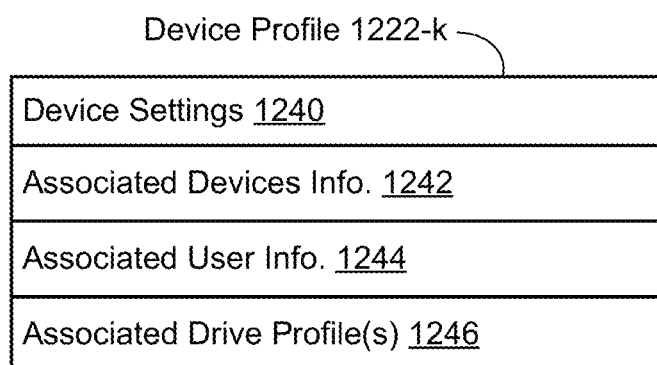

FIGS. 12A-12B are block diagrams illustrating a server system 910 in accordance with some embodiments. In some implementations, the server system 910 includes one or more processors (e.g., CPUs, ASICs, FPGAs, microprocessors, and the like) 1102, one or more network interfaces 1204, memory 1208, and one or more communication buses 1206 for interconnecting these components (sometimes called a chipset). In some implementations, the server system 910 includes one or more the user interface(s) includes one or more output devices and/or one or more input devices.

The network interface(s) 1204 enable the server system 910 to communicate with other devices (e.g., dental care devices 10 and/or dispenser device 904). In some implementations, the network interface(s) 1204 are capable of data communications using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, MiWi, etc.) custom or standard wired protocols (e.g., Ethernet, HomePlug, etc.), and/or any other suitable communication protocol, including communication protocols not yet developed as of the filing date of this document.

The memory 1208 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 1208, or alternatively the non-volatile memory within memory 1208, includes a non-transitory computer-readable storage medium. In some implementations, memory 1208, or the non-transitory computer-readable storage medium of the memory 1208, stores the following programs, modules, and data structures, or a subset or superset thereof:

Operating system 1210 including procedures for handling various basic system services and for performing hardware dependent tasks;

Network communication module 1212 for connecting the server system 910 to other systems and devices (e.g., client devices, dental care devices, dispenser devices, electronic devices, and systems connected to one or more networks 908) via one or more network interfaces 1204 (wired or wireless);

Device management module 1214 for managing a plurality of dental care devices (e.g., dental care device 10 and/or dental care device 100), dispenser devices 904, and/or other user devices (e.g., associated mobile devices), including sending, receiving, and processing data from the devices;

Third-party management module 1214 for managing associated third-parties, such as third-party dental health providers 918 and third-party dental suppliers 916, including sending, receiving, and processing data from the third-party devices;

User module 1213 for managing user information, such as user preferences, user settings, user dental information, user identifiers, user drive profiles, user dispensing profiles, and the like (e.g., a HIPPA-compliant module); and Server database 1216, including but not limited to:
Accounts information 1218 for storing account information for user accounts, including user profiles 1220, user account information, information and settings for linked devices and electronic devices (e.g., device identifications), device specific secrets, relevant user and hardware characteristics (e.g., service tier, device model, storage capacity, processing capabilities, etc.), user interface settings, dental health information, dental provider information, and the like;

Device information 1222 for storing data associated with each electronic device (e.g., each dental care device 10) of each user account, as well as data processing models, processed data results, and other relevant metadata (e.g., names of data results, location of electronic device, duration, settings of the electronic device, etc.) associated with the data, where (optionally) all or a portion of the data and/or processing associated with the dental care device are stored securely, and/or storing device information related to one or more dental care devices, e.g., device identifiers and device specific secrets, independently of whether the corresponding devices have been associated with any user account; and Inventory information 1224 for storing inventory information for associated dental care devices, dispenser devices, oral care agent ingredients, fabrication information and/or molds.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 1208, optionally, stores a subset of the modules and data structures identified above. Furthermore, the memory 1208, optionally, stores additional modules and data structures not described above.

FIG. 12B illustrates various data structures used by the server system 910 in some embodiments, including a user profile 1220-*j* and a device profile 1222-*k*. The user profile 1220-*j* corresponds to a user T associated with the dental system 900, such as a user of a dental care device 10, a user of a dental care device 100, a user of a dispenser device 904, and the like. In some embodiments, the user profile 1220-*j* includes user preferences 1226, user settings 1228, user dental information 1230, drive profile information 1232, associated devices information 1234, and associated oral care agents information 1236, and associated dental professionals information 1238. In some embodiments, the user profile 1220-*j* includes only a subset of the above data. In some embodiments, the user profile 1220-*j* includes additional user information not shown, such as information regarding other users associated with the user 'j'.

The user preferences 1226 include explicit user preferences input by the user as well as implicit and/or inferred user preferences determined by the dental system 900 (e.g., server system 910 and/or dental care device 10). In some embodiments, the inferred user preferences are based on historical user activity and/or historical activity of other users. The user settings 1228 include information regarding settings set by the user T such as notification settings, device settings, and the like. In some embodiments, the user settings 1228 include device settings for devices associated with the user 'j'. In some embodiments, the user dental information 1230 includes one or more dental images (e.g., x-rays or visual images), dental records, geometry information for the teeth and/or jaw of the user 'j'. In some embodiments, the drive profile information 1232 includes frequency and timing information for operation of dental care devices of the user 'j' (e.g., vectors and/or tables describing the drive profiles 1048 illustrated in FIG. 10B).

Associated devices information 1234 includes information regarding devices associated with the user T such as dental care devices, dispenser devices, and/or mobile devices (e.g., mobile devices with an associated dental application installed thereon). In some embodiments, associated devices information 1234 includes a link, pointer, or reference to a corresponding device profile 1222. Associated oral care agents information 1236 includes information regarding oral care agents associated with user 'j', such as oral care agent formulations for user 'j'. Associated dental professionals information 1238 includes information regarding dental professionals (e.g., dentists and dental hygienists) associated with user 'j'.

The device profile 1222-*k* corresponds to a device 'k' associated with the dental system 900, such as a dental care device, a dispenser device, a mobile device, and the like. In some embodiments, the device profile 1222-*k* includes device settings 1240, associated devices information 1242, associated user information 1244, and associated drive profile(s) 1246. In some embodiments, the device profile 1222-*k* includes only a subset of the above data. In some embodiments, the device profile 1222-*k* includes additional device information not shown such as information regarding whether the device is currently active.

Device settings 1240 include information regarding the current settings of device 'k' such as mode of operation information and the like. In some embodiments, the device settings 1240 are user-specific and are set by respective users of the device 'k'. Associated devices information 1242 includes information regarding other devices associated with device 'k' such as other devices assigned to a same user as the device 'k'. In some embodiments, associated devices information 1242 includes a link, pointer, or reference to a respective device profile 1222 corresponding to the associated device.

Associated user information 1244 includes information regarding users associated with the device such as users operating the device, receiving notifications from the device, users registered with the device, and the like. In some embodiments, associated user information 1244 includes a link, pointer, or reference to a user profile 1220 corresponding to the associated user. Associated drive profile(s) 1246 includes information regarding drive profiles associated with the device 'k' and/or users of the device.

Figure 13B:
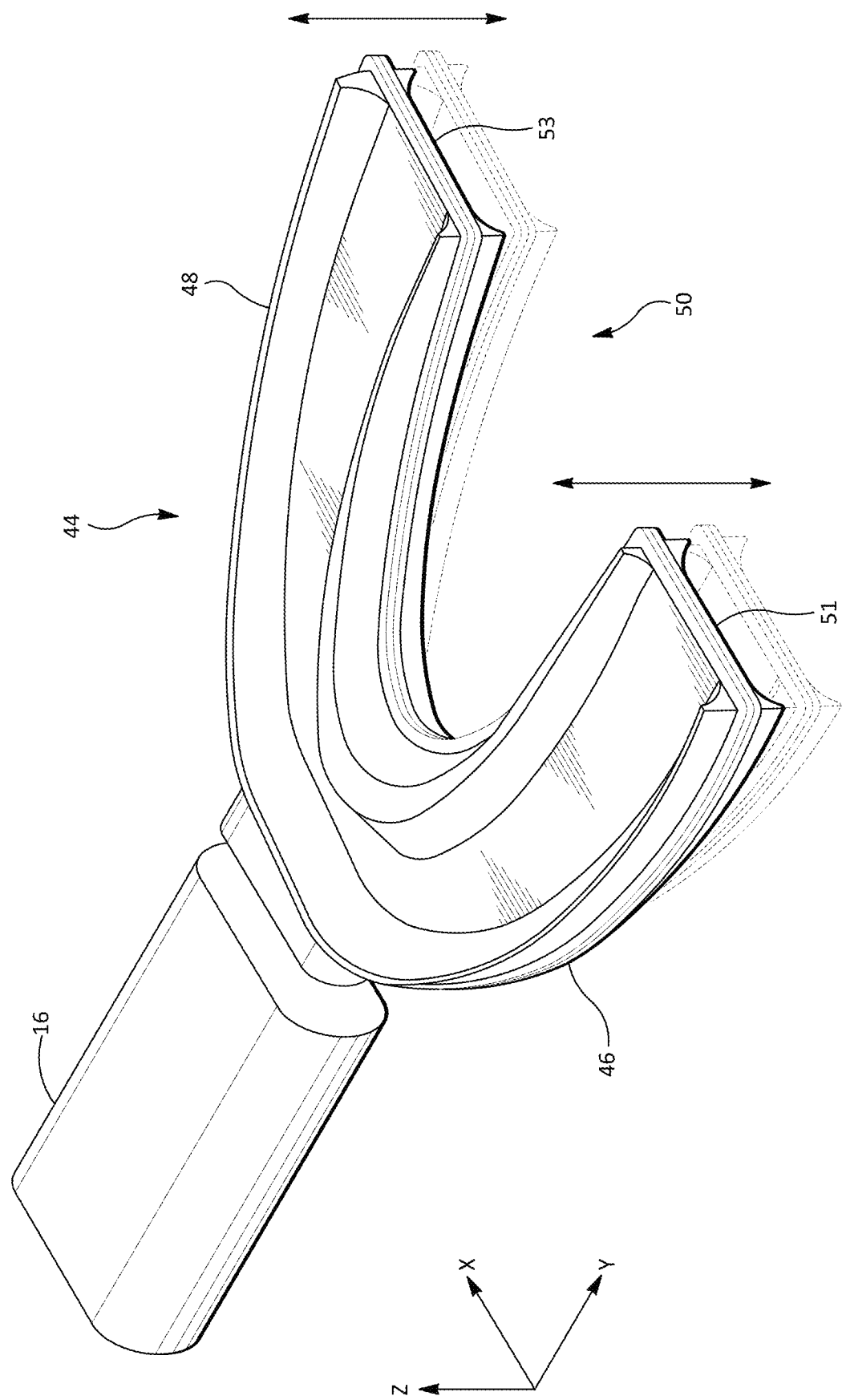
FIGS. 13B-13G are schematic views illustrating representative vibrational modes of a representative dental care device in accordance with some embodiments.

FIG. 13A is table illustrating example frequencies for various representative modes of operation of the dental care device of FIG. 10A in accordance with some embodiments. In the example of FIG. 13A, 300 Hz corresponds to a flap in-phase mode, 400 Hz corresponds to a flap out-of-phase mode, 500 Hz corresponds to a sweep mode, and 1100 Hz corresponds to a twist mode. The various modes are described in more detail in reference to FIGS. 13B-13G.

FIGS. 13B-13G are schematic views illustrating representative vibrational modes of a representative dental care device (e.g., a dental care device 10) in accordance with some embodiments. In some embodiments, a structure, such as the mouthpiece assembly 12 (FIG. 1A) and the structure plate (also sometimes called a chassis) 44, is configured to have one or more characteristic vibration modes, sometimes called resonant modes, which occur at respective natural frequencies of the structure. For example, a structure can be configured to have characteristic modes that respectively occur at the natural frequencies $f1, f2, f3, \ldots, fn$, where $f1$ is the fundamental frequency of the fundamental (e.g., lowest-frequency) characteristic mode, and $f2$-$fn$ are the frequencies of respective higher-order characteristic modes; although $f2$-$fn$ can be harmonics of $f1$, they need not be.

When excited at such a natural frequency by a vibration source such as a drive assembly 1016 (e.g., a motor with an unbalanced weight attached to its spindle), the structure vibrates in a predictable pattern. In some embodiments, the structure is configured to vibrate in a respective desired pattern at each of one or more selected natural frequencies. Each pattern depends on physical characteristics of the structure. Examples of such physical characteristics include the dimensions of the structure, the shape of the structure, the material from which the structure is formed, the distribution of the structure's mass, and the stiffness of the structure. In some embodiments, different profiles operate at different frequencies and/or amplitudes. In some circumstances and embodiments, the different frequencies change the location and amount of the motion as it gets near resonance points. In some embodiments, the drive frequency changes during a cleaning cycle in accordance with a preset drive profile.

In some embodiments, the one or more of such physical characteristics of the chassis 44 are selected so as to configure the chassis, and thus the mouthpiece assembly 12, to vibrate in a respective desired pattern at each of one or more selected frequencies, where each characteristic vibration mode corresponds to a respective cleaning mode of the teeth-cleaning device 14, e.g., as illustrated in FIG. 13A.

Referring to FIG. 13B, while the chassis 44 is operating in a first characteristic mode 50 corresponding to a frequency $f1$, the chassis arms 46 and 48 oscillate, e.g., flap up and down in-phase, and thus impart an in-phase up-and-down flapping motion to the upper and lower mouthpieces 40 and 42, in response to a first excitation frequency (e.g., from the one or more actuators in the electronics enclosure 16). As used herein, "in-phase" means that the front edges 51 and 53 of the chassis arms 46 and 48, respectively, have approximately the same z-axis coordinate at any given time. In some embodiments, the frequency $f1$ is in an approximate range of 90-400 Hz, and the excitation frequency generated by the one or more motors is approximately equal to $f1$. When the excitation frequency does not equal $f1$, then the arms 46 and 48 of the chassis 44, and thus the mouthpiece assembly 12, may flap up and down at the excitation frequency.

Figure 13C:
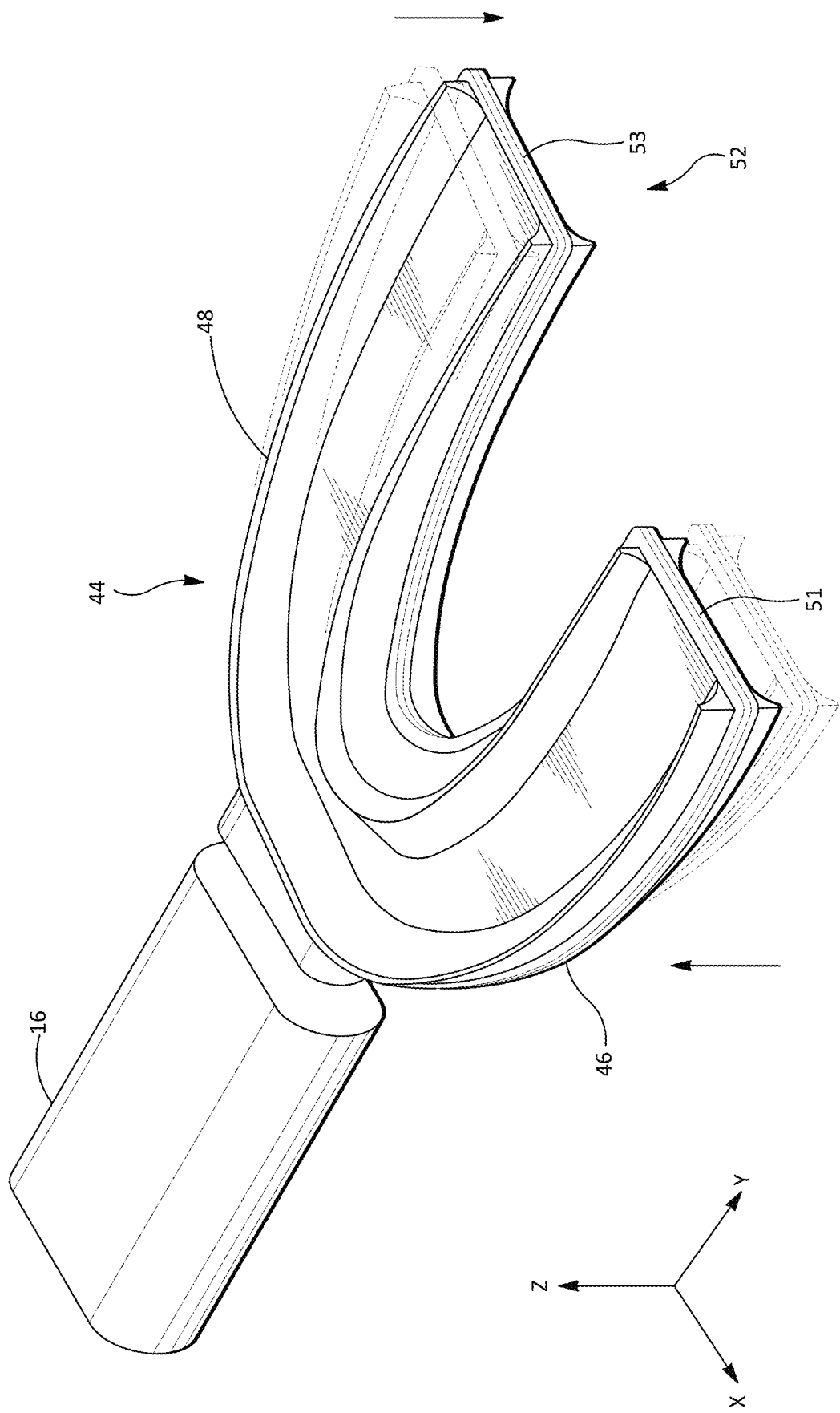

Referring to FIG. 13C, while the chassis 44 is operating in a second characteristic mode 52 corresponding to a frequency $f2$, the arms 46 and 48 oscillate, e.g., flap up and down out-of-phase, and thus impart an out-of-phase up-and-down flapping motion to the upper and lower mouthpieces 40 and 42, in response to a second excitation frequency from the one or more motors in the electronics enclosure 16. As used herein, "out-of-phase" means that the front edges 51 and 53 of the arms 46 and 48 at any given time have approximately the same value but a different sign. For example, at a time 't' the front edge 51 of the arm 46 can have a z-coordinate of approximately +1 and the front edge 53 of the arm 48 can have a z-coordinate of approximately −1. In some embodiments, the frequency $f2$ is in an approximate range of 180-500 Hz and can be a harmonic of $f1$ (although this is not required), and the excitation frequency generated by the one or more motors is approximately equal to $f2$. When the excitation frequency does not equal $f2$, then the arms 46 and 48 of the chassis 44, and thus the mouthpiece assembly 12, may flap up and down at the excitation frequency.

Figure 13D:
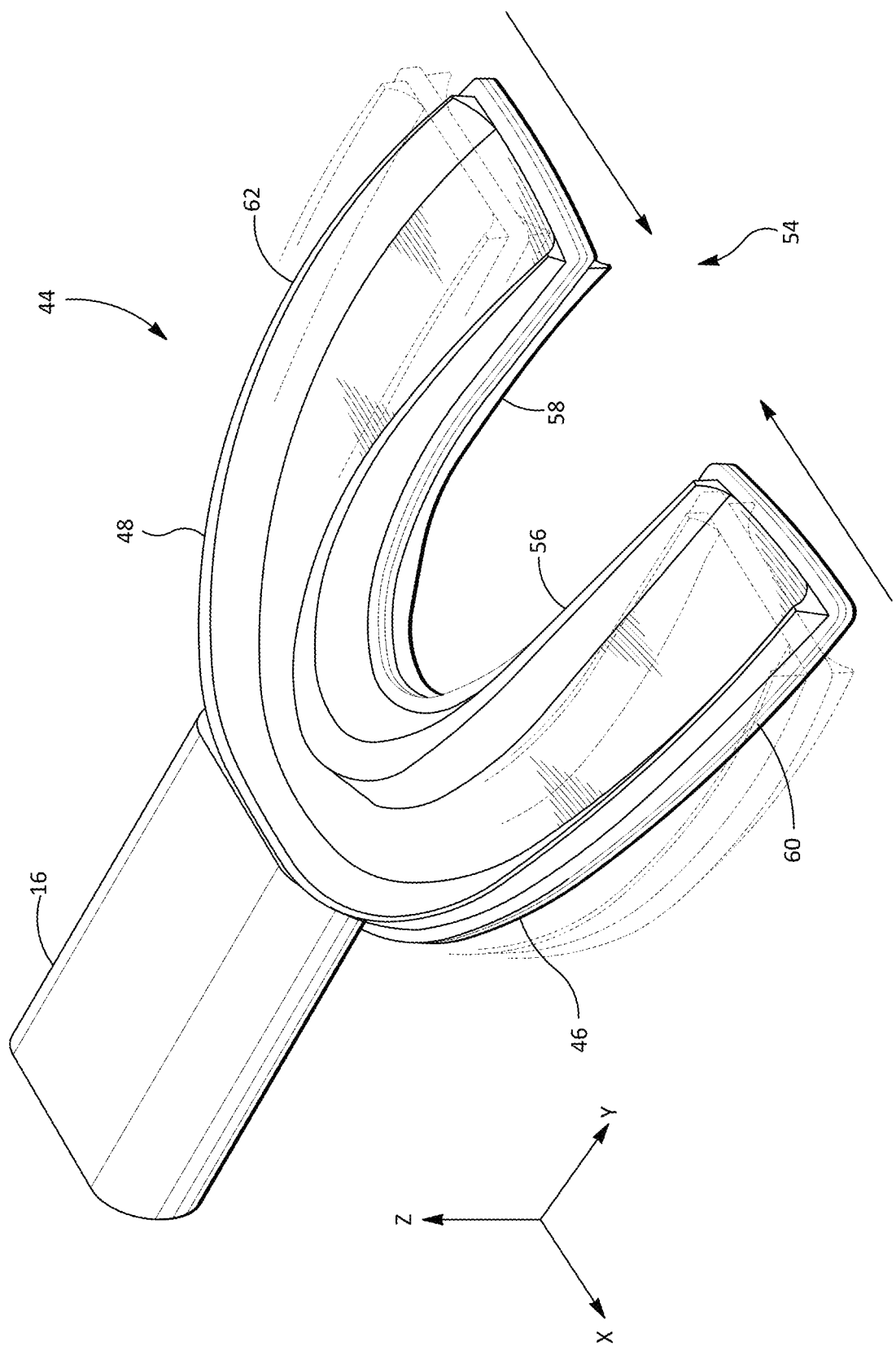

Referring to FIG. 13D, while the chassis 44 is operating in a third characteristic mode 54 that occurs at a frequency $f3$, the arms 46 and 48 sweep toward and away from each other in the x-dimension out of phase, and thus impart an out-of-phase sweeping motion to the upper and lower mouthpieces 40 and 42, in response to a third excitation frequency from the one or more motors in the electronics enclosure 16. In this example, out-of-phase means that corresponding points on the inner edges 56 and 58 of the arms 46 and 48 at any given time have approximately the same displacement in the x-dimension but with a different sign. For example, at a time T the point of the edge 56 has a displacement in the x-dimension of approximately +1 and the corresponding point of the edge 58 has a displacement in the x-dimension of approximately −1. Corresponding points of the outer edges 60 and 62 of the chassis arms 44 and 46 are likewise out-of-phase. In some embodiments, the frequency f3 is in an approximate range of 270-600 Hz and can be a harmonic of f1 (although this is not required), and the excitation frequency generated by the one or more motors is approximately equal to f3. When the excitation frequency does not equal f3, then the arms 46 and 48 of the chassis 44, and thus the mouthpiece assembly 12, may sweep back and forth at the excitation frequency.

Figure 13E:
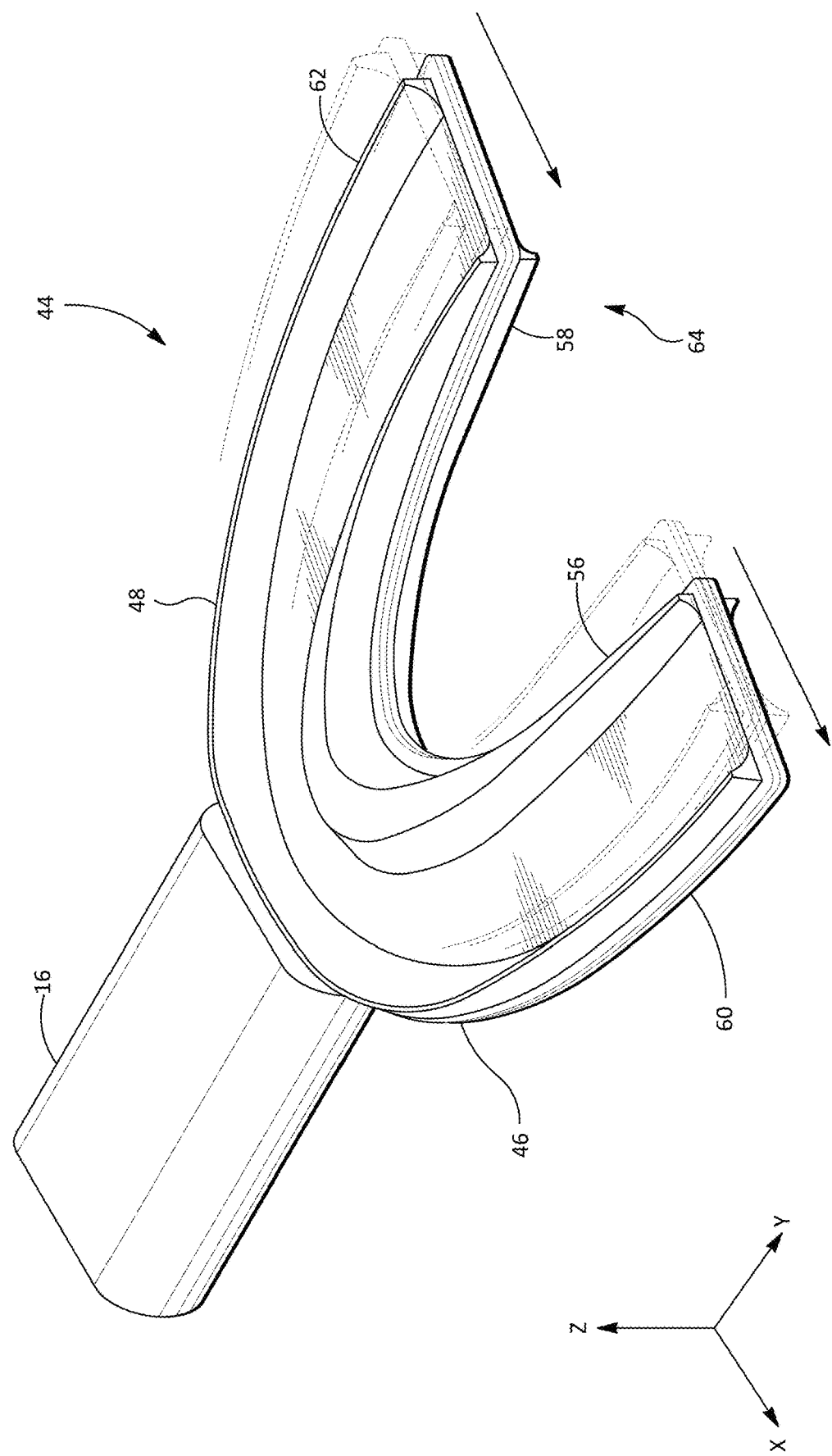

Referring to FIG. 13E, while the chassis 44 is operating in a fourth characteristic mode 64 that corresponds to a frequency f4, the chassis arms 46 and 48 sweep in the x-dimension in phase with one another, and thus impart an in-phase sweeping motion to the upper and lower mouthpieces 40 and 42, in response to a fourth excitation frequency from the one or more motors in the electronics enclosure 16. In this example, in-phase means that corresponding points of the inner edges 56 and 58 of the arms 44 and 46 at any given time have approximately the same displacement in the x-dimension with a same sign. For example, at a time 't' point of the edge 56 has a displacement in the x-dimension of approximately +1 and a corresponding point of the edge 58 also has a displacement in the x-dimension of approximately +1. Corresponding points of the outer edges 60 and 62 of the chassis arms 46 and 48 are likewise in-phase. In some embodiments, the frequency f4 is in an approximate range of 360-700 Hz and can be a harmonic of f1 (although this is not required), and the excitation frequency generated by the one or more motors is approximately equal to f4. When the excitation frequency does not equal f4, then the arms 46 and 48 of the chassis 44, and thus the mouthpiece assembly 12, may sweep back and forth at the excitation frequency.

Figure 13F:
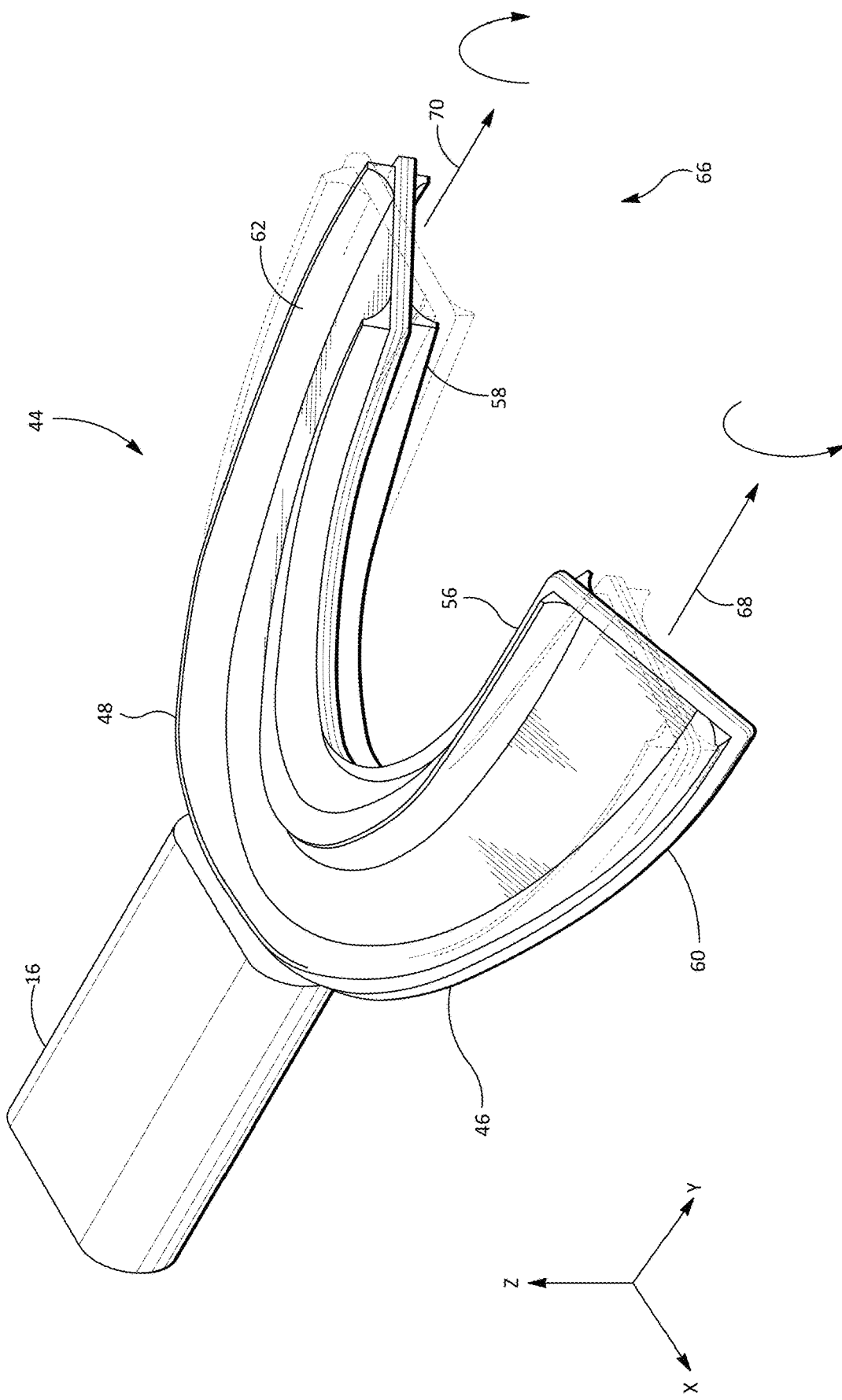

Referring to FIG. 13F, while the chassis 44 is operating in a fifth characteristic mode 66 that corresponds to a frequency f5, the arms 46 and 48 twist about respective axes 68 and 70 in-phase, and thus impart an in-phase twisting motion to the upper and lower mouthpieces 40 and 42, in response to a fifth excitation frequency from the one or more motors in the electronics enclosure 16. In this example, in-phase means that the z-coordinates of corresponding points of the inner edges 56 and 58 of the arms 46 and 48 at any given time have approximately the same value and same sign. For example, at a time 't' a point of the edge 56 has a z-coordinate of approximately +1 and a corresponding point of the edge 58 also has a z-coordinate of approximately +1. Corresponding points of the outer edges 60 and 62 of the chassis arms 46 and 48 are likewise in-phase. In some embodiments, the frequency f5 is in an approximate range of 810-1200 Hz and can be a harmonic of f1 (although this is not required), and the excitation frequency generated by the one or more motors is approximately equal to fs. If the excitation frequency does not equal fs, then the arms 46 and 48 of the chassis 44, and thus the mouthpiece assembly 12, may twist at the excitation frequency.

Figure 13G:
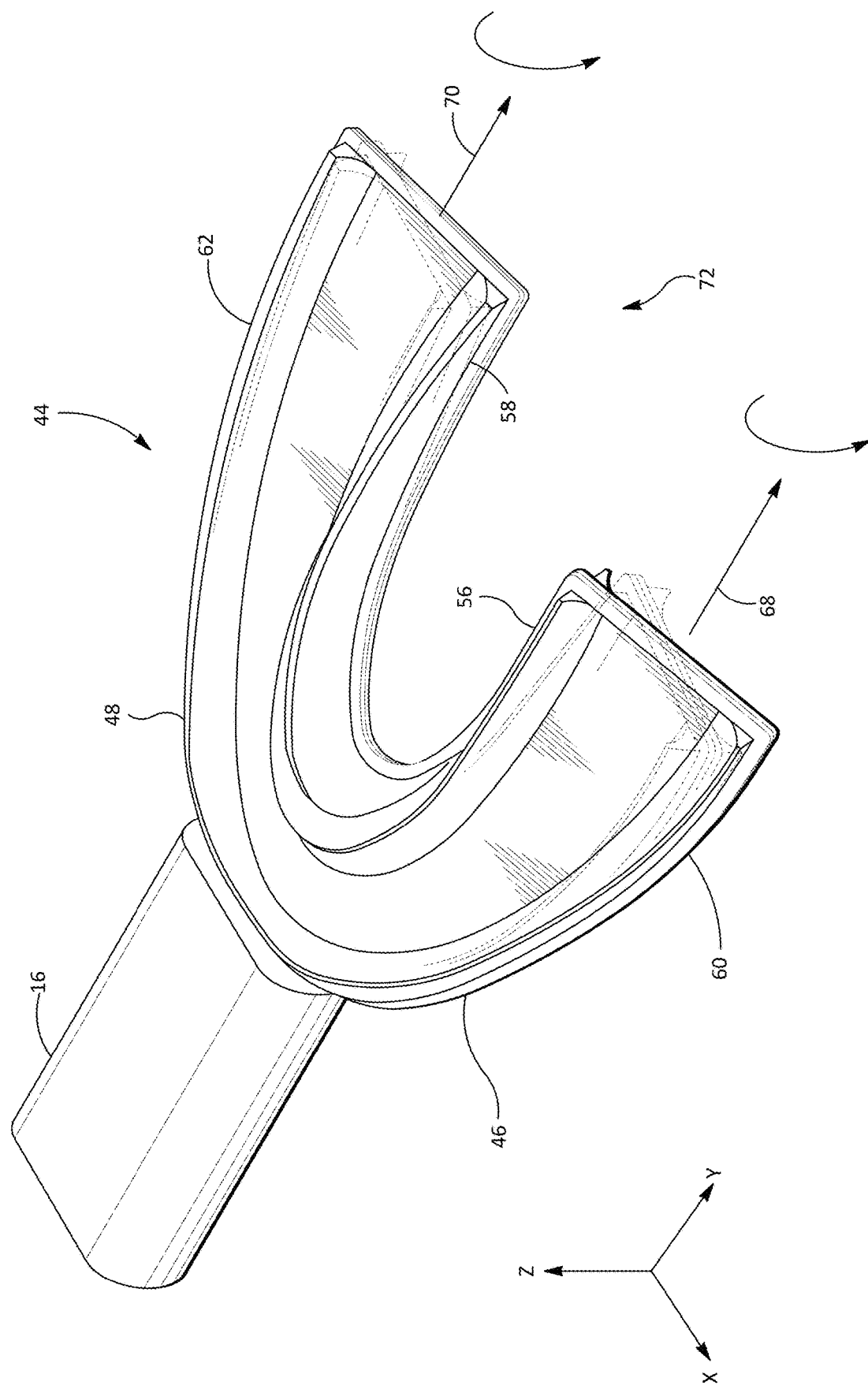

Referring to FIG. 13G, while the chassis 44 is operating in a sixth characteristic mode 72 that corresponds to a frequency f6, the chassis arms 46 and 48 twist about the respective axes 68 and 70 out-of-phase, and thus impart an out-of-phase twisting motion to the upper and lower mouthpieces 40 and 42, in response to a sixth excitation frequency from the one or more motors in the electronics enclosure 16. In this example, out-of-phase means that the z-coordinates of corresponding points of the inner edges 56 and 58 of the chassis arms 46 and 48 at any given time have approximately the same value and different sign. For example, at a time 't' point of the edge 56 has a z-coordinate of approximately +1 and a corresponding point of the edge 58 has a z-coordinate of approximately −1. Corresponding points of the outer edges 60 and 62 of the chassis arms 46 and 48 are likewise out-of-phase. In some embodiments, the frequency f6 is in an approximate range of 900-1300 Hz and can be a harmonic of f1 (although this is not required), and the excitation frequency generated by the one or more motors is approximately equal to f6. When the excitation frequency does not equal f6, then the arms 46 and 48 of the chassis 44, and thus the mouthpiece assembly 12, may twist at the excitation frequency.

Referring to FIGS. 13A-13G, in some embodiments, the teeth cleaning device 14 is configured such that the electronic circuitry sweeps the chassis 44, and thus the mouthpiece assembly 12 through multiple cleaning modes by changing, at respective configurable times relative to a start time, the excitation frequency generated by the one or more motors in the electronics enclosure 16, e.g., in accordance with a drive profile 1048. In some embodiments, the electronics enclosure 16 includes a button or other input device that enables a user to manually select the cleaning mode, or to manually step through a sequence for which the teeth cleaning device 14 is configured.

In some embodiments, the device 14 is capable of operating in one or more cleaning modes not described in conjunction with FIGS. 13A-13G (e.g., vibration of the center of the mouthpiece assembly 12 rather than the ends). In some circumstances, the natural-frequency range for one or more of the modes can be different than described. In some embodiments, the above-described modes are ordered differently relative to natural frequency (e.g., the twist modes have lower natural frequencies than the sweep or flap modes).

In some embodiments, the mouthpiece assembly 12 is configured to take into account physical characteristics (e.g., mass) of the elastic polymer such that the cleaning modes have desired characteristics. In some embodiments, the chassis 44 is configured to have modes that are custom tailored for a particular person. In some embodiments, the chassis 44 is formed via an automated process, for example, using computer-aided design tools. In some embodiments, electronic circuitry in the electronics enclosure 16 (e.g., drive assembly 1016) is configured to drive the one or more motors to induce multiple characteristic modes simultaneously.

Although the natural frequency ranges of the characteristic modes are described as being in the sonic frequency range (e.g., <20 KHz) in reference to FIGS. 13A-13G, in some embodiments, one or more of the characteristic modes have a respective fundamental frequency in the ultrasonic frequency range (e.g., >20 KHz), or have one or more frequency components (e.g., fundamental and harmonics) in the sonic frequency range and one or more other frequency components in the ultrasonic frequency range. Having at least one characteristic mode with at least one frequency component in the ultrasonic frequency range can facilitate removal of plaque from the teeth, and from other parts of the mouth, as described above.

In some embodiments, the characteristic modes, excitation frequencies of the characteristic modes, and the sequence of characteristic modes through which the teeth cleaning device 14 proceeds are customized for a user (e.g., in accordance with a customized drive profile).

For example, a user can use the teeth cleaning device 14 with initial mode and sequence settings for a period of time (e.g., three months) and go to the dentist for a checkup, and the dentist can modify the settings if the dentist thinks that the cleaning efficacy of the teeth cleaning device can be improved for the person. The user and dentist can repeat the checkup-and-setting-modification procedure as many times as the dentist or user believes is necessary to maximize the cleaning efficacy of the teeth cleaning device 14 for the person. Alternatively, the checkup-and-setting-modification procedure can occur via the internet/cloud. For example, instead of visiting the dentist, the user can take photographs of his/her mouth and teeth with the teeth cleaning device 14 or with another device (e.g., a smart phone) and upload the photographs to the dentist, who can modify the settings of the teeth cleaning device via the internet/cloud. Or the user or teeth cleaning device 14 can capture information other than, or in addition to, photographic information, where this other information is indicative of the cleaning efficacy of the teeth cleaning device, and the user or teeth cleaning device can provide this information to the user's dentist via the internet/cloud. Where the teeth cleaning device 14 provides such information to the dentist automatically (e.g., via a wireless router in the user's home), then this checkup-and-setting-modification procedure can be transparent to the person. And another parameter than the dentist can modify is the formula of a custom toothpaste, or other oral care agent, that the user uses while cleaning his/her teeth with the teeth cleaning device 14.

In some embodiments, characteristics (e.g., density, thickness, shape) of the arms 46 and 48 of the chassis 44 are configured to induce local complex modal structures that in turn generate local changes in vibration amplitude and speed during one or more characteristic modes.

Figure 14A:
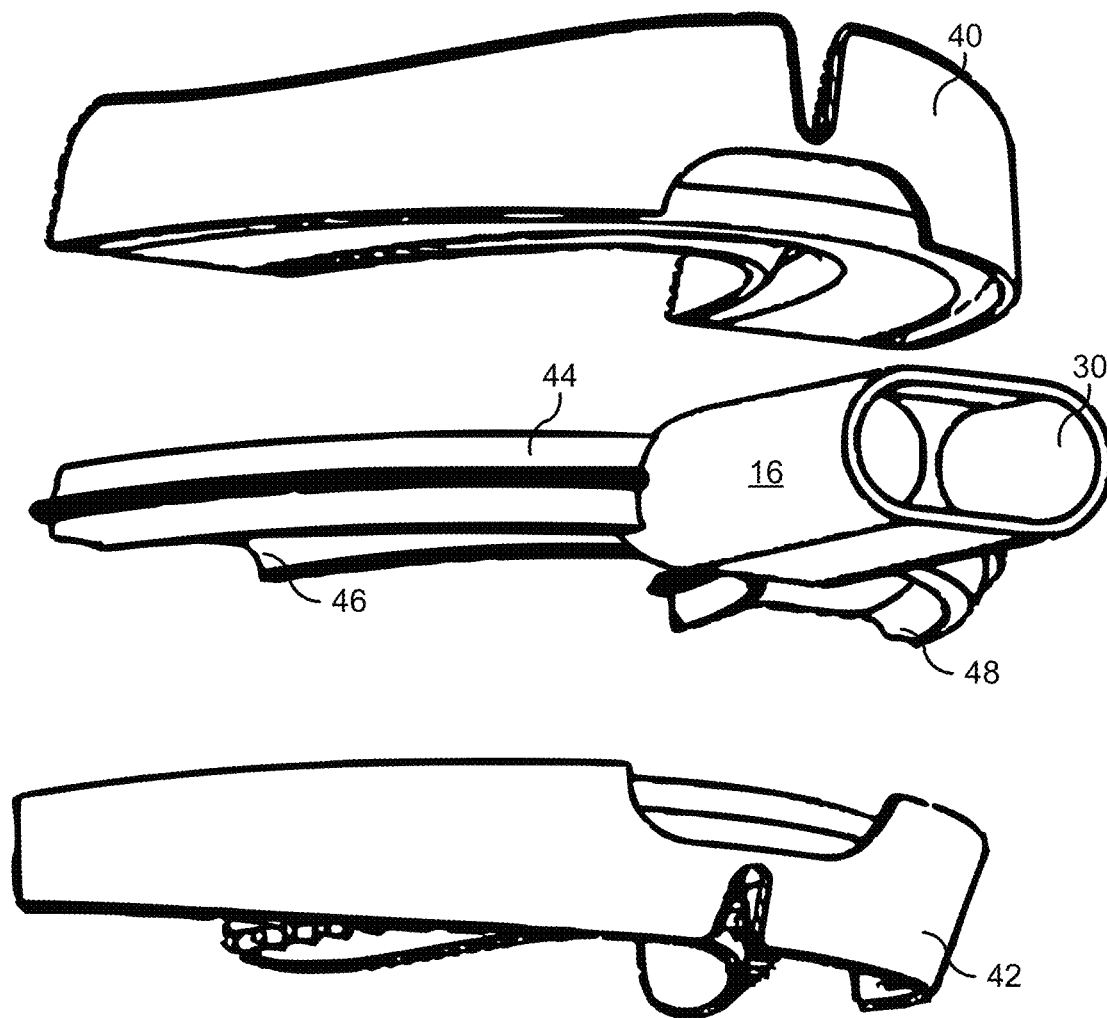
FIGS. 14A-14B are exploded schematic views of a representative dental care device in accordance with some embodiments.
Figure 14B:
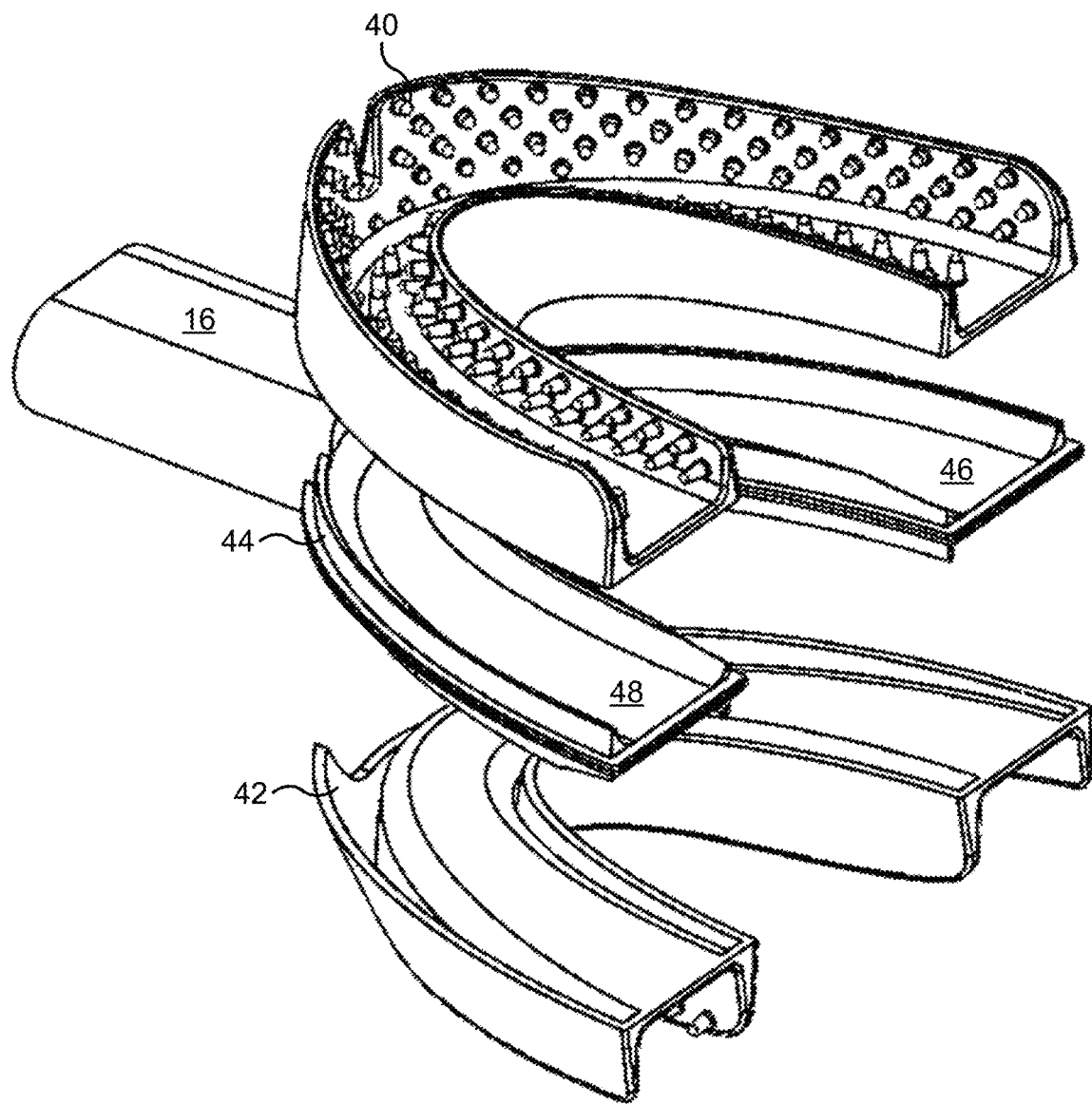
Figure 15A:
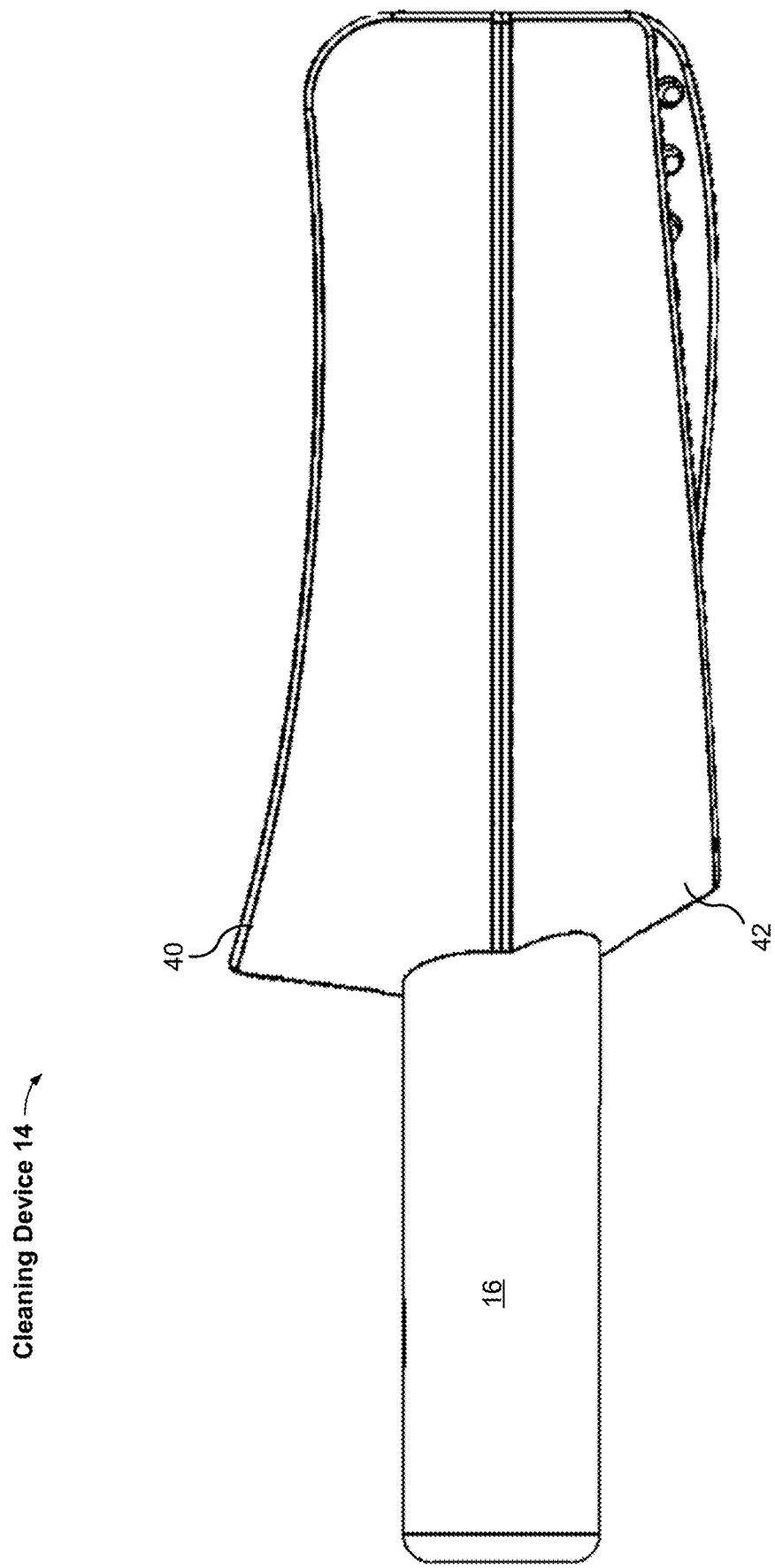
FIGS. 15A-15D are schematic views of a representative dental care device in accordance with some embodiments.
Figure 15B:
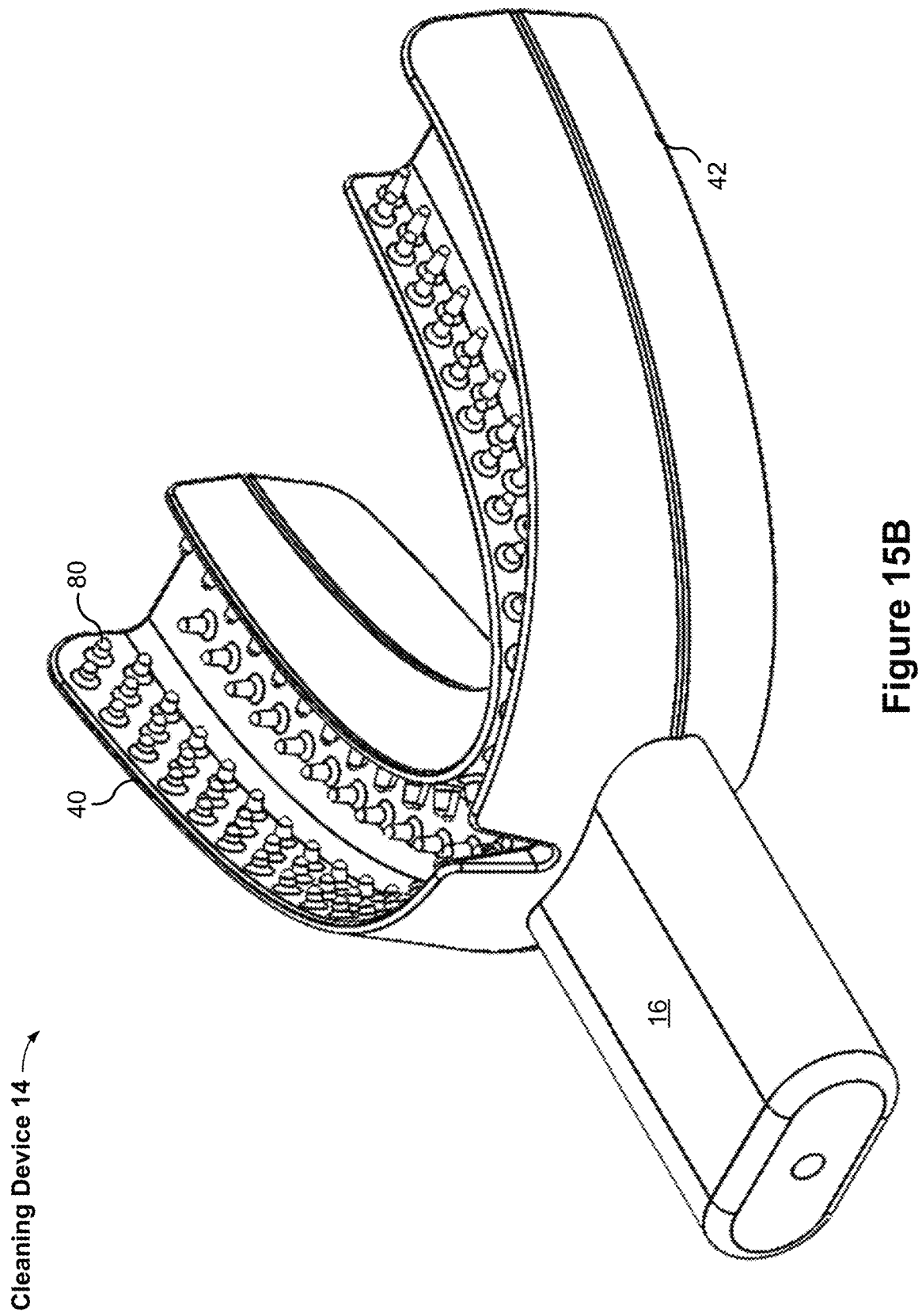
Figure 15C:
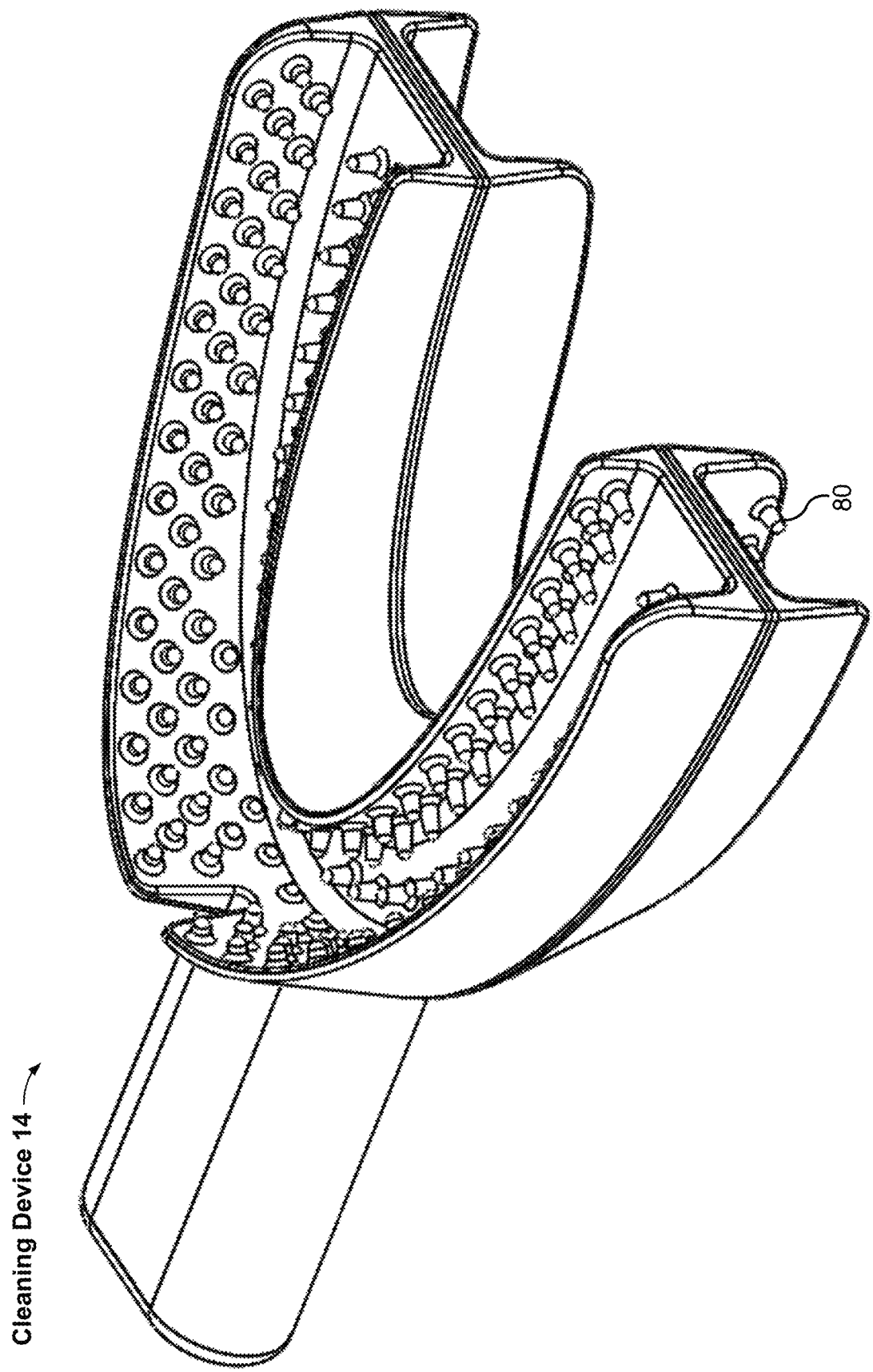
Figure 15D:
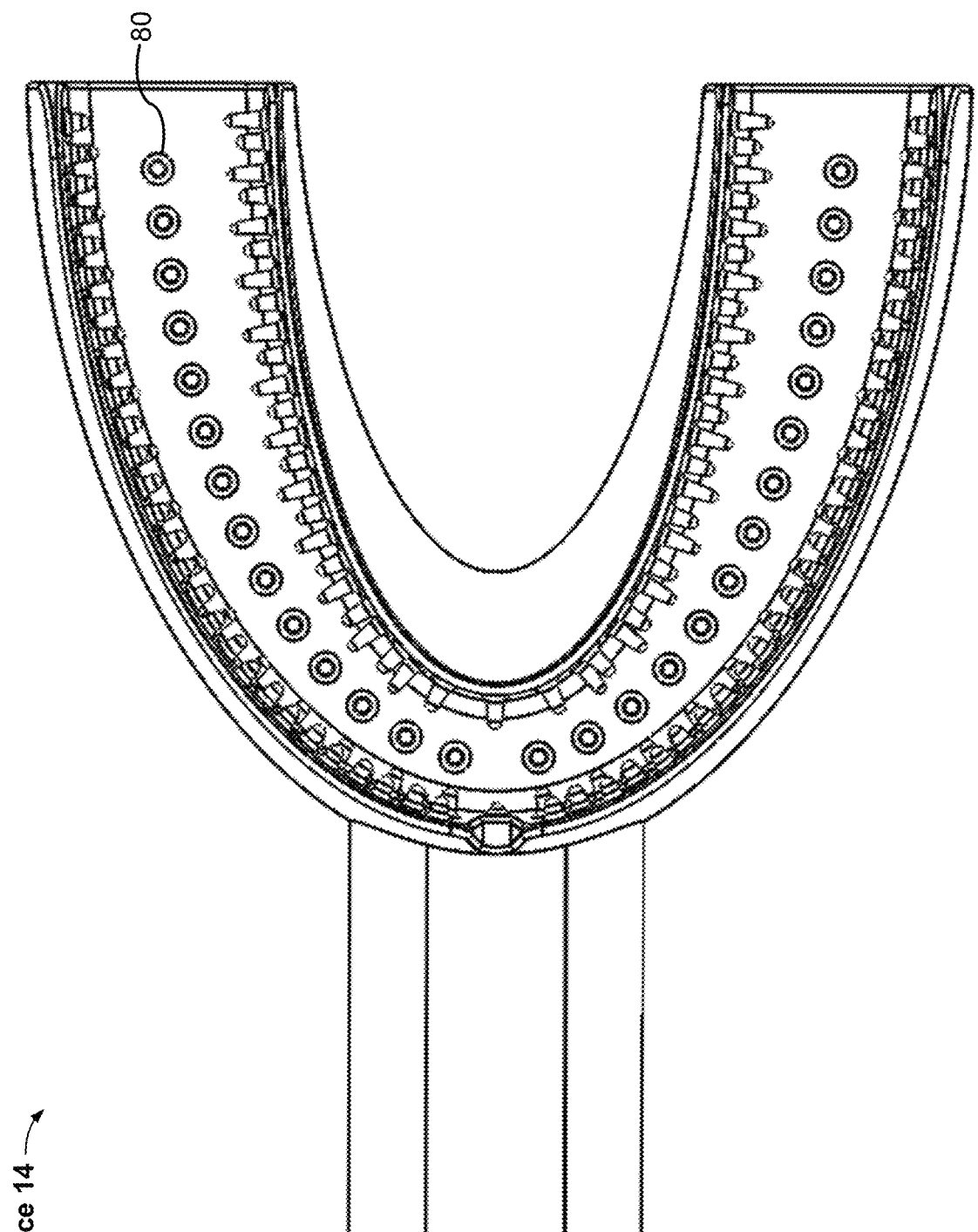

FIGS. 14A-14B are, respectively, rear and front partially exploded views of a dental care device, such as dental care device 10, in accordance with some embodiments. Referring to FIG. 14A, in accordance with some embodiments, the electronics enclosure 16 includes a cylindrical chamber 30, for receiving and housing a drive assembly (e.g., drive assembly 1016). In some embodiments, the drive assembly is mounted directly to a printed circuit board on which the electronic circuitry is mounted.

In some embodiments, the drive assembly includes one or more vibratory motors configured to cause the mouthpiece assembly 12 to move according to one or more vibratory (characteristic) cleaning modes. For example, the spindle of each motor can be fitted with a respective unbalanced (e.g., unevenly distributed radially, circumferentially, or both radially and circumferentially, relative to spindle) weight that causes the motor to vibrate sinusoidally at a frequency that is related to the angular velocity wt at which the spindle rotates according to the following equation:

Equation 1—Angular Velocity $$R(t) = A \sin(wt) \quad (1)$$

where R(t) is the radial displacement of the spindle as a function of time at a fixed angular location about the spindle. By setting the angular velocities of the motors, electronic circuitry within the electronics enclosure 16 can set the frequency of R(t), and, therefore, can select the characteristic mode, or characteristic modes, in which the mouthpiece assembly 20 operates. Therefore, the tooth-cleaning device 14 is configured to have unique characteristics utilizing vibratory-machine dynamics.

Still referring to FIG. 14A, alternate embodiments of the electronics enclosure 16 are contemplated. For example, the electronics enclosure 16 can be configured to house fewer or more than two motors. Furthermore, where the electronics enclosure 16 houses two or more motors, each of these motor can have any suitable respective orientation relative to any of the other motors, even if such suitable respective orientation is other than a parallel orientation. For example, the spindle of one motor may make an angle with the spindle of another motor, where the angle is less than 180°.

Moreover, at least one of the motors can have a different size than one or more of the other motors. In addition, in at least one cleaning mode, at least one of the motors can operate at a different speed than one or more of the other motors.

Referring to FIGS. 14A-14B, the mouthpiece assembly 12 includes an upper mouthpiece 40, a lower mouthpiece 42, and a chassis 44 to which the upper and lower mouthpieces are attached or otherwise secured. The upper mouthpiece 40 is designed to clean the upper set, or upper row, of a user's teeth. In some embodiments, the mouthpiece 40 is made from any suitable material, such as a flexible material like medical/dental-grade silicone or elastic polymer. In some embodiments, the mouthpiece 40 is designed for a custom fit with the upper teeth and maxilla of the person. In accordance with some embodiments, the upper mouthpiece 40 has a shaped back surface that is configured for attachment to an upper side of the chassis 44 in any suitable manner, such as with an adhesive or fasteners. In some embodiments, the mouthpiece assembly 12 is configured to perform gum massage of both upper and lower gums (e.g., on inner and outer gum lines—mesial and distal). In some circumstances, gum massage results in increase of circulation in the gums and thus improves gum health for the user.

In some embodiments, the lower mouthpiece 42 is designed to clean the lower set, or lower row, of a user's teeth. In some embodiments, the mouthpiece 42 is made from any suitable material, such as a flexible material like silicone or elastic polymer. In some embodiments, the mouthpiece 42 is designed for a custom fit with the lower teeth and mandible of the person. In accordance with some embodiments, the lower mouthpiece 42 has a shaped back surface that is configured for attachment to a lower side of the chassis 44 in any suitable manner, such as with an adhesive or fasteners.

In accordance with some embodiments, the chassis 44 includes two arms 46 and 48, and is coupled to the one or more motors housed in the electronics enclosure 16 in a manner that allows the one or more motors, when active, to induce one or more characteristic modes in the chassis, and therefore, to induce one or more cleaning modes in the mouthpiece assembly 12. In some embodiments, the chassis 44 is made from any suitable material such as a polymer, plastic, or a metal, and can have any suitable shape and dimensions.

In some embodiments, the teeth-cleaning device 14 is configured as a single integral unit such that components (e.g., the mouthpiece assembly 12) of the teeth-cleaning device are not independently replaceable. Therefore, when the device 14 wears out, a user replaces the entire device. For example, a single-integral-unit teeth-cleaning device 14 can be designed to be replaced once every approximately 3-6 months.

In some embodiments, the teeth-cleaning device 14 is configured such that one or more of its components are independently replaceable. For example, the device 14 can be configured such that the mouthpiece assembly 12 is replaceable. Or, the device 14 can be configured such that the upper mouthpiece 40 and the lower mouthpiece 42 are independently replaceable. For example, the mouthpiece assembly 12, or the upper and lower mouthpieces, can each be designed to be replaced once every approximately 3-6 months.

In some embodiments, the teeth-cleaning device 14 is configured to indicate to a user when it is time to replace the device, or one or more components of the device (e.g., the upper and lower mouthpieces 40 and 42). In some embodiments, electronic circuitry in the electronics enclosure 16 counts the number of times that the teeth-cleaning device 14 is activated for use by a particular person, compares a count value to a count threshold, and generates a time-for-replacement indicator (e.g., a sound, a light, a special vibration pattern, an indicator uploaded to user's smartphone via the cloud) in response to the count value equaling or exceeding the threshold. In some embodiments, the electronic circuitry is configured to generate a time-for-replacement warning (e.g., a sound, a light, a special vibration pattern, an indicator uploaded to user's smartphone via the cloud) in response to the difference between the count value and the count threshold being less than or equal to a difference threshold. In some embodiments, the electronic circuitry is configured to generate a cloud order (e.g., via a smart phone or mobile device communicatively linked to the device 14) for a replacement mouth piece 40 or 42, or a replacement mouthpiece assembly 12, so that the user will have received the replacement by the time that the mouthpiece 40 or 42, or the mouthpiece assembly 12, is ready to be replaced. In some embodiments, at least one of the upper and lower mouthpieces 40 and 42 is configured to exhibit a particular wear pattern (e.g., changing colors) to notify a user when it is time to replace the device 14 or one or more components thereof. In some embodiments, the device 14 is configured to use any other suitable technique for determining when it is time to replace the device or a component thereof, and for indicating the same to a person.

In some embodiments, the chassis 44 has a wider or narrower width than the mouthpieces 40 and 42. In some embodiments, the upper and lower mouthpieces 40 and 42 are formed as an integral mouthpiece unit having a pocket configured to receive the chassis such that the mouthpiece unit can be slipped onto the chassis.

FIGS. 15A-15D are schematic views of a representative dental care device in accordance with some embodiments. In accordance with some embodiments, the upper mouthpiece 40 includes cleaning tips 80, which are configured to contact a user's teeth and to scrub away substances (e.g., plaque, tartar, food particles, food residue, stains, bacteria, viruses) from the surfaces of the user's teeth during operation of the teeth-cleaning device 14 (e.g., while the one or more motors in the electronics enclosure 16 are driving the mouthpiece assembly 12 in a cleaning mode).

In accordance with some embodiments, the lower mouthpiece 42 also includes cleaning tips 80. In accordance with some embodiments, the cleaning tips 80 protrude from the inner walls of the mouthpieces 40 and 42, and are integral with the respective mouthpieces. In some embodiments, the cleaning tips 80 are formed from any suitable material, such as silicone or elastic polymer. In some embodiments, one or more of the cleaning tips are attached to, or otherwise secured to, the respective mouthpiece. For example, a hole can be formed in a wall of a mouthpiece, and a cleaning tip 80 can be installed in the hole. The cleaning tips 80 can be similar to the conventional bristles of a conventional toothbrush, but, as described below, the cleaning tips can be significantly different from conventional bristles.

Each cleaning tip 80 may have any dimensions, shape, and other characteristics suitable for cleaning teeth. In some embodiments, the cleaning tips 80 are custom configured for a particular user's dentition (e.g., teeth and jaw geometry). In some embodiments, the cleaning tips 80 in one location have different sizes or different shapes from the cleaning tips in another location, and/or the cleaning tips in one location are configured to vibrate, or otherwise to move, differently during a cleaning mode than the cleaning tips in another location. In some embodiments, one or more of the cleaning tips 80 have a shape that includes a paddle, circular, tubular, fin-like, conical, trapezoidal, and pyramid. The cleaning tips 80 are optionally solid or partially hollow. For example, a cleaning tip 80 can be a solid protrusion or a hollow protrusion of the surface of a respective one of the mouthpieces 40 and 42.

In some embodiments, the surface of a cleaning tip 80 is an extension of the surface of a respective one of the mouthpieces 40 and 42. In some embodiments, cleaning tips 80 configured for extending between two of a user's teeth are elongated, and different cleaning tips are configured for vibrating at different speeds and amplitudes as a function of tooth type and tooth surface. In some embodiments, the cleaning tips 80 and other characteristics (e.g., the local stiffness) of the mouthpieces 40 and 42, and the characteristic modes of the teeth-cleaning device 14, are configured to provide vibration patterns that produce superior cleaning of each one of a user's teeth.

The operation of the teeth-cleaning device 14 is described below, according to some embodiments. First, a user grasps the electronics enclosure 16 with his/her hand or fingertips, and inserts the mouthpiece assembly 12 into his/her mouth with the upper mouthpiece 40 facing upward and the lower mouthpiece 42 facing downward. Before inserting the mouthpiece assembly 12 into his/her mouth, the user optionally dispenses toothpaste, or another oral care agent, inside of the troughs formed by the upper and lower mouthpieces 40 and 42. Next, the user gently bites down on the mouthpiece assembly 12 to seat the upper mouthpiece 40 and the lower mouthpiece 42 with his/her upper and lower sets of teeth, respectively. Then, the user activates the teeth-cleaning device 14, for example, by pressing a button on the electronics enclosure 16. After activating the device 14, the user can continue to hold the electronics enclosure 16, or can let go of the electronics enclosure such that the user holds the device in position solely with his/her mouth.

In this example, in response to the user activating the teeth-cleaning device 14, electronic circuitry in the electronics enclosure 16 activates the one or more motors in the electronics enclosure and causes the motors to excite the mouthpiece assembly 12 at a frequency f1, which causes the mouthpiece assembly to move according to a first cleaning mode. Next, after a set time that is optionally configurable (e.g., by programming the time into the teeth-cleaning device's electronic circuitry), the electronic circuitry in the electronics enclosure 16 causes the one or more motors in the electronics enclosure 16 to excite the mouthpiece assembly 12 at a frequency f2, which causes the mouthpiece assembly to move according to a second cleaning mode.

In this example, the electronic circuitry in the electronics enclosure 16 continues stepping through the cleaning modes (if there are more than two cleaning modes) until it has cycled through all of the cleaning modes in the cycle, which can be programmed into the teeth-cleaning device's electronic circuitry. Then, the electronic circuitry in the electronics enclosure 16 automatically deactivates the teeth-cleaning device 14 such that the device ceases movement. Next, the user recognizes the cessation of movement of the teeth-cleaning device 14 as the end of the cleaning cycle, and removes the device from his/her mouth. The device is effectively automatically cleaning the dentition without any need of direct user intervention.

In some embodiments, the electronics enclosure 16 is made long enough for a user to grasp with his/her hand like the user would a conventional toothbrush handle. In some embodiments, the electronic circuitry in the electronics enclosure 16 activates a particular cleaning mode more than once during a cleaning cycle. In some embodiments, the electronic circuitry in the electronics enclosure 16 activates the cleaning modes in an order other than from lowest mode frequency to highest mode frequency.

In some embodiments, a healthcare professional prescribes a customize cleaning cycle (e.g., the number, type, order, and duration of the cleaning modes, the time delays between consecutive cleaning modes, and the total cycle time) for a user based on, for example, dental characteristics and/or preferences of the person. Examples of such characteristics include the contours of the user's teeth, the user's diet, the chemistry of the user's mouth, the user's dental history, and the user's health history. Furthermore, although described as being protruding only from the inner walls of the upper and lower mouthpieces 40 and 42, the cleaning tips 80 can protrude from one or more outer walls of one or both of the mouthpieces.

In some embodiments, at least some of the cleaning tips 80 are configured to clean, or to stimulate (e.g., massage), other parts of the user's mouth such as the gums, tongue, and cheeks. In some embodiments, the teeth-cleaning device 14 is configured to provide water, or another liquid (such as mouthwash), out of one or more of the cleaning tips 80.

Figure 16A:
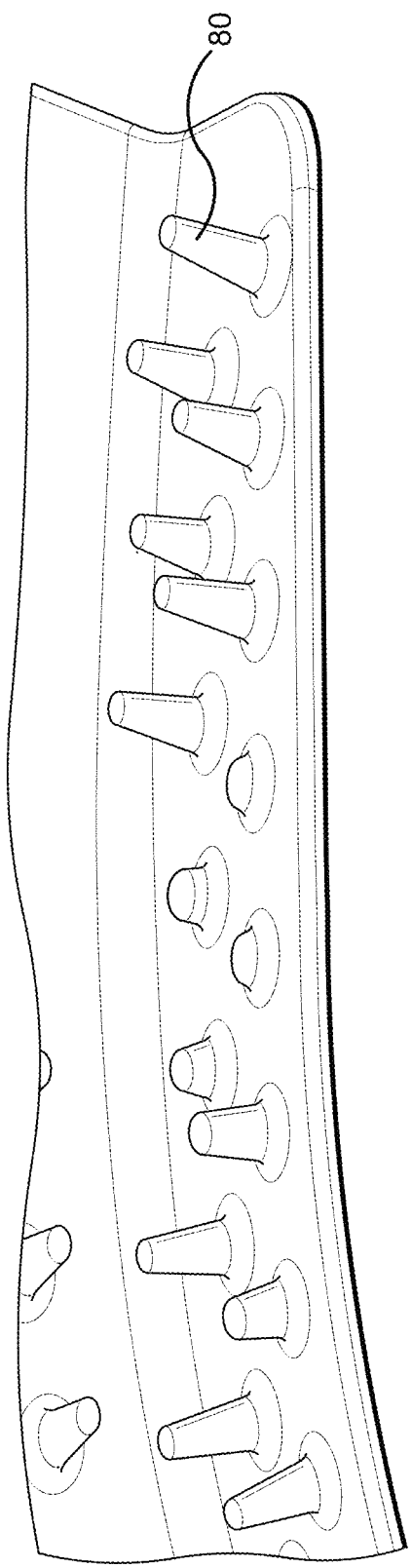
FIG. 16A is a schematic view of representative cleaning tips for a representative dental care device in accordance with some embodiments.
Figure 16B:
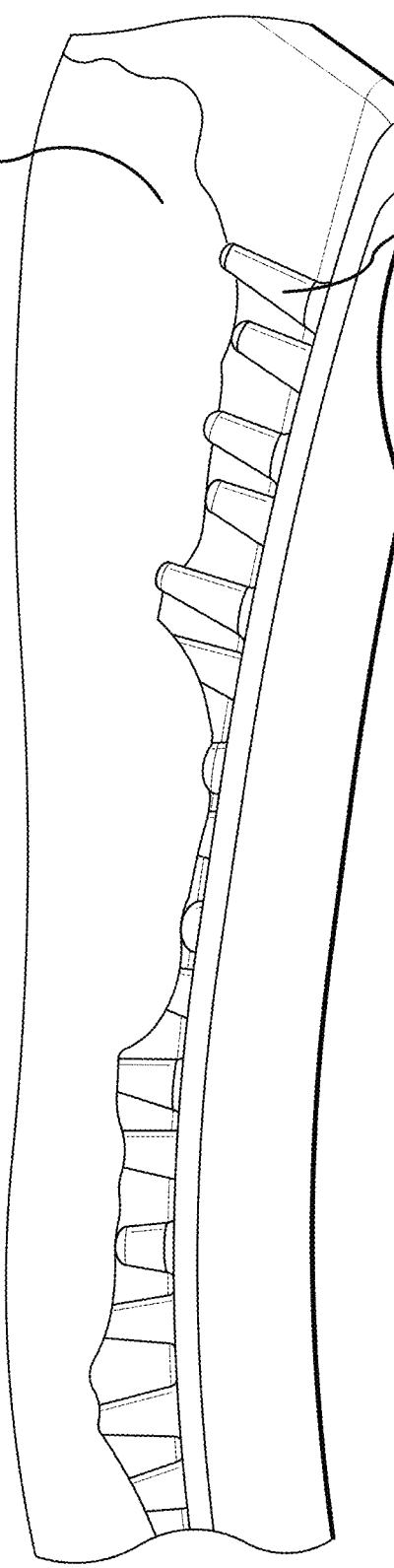
FIG. 16B is a schematic view of the cleaning tips of FIG. 16A engaging a user's teeth during operation of the dental care device in accordance with some embodiments.

FIG. 16A is a close-up view of the cleaning tips 80 of the upper mouthpiece 40 in accordance with some embodiments. FIG. 16B is a close-up view of the cleaning tips 80 engaging a user's teeth 90 in accordance with some embodiments. In some embodiments, the cleaning tips 80 are configured to have different lengths such that as a group, the cleaning tips follow the contours of a user's teeth 90. Such custom-length cleaning tips 80 can provide faster, and overall better, cleaning compared to cleaning tips having a uniform size. In some embodiments, cleaning tips 80 that are near spaces between a user's teeth are configured to have lengths long enough to extend, and to clean, between teeth. In some embodiments, cleaning tips 80 that are near a user's gum line (e.g., where the gum ends and the teeth are exposed) are configured to have lengths long enough to extend, and to clean, below the gum line.

In some embodiments, characteristics of the cleaning tips 80 other than length are customized for a particular person. Examples of such characteristics include width, height, shape, stiffness, material from which the cleaning tips are made, and pitch between adjacent cleaning tips.

In accordance with some embodiments, fabrication of the cleaning device 14 is now described. First, one generates an electronic three-dimensional (3-D) representation of a user's teeth (and optionally other parts of the user's mouth such as gums, cheek, and tongue). In some embodiments, the user, a dentist, or other dental professional, scans the user's teeth with a 3-D scanner. In some embodiments, the user, a dentist, or other dental professional, takes an impression of the user's teeth, and sends the impression to a facility that scans the impression to generate a corresponding electronic 3-D representation of the user's teeth. In some embodiments, the user takes the impression using a do-it-yourself impression kit, and sends the impression to a facility that scans the impression to generate a corresponding electronic 3-D representation of the user's teeth.

Next, the 3-D representation of the user's teeth is provided to a computer having circuitry configured to analyze the representation, and to generate, in response to the analysis, a 3-D representation of the mouthpieces 40 and 42 (or optionally of the entire mouthpiece assembly 12). For example, the computer can be a cloud server to which one uploads the 3-D representation of the user's teeth in a suitable format.

Then, the computer circuitry, which is configured to execute software, is configured by firmware, or is configured by firmware and to execute software, analyzes the 3-D representation and, in response to this analysis, generates a 3-D representation of at least the upper and lower mouthpieces 40 and 42, and, optionally, of the entire mouthpiece assembly 12 (e.g., combination of the mouthpieces and the chassis 44). For example, the computer circuitry can determine the shapes and other characteristics (e.g., local thickness, local stiffness, local density) of the upper and lower mouth pieces 40 and 42, the characteristics (e.g., local stiffness, local width, local thickness, local density) of the chassis 44, and the lengths, other dimensions, and other characteristics (e.g., local shape, local thickness, local stiffness, local density), of the cleaning tips 80 in response to this analysis. In this example, 'local' means that the value of a respective quantity (e.g., stiffness) in one location of an item (e.g., cleaning tip) can be different from the value of the same quantity in another location of the same item. For example, a cleaning tip 80 can be thinner at a location closer to its base (e.g., where the cleaning tip meets the rest of the respective mouthpiece 40 or 42), and can be thicker at a location farther from its base.

Next, the computer circuitry optionally displays, or otherwise renders, the 3-D representation of the mouthpieces 40 and 42 (and optionally of the entire mouthpiece assembly 12) to enable a dentist, or other dental professional, to make revisions to the 3-D representation. For example, a dentist can add one or more extra cleaning tips 80 to a region of a mouthpiece corresponding to a region of the user's teeth that historically has experienced heavy tartar buildup. Additional details for generating the 3-D representation of at least the upper and lower mouthpieces 40 and 42 are discussed in further detail below with reference to FIGS. 25 through 27D.

Then, the computer circuitry converts the 3-D representation of the mouthpieces 40 and 42 (and optionally of the entire mouthpiece assembly 12) into a file suitable for a machine that is configured to form the mouthpieces (or the entire mouthpiece assembly). An example of such a machine is a 3-D printer, which may be located in a manufacturing facility or in a user's home. Another example of such a machine is an injection-molding machine. Alternately, the 3-D printer can print a mold from which the mouthpieces can be cast using traditional technologies such as injection-molding, liquid-silicone rubber molding, or similar casting approaches.

In some embodiments, the mouthpieces (or the entire mouthpiece assembly) are 3-D printed using a powder bed fusion process. In some embodiments, the powder bed fusion process is a multi jet fusion (MJF) process, similar to that described in US 2018/027602 A1, incorporated here in its entirety. In some embodiments, the powder bed fusion process is a selective laser sintering (SLS) process, a selective laser melting (SLM) process, or an electron beam melting (EBM) process. A powder bed fusion process, like MJF, allows for complex designs and a high level of detail, which are ideal for fabricating the mouthpieces (or the entire mouthpiece assembly). For example, powder bed fusion allows for complex designs, meaning that the entire mouthpiece assembly (e.g., including the cleaning trays and cleaning elements) is 3-D printed as a single unit. The high level of detail also allows for 3-D printing high fidelity cleaning elements, which are not achievable with traditional fabrication methods (e.g., injection molding, machining, etc.) or are cost prohibitive when each mouthpiece assembly design is unique to each user. Powder bed fusion is advantageous over other 3-D printing processes, as the powder material provides support for the mouthpiece (and bristles) during printing, without the need for complex scaffolding or other external support. Through trial and error using numerous 3-D printing technologies, the inventors discovered that powder bed printing provided unexpected results of being able to obtain cleaning elements with less than 0.5 mm diameters, and even less than 0.2 mm diameters.

In some embodiments, the powder bed fusion process uses biocompatible materials as the powder material. In some embodiments, the biocompatible material is a biocompatible thermoplastic polyurethane (TPU).

Next, the machine forms the mouthpieces 40 and 42 (or optionally the entire mouthpiece assembly 12) such that, in some embodiments, the formed mouthpieces 40 and 42 are personalized/customized to the user's teeth, to one or more other parts of the user's mouth, and/or to the user's jaw structure. In the cases where the machine is remote from the user, the formed mouthpieces or mouthpiece assembly is sent to the user, e.g., via mail.

In some embodiments, based on an analysis of the 3-D representation of a user's teeth, the computer circuitry and/or a dental professional determines a custom cleaning cycle (e.g., a drive profile and/or dispensing profile) for the person. In some embodiments, the dental care device 10 is configured to operate according to this cycle via, e.g., an internet connection.

In some embodiments, based on an analysis of the scans, usage, and other user/device data, the software automatically predicts and recommends dental procedures relevant to the user. For example, the software predicts decline in gum health and/or predicts improvement in smile and facial features if the user does teeth straightening or crowns or veneers.

In some embodiments, the cleaning tips have uniform lengths and other characteristics, for example, in a lower-cost version of the teeth-cleaning device 14. In some embodiments, groups of cleaning tips 80 are each designed for providing a best cleaning for that group during a respective one of the above-described characteristic modes. For example, for a particular tooth, such as a molar, there can be a respective group of cleaning tips 80 for each characteristic mode, and the cleaning tips of each group can be distributed, e.g., in a homogenous manner, with the cleaning tips of the other groups such that all areas of the molar experience suitable cleaning during each characteristic mode. In some embodiments, as described above, the upper mouthpiece 40 and the cleaning tips 80 associated with the upper mouthpiece are formed as a single, integral unit (e.g., unibody construction), as is the lower mouthpiece 40 and the cleaning tips 80 associated with the lower mouthpiece; or, the entire mouthpiece assembly 12 (upper and lower mouthpieces 40 and 42 and cleaning tips 80) is formed as a single, integral unit.

In some embodiments, the computer circuitry is configured to determine when a part (e.g., the upper mouthpiece 40, the lower mouthpiece 42) of the teeth-cleaning device 14 is scheduled for replacement or updating, is failing, or has failed, and is optionally configured to reorder the part automatically (e.g., via an online reordering portal), alert the user, and/or alert a dental health provider or supplier. In some embodiments, when the part needs updating (e.g., a mouthpiece needs modification by a dentist), then an application on a cloud or other computer server is configured to take steps (e.g., contact the user's dentist) to generate an updated part.

Figure 17:
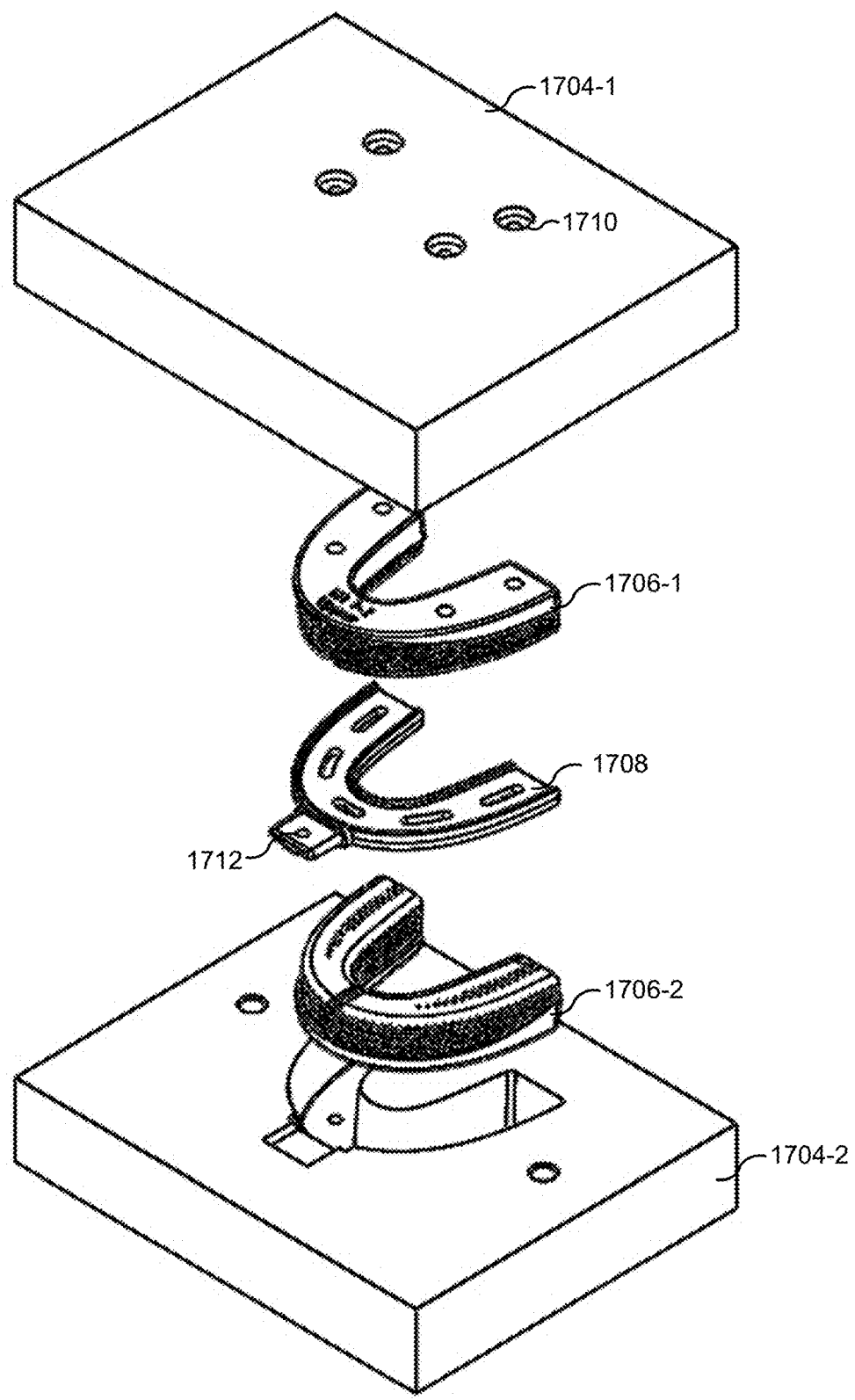
FIG. 17 is an exploded schematic view illustrating a representative dental mold system in accordance with some embodiments.

FIG. 17 is an exploded schematic view illustrating a dental mold system 1702 in accordance with some embodiments. The dental mold system 1702 is configured to produce (e.g., fabricate) at least a portion of the dental care device 10 (e.g., the mouthpiece assembly 12). The dental mold system 1702 includes dental mold plates 1704, dental mold insert molds 1706, and a structure plate 1708 (e.g., a chassis 44). In some embodiments, the dental mold plates 1704 are composed of metal. In some embodiments, the dental mold plates 1704 are selected for a particular user based on the geometry of the user's jaw and/or teeth. For example, smaller dental mold plates 1704 are selected for a child and larger plates are selected for an adult. In some embodiments, the dental mold plates 1704 are selected based on a size of the structure plate 1708 and/or the dental mold inserts 1706 (e.g., a larger structure plate 1708 requires a larger set of dental mold plates 1704). In some embodiments, the dental mold plates 1704 are configured to secure the dental mold inserts 1706 in place around the structure plate 1708 for molding a mouthpiece around the structure plate 1708. In accordance with some embodiments, the dental mold plates 1704 include one or more apertures 1710 for injecting a molding substance (e.g., an elastic polymer) into the dental mold inserts. In some embodiments, the dental mold system 1702 includes one or more fasteners for securing the plates to one another during fabrication of a portion of the dental care device 10.

In some embodiments, the dental insert molds 1706 are fabricated (e.g., 3-D printed or machined) based on a user's dental information (e.g., the geometry of the user's jaw and teeth). In some embodiments, the dental insert molds are composed of a plastic, metal, or a polymer. In some embodiments, the dental insert molds comprise a plurality of apertures for forming the cleaning tips 80 of the mouthpiece assembly. The design and manufacture of the dental mold inserts 1706 are discussed in further detail below with reference to FIGS. 25 through 27D.

In some embodiments, the structure plate 1708 is selected for a particular user based on the geometry of the user's jaw and/or teeth. For example, a smaller structure plate 1708 is selected for a child and a larger plate is selected for an adult. In accordance with some embodiments, the structure plate 1708 includes a connector 1712 configured to couple the structure plate 1708 to one or more of the components shown in FIG. 10A (e.g., the drive assembly 1016, the energy assembly 1020, the memory 1030, etc.).

Figure 18A:
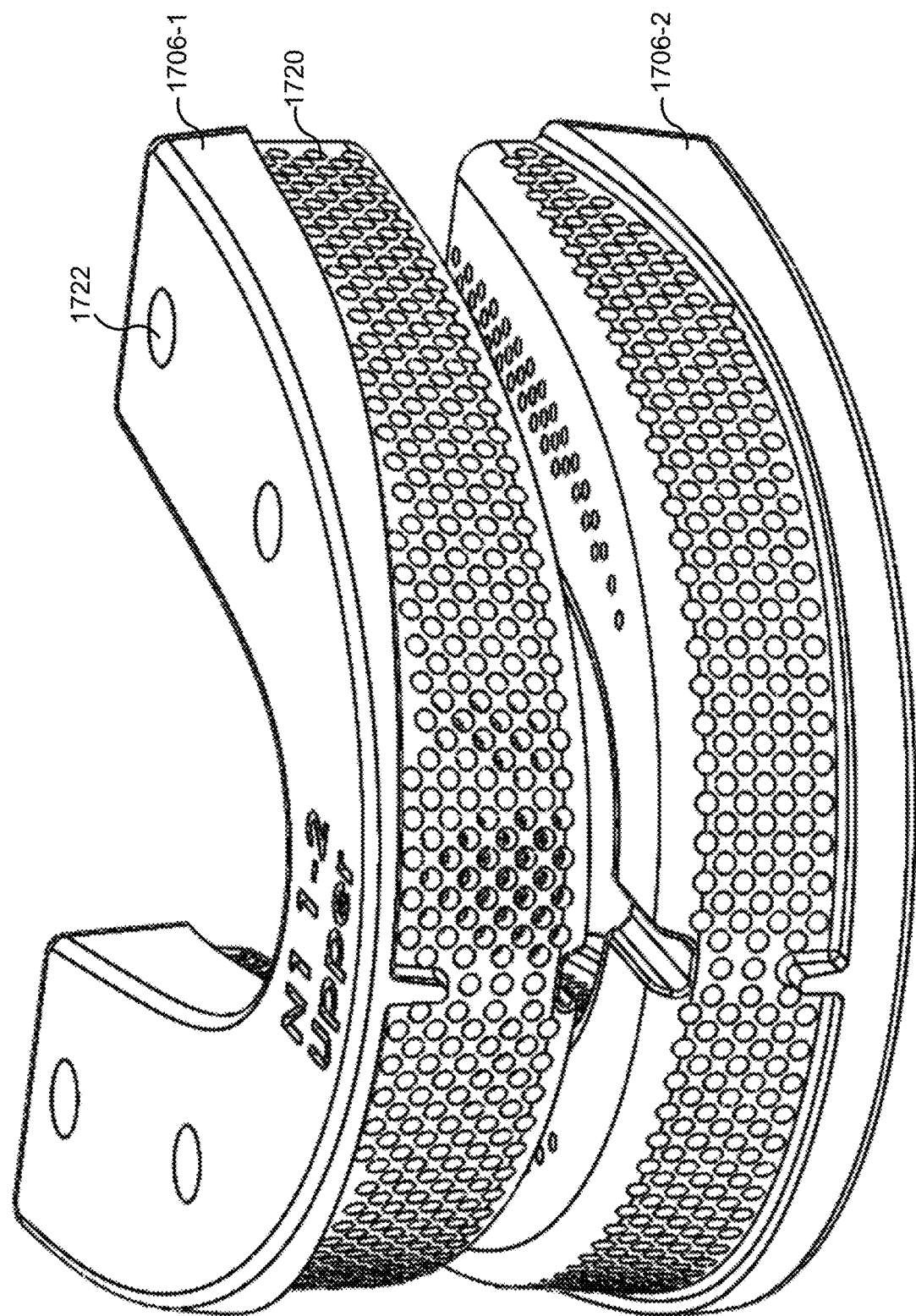
FIGS. 18A-18B are schematic views illustrating representative dental insert molds in accordance with some embodiments.
Figure 18B:
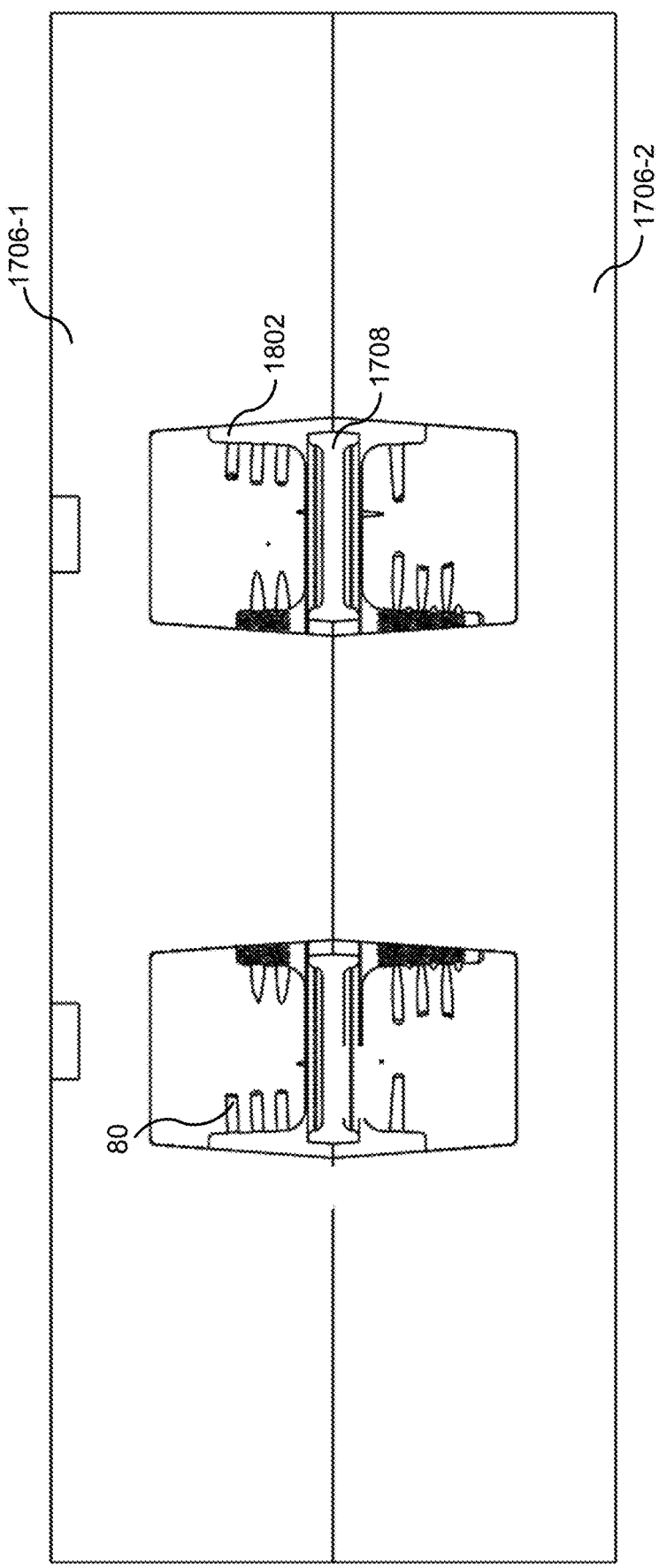

FIGS. 18A-18B are schematic views illustrating dental insert molds 1706 in accordance with some embodiments. FIG. 18A shows a front perspective view of the dental insert molds 1706. As shown in FIG. 18A, the dental insert molds 1706 include a plurality of apertures 1720 for use in forming the cleaning tips 80 of the dental care device 10 in accordance with some embodiments. In some embodiments, each dental insert mold 1706 is customized for a particular person, e.g., is fabricated in accordance with the user's dental information. The custom dental insert molds 1706 enable fabrication of custom mouthpiece assemblies and thus custom dental care devices 10. In some embodiments, the dental insert molds 1706 includes one or more apertures for affixing the dental insert molds to the mold plates 1704. In some embodiments, the dental insert molds 1706 includes one or more apertures for injecting molding material, such as an elastic polymer.

FIG. 18B shows a cross-sectional view of the dental insert molds 1706 encasing a mouthpiece assembly in accordance with some embodiments. The mouthpiece assembly in FIG. 18B includes a structure plate 1708 enclosed in a polymer 1802 having a plurality of cleaning tips 80 in accordance with some embodiments. In some embodiments, the cleaning tips 80 each have a size and shape configured in accordance with a user's dental information, such as the shape and positioning of the user's teeth, the sensitivity of the user's gums, the dental health of the user's teeth and gums, and the like.

Figure 19A:
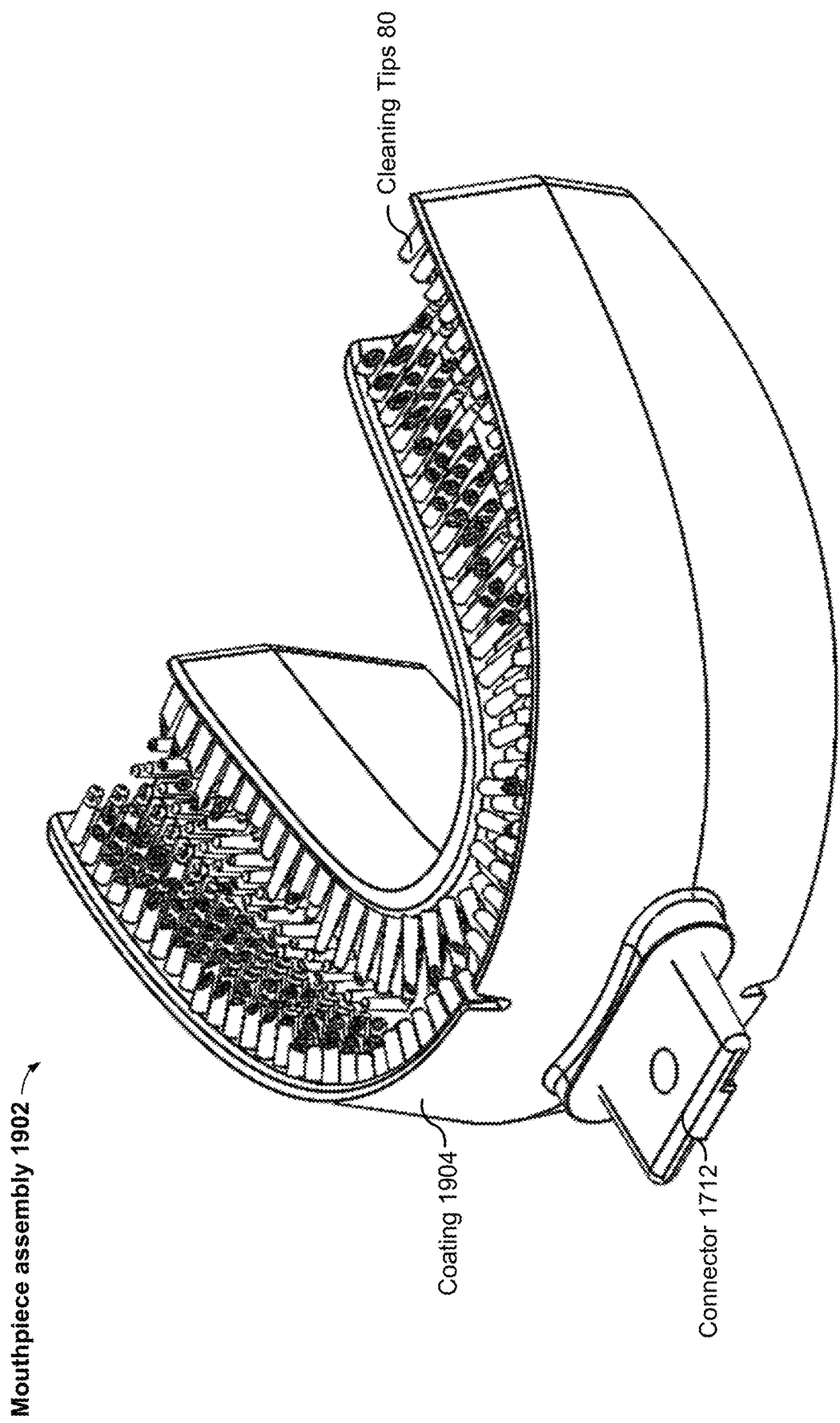
FIGS. 19A-19C are schematic views illustrating a representative mouthpiece assembly in accordance with some embodiments.
Figure 19B:
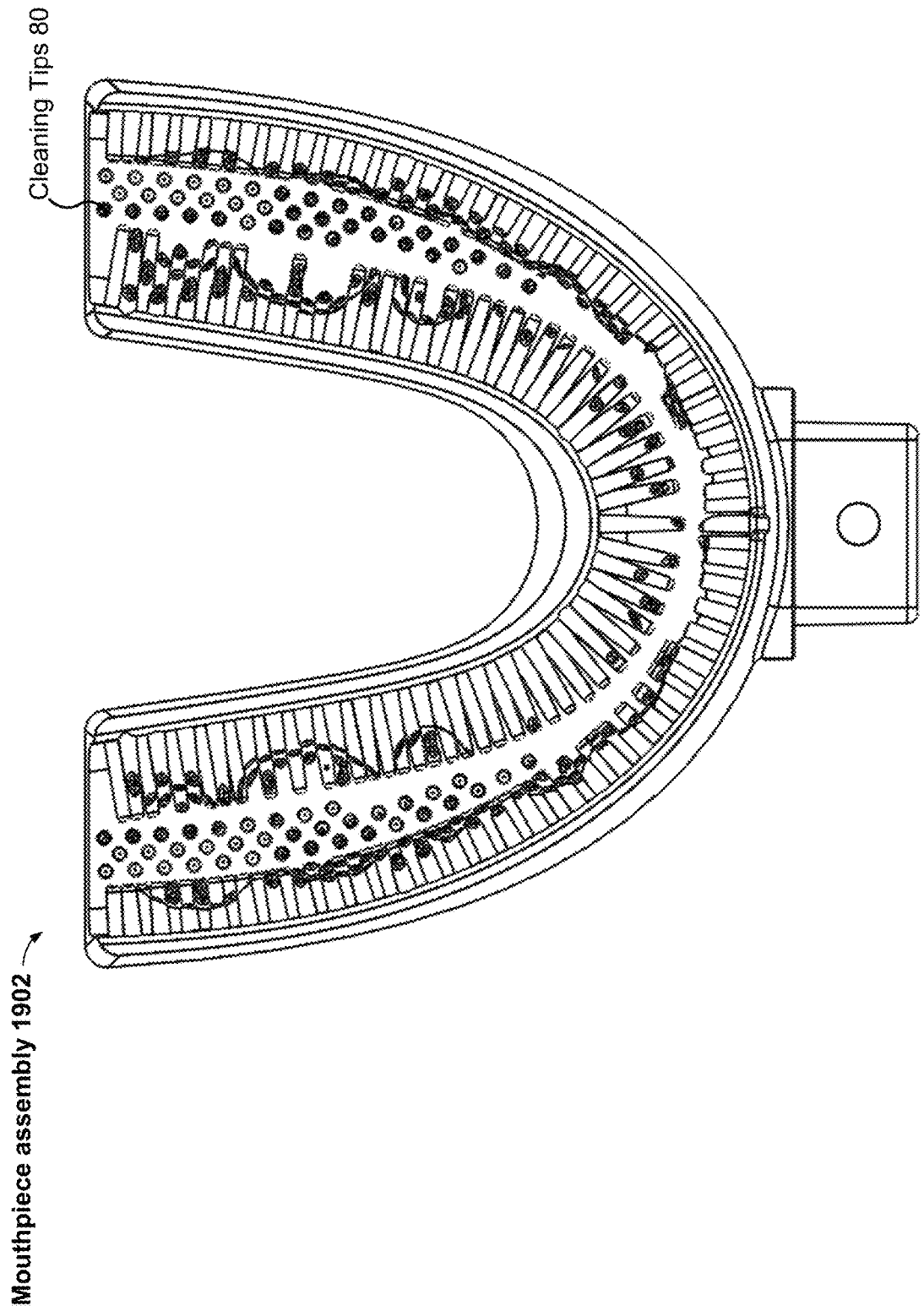
Figure 19C:
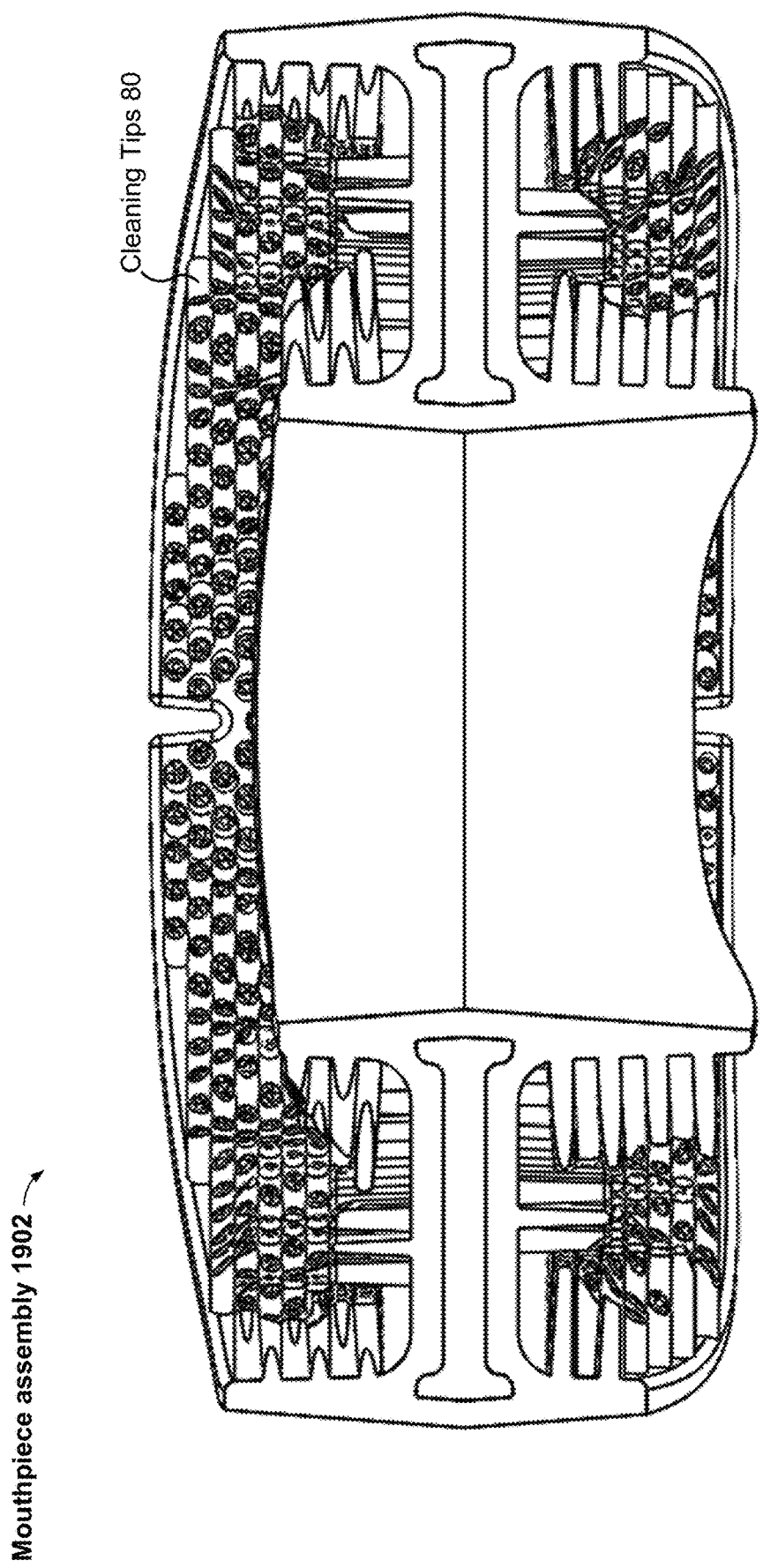

FIGS. 19A-19C are schematic views illustrating a mouthpiece assembly 1902 in accordance with some embodiments. FIG. 19A shows a front perspective view, FIG. 19B shows a top-down view, and FIG. 19C shows a cross-sectional view of the mouthpiece assembly 1902. The mouthpiece assembly 1902 includes the connector 1712 configured to couple the assembly 1902 to one or more of the components shown in FIG. 10A (e.g., the drive assembly 1016, the energy assembly 1020, the memory 1030, etc.). The mouthpiece assembly 1902 also includes a coating 1904 (e.g., an elastic polymer coating) around a structure plate 1708, the coating 1904 including multiple cleaning tips 80.

Accordingly, in some embodiments, a dental care device for cleaning teeth that is customized for a particular user includes: (1) a structure plate (e.g., plate 1708) configured to be inserted into a mouth of a user, where the structure plate includes an attachment tab configured to couple the dental care device to an external drive assembly; and (2) an upper (elastic polymer) cleaning portion above the structure plate and a lower cleaning portion below the structure plate, the upper and lower cleaning portions each including a plurality of cleaning tips (e.g., cleaning tips 80), where the upper and lower cleaning portions are customized in accordance with dental details of a particular user.

In some embodiments, the upper and lower cleaning portions are configured to match the teeth and jaw geometry of the particular user. In some embodiments, the upper and lower portions are composed of an elastic polymer (e.g., an elastomer) customized to the particular user based on the dental information of the particular user. In some embodiments, the elastomer is composed of biocompatible silicone.

In some embodiments, at least one characteristic of the plurality of cleaning tips is based on the dental details of the particular user (e.g., the stiffness or shape of individual cleaning tips and/or clustering of tips). In some embodiments, a length of the cleaning tips ranges from 0.5 mm to 6 mm. In some embodiments, the cleaning tips have a fin shape, a cylindrical shape with a rounded end, a rectangular shape, etc. In some embodiments, the cleaning tips are tapered. In some embodiments, the dental details are a teeth profile and customization is conforming to teeth profile.

In some embodiments, the dental care device further includes an operating component including a drive assembly (e.g., drive assembly 1016, FIG. 10A), one or more energy sources (e.g., batteries 1022), and control circuitry (e.g., processor(s) 1002). In some embodiments, the drive assembly includes one or more offset weight motors and/or magnetic motors. In some embodiments, the drive assembly includes one or more power ports (e.g., USB and/or inductive charging ports). In some embodiments, the dental care device further includes one or more indicators (e.g., one or more LEDs) configured to indicate a status of the device (e.g., needs cleaning, needs charging, needs replaced, operational update available, etc.).

In some embodiments, the drive assembly further includes one or more sensors (e.g., sensor(s) 1004, FIG. 10A) configured to collect dental information of the particular user. In some embodiments, the one or more sensors are configured to obtain breath data for analysis. In some embodiments, the one or more sensors to determine number of device uses.

In some embodiments, the drive assembly is configured to generate a vibrational motion for the elastomer portion. In some embodiments, the vibrational motion is configured to improve dental health of the user (e.g., clean teeth, remove plaque, massage gums, etc.). In some embodiments, generating a vibrational motion includes adjusting a current and/or voltage supplied to one or more motors of the device.

In some embodiments, the drive assembly further includes memory (e.g., the memory 1030, FIG. 10A); and the control circuitry is configured to generate vibration motion in accordance with a drive profile (e.g., a drive profile 1048) stored in the memory.

In some embodiments, the drive profile is based on dental information of the particular user. In some embodiments, the drive profile is based on user preferences and dental health.

In some embodiments, the drive profile includes drive frequency and duration information, e.g., as illustrated in FIG. 10B. In some embodiments, the drive profile is based on one or more characteristics of the cleaning tips. In some embodiments, the drive profile is based on one or more characteristics an oral care agent assigned to the particular user. In some embodiments, the drive profile includes a customized sequence of vibrational frequencies adapted to ensure proper cleaning. In some embodiments, the vibrational frequencies include one or more sonic frequencies and/or one or more ultrasonic frequencies (e.g., as described above with respect to FIGS. 13A-13G).

In some embodiments, the drive assembly further includes communication circuitry (e.g., communication interface(s) 1026); and the communication circuitry is configured to receive dental information for the particular user (e.g., receive a drive profile, user preferences, dental health information, etc. from a mobile app). In some embodiments, the communication circuitry includes one or more wireless antennas (e.g., antenna(s) 1028) configured to utilize one or more communication protocols (e.g., WiFi, Bluetooth, etc.). In some embodiments, the communication circuitry includes one or more communication ports (e.g., USB ports).

In some embodiments, the communication circuitry is configured to transmit operational data of the dental care device to a remote computer system (e.g., server system 910, FIG. 9). In some embodiments, the control circuitry collects operational/feedback information for use in customizing the shape of the elastomer and/or the drive profile for the particular user. In some embodiments, the operation data is transmitted to a dentist or dental agent of the particular user.

In some embodiments, the dental care device is configured such that different vibrational frequencies cause different regions of the elastomer portion to vibrate. For example, only a first region vibrates in response to a first frequency and only a second region vibrates in response to a second frequency.

In some embodiments, the structure plate is configured to provide structural support to the elastomer portion (e.g., has less flexibility (is stiffer) than the elastomer portion). In some embodiments, the upper and lower portions are configured to extend around surfaces of the teeth of the particular user.

Figure 20A:
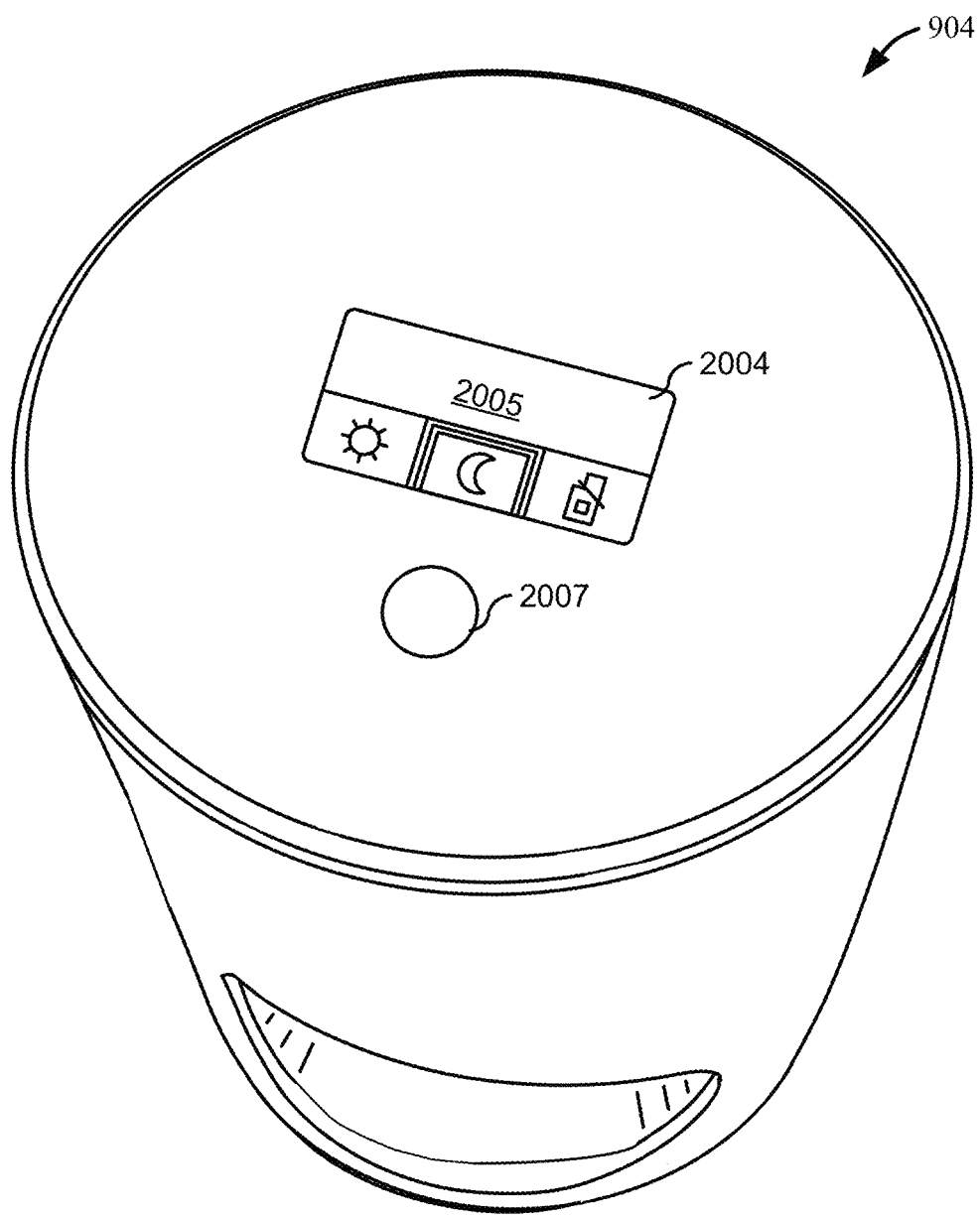
FIG. 20A is a perspective view of a representative dispenser device in accordance with some embodiments.
Figure 20B:
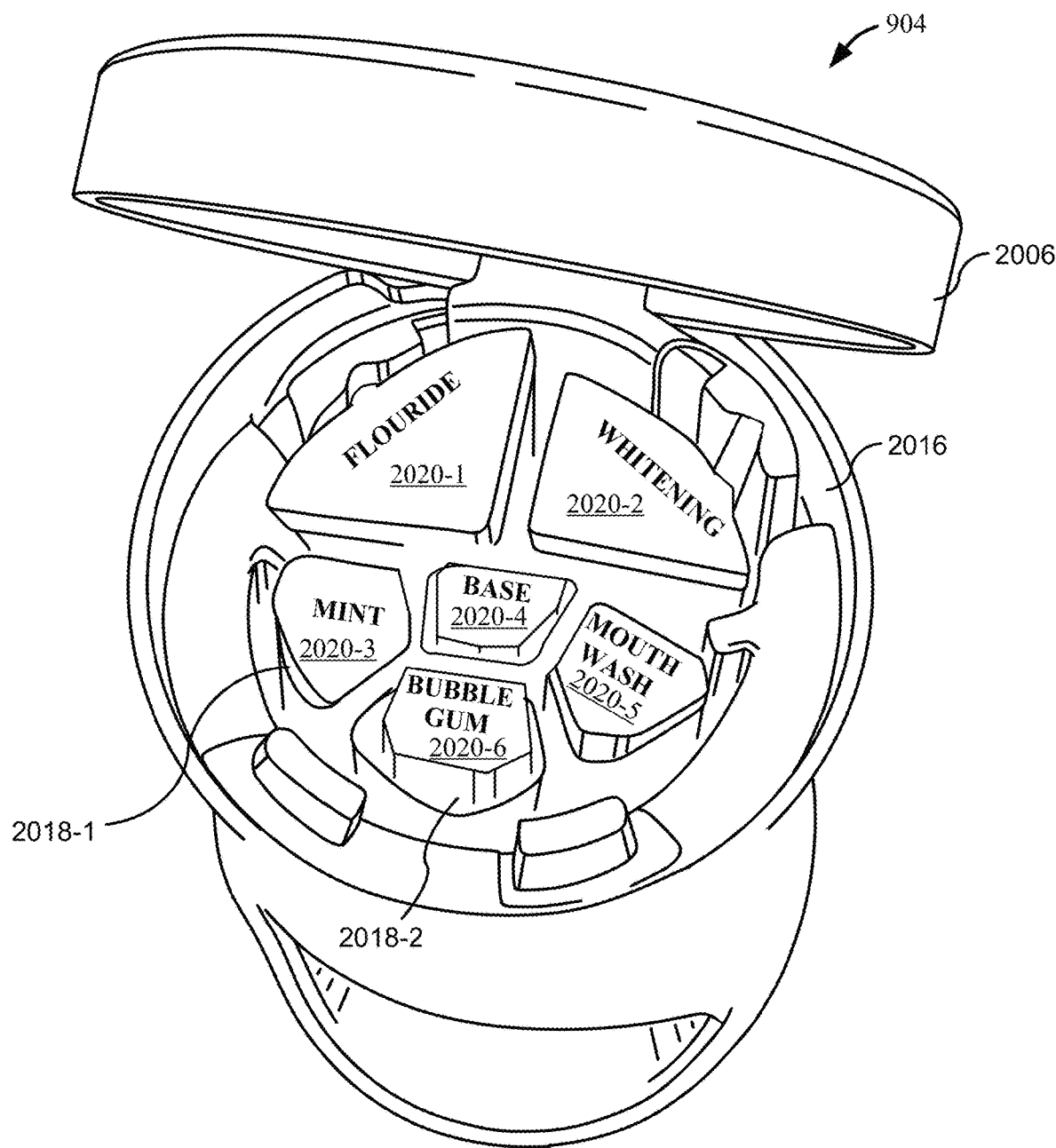
FIG. 20B is a perspective view of the dispenser device of FIG. 20A with its cover open in accordance with some embodiments.

FIG. 20A is a perspective view of an oral care agent (e.g., toothpaste) dispenser 904 in accordance with some embodiments. In some embodiments, the dispenser 904 is a smart device that is programmable, or otherwise configurable, to mix a custom oral care agent formulation from one or more ingredients, and to dispense, in a hands-free manner, a custom amount of custom oral care agent. FIG. 20B is a perspective view of the dispenser device of FIG. 20A with its cover open in accordance with some embodiments.

Referring to FIGS. 20A-20B, in addition to the cover 2006, the dispenser 904 includes a user interface 2004 (e.g., an electronics interface), a chamber 2016 having cartridge slots 2018, and ingredient cartridges 2020 disposed in the cartridge slots. The dispenser 904 further includes electronic circuitry, as illustrated in FIG. 11, for controlling the operation and function of the dispenser.

The electronic interface 2004 optionally includes a display 2005 and one or more buttons 2007. In some embodiments, the display 2005 is configured to display a menu, and the buttons 2007 are configured to enable a user to navigate the menu and to select one or more menu choices or items. For example, if multiple persons (e.g., multiple family members) use the dispenser 904, then a user can use one or more of the button(s) 2007 to navigate the menu and to select, from the menu, his/her name (or other identifier) so as to configure the dispenser to dispense his/her previously entered custom formulation and custom amount of oral care agent. In some embodiments, a user is enabled to use one or more of the button(s) 2007 to navigate the menu to enter/program a custom oral care agent formulation and/or a custom dispense amount. In some embodiments, a user is enabled use the button(s) 2007 to determine a status of the dispenser 904, such as whether any of the ingredient cartridges 2020 are running low or need to be replaced, or whether any components of the dispenser are malfunctioning.

The cartridge slots 2018 of the chamber 2016 are configured to hold, and to dispense ingredients from, the ingredient cartridges 2020. In some embodiments, the cartridge slots and the ingredient cartridges are analogous to toner-cartridge slots and toner cartridges of a color printer that mixes toner from one or more of the cartridges in programmed amounts to create colors of a color palette, and that prints these colors on print media (e.g., paper). In some embodiments, the dispenser 904 is configured to combine ingredients from one or more of the ingredient cartridges 2020 in programmed amounts to create one or more custom oral care agent formulations, and to dispense these one or more custom oral care agents onto brush heads of toothbrushes (typically one custom oral care agent per brush head).

In some embodiments, the cartridge slots 2018 each include a pump mechanism that is configured to draw an ingredient out of a respective one of the cartridges 2020 into a mixing chamber (not shown in FIGS. 20A-20B), in which a mixing mechanism is configured to mix the ingredient with other ingredients entering the chamber. In some embodiments, the pump mechanism of each cartridge slot 2018 is configured to draw an ingredient out of a respective one of the cartridges 2020 and, together with the pump mechanisms of other active ones of the cartridge slots, to generate a single flow of the combined ingredients, where each cartridge slot regulates a rate of flow of the ingredient from the associated cartridge according to an oral care agent formulation. In some embodiments, the pump mechanism of each cartridge slot 2018 is configured to draw out most, if not all, of the ingredient from the corresponding ingredient cartridge so that there is little or no waste of the ingredient. In some embodiments, each cartridge slot 2018 includes a needle, or other device, configured to penetrate the corresponding ingredient cartridge and to form a conduit through which the respective pump mechanism draws the ingredient from the cartridge.

The ingredient cartridges 2020 are configured to hold respective oral care agent ingredients, and to interface with the cartridge slots 2018 in a removable manner such that a pump mechanism (or other suitable mechanism) can draw out the respective ingredients from the cartridges. In some embodiments, the cartridge slots are sized or shaped differently such that only a particular type of ingredient cartridge 2020 is enabled to be inserted into a particular cartridge slot 2018. In some embodiments, the cartridge slots are keyed to a particular type of ingredient cartridge 2020 so as track the location of ingredients and to prevent use of improper ingredients in a particular formulation. In some embodiments, the cartridge slots and cartridges are configured to enable a user to replace the cartridges when their ingredients are respectively spent. Examples of the ingredients that the ingredient cartridges 2020 can hold are, respectively, a tooth-whitening agent (cartridge 2020-2), a mouthwash or a mouth rinse (cartridge 2020-5), a flavoring (cartridges 2020-6 and 2020-3), a fluoride compound (cartridge 2020-1), and an oral care agent base (cartridge 2020-4).

In some embodiments, the dispenser 904 includes more or fewer than six cartridge slots 2018. In some embodiments, the cartridges 2020 hold ingredients other than those described above (e.g., a numbing compound for sensitive teeth). In some embodiments, the dispenser 904 does not include every ingredient in each of the custom oral care agents that it generates.

Figure 21A:
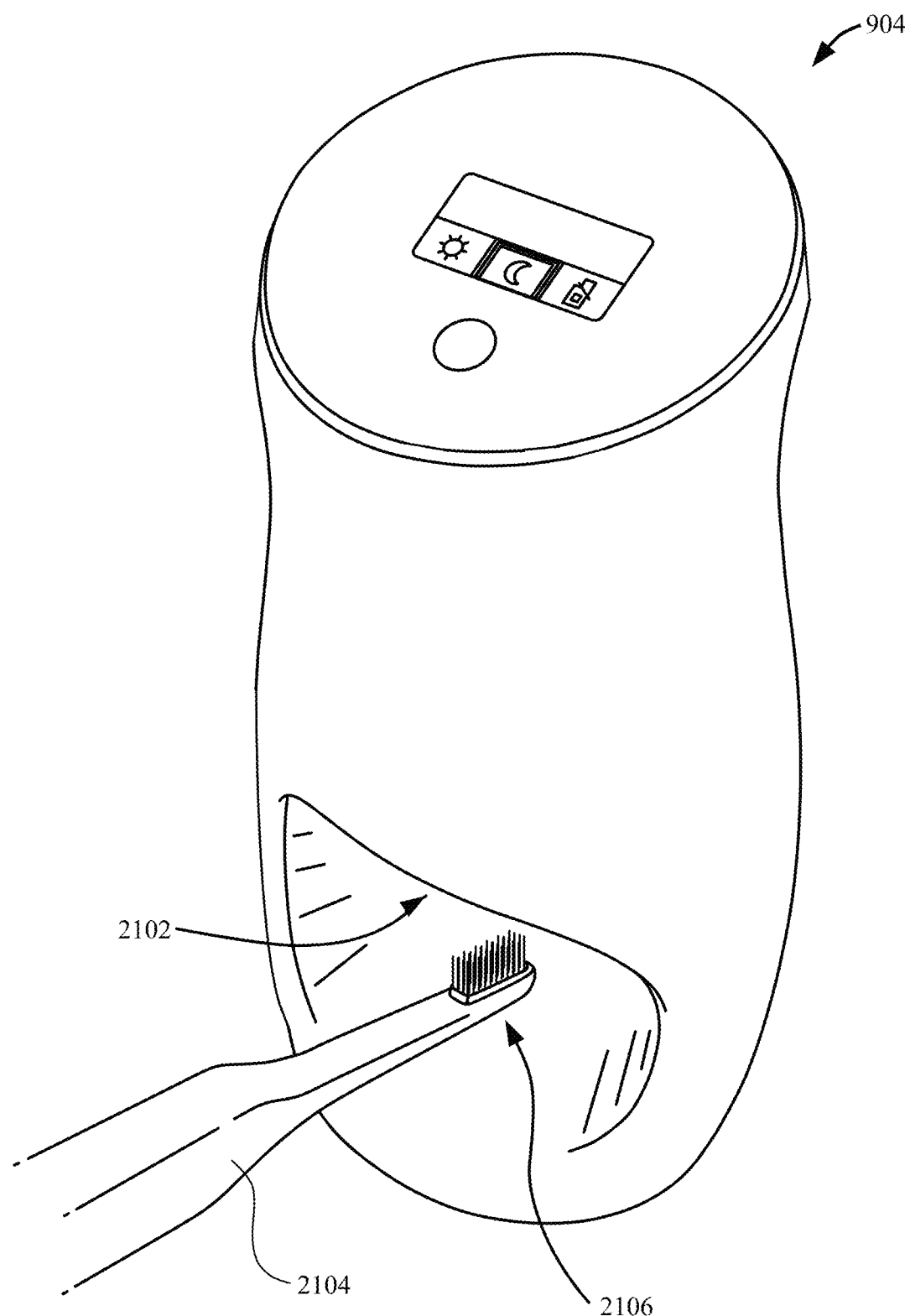
FIGS. 21A-21B are perspective views of the dispenser device of FIG. 20A with dental care devices disposed under a dispensing port of the dispenser device in accordance with some embodiments.
Figure 21B:
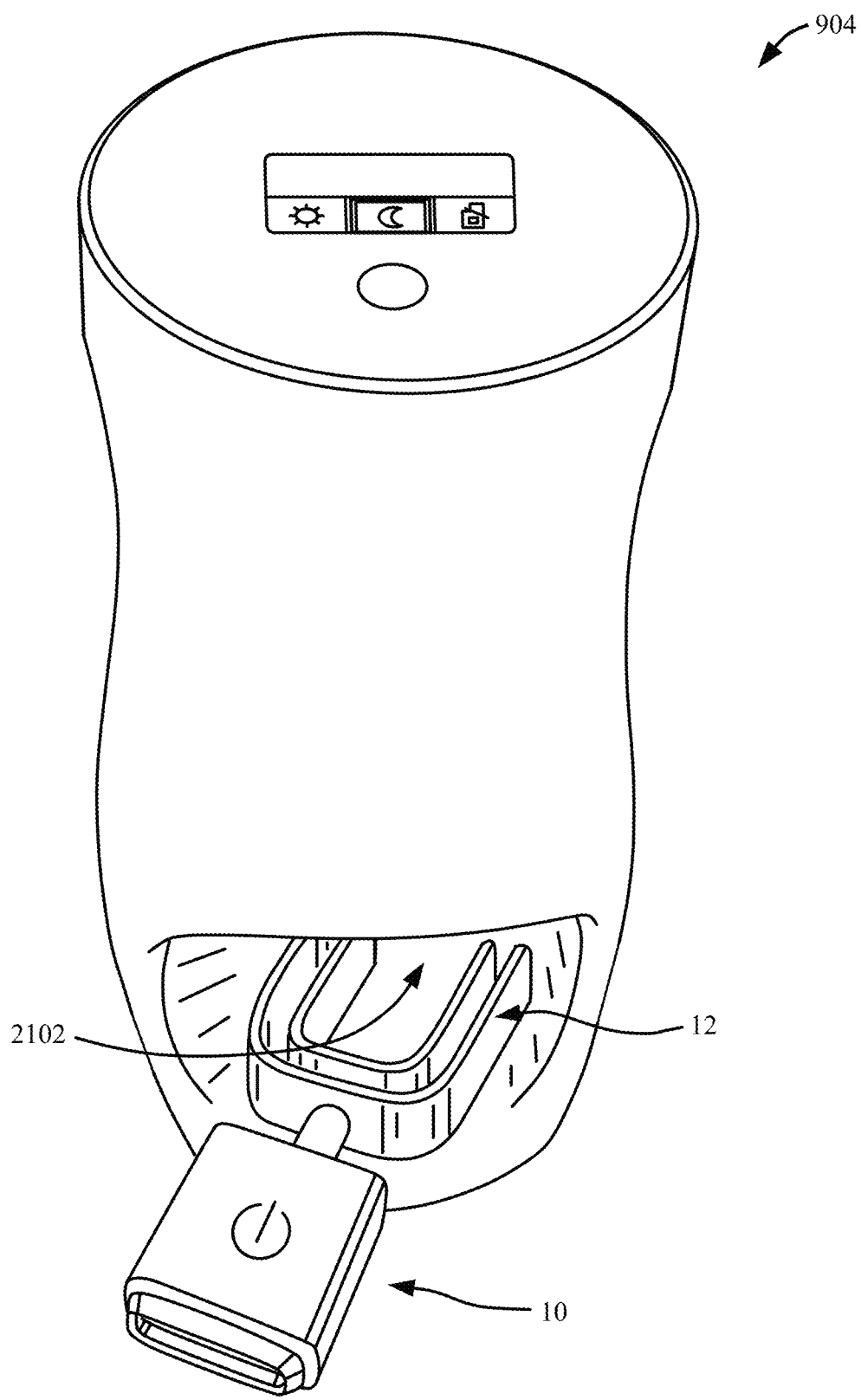

FIGS. 21A-21B are perspective views of the dispenser device of FIG. 20A with dental care devices disposed under a dispensing port of the dispenser device in accordance with some embodiments. FIG. 21A shows a conventional toothbrush 2104 with its brush head 2106 under a dispensing port 2102 of the dispenser 904 in accordance with some embodiments. FIG. 21B shows a dental care device 10 with its mouthpiece assembly 12 under a dispensing port 2102 of the dispenser 904 in accordance with some embodiments. In some embodiments, the dispenser 904 includes a sensor (e.g., sensor(s) 1104, FIG. 11) that is configured to detect when the mouthpiece assembly 12 is in a proper position to receive oral care agent. Examples of such a sensor include an optical sensor and a camera.

In some embodiments, the dispenser 904 includes a sensor (e.g., sensor(s) 1104, FIG. 11) that is configured to detect when the brush head 2106 of the toothbrush 2104 (or the brush head of any other toothbrush) is in a proper position to receive oral care agent. Examples of such a sensor include an optical sensor, a PIR sensor, a camera, and the like.

In some embodiments, the sensor is configured, in response to detecting that the brush head 2106 is in a proper position, to generate a sensor signal, and to send the sensor signal to electronic circuitry (e.g., processor(s) 1102) onboard the oral care agent dispenser 904.

In some embodiments, the electronic circuitry is configured, in response to receiving the sensor signal, to cause the dispenser 904 to generate, and to dispense, a custom amount of custom oral care agent (e.g., in accordance with a dispensing profile 1148) onto the brush head 2106 of the toothbrush 2104. In some embodiments, the electronic circuitry is configured to first activate the ingredient-pumping mechanisms associated with one or more of the cartridge slots 2018, which, while activated, draw ingredients out of the corresponding cartridges 2020. In some embodiments, the electronic circuitry is configured next to cause a mixing or other mechanism of the oral care agent dispenser 10 to generate a set amount of oral care agent according to a set formulation (e.g., a dispensing profile 1148). In some embodiments, the electronic circuitry is configured then to cause a dispensing or other mechanism of the dispenser 904 to dispense the set/custom amount of the custom oral care agent from the dispensing port 2102 onto the brush head 2106. In some embodiments, the oral care agent formulation and the amount of oral care agent to be dispensed are programmable by the user and/or a dental professional.

In some embodiments, the electronic circuitry is configured, in response to receiving the sensor signal, to cause the dispenser 904 to generate, and to dispense, a custom amount of custom oral care agent onto the mouthpiece assembly 12. In some embodiments, the electronic circuitry is configured to first activate the ingredient-pumping mechanisms associated with one or more of the cartridge slots 2018, which mechanisms, while activated, draw respective ingredients out of the corresponding cartridges 2020. In some embodiments, the electronic circuitry is configured next to cause a mixing or other mechanism of the dispenser 904 to generate a set amount of oral care agent according to a set formulation. In some embodiments, the electronic circuitry is configured then to cause a dispensing or other mechanism of the dispenser 904 to dispense the set/custom amount of the custom oral care agent from the dispensing port 2102 into the trough of the mouthpiece assembly 12.

In some embodiments, after the oral care agent dispenser 904 dispenses oral care agent into the mouthpiece assembly 12, the user can turn over the dental care device 10 over and cause the dispenser to dispense a custom amount of custom oral care agent into the opposite side of the mouthpiece. In some embodiments, the dispenser 904 is configured to dispense different amounts or different oral care agent formulations onto the opposite sides of the mouthpiece.

In some embodiments, the electronic circuitry onboard the dispenser 904 includes communication circuitry configured for wired or wireless communication with a device remote from the dispenser. For example, the dispenser 904 can communicate with a smart phone via a Bluetooth® or WiFi link, and, via the smart phone, can upload and download data, such as program data, configuration data, and data indicative of the status of the dispenser.

In some embodiments, using the communication circuitry, the electronic circuitry notifies a supply server (e.g., a cloud server) automatically when the amount of ingredient in a particular ingredient cartridge is below a threshold level, and the server can have a replacement cartridge sent to the user in time to avoid the installed cartridge emptying before the replacement cartridge arrives.

In some embodiments, a dentist or other dental professional can determine a custom oral care agent formulation based on a user's dental history and other factors (e.g., health, tooth structure, flavor preference), and provide the formulation to the oral care agent dispenser 904 in a manner that is transparent to the person. For example, the dentist or other dental professional can upload the formulation to a cloud server, which can generate configuration data from the formulation and can upload the configuration data to the dispenser 904 via the internet, a smart phone or wireless router, and the dispenser's communication circuitry. The dispenser 904 can then execute the configuration data if it is in the form of executable instructions, or otherwise can configure itself according to the configuration data. In some embodiments, in response to the user identifying him/herself (e.g., by selecting his/her name or identifier via the menu and buttons on the dispenser) and properly placing his toothbrush or dental care device under the dispensing port 2102, the dispenser 904 generates oral care agent according to the custom amount and custom formulation and dispenses the custom amount of oral care agent onto the brush head 2106 or the mouthpiece assembly 12.

In some embodiments, the dispenser 904 is configured to dispense oral care agent simultaneously into both sides of the mouthpiece assembly 12. In some embodiments, the dispenser 904 is configured to dispense a standard (non-custom) toothpaste.

In accordance with some embodiments, the dispenser 904 operates as follows. In some embodiments, upon power up, electronic circuitry onboard the oral care agent dispenser 904 executes a start-up routine. In some embodiments, as part of the start-up routine, the dispenser 904 checks its status, determines whether any of its components are not functioning properly, and determines whether any of the cartridges 2020 are low enough on ingredient to warrant ordering a replacement cartridge (e.g., below a threshold amount or weight). In some embodiments, if the electronic circuitry determines that any components are not functioning properly, or that any replacement cartridges need to be ordered, then the circuitry uploads such information or reorder to a cloud server via a wired or wireless link and a device such as a router or smart phone.

In some embodiments, if the cloud server has any configuration files (e.g., corresponding to an oral care agent formulation, a software or firmware update) for the dispenser 904, then the cloud server notifies the dispenser, which downloads the configuration file(s).

In some embodiments, if the electronic circuitry determines that any of the cartridges 2020 need replacing, a user opens the cover 2006 and replaces the one or more cartridges. For example, the electronic circuitry can cause the display 2005 to display a message indicating which cartridge or cartridges 2020 to replace.

In some embodiments, the user uses the buttons 2007 to navigate a menu on the display 2005 to select the function that the user wants the dispenser 904 to perform. For example, the user can enter an oral care agent formulation, or can enter or select his/her name, or another identifier, to configure the dispenser 904 for dispensing oral care agent in an amount, and having a formulation, that are customized for him/her.

In some embodiments, the user places the brush head 2106 of a toothbrush 2104, or a mouthpiece assembly 12 of a dental care device 10, under the dispenser 2102. In some embodiments, in response to a sensor detecting that the brush head 2106 or mouthpiece assembly 12 is in the proper position, the dispenser 904 activates the pump assembly (and mixing assembly, if included in the dispenser) to generate and dispense a custom amount of oral care agent having a custom formulation, where the custom amount and custom formulation correspond to the person. If the dispenser 904 does not activate the pump assembly, then the user may need to reposition the brush head 2106 or mouthpiece assembly 12 until the user is notified that the position is proper (e.g., hears the dispenser 904 dispensing oral care agent).

In some embodiments, after the dispenser 904 stops dispensing oral care agent, the user removes the brush head 2106 or mouthpiece assembly 12 from beneath the dispenser, and cleans his/her teeth.

Accordingly, in some embodiments, oral care agent dispenser device (e.g., dispenser 904) includes: (1) multiple chambers (e.g., cartridge slots 2018) each configured to receive a cartridge (e.g., cartridges 2020) containing a different oral care agent ingredient of a plurality of oral care agent ingredients; (2) memory (e.g., memory 1130) configured to store an oral care agent formulation that includes one or more of the plurality of oral care agent ingredients (e.g., a dispensing profile 1148); and (3) a dispenser positioned above an oral care agent dispensing region, the dispenser configured to dispense one or more of the plurality of oral care agent ingredients in accordance with the oral care agent formulation.

In some embodiments, each cartridge is keyed such that it can only fit into its corresponding chamber (cartridge slot). In some embodiments, each cartridge is configured for one-time use and the dispenser is configured to eject used cartridges into a garbage tray. In some embodiments, the cartridges are configured to be refillable. In some embodiments, each cartridge has a foil seal at one end configured such that, when inserted into the dispenser, the foil seal is broken (e.g., pierced). In some embodiments, each cartridge comprises a syringe and the dispenser device is configured to move a plunger of the syringe down in set increments to eject oral care agent (e.g., via an actuator 1118). In some embodiments, the dispenser device utilizes a geared servo-motor to drive the plunger at side of syringe. In some embodiments, each syringe is pressurize-sealed and the dispense employs a pump with valves to push a syringe plunger down. In some embodiments, a cartridge comprises flexible tubing containing the corresponding oral care agent ingredient and the dispenser is configured to employ a roller to squeeze the ingredient from the tubing. In some embodiments, the dispenser device includes a tortious path mixer for mixing ingredients prior to dispensing.

In some embodiments, the plurality of oral care agent ingredients includes one or more whitening agents, one or more numbing agents, one or more flavorings, one or more fluoride compounds, breath freshener components, tartar control components, polishing particulates, and the like. In some embodiments, the oral care agent formulation is assigned (e.g., prescribed) to a particular user. In some embodiments, the memory stores multiple oral care agent formulations, each for a different user (e.g., a different member of a household).

In some embodiments, the dispenser device further includes communication circuitry (e.g., communication interface(s) 1126) configured to receive oral care agent formulation information (e.g., oral care agent formulation information) for one or more users from a remote source. In some embodiments, the oral care agent formulation information is a dentist prescribed formulation of one or more of the plurality of oral care agent ingredients.

In some embodiments, the dispenser device is configured to only dispense prescription-approved material, e.g. prescription fluoride treatment, after identifying the user and/or dental care device.

In some embodiments, the dispenser comprises at least one actuator (e.g., actuator(s) 1118). In some embodiments, the one or more dispensing components includes one or more motors. In some embodiments, the dispenser includes an individual pump for each ingredient. In some embodiments, the dispenser includes a single pump for use with all ingredients. In some embodiments, the dispenser includes a liquid reservoir (e.g., a water reservoir) configured to flush undeposited oral care agent after use. In some embodiments, the dispenser includes a liquid reservoir configured to for mixing with the oral care agent ingredients as part of the oral care agent formulation (e.g., to adjust viscosity).

In some embodiments, the dispenser further includes control circuitry (e.g., processor(s) 1102) configured to selectively activate the dispenser. In some embodiments, the dispenser is configured to combine respective portions of one or more of the plurality of oral care agent ingredients into a dispensed oral care agent in accordance with the oral care agent formulation information; and the control circuitry is further configured to dispense an amount of the dispensed oral care agent in accordance with profile information of a user (e.g., a dispensing profile 1148) stored in the memory. For example, the profile information includes information regarding one or more user preferences and/or user dental prescription information.

In some embodiments, the dispenser further includes a user interface 2004 configured to present information to a user and receive user commands. In some embodiments, the user interface includes one or more physical buttons (e.g., button(s) 1108), microphones (e.g., microphone(s) 1112), speakers (e.g., speaker(s) 1114), displays, touch screens, and the like.

In some embodiments, the control circuitry is configured to selectively activate the dispenser in response to a user command received via the user interface. In some embodiments, the control circuitry is configured to identify the user who issued the command prior to activating the dispensing components (e.g., to dispense customized oral care agent for the user). In some embodiments, the dispenser device identifies the user via an inputted passcode, voice recognition, dental care device recognition, and the like.

In some embodiments, the user interface is further configured to receive one or more user preferences from the particular user. For example, receive one or more flavoring and/or consistency preferences.

In some embodiments, the dispenser further includes one or more sensors (e.g., sensor(s) 1104) configured to determine whether a dental cleaning device is present. In some embodiments, the one or more sensors comprise one or more passive infrared (PIR) sensors, barcode readers, near field communication (NFC) circuitry, and the like. In some embodiments, determining that the dental cleaning device is present comprises determining that the dental cleaning device is positioned to receive the oral care agent dispensed by the dispensing components (e.g., positioned as shown in FIGS. 21A-21B). In some embodiments, the dispenser includes an NFC and/or barcode reader to read unique identifier in toothbrush and dispense a corresponding oral care agent formulation.

In some embodiments, the control circuitry is configured to automatically dispense one or more of the plurality of oral care agent ingredients in response a determination that the dental cleaning device is present in the dispensing zone (e.g., that the cleaning device is positioned under the dispenser output).

In some embodiments, the oral care agent dispenser device is configured to determine whether one or more of the plurality of oral care agent ingredients is below a threshold amount (e.g., will be exhausted within 5 days, 7 days, or 15 days). In some embodiments, the device counts a number of uses to determine if an ingredient is below a threshold amount (low). In some embodiments, the device uses one or more sensors (e.g., via weight or line-of-sight determinations) to determine if an ingredient is low.

In some embodiments, the control circuitry is further configured to generate a notification for a particular oral care agent ingredient in accordance with a determination that the particular oral care agent ingredient is below a threshold amount. For example, the control circuitry is configured to generate a notification to the user via the user interface or the communication circuitry; and/or generate a notification to a dental provider via the communication circuitry.

In some embodiments, the control circuitry is further configured to request more of a particular oral care agent ingredient in accordance with a determination that the particular oral care agent ingredient is below a threshold amount (e.g., using the communication circuitry). In some embodiments, the control circuitry automatically orders more of the ingredient from a dental provider (without a specific request from the user). In some embodiments, the dispenser is configured to wirelessly communicate with a user's device (e.g., user device 906) to notify the user know that an ingredient is running low.

In some embodiments, the communication circuitry is further configured to communicatively couple the oral care agent dispenser device to a dental cleaning device (e.g., a dental care device 10). In some embodiments, the oral care agent formulation information is based in part on a drive profile received from the dental cleaning device. In some embodiments, the drive profile is based in part on the oral care agent formulation information. In some embodiments, the dispenser 904, the dental care device 10, or the server system 910 determines a drive profile for the dental care device 10 based in part on the oral care agent formulation information. In some embodiments, the dispenser 904, the dental care device 10, or the server system 910, determines oral care agent formulation information based in part on a drive profile for a user of the dental care device 10.

In some embodiments, in response to detecting a mouthpiece assembly 12 in position under a dispenser, the dispenser dispenses oral care agent in accordance with the shape of the mouthpiece (e.g., in U-shape). In some embodiments, the dispenser dispenses oral care agent from top and bottom. In some embodiments, the dispenser moves in a predetermined path along the detected brush head or mouthpiece. In some embodiments, the dispenser includes two nozzles, where one nozzle is positioned under the mouthpiece and the other nozzle is positioned above the mouthpiece when the mouthpiece is in position to receive the oral care agent. In some embodiments, the dispenser includes a nozzle positioned to the right of the mouthpiece and/or a nozzle positioned to the left of the mouthpiece when the mouthpiece is in position to receive the oral care agent.

In some embodiments, the dispenser device includes a component configured to store a dental care device 10 (e.g., a storage compartment and/or mount). In some embodiments, the dispenser device is configured to operate as a base unit 750 (FIGS. 7A-7B) and/or a housing 815 (FIGS. 8A-8D). In some embodiments, the dispenser device is configured to have some or all of the functionality of the base unit 750 (FIGS. 7A-7B) and/or the housing 815 (FIGS. 8A-8D). In some embodiments, the dispenser device is configured to charge the dental care device 10 (e.g., via inductive charging, an electrical port (e.g., a USB port), or an AC adapter) while the dental care device is stored. In some embodiments, the dispenser device is configured to clean and/or disinfect dental care device 10 (e.g., using ultraviolet light and/or a cleaning solution).

Figure 22:
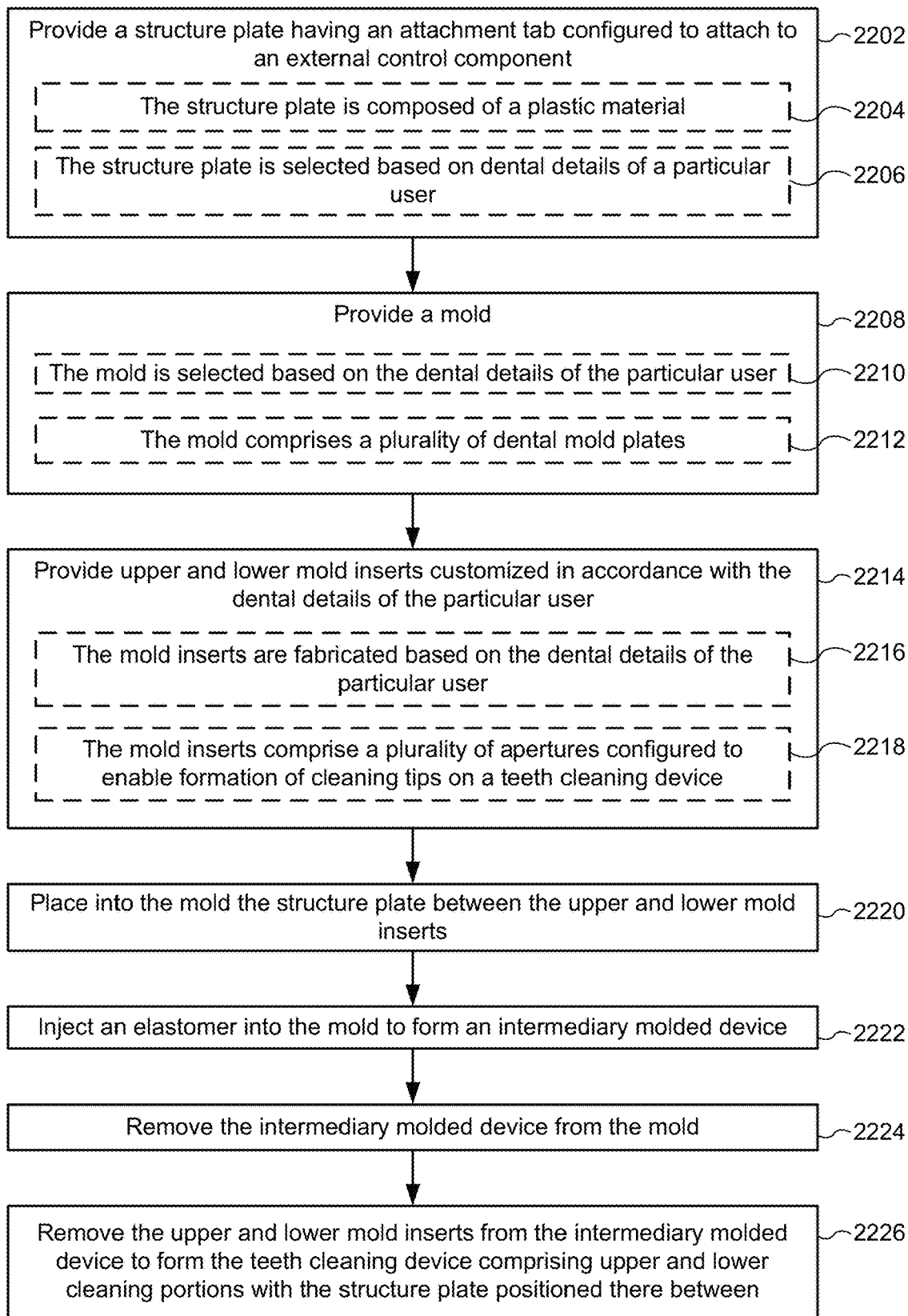
FIG. 22 is a flowchart illustrating a method for fabricating a representative teeth cleaning device in accordance with some embodiments.

FIG. 22 is a flowchart illustrating a method 2200 for fabricating a representative teeth cleaning device in accordance with some embodiments. A structure plate (e.g., structure plate 1708) having an attachment tab (e.g., connector 1712) configured to attach to a control component (e.g., an external drive mechanism) is provided (2202). In some embodiments, the structure plate is composed of (2204) a plastic material. In some embodiments, the plate is injection molded out of a plastic material that is more ridged than the elastomer. In some embodiments, the structure plate is selected (2206) from a set of pre-made structure plates based on dental details of a particular user. In some embodiments, the set of pre-made structure plates (e.g., 5 or 10 plates) are configured to cover a wide range of jaw sizes and shapes (e.g., from children to adults). In some embodiments, the dental details of the particular user include information regarding locations and shapes of the particular user's teeth (e.g., obtained via 3-D scanning the user's mouth). In some embodiments, the structure plate has a general U-shape or Y-shape. In some embodiments, the structure plate has a jaw-shape. Additional details for fabricating a representative teeth cleaning device are provided below with reference to FIGS. 25 through 27D. Also, additional details regarding a design of the attachment tab (e.g., connector 1712) are provided in U.S. patent application Ser. No. 17/192,645, which is incorporated herein by reference in its entirety.

A mold is provided (2208). In some embodiments, the mold is selected (2210) from a set of pre-made molds based on the dental details of the particular user. In some embodiments, the mold is selected based on the provided structure plate (e.g., based on a size or shape of the structure plate). In some embodiments, the mold comprises (2212) a plurality of dental mold plates (e.g., plates 1704, FIG. 17).

Upper and lower mold inserts customized in accordance with the dental details of the particular user (e.g., mold inserts 1706) are provided (2214). In some embodiments, the mold inserts are fabricating via a 3-D printing process. In some embodiments, multiple customized dental care devices are fabricating for a particular user using the same mold inserts. In some embodiments, the mold inserts are fabricated (2216) based on the dental details of the particular user, e.g., the geometry of the user's teeth and jaw, the dental health of the user's teeth and gums, and dental history of the user. In some embodiments, the mold inserts comprise (2218) a plurality of apertures (e.g., apertures 1720) configured to enable formation of (custom) cleaning tips on a teeth cleaning device via the molding process. The design and manufacture of the upper and lower mold inserts are discussed in further detail below with reference to FIGS. 25 through 27D.

The structure plate is placed (2220) into the mold between the upper and lower mold inserts. An elastomer is injected (e.g., pressure injected or vacuum injected) into the mold to form an intermediary molded device (2222). The intermediary molded device is removed (2224) from the mold. The upper and lower mold inserts are removed (2226) from the teeth cleaning device to form the teeth cleaning device (e.g., the mouthpiece assembly 1902, FIG. 19A) comprising upper and lower cleaning portions with the structure plate positioned there between. In some embodiments, the upper and lower cleaning portions comprise a single continuous elastomer coating (e.g., coating 1904). For example, an elastomer coating configured to, without any seams, surround the arms of the support plate and extend around surfaces of the user's teeth during user.

In some embodiments, the upper and lower cleaning portions include a plurality of cleaning tips (e.g., cleaning tips 80) formed from apertures (also sometimes called cavities herein) in the upper and lower mold inserts. In some embodiments, the apertures are configured in accordance with the user's dental information.

Figure 23:
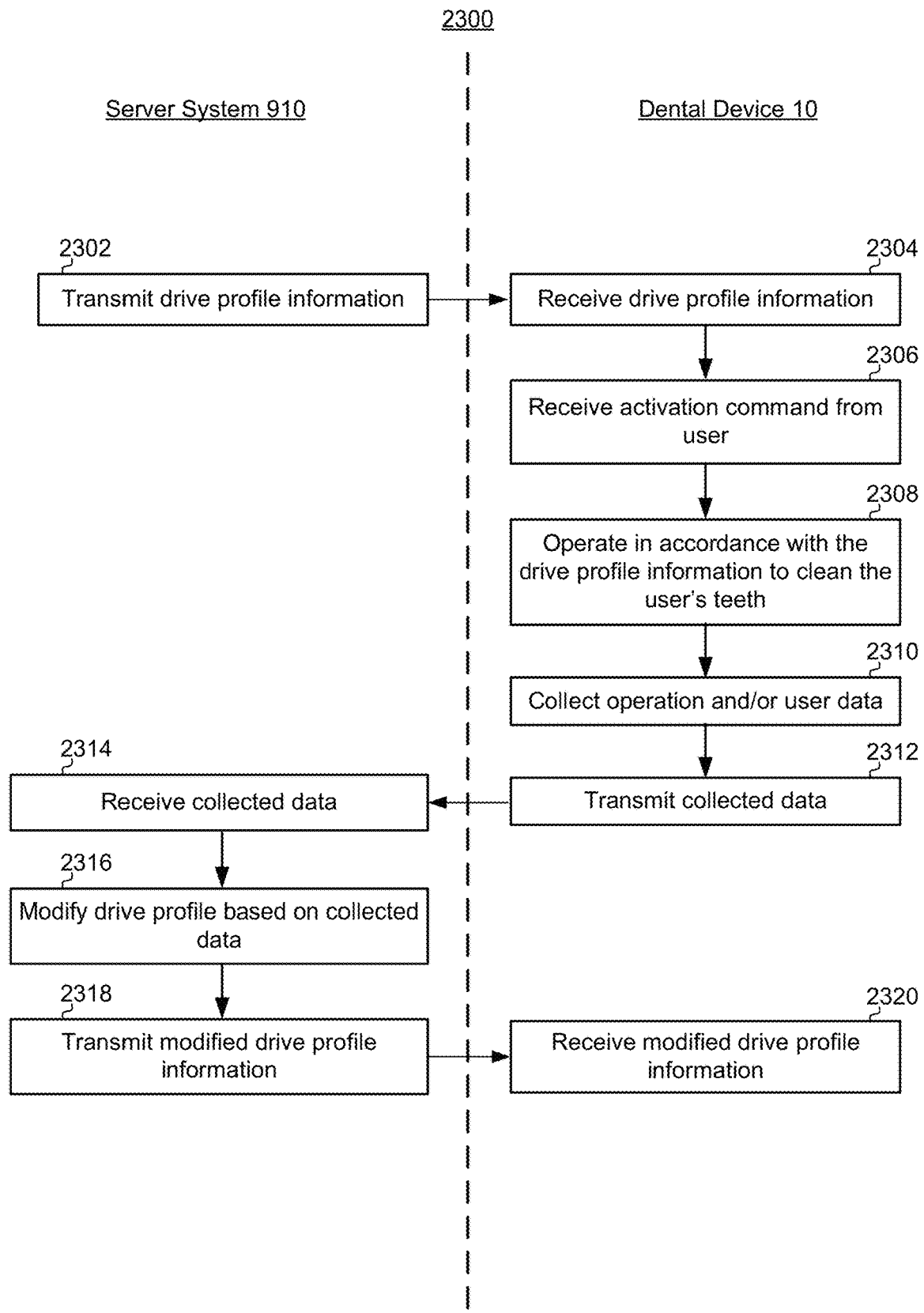
FIG. 23 is a flowchart illustrating a method for operating a representative dental care device in accordance with some embodiments.

FIG. 23 is a flowchart illustrating a method 2300 for operating a representative dental care device in accordance with some embodiments. A server system (e.g., server system 910) transmits (2302) drive profile information (e.g., drive profile information 1232) to a dental care device (e.g., dental care device 10 or dental care device 100). In some embodiments, the server system transmits the information via the network interface(s) 1204 in conjunction with the network communication module 1212. In some embodiments, the drive profile information is provided by a dental health professional. In some embodiments, the drive profile information is generated at the server system based on dental details of a user of the dental care device. In some embodiments, the drive profile information includes frequency and timing information for operating the dental care device to clean the user's teeth. In some embodiments, the drive profile information includes voltage and/or current information for operating a drive assembly 1016 of the dental care device (e.g., to produce desired frequencies and timings).

The dental care device receives (2304) the drive profile information from the server system. In some embodiments, the dental care device receives the information via the communication interface(s) 1026 operating in conjunction with the communication module 1034. In some embodiments, the dental care device stores the drive profile information in memory 1030. In some embodiments, the dental care device utilizes the drive profile information to update one or more drive profiles 1048 stored in memory 1030.

The dental care device receives (2306) an activation command from the user. In some embodiments, the activation command comprises a voice command or selection of an activation affordance (e.g., a physical button) on the dental care device. In some embodiments, the activation command comprises an implicit activation command (e.g., the dental care device determines that it is inserted into the user's mouth).

The dental care device operates (2308) in accordance with the drive profile information to clean the user's teeth. In some embodiments, the dental care device vibrates at a plurality of sonic and/or ultrasonic frequencies (e.g., in accordance with a drive profile 1048).

The dental care device collects (2310) operation and/or user data. In some embodiments, the operation data includes information regarding how often the user operates the dental care device. In some embodiments, the operation data includes information obtained from one or more sensors of the dental care device (e.g., one or more breath analyzers). In some embodiments, the user data includes one or more user settings and/or preferences. In some embodiments, the user data includes dental information supplied by the user to the dental care device. In some embodiments, the dental care device modifies one or more drive profiles of the user based on the collected information.

The dental care device transmits (2312) the collected data to the server system. In some embodiments, the dental care device transmits the collected data via the communication interface(s) 1026 operating in conjunction with the communication module 1034. The server system receives (2314) the collected data from the dental care device. In some embodiments, the server system receives the collected data via the network interface(s) 1204 in conjunction with the network communication module 1212.

The server system modifies (2316) a drive profile (or drive profile information) for the user based on the collected data. In some embodiments, the server system modifies one or more frequency, amplitude, timing, voltage, or current parameters of the drive profile based on the collected data. In some embodiments, the server system requests updated dental information from the user (or a dental care provider of the user) based on the collected data. For example, the collected data indicates that the user has recently experienced pain or discomfort when using the dental care device, thereby indicating that the user's dental health or situation has changed. Based on this indication, the server system requests updated dental information to so that it can adjust the drive profile (or order a new dental care device mouthpiece) based on the updated information. In some embodiments, the server system requests an updated mouthpiece for the dental care device based on the collected information.

The server system transmits (2318) the modified drive profile information (e.g., drive profile information 1232) to the dental care device. In some embodiments, the server system transmits the modified information via the network interface(s) 1204 in conjunction with the network communication module 1212. The dental care device receives (2320) the modified drive profile information from the server system. In some embodiments, the dental care device receives the information via the communication interface(s) 1026 operating in conjunction with the communication module 1034.

In some embodiments, the dental care device stores the modified drive profile information in memory 1030 (e.g., in place of, or in addition to, the previously received drive profile information). In some embodiments, the dental care device utilizes the modified drive profile information to update one or more drive profiles 1048 stored in memory 1030.

Figure 24:
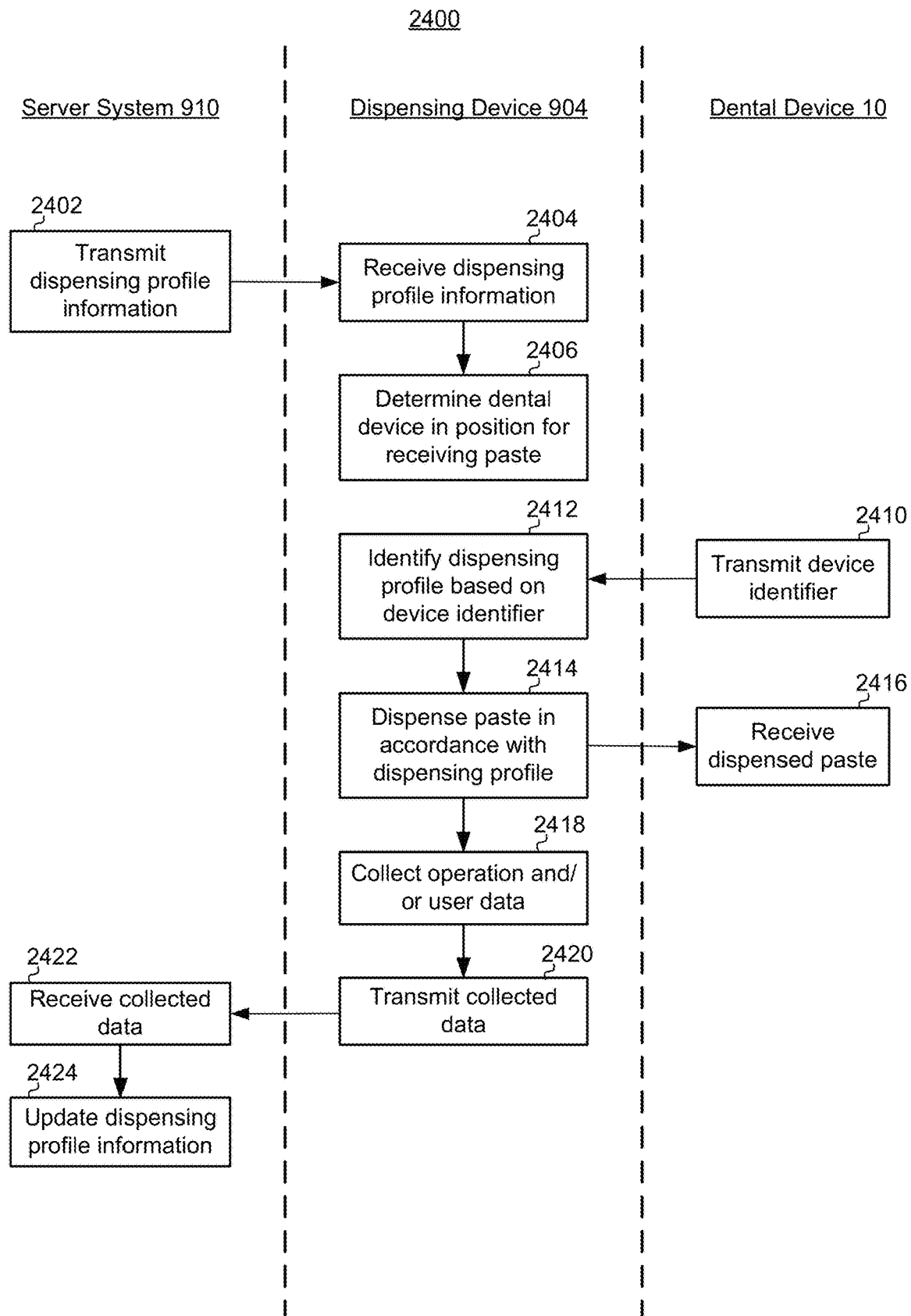
FIG. 24 is a flowchart illustrating a method for operating a representative dispenser device in accordance with some embodiments.

FIG. 24 is a flowchart illustrating a method 2400 for operating a representative dispenser device in accordance with some embodiments. A server system (e.g., server system 910) transmits (2402) dispensing profile information to a dispenser device (e.g., oral care agent dispenser device 904). In some embodiments, the server system transmits the information via the network interface(s) 1204 in conjunction with the network communication module 1212. In some embodiments, the dispensing profile information is provided by a dental health professional. In some embodiments, the dispensing profile information is generated at the server system based on dental details, and optionally preferences, of a user of the dispenser device (e.g., dental details provided by the user and/or one or more dental health professionals). In some embodiments, the drive profile information includes ingredient and quantity information for combining and dispensing oral care agent ingredients. In some embodiments, the dispensing profile information includes voltage and/or current information for operating a drive assembly 1116 of the dispenser device (e.g., to produce the desired amount of each oral care agent ingredient).

The dispenser device receives (2404) the dispensing profile information. In some embodiments, the dispenser device receives the information via the communication interface(s) 1126 operating in conjunction with the communication module 1134.

The dispenser device determines (2406) that a dental care device (e.g., dental care device 10 or dental care device 100) is in position to receive oral care agent from the dispenser device. In some embodiments, the dispenser device determines that the dental care device is in position based on one or more sensors 1104 of the dispenser device. In some embodiments, the dispenser device determines that the dental care device is in position based on one or more inputs to the user interface(s) 1106. In some embodiments, the dispenser device is notified by the dental care device that it is in position to receive dispensed oral care agent.

The dental care device optionally transmits (2410) a device identifier to the dispenser device. In some embodiments, the device identifier is transmitted via a barcode on the dental care device and a barcode scanner on the dispenser device. In some embodiments, the device identifier is transmitted via NFC protocol. In some embodiments, the device identifier is transmitted via a radio frequency identity (RFID) protocol. In some embodiments, the user of the dental care device submits an identifier to the dispenser device (e.g., via voice input, a passcode entered via the user interface(s) 1106, or the like).

The dispenser device receives the device (or user) identifier and identifies (2412) the dispensing profile based on the identifier. In some embodiments, the dispenser device stores a plurality of dispensing profiles (e.g., dispensing profiles 1148) and each dispensing profile corresponds to a unique identifier. In some embodiments, the dispenser device matches the identifier with an identifier in the dispensing profile. In some embodiments, the dispenser device stores multiple dispensing profiles for a single user and selects one of the multiple dispensing profiles based on additional information (e.g., a time of day, day of the week, a user selection, a user preference, dental information of the user, a type of the dental care device provided to receive the oral care agent, and the like).

The dispenser device dispenses (2414) oral care agent ingredients in accordance with the identified dispensing profile. In some embodiments, the dispensing profiles identifies a plurality of oral care agent ingredients to be dispensed and a corresponding amount to be dispensed for each oral care agent ingredient. In some embodiments, the dispenser device mixes the oral care agent ingredients prior to dispensing. In some embodiments, the dispenser device determines a shape of the dental care device (e.g., based on the identifier) and dispenses the ingredients in a shape corresponding to the shape of the dental care device.

The dispenser device collects (2418) operation and/or user data. In some embodiments, the operation data includes information regarding how often the user operates the dispenser device (and/or which dental care device the user is using with the dispenser device). In some embodiments, the operation data includes information obtained from one or more sensors of the dispenser device (e.g., sensors to determine amounts of ingredients remaining). In some embodiments, the user data includes one or more user settings and/or preferences. In some embodiments, the user data includes dental information supplied by the user to the dispenser device. In some embodiments, the dispenser device modifies one or more dispensing profiles of the user based on the collected information.

The dispenser device transmits (2420) the collected data to the server system. In some embodiments, the dispenser device transmits the collected data via the communication interface(s) 1126 operating in conjunction with the communication module 1134. The server system receives (2422) the collected data from the dispenser device. In some embodiments, the server system receives the collected data via the network interface(s) 1204 in conjunction with the network communication module 1212.

The server system updates (2424) a dispensing profile (or dispensing profile information) for the user based on the collected data. In some embodiments, the server system modifies one or more ingredients, amounts, voltage, or current parameters of the dispensing profile based on the collected data. In some embodiments, the server system requests updated dental information from the user (or a dental care provider of the user) based on the collected data. For example, the collected data indicates that the user has recently experienced yellowing of the teeth, thereby indicating that the user's dental health or situation has changed. Based on this indication, the server system requests updated dental information to so that it can adjust the dispensing profile, order new oral care agent ingredients, and/or order a new dental care device mouthpiece based on the updated information. In some embodiments, the server system requests an updated mouthpiece for the dental care device based on the collected information.

In some embodiments, the server system transmits the updated dispensing profile information to the dispenser device. In some embodiments, the server system transmits the modified information via the network interface(s) 1204 in conjunction with the network communication module 1212. The dispenser device receives the modified dispensing profile information from the server system. In some embodiments, the dispenser device receives the information via the communication interface(s) 1126 operating in conjunction with the communication module 1134.

In some embodiments, the dispenser device stores the modified dispensing profile information in memory 1130 (e.g., in place of, or in addition to, the previously received dispensing profile information). In some embodiments, the dispenser device utilizes the modified dispensing profile information to update one or more dispensing profiles 1148 stored in memory 1130.

Figure 25A:
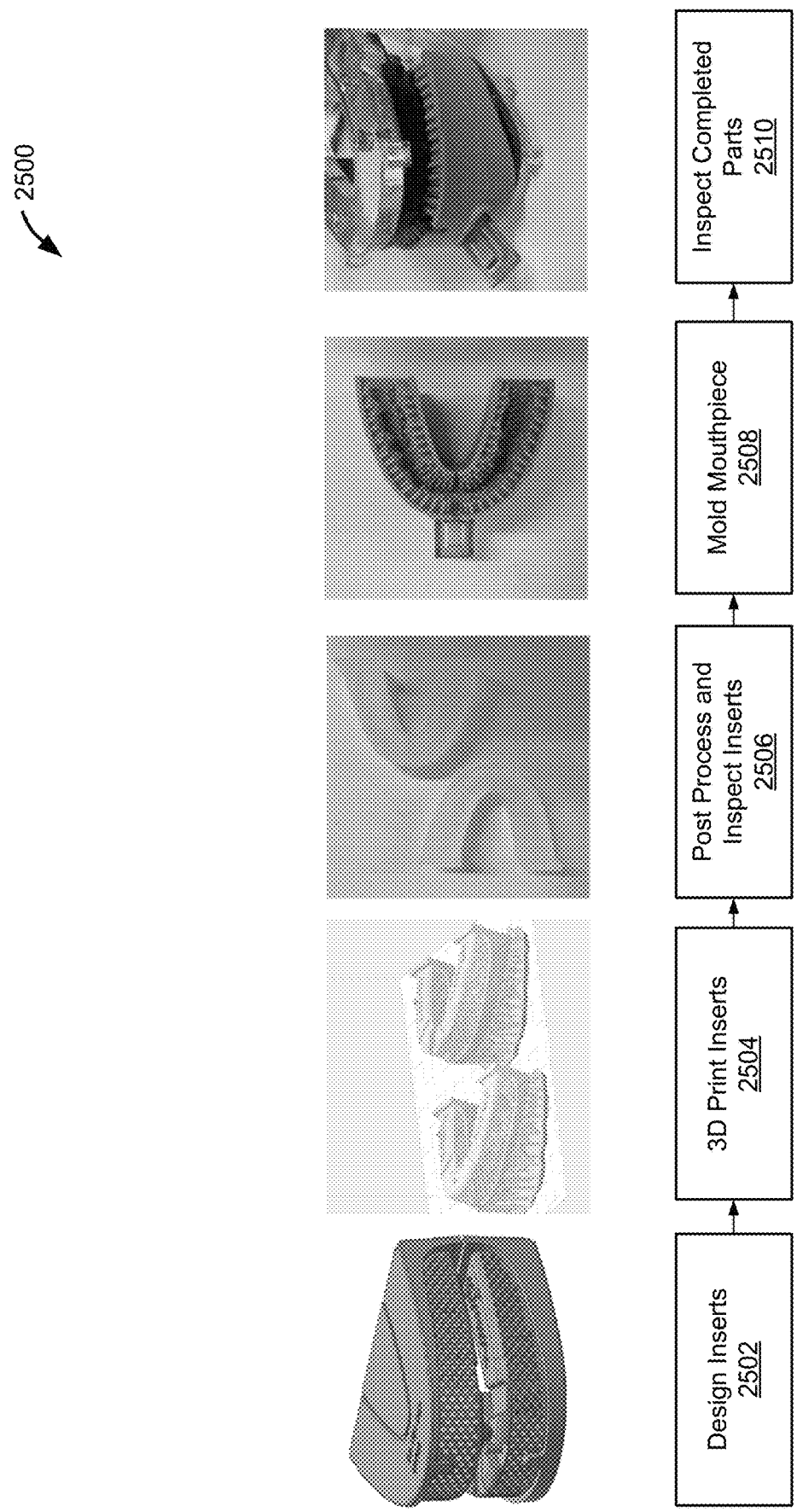
FIG. 25A shows a high-level overview of a manufacturing process for designing and fabricating a teeth cleaning device in accordance with some embodiments.

FIG. 25A shows a high-level overview of a manufacturing process 2500 for designing and fabricating a teeth cleaning device in accordance with some embodiments. The manufacturing process 2500 includes five main steps: (i) design inserts 2502, (ii) 3-D print the inserts 2504, (iii) inspect the printed inserts 2506, (iv) mold a mouthpiece 2508, and (v) inspect the completed part 2510 (i.e., the teeth cleaning device 2550). The discussion below focuses mainly on step 2502 and step 2504 (although the other steps, e.g., step 2506, may be touched on as well). Steps 2508 and 2510 are discussed in detail above, e.g., with reference to FIG. 22, and, consequently, for the sake of brevity, will not be repeated here. Note that the discussion below expands on the description above regarding the design and manufacture of teeth cleaning devices.

Figure 25B:
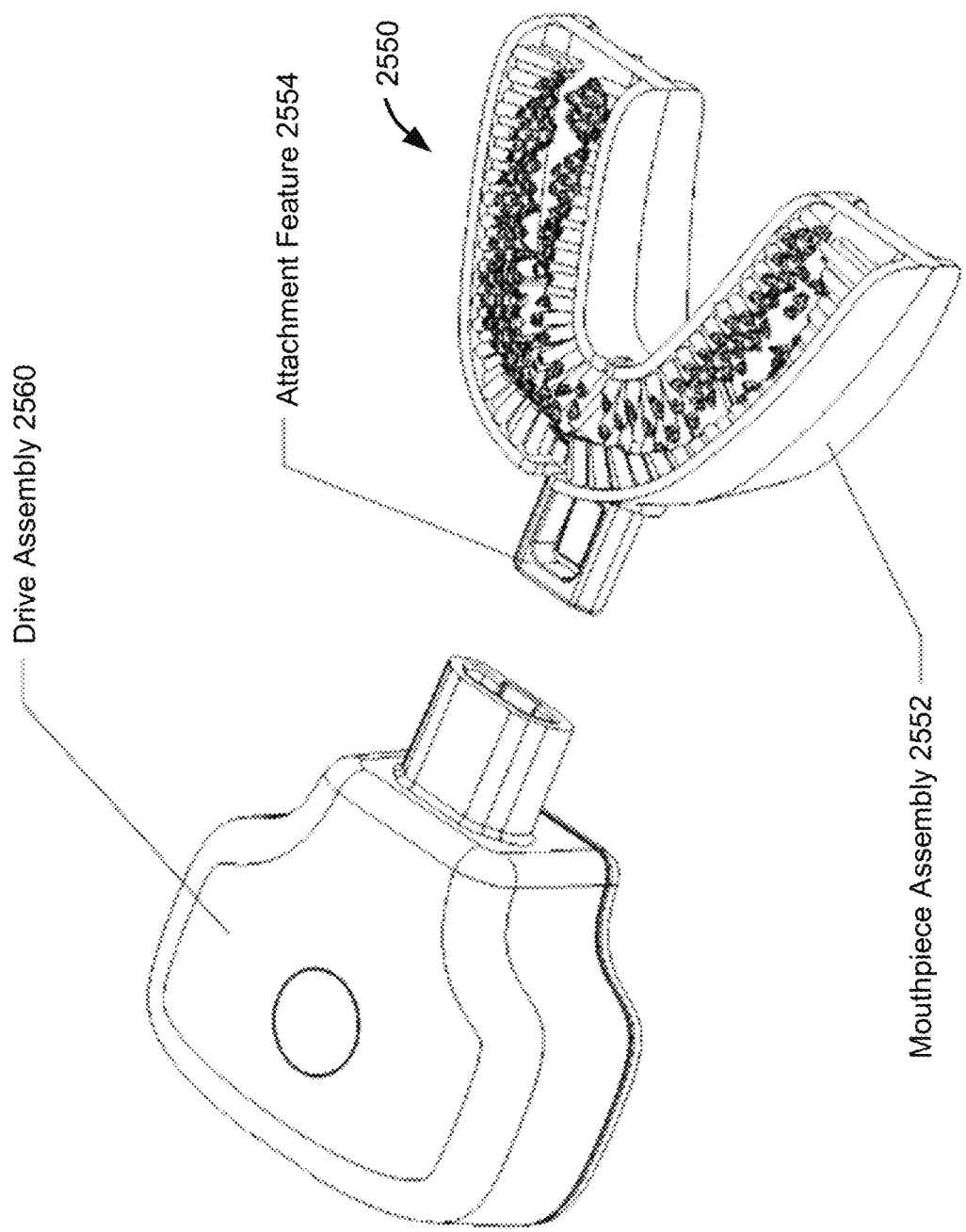
FIG. 25B shows a representative teeth cleaning device created using the manufacturing process of FIG. 25B.

FIG. 25B is provided to show a representative teeth cleaning device 2550 created using the manufacturing process 2500. As shown in FIG. 25B, the representative teeth cleaning device 2550 includes a mouthpiece assembly 2552, which is an example of the mouthpiece assembly 12, and an attachment feature 2554, which is an example of the coupling 15. FIG. 25B also includes a drive assembly 2560, which is an example of the drive assembly 1016. The drive assembly 2560 is configured to couple with the representative teeth cleaning device 2550 via the attachment feature 2554, and generate vibrations that cause at least portions of the mouthpiece assembly 2552 to vibrate to clean a user's teeth when positioned in the user's mouth. The manufacturing process 2500 mainly covers the process steps used to design and manufacture the mouthpiece assembly 2552.

Figure 26:
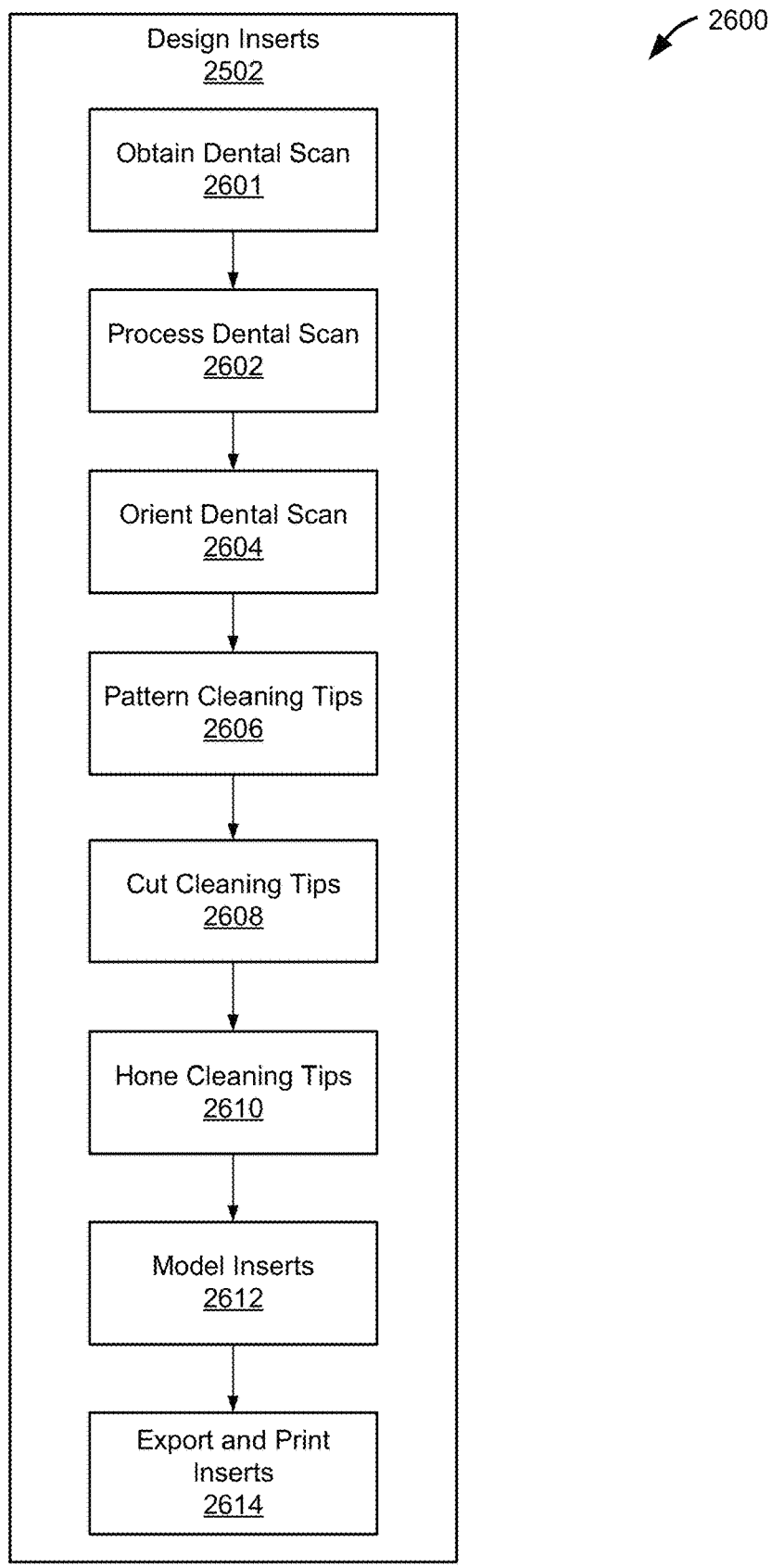
FIG. 26 shows a process for designing inserts used in the manufacture of a representative teeth cleaning device in accordance with some embodiments.

FIG. 26 provides more detail of how the inserts are designed at step 2502, per FIG. 25A. In particular, FIG. 26 shows a process 2600 for designing inserts used in the manufacture of a representative teeth cleaning device in accordance with some embodiments. FIGS. 27A-33 are included herein to support FIG. 26 as they provide additional insights into how 3-D representations of upper and lower mouthpieces are made (e.g., 3-D representations of upper mouthpiece 40 and lower mouthpiece 42), and how inserts (e.g., dental mold inserts 1706) are derived from the 3-D representations of upper and lower mouthpieces. In general, the process 2600 for designing the inserts includes obtaining a scan of a user's teeth (2601), processing the scan (2602), orientating upper and lower mouthpieces with respect to the user's teeth and mouth generally from the processed scan of the user's teeth (2604), modeling cleaning tips with the upper and lower mouthpieces (2606), removing portions of the cleaning tips according to a geometry of the user's teeth from the scan of the user's teeth (2608), honing and contouring the cleaning tips, as needed (2610), modeling the inserts according to the finished design of the upper and lower mouthpieces, including the cleaning tips (2612), and exporting the inserts for printing (e.g., on a 3-D printing machine). The paragraphs below expand on each of the steps.

The process 2600 begins with obtaining a dental scan (or some other 3-D representation) of a user's teeth (2601). Next, the scan of the user's teeth is processed (2602). As explained above with reference to FIGS. 16A and 16B, obtaining a dental scan may involve the user, a dentist, or other dental professional, scanning the user's teeth with a 3-D scanner (e.g., a laser scanner). Alternatively, the user, a dentist, or other dental professional, takes an impression of the user's teeth, and then sending the impression to a facility that scans the impression to generate a corresponding electronic 3-D representation of the user's teeth. The dental scan of the user's teeth is generally referred to herein as a dental model of the user's teeth, dental details of the user's teeth, or simply a scan of the user's teeth.

Regardless of the how the scan/3-D representation of the user's teeth is obtained at step 2601, step 2602 also includes processing the scan. The scan is processed to ensure that the scan can be used in the design and fabrication steps that follow. Like step 2601, processing the dental scan may involve the user, a dentist, or other dental professional, interacting with computer software to process the scan. Alternatively, a computer program analyzes the scan of the user's teeth, and processes (without human intervention) the scan of the user's teeth as needed.

Figure 27B:
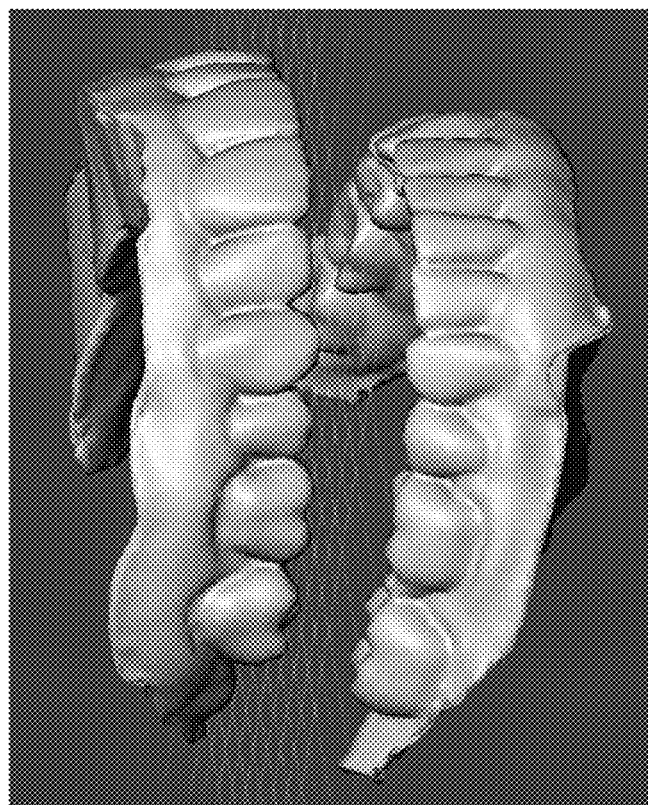
FIG. 27B shows the scan of the user's teeth after processing.
Figure 27A:
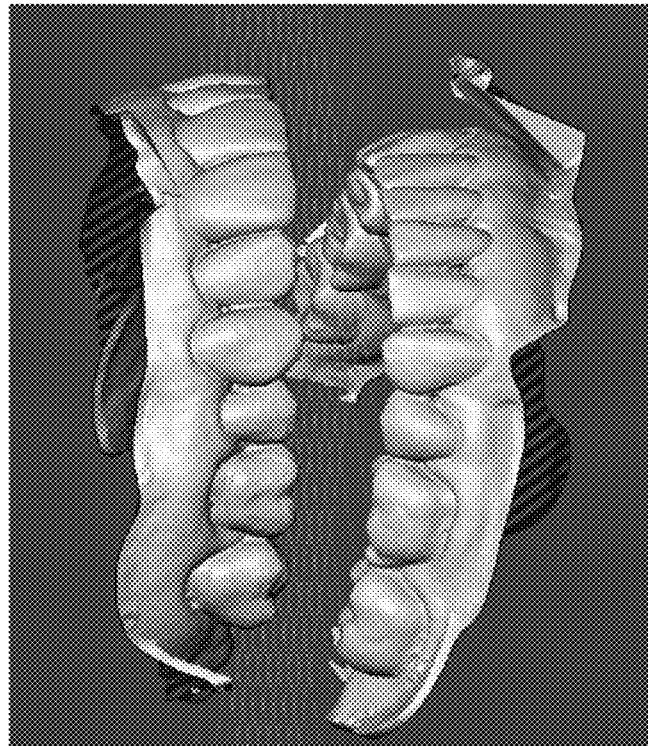

FIG. 27A shows a scan of a user's teeth before processing (i.e., shows a raw scan), while FIG. 27B shows the scan of the user's teeth after processing (i.e., shows a processed scan). In FIG. 27A, the raw scan of the user's teeth provides a highly detailed representation of the user's teeth, while the processed scan of the user's teeth in FIG. 27B provides a smoothed representation of the user's teeth (relative to the raw scan). In some embodiments, processing the scan (or other 3-D representation) of the user's teeth includes removing extraneous surfaces from the raw scan of the user's teeth. Alternatively, or in addition, processing the scan (or other 3-D representation) of the user's teeth may include filling surfaces of the user's teeth in the scan to create a solid model. Removing extraneous surfaces from the raw scan and/or filing the surfaces of the user's teeth in the raw scan has several benefits, including that a file size of the resulting 3-D representation can be reduced by up to 95%, which significantly reduces computer processing requirements, while also maintaining an adequate level of detail to create the upper and lower mouthpieces (e.g., the processing in step 2602 does not compromise critical geometries and other features needed for creating the upper and lower mouthpieces). Note that the In some embodiments, processing the scan (or other 3-D representation) of the user's teeth includes offsetting the teeth geometry in the scan by a predefined distance(s) (e.g., between 0.1 mm and 1 mm, preferably 0.7 mm). In some instances, offsetting the teeth geometry in the scan results in the user's teeth in the processed scan being slightly smaller than the user's teeth actual size. The offsetting is performed so that the cleaning tips (discussed below) achieve a positive contact pressure on facial and lingual surfaces of the user's teeth (i.e., the cleaning tips are designed based, at least in part, according to the offset teeth geometry in the processed scan). Note that offsetting the teeth geometry in the scan may involve offsetting upper teeth geometry in the scan by a first amount and offsetting lower teeth geometry in the scan by a second amount, which differ from the first amount. Furthermore, offsetting the teeth geometry in the scan may involve using different offsets for different types of teeth or different sections of the mouth.

Figure 28B:
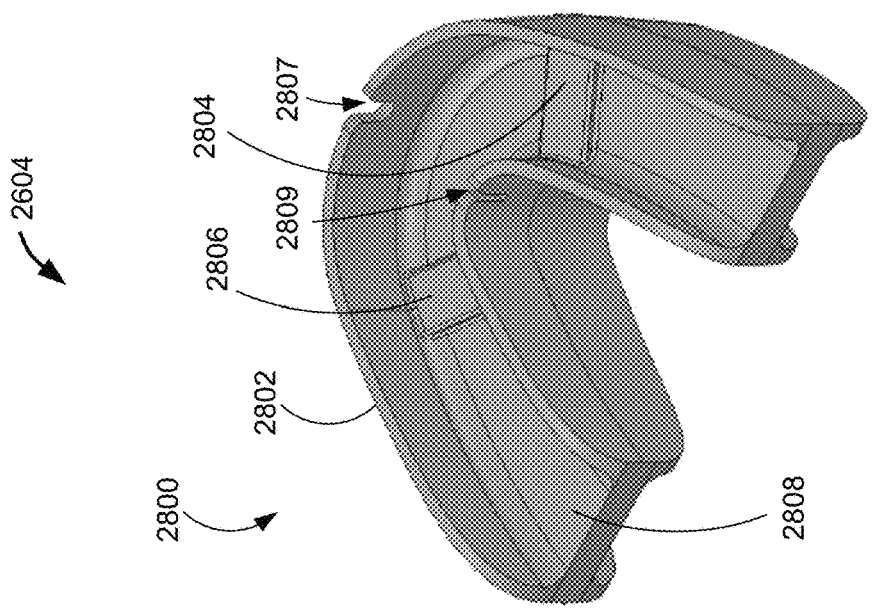
FIG. 28B shows a digital representation of a mouthpiece assembly in accordance with some embodiments.
Figure 28A:
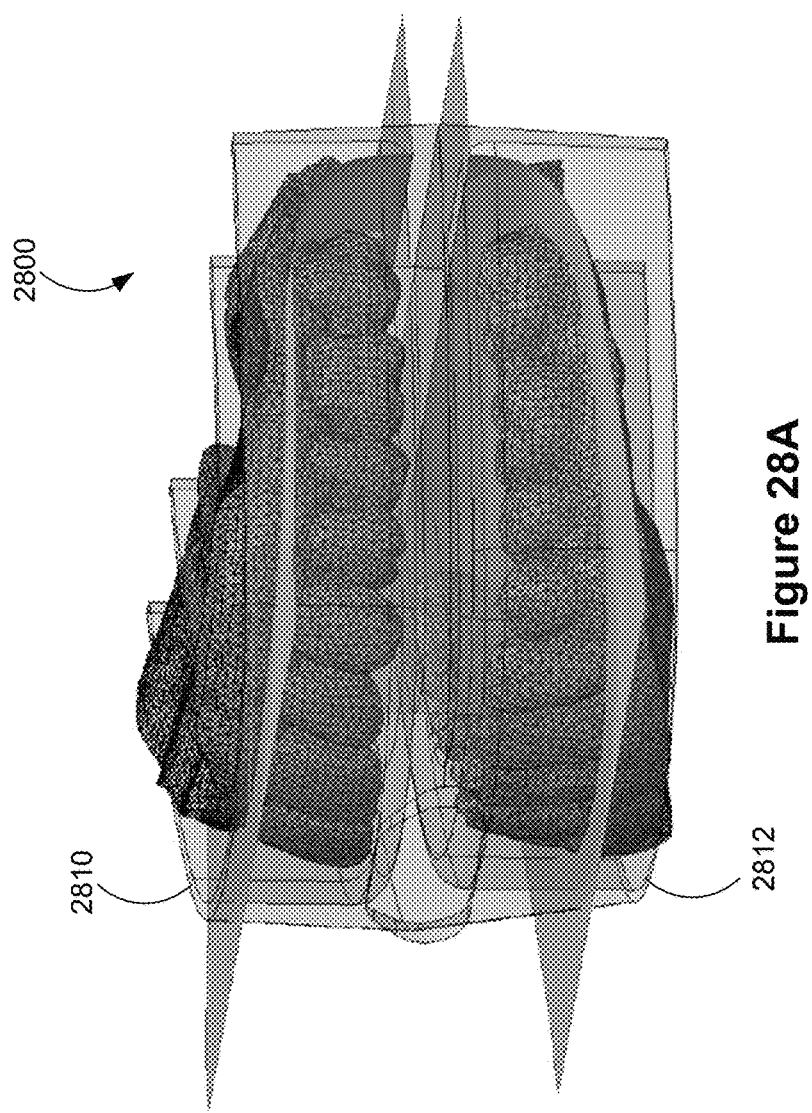
FIG. 28A shows one example of a scan of a user's teeth oriented with a mouthpiece assembly.

Turning back to FIG. 26, the process 2600 also includes orienting the scan of the user's teeth inside a mouthpiece (2604), as shown with reference to FIGS. 28A and 28B. In some embodiments, orienting the scan involves the user, a dentist, or other dental professional, manually interacting with a computer program to orient the scan of the user's teeth with the mouthpiece in a desired configuration. In some other embodiments, orienting the scan involves the computer program analyzing the scan of the user's teeth, and positioning (without human intervention) the scan of the user's teeth with the mouthpiece in a desired configuration. FIG. 28A shows one example of a scan of a user's teeth oriented with a mouthpiece assembly 2800. As shown, the mouthpiece assembly 2800 includes an upper mouthpiece 2810 and a lower mouthpiece 2812.

In some embodiments, one or more features of the mouthpiece assembly 2800 (which is a 3-D representation of the mouthpiece assembly 2552) are determined as a result of the orienting at step 2604. For example and with reference to FIG. 28B, a top edge 2802 of the upper mouthpiece 2810 is set according to an upper gumline of the user, which is derived from the scan of the user's teeth. Note that a height of the top edge 2802 of the mouthpiece assembly 2800 is set once the scan is properly oriented (again, at step 2604). Likewise, a top edge of the lower mouthpiece 2812 (not shown) is set according to an lower gumline of the user, which is derived from the scan of the user's teeth.

In another example and still with reference to FIG. 28B, bite points of the mouthpiece assembly 2800 are added according to a layout of the user's teeth. In particular, a layout of the user's canines and lower front teeth, which is again determined from the scan of the user's teeth, is used to determine appropriate locations for the bite points in the mouthpiece assembly 2800. For example, the bite points 2804 and 2806, which are raised areas on a bite surface 2808 of the upper mouthpiece 2810, are located at specific locations on the bite surface 2808 of the upper mouthpiece 2810 and form points for a user to bite down on (e.g., when the representative teeth cleaning device is completed and is being used by a user). The lower mouthpiece 2812 also includes one or more bite points. The raised surfaces of the bite points help the user to obtain a proper bite on the upper and lower mouthpieces so that optimal positioning and depth of the user's teeth within the mouthpiece assembly 2800 is achieved (e.g., so that cleaning tips of the representative teeth cleaning device are properly positioned with respect to the tooth surfaces). Stated differently, the bite points are specifically located on the top and bottom bite surfaces to allow the mouthpiece assembly 2800 to move when the user bites down onto the bite points. This movement causes the mouthpiece assembly 2800 to be properly positioned in the user's mouth. Aside from helping to properly position the mouthpiece assembly 2800, the bite points also help counter weight of the drive assembly and reduce a tendency of the device to tip downward during use.

Note that one or more features of the upper mouthpiece 2810 may differ from one or more features of the lower mouthpiece 2812. For example, the one or more bite points 2804 and 2806 on the upper mouthpiece 2810 may have a first configuration while the one or more bite points on the lower mouthpiece 2812 may have a second configuration that differs from the first configuration. Example bite points 2912, 2914, and 2916 on the lower mouthpiece 2812 are shown in FIG. 29C. As shown there, the lower mouthpiece 2812 includes three bite points 2912, 2914, and 2916, which are slender raised areas shaped for the user's lower front teeth. In other example, a top edge 2802 of the upper mouthpiece 2810 may have a first configuration while a bottom edge of the lower mouthpiece 2812 may have a second configuration that differs from the first configuration. Indeed, because the representative teeth cleaning device is completely personalized to a particular user's teeth (and mouth generally), the lower mouthpiece 2812 and the upper mouthpiece 2810 may have many different structural characteristics (and potentially some common structural characteristics), which are based on differences (and potential similarities) between the user's top and bottom teeth, gums, etc.

In some embodiments, a width of the bite surfaces of the lower mouthpiece 2812 and the upper mouthpiece 2810 varies according to a surface area of the user's teeth. For example, the bite surfaces are wider toward the ends of the lower mouthpiece 2812 and the upper mouthpiece 2810 to accommodate molars, while the bite surfaces are thinner toward the middle of the lower mouthpiece 2812 and the upper mouthpiece 2810 as front teeth are typically skinny.

As also shown in FIG. 28B, a first vertical slot 2807 is defined on the facial wall of the upper mouthpiece 2810 and a second vertical slot 2809 is defined on the lingual wall of the upper mouthpiece 2810. While not shown, the lower mouthpiece 2812 can have the same slot arrangement. In some embodiments (as shown in FIG. 28B), the slots 2807, 2809 are positioned along a centerline of the upper mouthpiece 2810 and are configured to increase motion of the facial wall and the lingual wall of the upper mouthpiece 2810 (and the lower mouthpiece 2812), thereby improving comfort of the mouthpiece assembly 2800 as a whole.

Figure 29B:
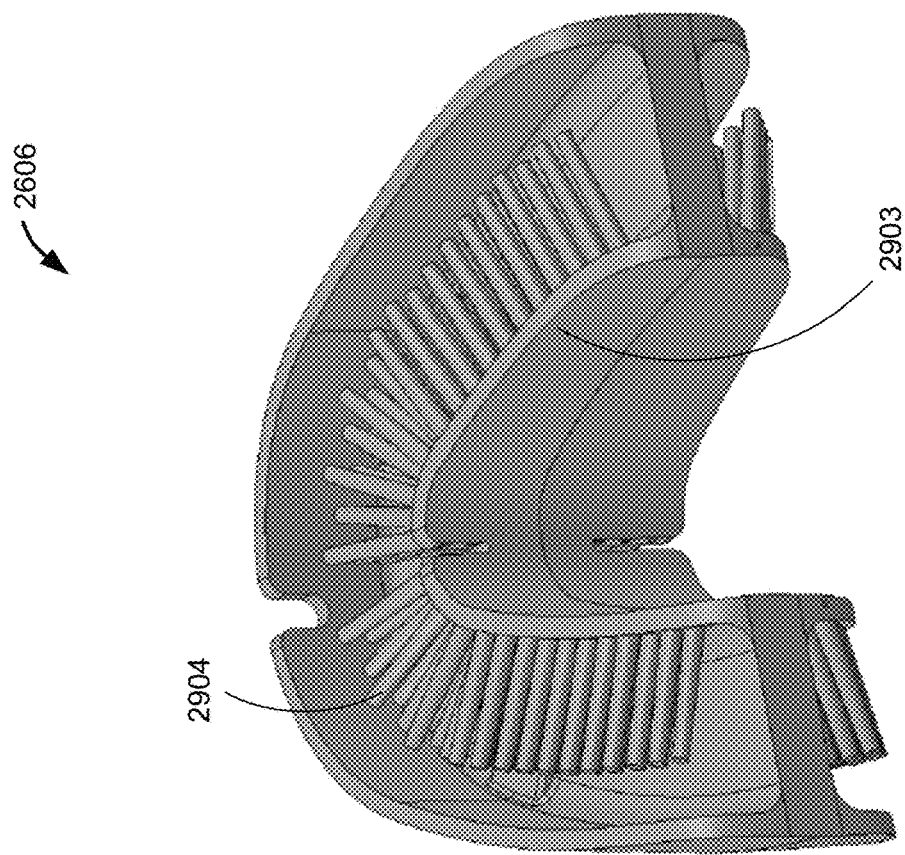
FIGS. 29A-29C show different sets of cleaning tips in digital representations of a mouthpiece assembly in accordance with some embodiments.
Figure 29A:
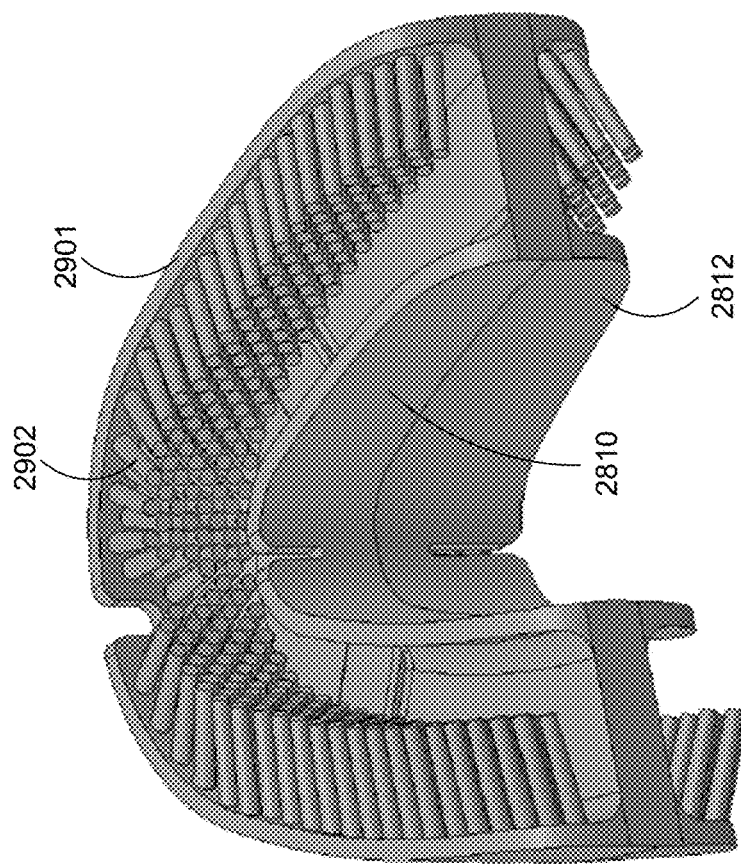
Figure 29C:
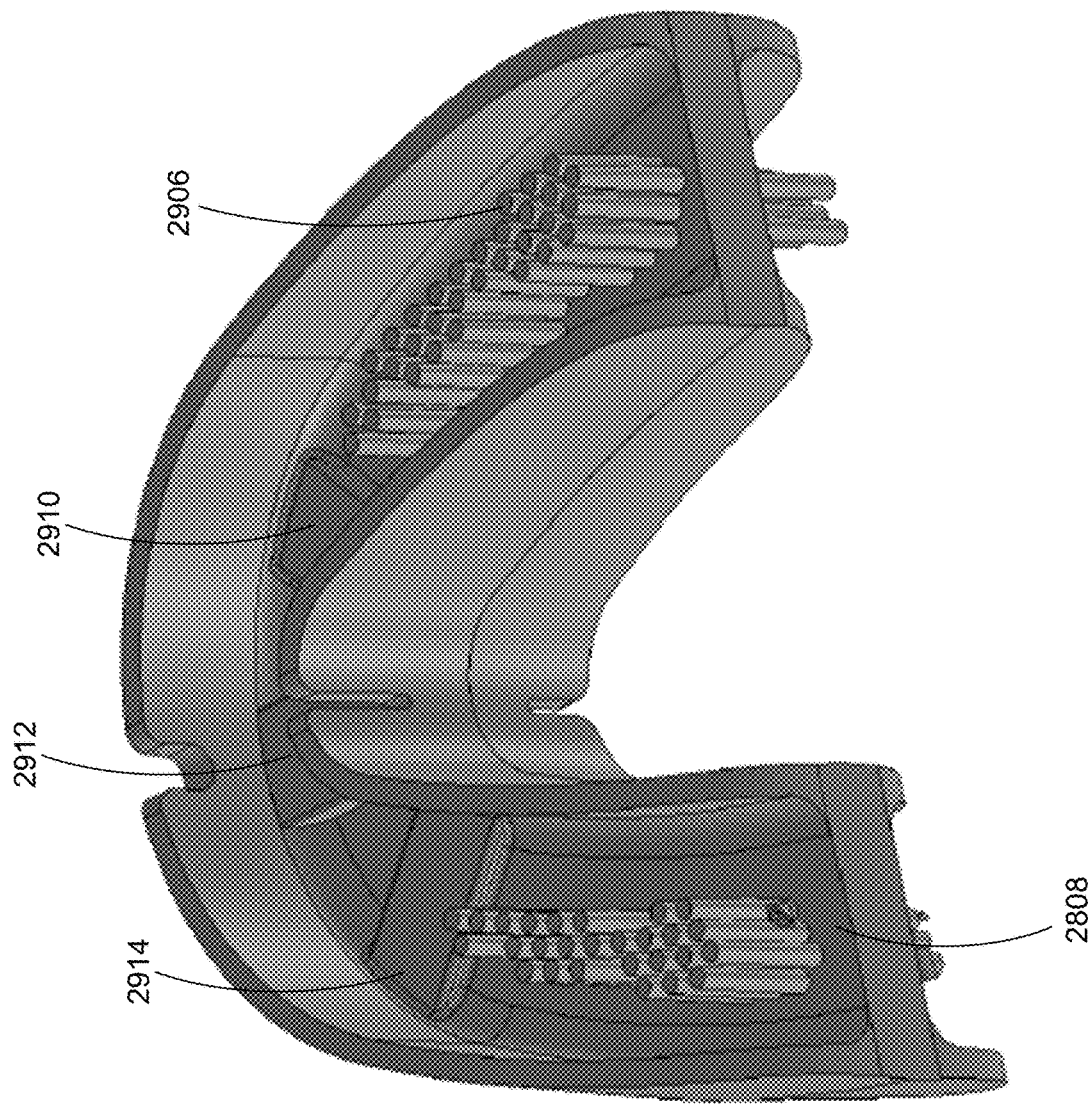

Referring to FIG. 26, the process 2600 also includes patterning the cleaning tips in the 3-D representation of the mouthpiece assembly (2606), as shown with reference to FIGS. 29A-29C (again, the mouthpiece assemblies 2800 shown in FIGS. 29A-29C are 3-D representations of the mouthpiece assembly 2550). In some embodiments, patterning the cleaning tips involves the user, a dentist, or other dental professional, manually interacting with a computer program to create the desired patterns. In other embodiments, the computer program analyzes the scan of the user's teeth (as processed and oriented), and generates (with minimal to no human intervention) patterns/configurations for the cleaning tips based on the said analyzing.

In particular, FIG. 29A shows first cleaning tips 2902 integrally formed with and extending from an outer wall 2901 of the mouthpiece assembly 2800, FIG. 29B shows second cleaning tips 2904 integrally formed with and extending from an inner wall 2903 of the mouthpiece assembly 2800, and FIG. 29C shows third cleaning tips 2906 integrally formed with and extending from the bite surface 2808 of the mouthpiece assembly 2800. Note that the bite surface of the upper mouthpiece 2810 is shown in FIGS. 29A and 29B, while a bite surface of the lower mouthpiece 2812 is show in FIG. 29C. The upper mouthpiece 2810 and the lower mouthpiece 2812 both include distinct instances of the first cleaning tips 2902, the second cleaning tips 2904, and the third cleaning tips 2906. In some embodiments (at this stage of the design process), the first cleaning tips 2902, the second cleaning tips 2904, and the third cleaning tips 2906 on the lower mouthpiece 2812 match the first cleaning tips 2902, the second cleaning tips 2904, and the third cleaning tips 2906 on the upper mouthpiece 2810 (at least during this stage of the design process). In some other embodiments, the first cleaning tips 2902, the second cleaning tips 2904, and/or the third cleaning tips 2906 on the lower mouthpiece 2812 differ from the first cleaning tips 2902, the second cleaning tips 2904, and the third cleaning tips 2906 on the upper mouthpiece 2810 (again, at least during this stage of the design process).

Regardless of whether they are located on the upper mouthpiece 2810 or the lower mouthpiece 2812, the first cleaning tips 2902 are configured to clean facial surfaces of the user's teeth, the second cleaning tips 2904 are configured to clean lingual surfaces of the user's teeth, and the third cleaning tips 2906 are configured to clean bite surfaces of the user's teeth. Notably, the cleaning tips shown in FIGS. 29A-29C are patterned individually according to the specific characteristics of the user's teeth, which are derived from the dental model of the user's teeth. In other words, a layout (i.e., distribution density, spatial arrangement) of each set of cleaning tips is personalized for a specific surface of the user's teeth, and, consequently, each set of cleaning tips may be different in the mouthpiece assembly 2800.

In terms of physical characteristics, the cleaning tips are made from the same material as the mouthpiece assembly 2800 in some embodiments, while in other embodiments the cleaning tips are made from a different material from the mouthpiece assembly 2800. In some embodiments, the cleaning tips have a diameter between approximately 1 mm and 2 mm (preferably approximately 1.4 mm) at the base, with a 1 degree taper from the base to the tip. The tapered design of the cleaning tips helps with removal of molded parts (e.g., mouthpiece assembly 2552) from the printed inserts, which is discussed at steps 2508 and 2510 (i.e., without the tapered designed, the cleaning tips tend to stick in apertures of the printed inserts after an injection molding operation).

In some embodiments, the first cleaning tips 2902 and the second cleaning tips 2904 are angled with respect to the bite surfaces of the upper and lower mouthpieces, respectively. For example, with reference to FIGS. 29A and 29B, the first cleaning tips 2902 and the second cleaning tips 2904 on the upper mouthpiece 2810 are angled upwards (away from the bite surface 2808), while the first cleaning tips 2902 and the second cleaning tips 2904 on the lower mouthpiece 2812 are angled downwards (again, away from the bite surface of the lower mouthpiece 2812). A magnitude of the angle between the cleaning tips and the respective bite surface can depend on the scan of the user's teeth, as the angling is used to target plaque removal at the user's gumline. As one example, the angle can range between 5 and 25 degrees (preferably 15 degrees). Note that some of the first cleaning tips 2902 and the second cleaning tips 2904 may not be angled (e.g., those tips that will not interact with the gumline).

In some embodiments, the first cleaning tips 2902, the second cleaning tips 2904, and the third cleaning tips 2906, are arranged in a first pattern. For example, the first cleaning tips 2902, the second cleaning tips 2904, and the third cleaning tips 2906 may be each arranged in a diamond pattern, such that the cleaning tips are closely packed together (e.g., cleaning tips of the first cleaning tips 2902 may have a center-to-center spacing of approximately 1 mm, 1.5 mm, 2 mm, 2.5 mm, or 3 mm). In some other embodiments, the first cleaning tips 2902 and the second cleaning tips 2904 are arranged in the first pattern, while the third cleaning tips 2906 are arranged in a second pattern different from the first pattern (or some other combination of patterns between the different cleaning tips). Note that the first cleaning tips 2902, the second cleaning tips 2904, and the third cleaning tips 2906 are all arranged differently in some embodiments (e.g., one set uses the diamond pattern, while another set uses some different pattern).

Figure 30:
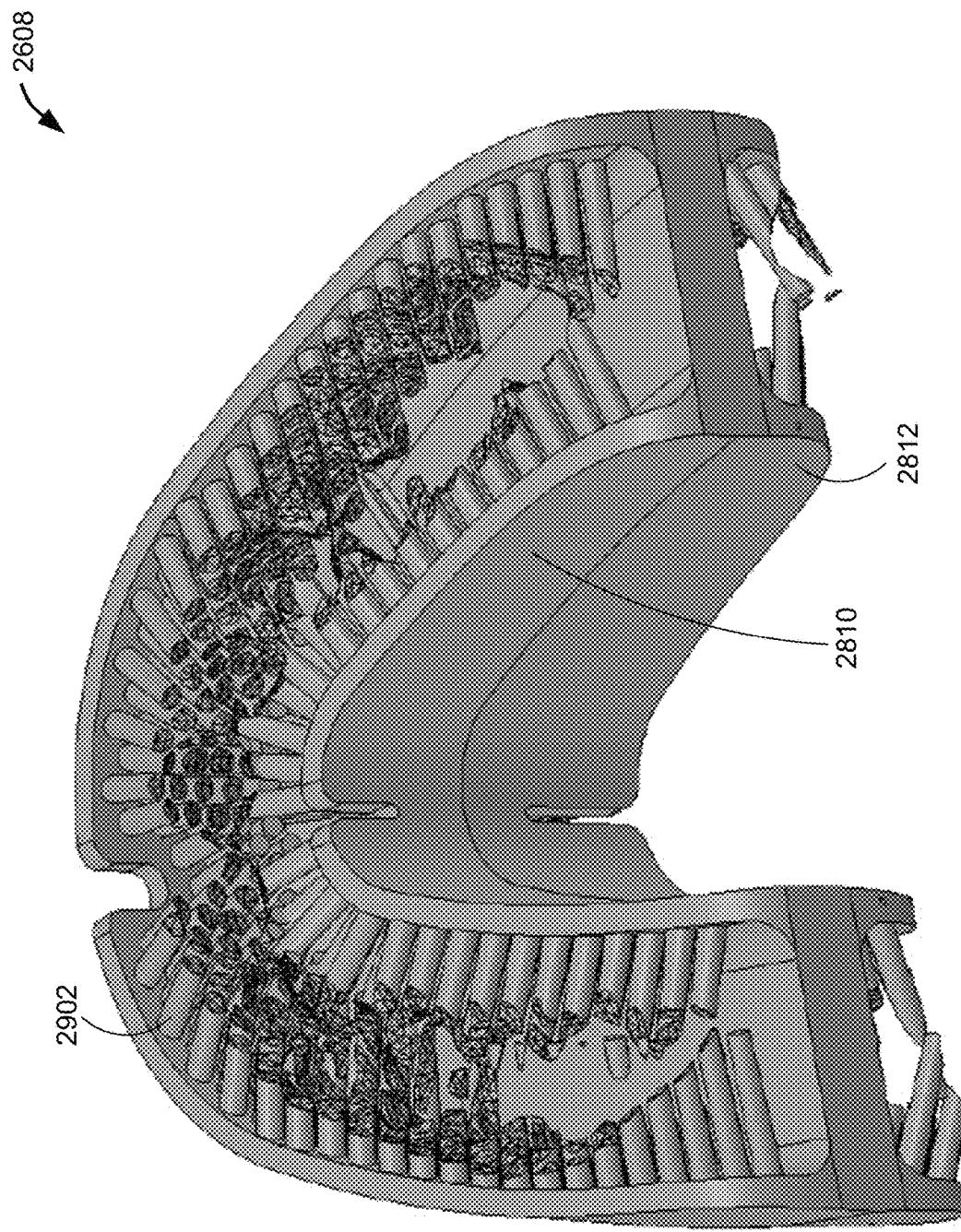
FIG. 30 shows how lengths of the cleaning tips are modeled and modified in a digital representation of a mouthpiece assembly in accordance with some embodiments.

Turning back to FIG. 26, the process 2600 also includes cutting the cleaning tips in the 3-D representation of the mouthpiece assembly 2800 according to the dental model of the user's teeth (2608), as shown with reference to FIG. 30. "Cutting" as used herein means removing portions of the modeled cleaning tips from the 3-D representation of the mouthpiece assembly 2800. In some embodiments, cutting the cleaning tips involves the user, a dentist, or other dental professional, manually interacting with a computer program to cut the cleaning tips in a desired manner/configuration. In other embodiments, the computer program analyzes the dental model of the user's teeth, and cuts (without human intervention) the patterned cleaning tips (from step 2606) in a desired manner/configuration.

FIG. 30 shows how lengths of the first cleaning tips 2902 and the second cleaning tips 2904 (originally designed in step 2606) are modified and customized according to a geometry of the user's teeth, which is derived from the dental model of the user's teeth. As discussed above with reference to step 2602, processing the scan (or other 3-D representation) of the user's teeth may include offsetting the teeth geometry in the scan by a predefined distances (e.g., between 0.1 mm and 1 mm, preferably 0.7 mm). Accordingly, in such instances, cutting the cleaning tips may also include cutting the tips with a corresponding offset (e.g., between −0.1 mm and −1 mm, preferably −0.7 mm). In some embodiments, the cutting is performed using a subtractive process whereby the cleaning tips are originally designed too long (at step 2606), and then the scan of the user's teeth is subtracted (at step 2608) from these originally designed cleaning tips to achieve the desired length and geometry for the cleaning tips. In other embodiments, cutting the cleaning tips does not include cutting the tips with a corresponding offset, such that the cleaning tips are longer than the distance to the user's teeth by the offset (e.g., between 0.1 mm and −1 mm, preferably 0.7 mm). The offset length addresses manufacturing tolerances to ensure the cleaning tips reach the user's. In some embodiments, cutting the cleaning tips includes cutting the tips with an offset less than the offset of the scan. This addresses potential user discomfort if the cleaning tips are too long, while still partially addressing manufacturing tolerances.

For ease of illustration, the third cleaning tips 2906 are not shown in FIG. 30, however, step 2608 can also include cutting the third cleaning tips 2906 in the 3-D representation of the mouthpiece assembly 2800 according to the scan of the user's teeth. In some embodiments, cutting the third cleaning tips 2906 includes cutting the tips with the same offset as the offset used on the first and second cleaning tips. In other embodiments, cutting the third cleaning tips 2906 includes cutting the tips without an offset, or some unique offset different from the offset used on the first and second cleaning tips. Cutting the third cleaning tips 2906 also includes cutting the tips 2906 with the nominal teeth geometry (i.e., cut according to the rises, falls, and contours of the user's teeth along his or her bite surface). The cutting of the third cleaning tips 2906 can also include the same subtractive process discussed above.

In some embodiments, with reference to FIG. 26, the process 2600 also includes removing any extraneous bodies, undercuts, and intersecting cleaning tips are from the 3-D representation of the mouthpiece assembly 2800. In some embodiments, this is performed by the user, a dentist, or other dental professional, manually interacting with a computer program to perform said cleaning. In other embodiments, the computer program analyzes the cut cleaning tips, and makes (without human intervention) the necessary adjustments to the cut cleaning tips based on the analyzing.

At bottom, step 2610 is included in the process 2600 to hone the design of the cleaning tips on the upper mouthpiece 2810 and the lower mouthpiece 2812 for manufacture. For example, in FIG. 30, some of the first cleaning tips 2902 extend too far away from the inner surface of the upper mouthpiece 2810, while some other tips were not cleaning cut at step 2608 (which can be attributed, at least in part, to pure reliance on the scan of the user's teeth). Accordingly, step 2610 corrects these minor defects (either manually or without human intervention) so that future operations, such as steps 2504 and 2508, can be properly performed.

Figure 31:
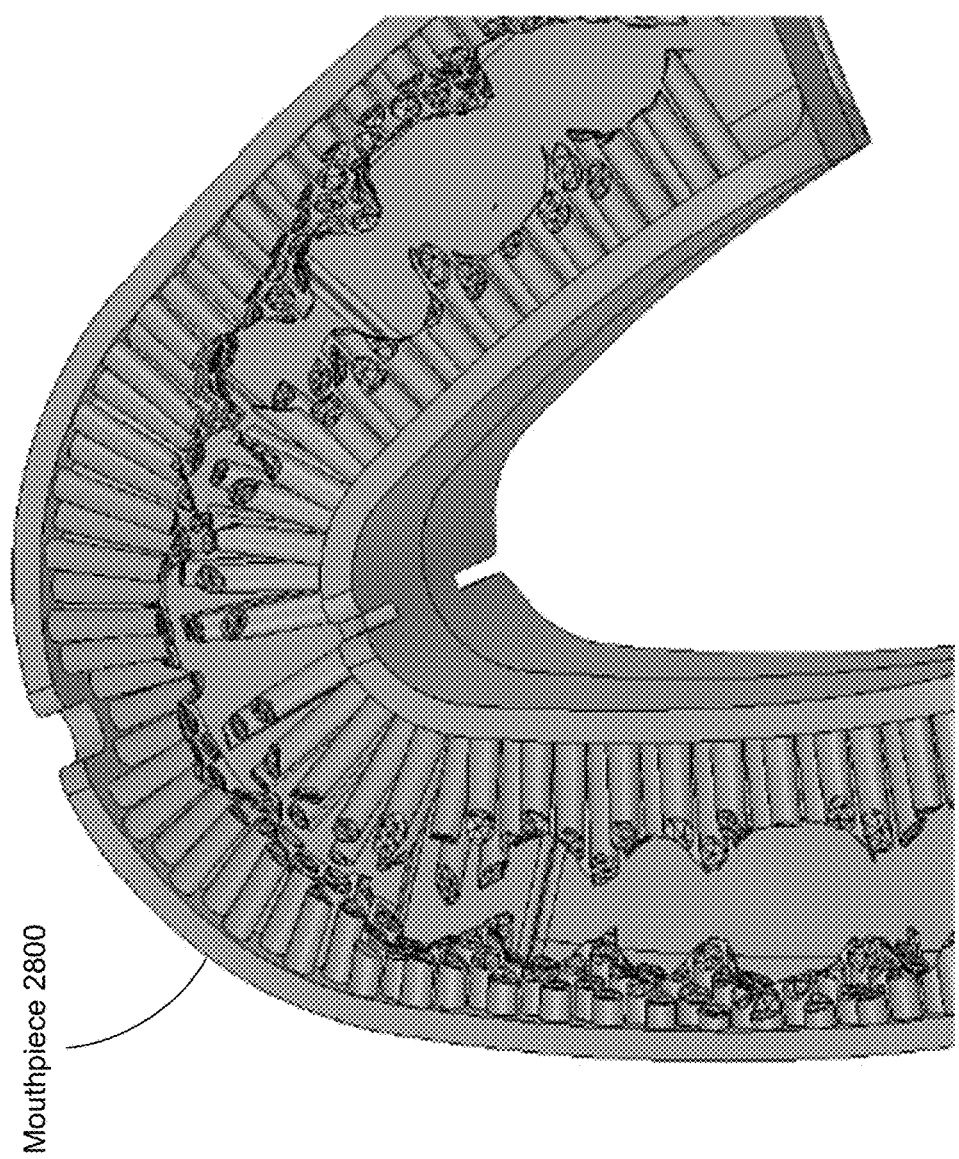
FIG. 31 shows how lengths of the cleaning tips are honed in a digital representation of a mouthpiece assembly in accordance with some embodiments.

Note that FIG. 31 shows a semi-complete 3-D representation of the mouthpiece assembly 2800 (the third cleaning tips are not shown for ease of illustration). In other words, the 3-D representation of the mouthpiece assembly 2800 shown in FIG. 31 (with the additional of the third cleaning tips) is used as the model for designing the inserts 3202, 3204, which are discussed below with reference to steps 2612 and 2614.

Figure 32:
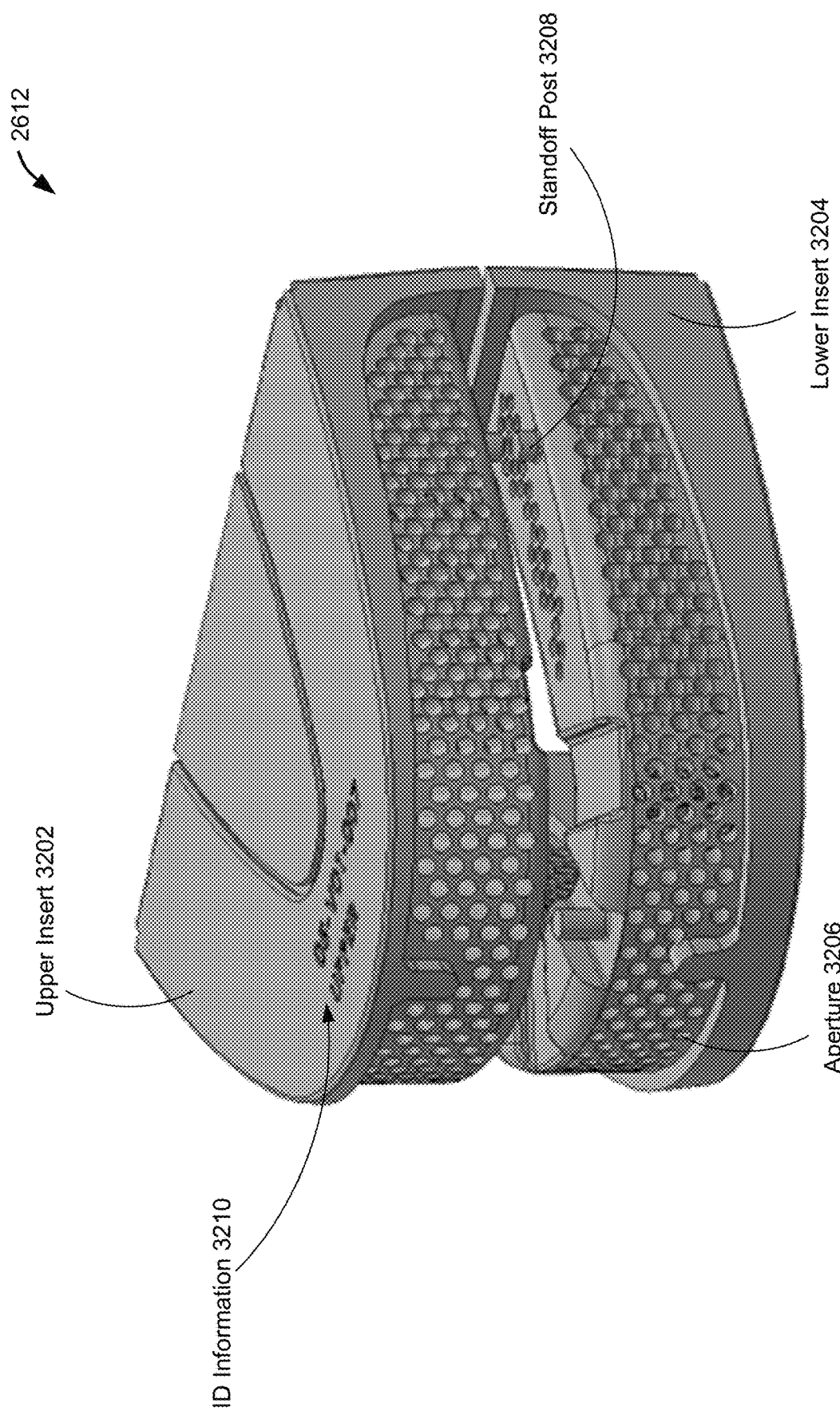
FIG. 32 shows digital representations of mold inserts in accordance with some embodiments

Referring to FIG. 26, the process 2600 then models/designs the inserts based on the 3-D representation of the mouthpiece assembly 2800 (2612), examples of which are shown with reference to FIG. 32. In some embodiments, the user, a dentist, or other dental professional, manually interacts with a computer program to perform the modeling. In other embodiments, the computer program analyzes the 3-D representation of the mouthpiece assembly 2800, and generates (without human intervention) the inserts based on the said analyzing.

As shown in FIG. 32, step 2612 produces 3-D representations of an upper insert 3202 and a lower insert 3204. In essence, the upper insert 3202 has a first geometry that complements a geometry of the upper mouthpiece 2810 (including the cleaning tips therein), while the lower insert 3204 has a second geometry that complements a geometry of the lower mouthpiece 2812 (including the cleaning tips therein). Stated differently, the upper insert 3202 is the inverse or negative of the upper mouthpiece 2810, while the lower insert 3204 is the inverse or negative of the lower mouthpiece 2812. The upper insert 3202 and the lower insert 3204 are examples of the mold inserts 1706-1 and 1706-2, which are discussed in detail with reference to FIGS. 18A and 18B. Like the mold inserts 1706, the upper insert 3202 and the lower insert 3204 comprise a plurality of apertures 3206 configured to form the cleaning tips designed during steps 2606, 2608, and 2610, via a molding process. The upper insert 3202 and the lower insert 3204 also have the structure necessary to form the other structures of the mouthpiece (e.g., bite points 2804 and 2806, bite surface 2808, outer wall 2901, inner wall 2903, etc.).

In some embodiments, modeling the inserts based on the 3-D representation of the mouthpiece assembly 2800 includes adding one or more additional features to the inserts. For example, an overall shape of the upper insert 3202 and the lower insert 3204 is selected according to the molds (e.g., molds 1704-1 and 1704-2) used during the injection molding process (e.g., step 2508). In addition, designing the inserts may involve adding an offset around the inserts to allow the inserts to easily fit inside the molds (i.e., some tolerances are added to the design of the inserts).

Figure 33:
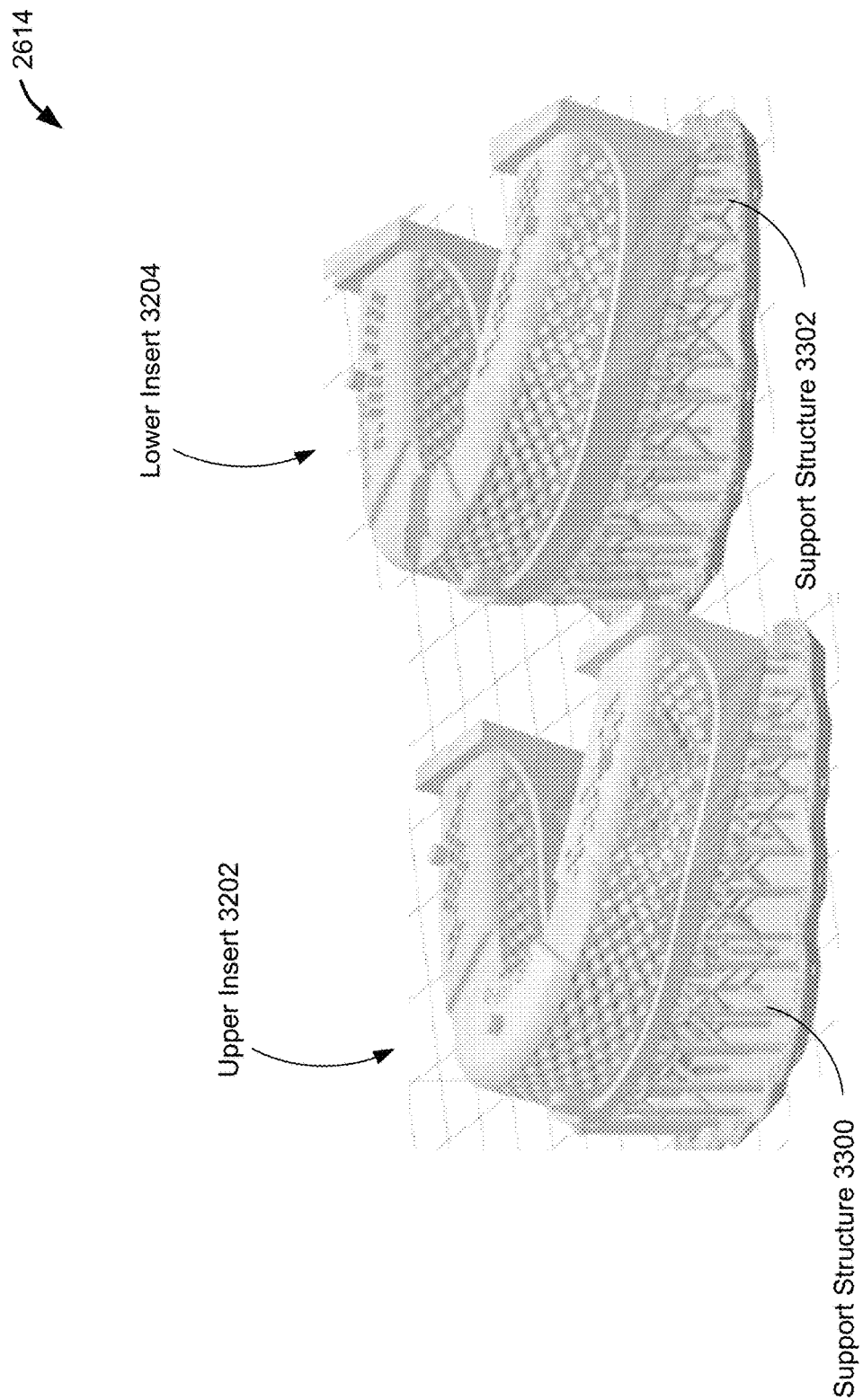
FIG. 33 shows 3-D printed models of the mold inserts in FIG. 32 in accordance with some embodiments.

In some embodiments, support structures are incorporated into the design of the inserts to give each insert more structure during the printing and post processing steps so the insert retains its desired shape. Examples of these support structures are shown in FIG. 33 (e.g., support structure 3300 and support structure 3302). In some embodiments, the upper insert 3202 and the lower insert 3204 are designed to include standoff posts 3208 that are used for holding the structure plate 1708 in the mold during an injection molding operation. In some embodiments, the upper insert 3202 and the lower insert 3204 are designed to include identification information 3210, which is used for internal cataloguing, inventory tracking processes, and customer identification. In some embodiments, the upper insert 3202 and the lower insert 3204 are designed to include one or more markers that are used to verify if warping occurred.

Referring back to FIG. 25A, the manufacturing process 2500 also includes, after completing step 2502 (the steps of which are detailed above with reference to FIGS. 26A-33), 3-D printing the upper insert 3202 and the lower insert 3204 (2504), as discussed above with reference to FIG. 22. After 3-D printing the upper insert 3202 and the lower insert 3204, the manufacturing process 2500 also may include inspecting the printed parts, and performing one or more post processing operations (e.g., removing extraneous features from the printing process). Thereafter, the manufacturing process 2500 includes molding a teeth cleaning device (e.g., the representative teeth cleaning device 2550) (2508) using the printed inserts, and inspecting the teeth cleaning device (2510). The molding process is discussed in further detail above with reference to FIG. 17 and FIG. 22 (among others).

FIGS. 34 through 36C are close-up views of different cleaning elements in accordance with some embodiment. In some embodiments, the patterning of the different cleaning elements is part of the design of the upper insert 3202 and the lower insert 3204. For example, during the 3-D printing process, structures used in the upper insert 3202 and the lower insert 3204 to create the cleaning elements include features to impart the patterning discussed below with reference to FIGS. 34 through 36C onto the finalized cleaning elements. In some embodiments, natural results of the manufacturing process are leveraged to create the patterning of the different cleaning elements. For example, during the 3-D printing process, ribbing features may result naturally as each successive layer is added, such that each rib is the width of the layer height.

Figure 34:
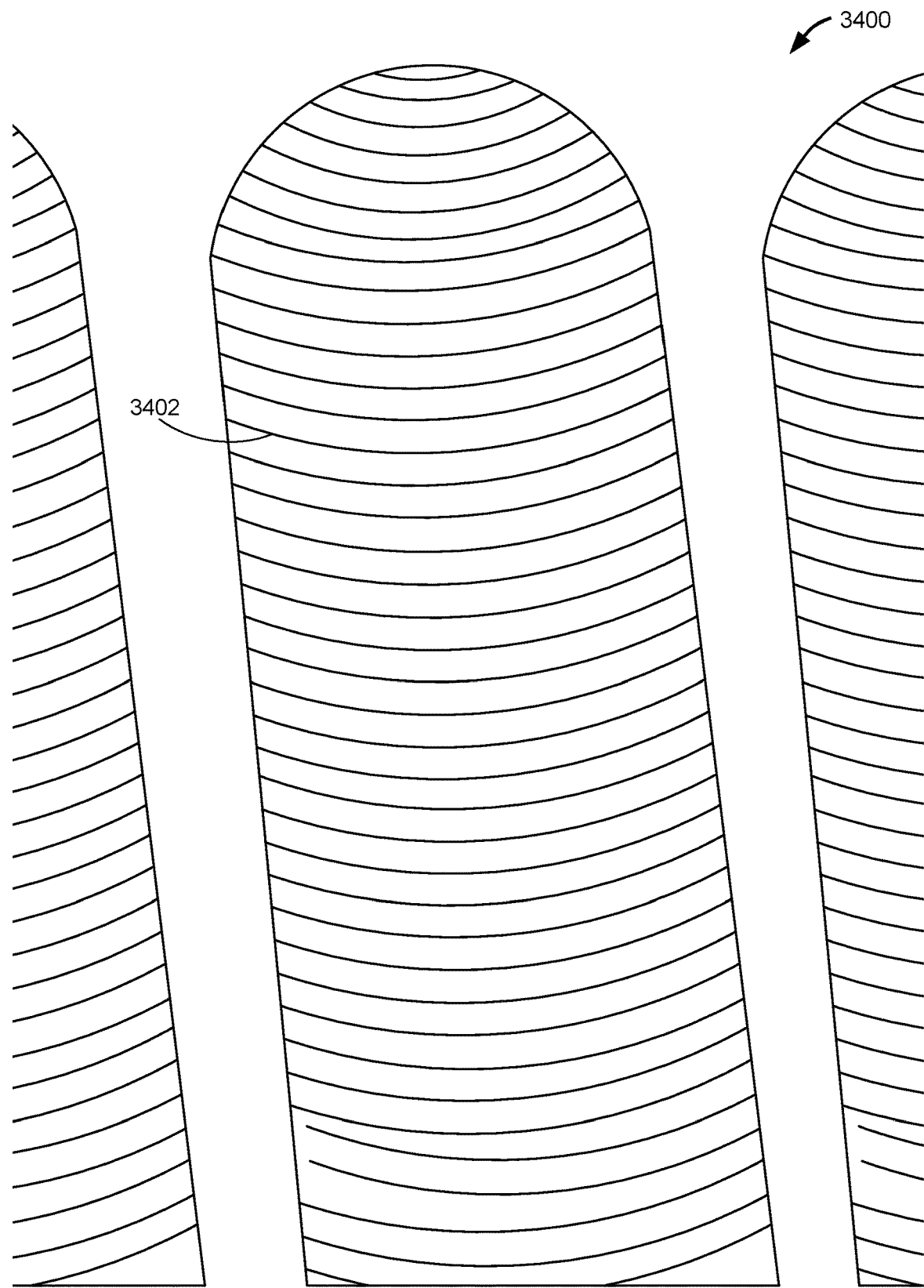
FIGS. 34, 35A-35B and 36A-36C are close-up views of different cleaning elements in accordance with some embodiments.

FIG. 34 shows an example cleaning tip 3400 that includes ribbing features 3402 that run perpendicular to a length of the cleaning tip 3400. In some embodiments, each of the cleaning tips in an example teeth cleaning device 2550 has the ribbing features 3402. Alternatively, in other embodiments, some of the cleaning tips in an example teeth cleaning device 2550 have the ribbing features 3402, while some other cleaning tips in the teeth cleaning device 2550 do not include any ribbing features, or they include some other ribbing features (such as those discussed below). The ribbing features 3402 are used to enhance a cleaning ability of the cleaning tip 3400.

Figure 35A:
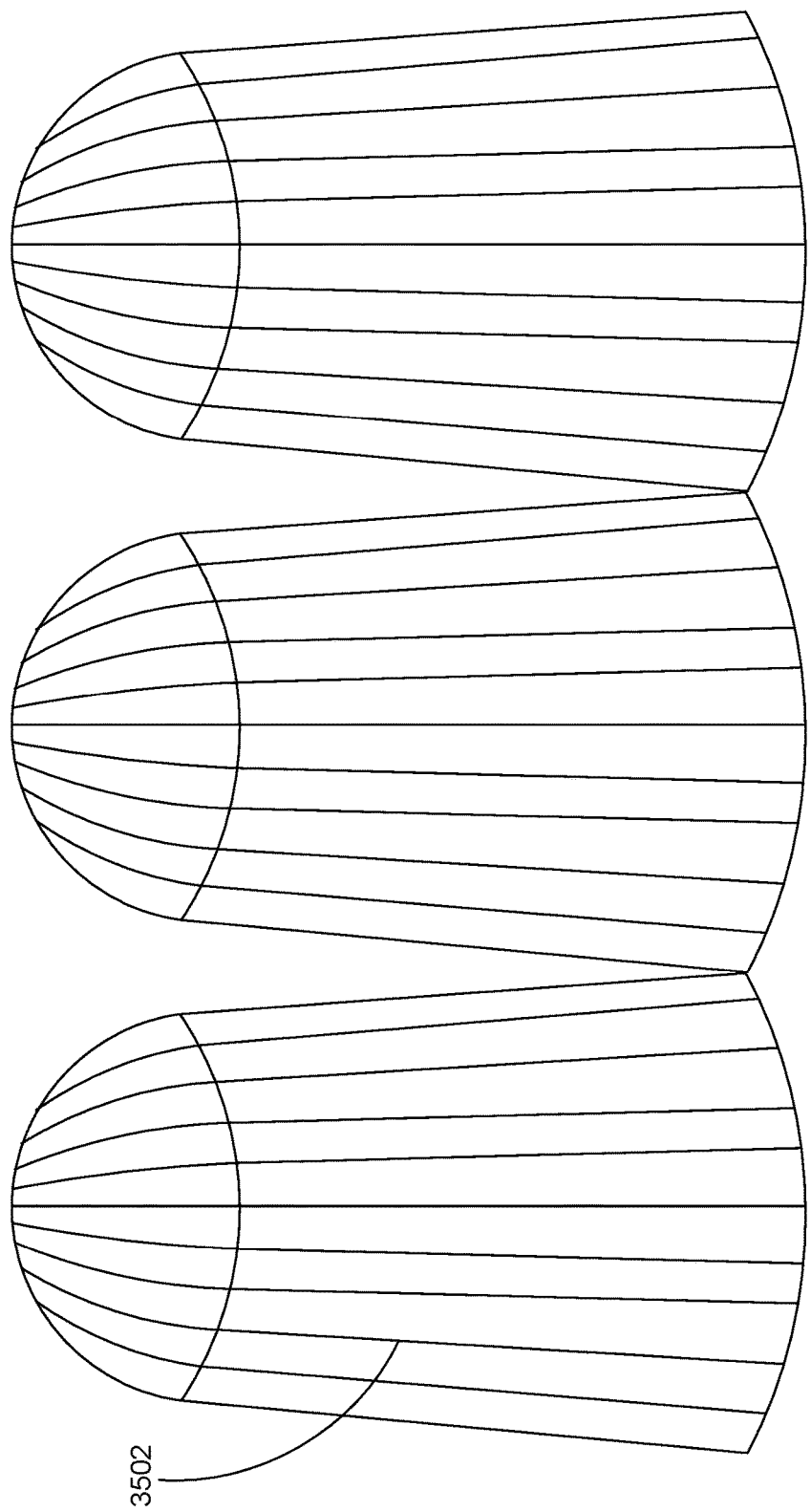
Figure 35B:
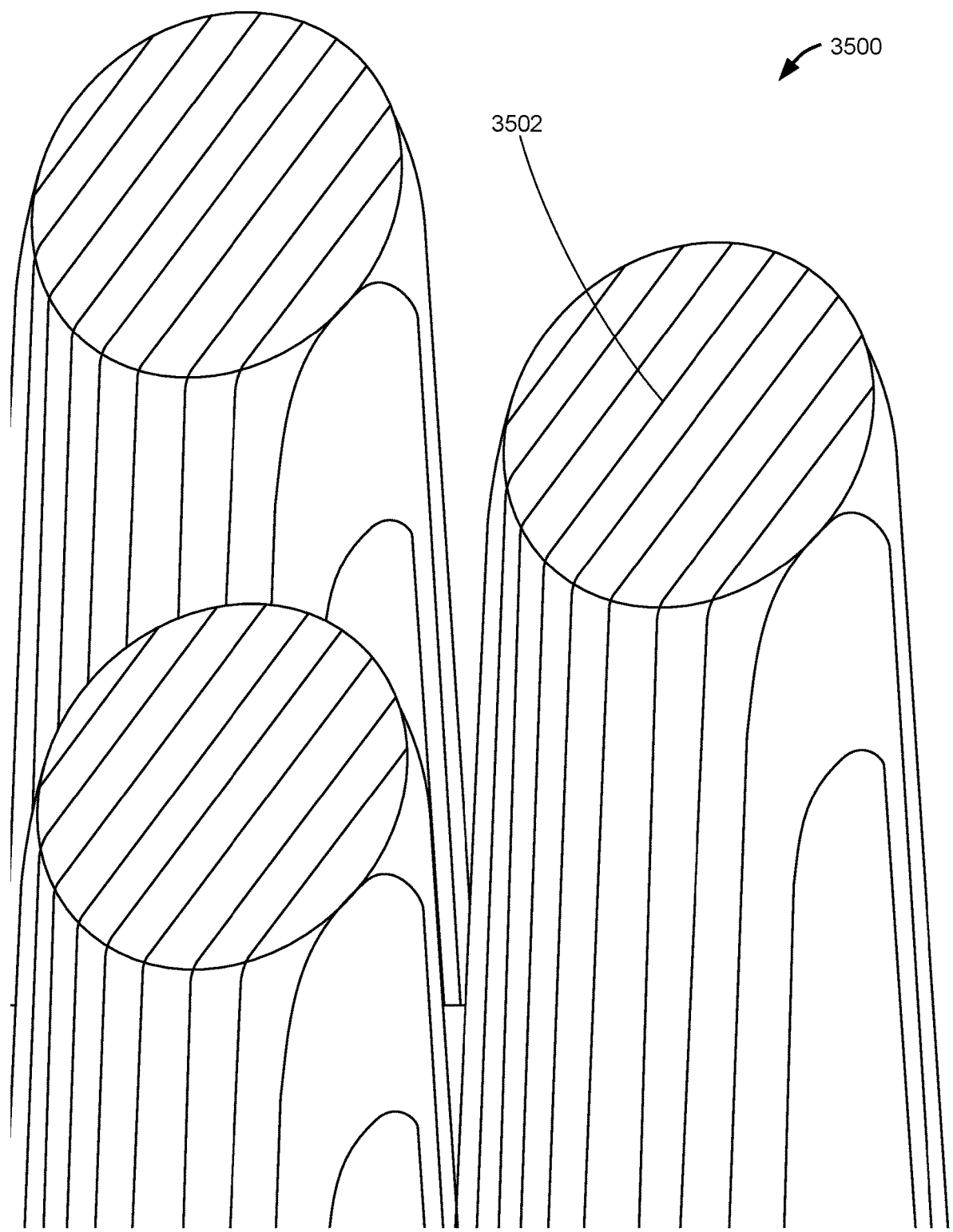

FIGS. 35A and 35B show example cleaning tips 3500 that include ribbing features 3502 that run parallel to the lengths of the cleaning tips 3500. In some embodiments, each of the cleaning tips in an example teeth cleaning device 2550 has the ribbing features 3502. Alternatively, in other embodiments, some of the cleaning tips in an example teeth cleaning device 2550 have the ribbing features 3502, while some other cleaning tips in the teeth cleaning device 2550 do not include any ribbing features, or they include some other ribbing features (such as those discussed above with reference to FIG. 34 or below with reference to FIGS. 36A-36C). The ribbing features 3502 are used to enhance a cleaning ability of the cleaning tip 3500.

Figure 36A:
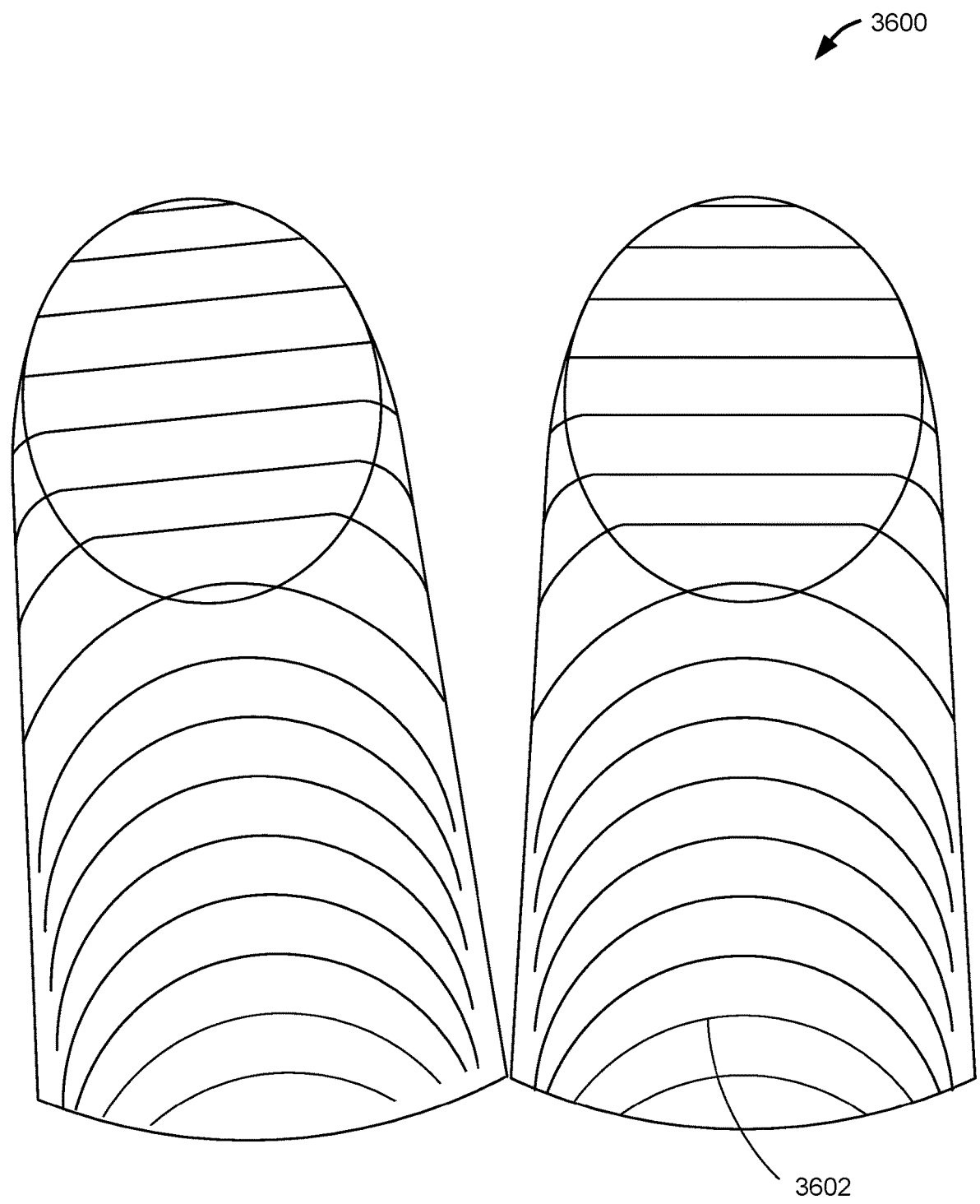
Figure 36B:
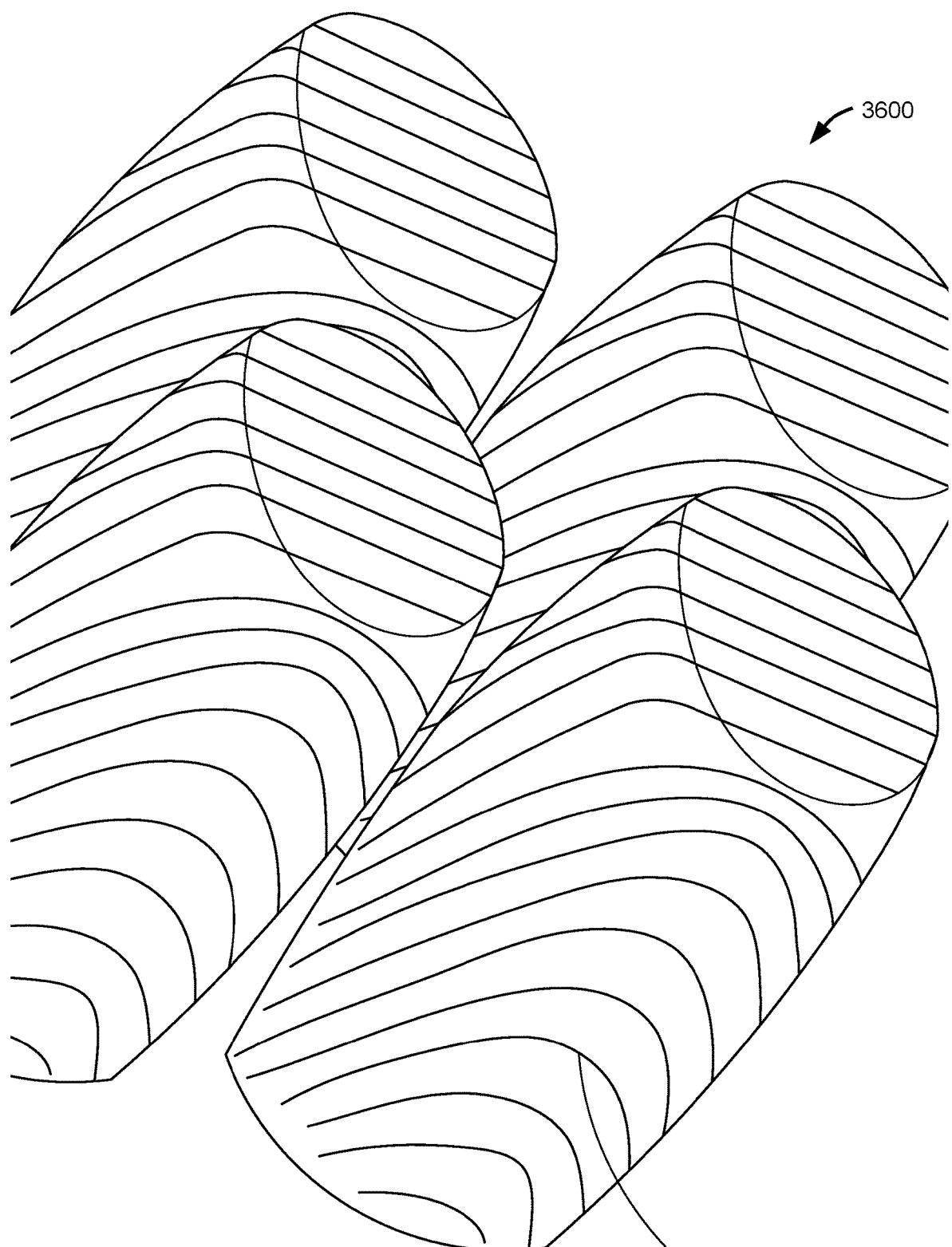
Figure 36C:
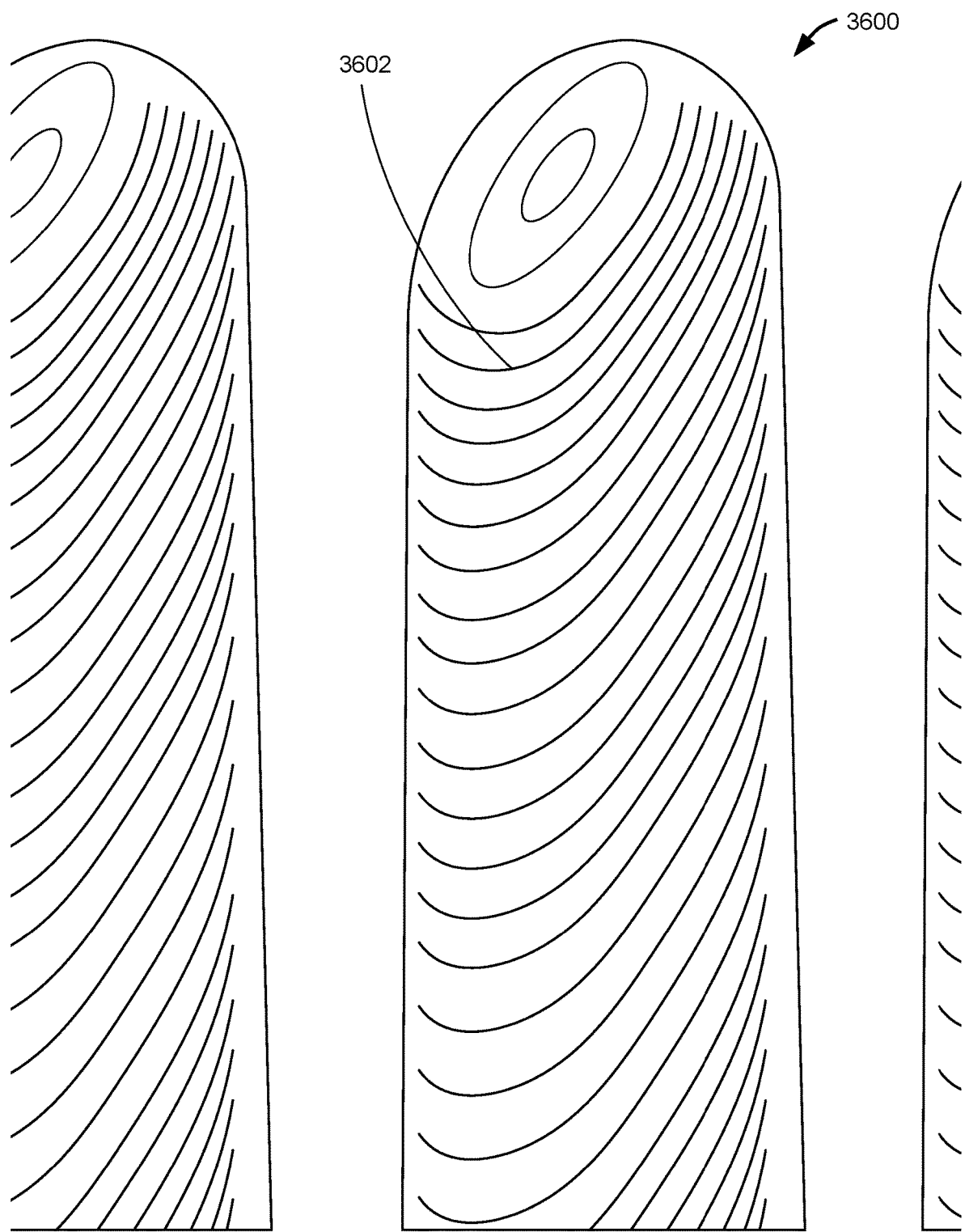

FIGS. 36A-36C show example cleaning tips 3600 that include ribbing features 3602 that are angled relative to lengths the cleaning tips 3600. In some embodiments (as shown in FIGS. 36A-36C), the ribbing features 3602 are scalloped shape. In other embodiments, the ribbing features 3602 are diagonal lines. In some embodiments, each of the cleaning tips in an example teeth cleaning device 2550 has the ribbing features 3602. Alternatively, in other embodiments, some of the cleaning tips in an example teeth cleaning device 2550 have the ribbing features 3602, while some other cleaning tips in the teeth cleaning device 2550 do not include any ribbing features, or they include some other ribbing features (such as those discussed with reference to FIG. 34 or with reference to FIGS. 35A and 35B). The ribbing features 3602 are used to enhance a cleaning ability of the cleaning tip 3600.

FIGS. 37A-37H show exemplary customizations for cleaning trays of a mouthpiece 3700 of a personalized toothbrush device. For ease of explanation, individual customizations are described below, but in some embodiments, multiple customizations are optionally combined.

In some embodiments, the possible customizations for the cleaning trays of the mouthpiece 3700 are customizations based at least in part on a first physical characteristic of a particular user's mouth. Some examples of the first physical characteristic of the particular user's mouth include: a length of the dental arch of the particular user's mouth, a width of the dental arch of the particular user's mouth, an occlusion classification of the particular user's mouth (e.g., overbite, underbite, etc.), tooth alignment of the particular user's teeth, the presence of dental correctors in the particular user's mouth, the presence of one or more third molars (e.g., wisdom teeth) in the particular user's mouth, a width of the particular user's teeth, and a gum line of the particular user's mouth.

In some embodiments, the possible customizations for the cleaning trays of the mouthpiece 3700, based at least in part on the first physical characteristic of the particular user's mouth, include: customizing a length of the top cleaning tray and/or bottom cleaning tray, customizing a width of the top cleaning tray and/or bottom cleaning tray, customizing a distance between the outer boundary wall and the inner boundary wall for the top cleaning tray and/or bottom cleaning tray, customizing an offset (e.g., offset in the vertical alignment) between the top cleaning tray and bottom cleaning tray, customizing a thickness of the outer boundary wall and/or the inner boundary wall for the top cleaning tray and/or bottom cleaning tray, customizing a density of the outer boundary wall or the inner boundary wall for the top cleaning tray or bottom cleaning tray, customizing an internal structure of the top cleaning tray or bottom cleaning tray, and/or adding one or more bite points (e.g., as discussed above with reference to FIG. 28B, and as discussed in further detail below) to the top cleaning tray or bottom cleaning tray.

Figure 37A:
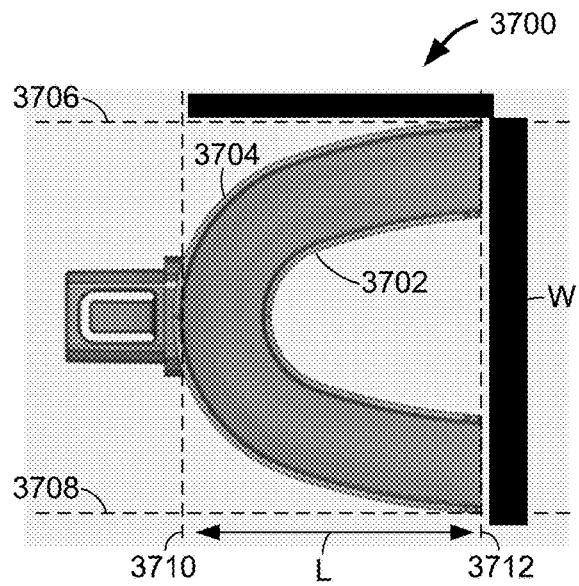
FIGS. 37A-37J show exemplary customizations for cleaning trays of a personalized toothbrush device.

FIG. 37A shows a generic cleaning tray of a mouthpiece 3700 of a toothbrush device, without any customization. The cleaning tray comprises an inner boundary wall 3702 and an outer boundary wall 3704. The reference lines 3706, 3708, 3710, and 3712 provide reference points for the size of the cleaning tray. In some embodiments, the length (e.g., as shown by the arrows "L") and/or width (e.g., as shown by the arrows "W") of the cleaning tray is customized for the particular user. FIG. 37B shows the cleaning tray for the mouthpiece 3700 after customizations, where both the width and the length of the mouthpiece have been increased (e.g., to fit the particular dental arch of the particular user).

Figure 37C:
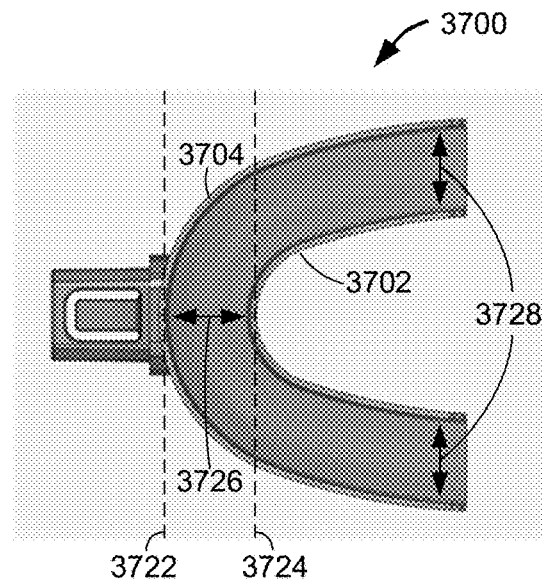
Figure 37B:
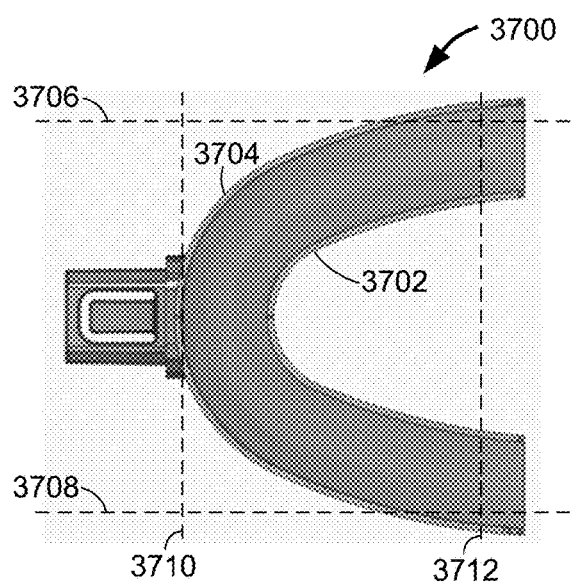
Figure 37D:
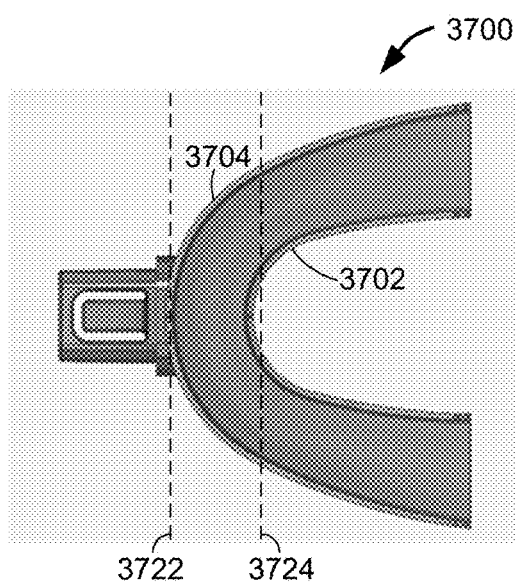

FIG. 37C shows the cleaning tray of the mouthpiece 3700, without any customization, and the reference lines 3722 and 3724, which provide reference points for the distance between the inner boundary wall 3702 and the outer boundary wall 3704. In some embodiments, the distance between the inner boundary wall 3702 and the outer boundary wall 3704 of the cleaning tray is customized for the particular user (e.g., by increasing or decreasing the distance 3726 between the inner boundary wall 3702 and the outer boundary wall 3704, as shown by the double arrows 3726). FIG. 37D shows the cleaning tray for the mouthpiece 3700 after customizations to the distance between the inner boundary wall 3702 and the outer boundary wall 3704, where the distance between the inner boundary wall 3702 and the outer boundary wall 3704 has been reduced in the region corresponding to the double arrow 3726 (shown in FIG. 37C). In some embodiments, the distance between the inner boundary wall 3702 and the outer boundary wall 3704 is different for different regions of the cleaning tray. For example, the distance can be reduced in the region corresponding to the double arrows 3726, but increased in the region corresponding to the double arrows 3728 (shown in FIG. 37C).

Figure 37F:
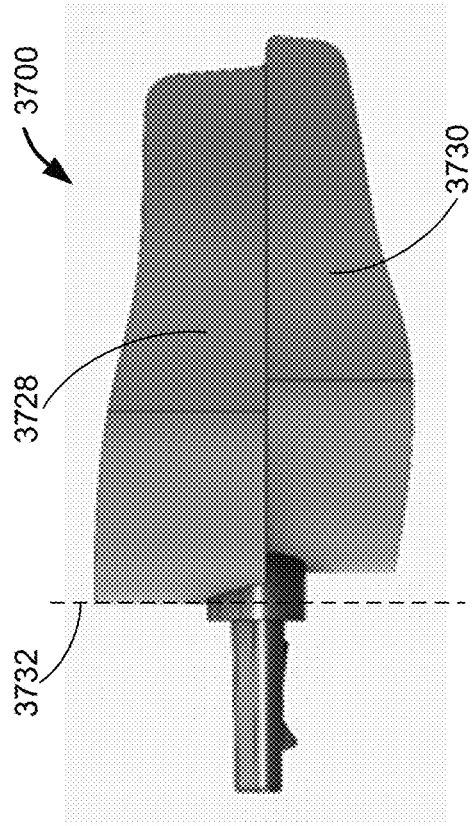
Figure 37H:
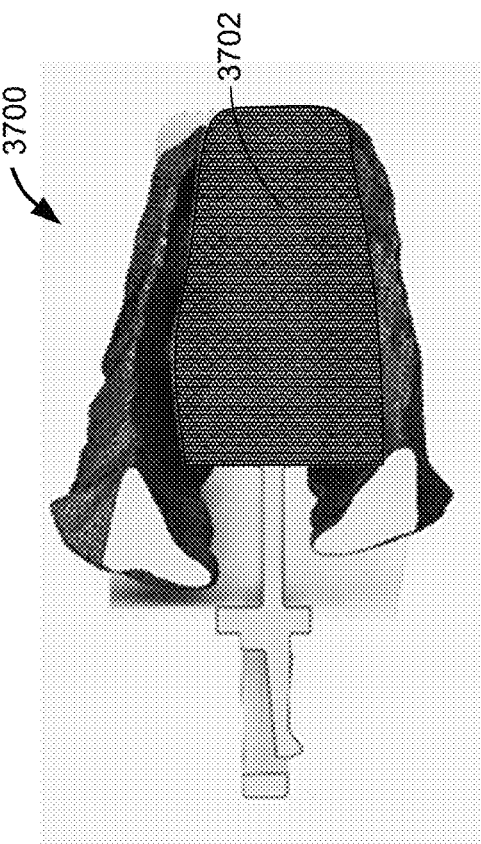
Figure 37E:
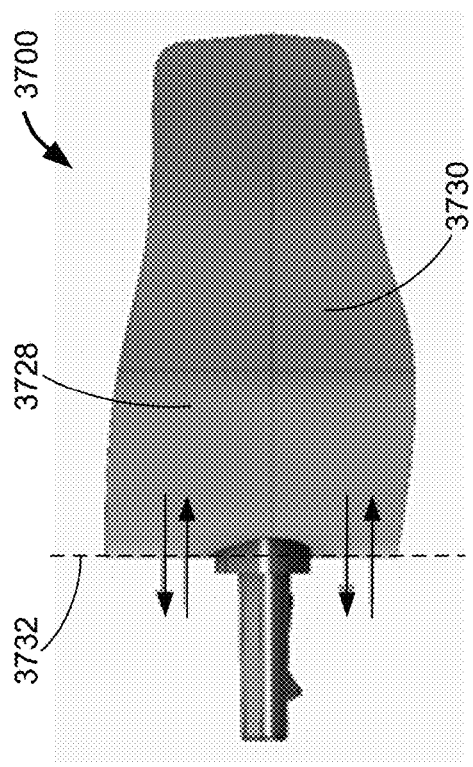

FIG. 37E shows the alignment of a top cleaning tray 3728 and a bottom cleaning tray 3730 of a mouthpiece of the personalized toothbrush device, prior to any customization. The reference line 3732 shows that the top tray 3728 and the bottom bray 3730 are vertically aligned prior to any customization. FIG. 37F shows a customized mouthpiece of the personalized toothbrush device, where the top tray 3728 and the bottom tray 3730 are offset. Such tray offset can be used to accommodate the particular bite of a particular user (e.g., to accommodate user's with malocclusion). For example, the mouthpiece of FIG. 37F shows possible customizations for a user with Class II malocclusion, sometimes referred to as distocclusion, retrognathism, overjet, or overbite. In other embodiments, the trays can be aligned to accommodate other types of malocclusion, such as Class I (neutrocclusion) or Class III malocclusion (prognathism/anterior crossbite/negative overjet/underbite).

Figure 37G:
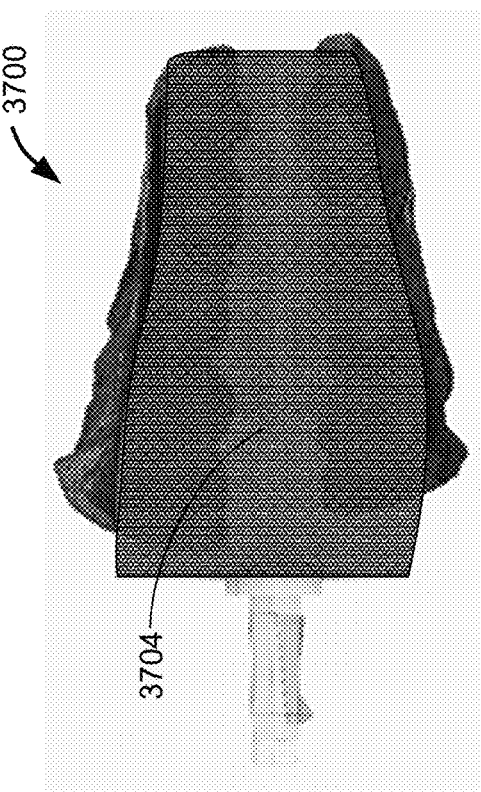

FIG. 37G shows that the shape of the mouthpiece of the personalized toothbrush device can also be customized, for example, based on the particular user's gumline. The outer boundary wall 3704 can be customized to have a shape that follows the facial gum line of the particular user's mouth, which helps prevent the outer boundary wall 3704 from causing discomfort to the user (e.g., due to the outer boundary wall 3704 being too tall and pressing into the upper and lower portions of the particular user's mouth during use). FIG. 37H shows analogous customizations for the inner boundary wall 3702. For example, the inner boundary wall 3702 can be customized to have a shape that follows the lingual gum line of the particular user's mouth.

Figure 37J:
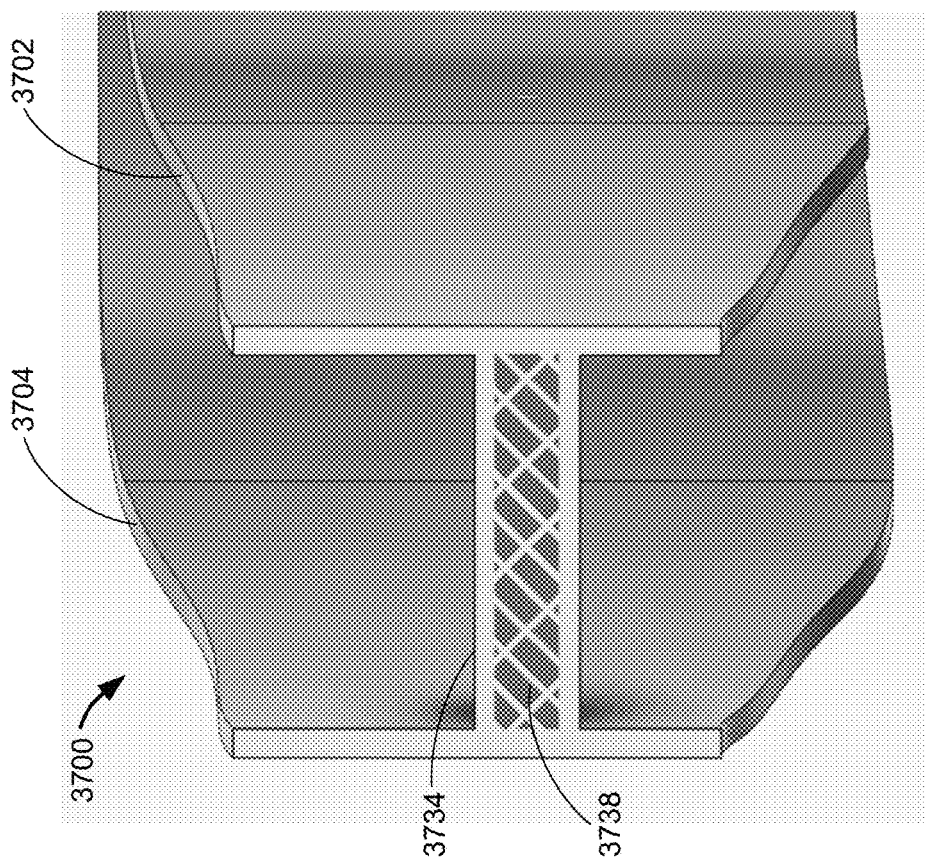
Figure 37I:
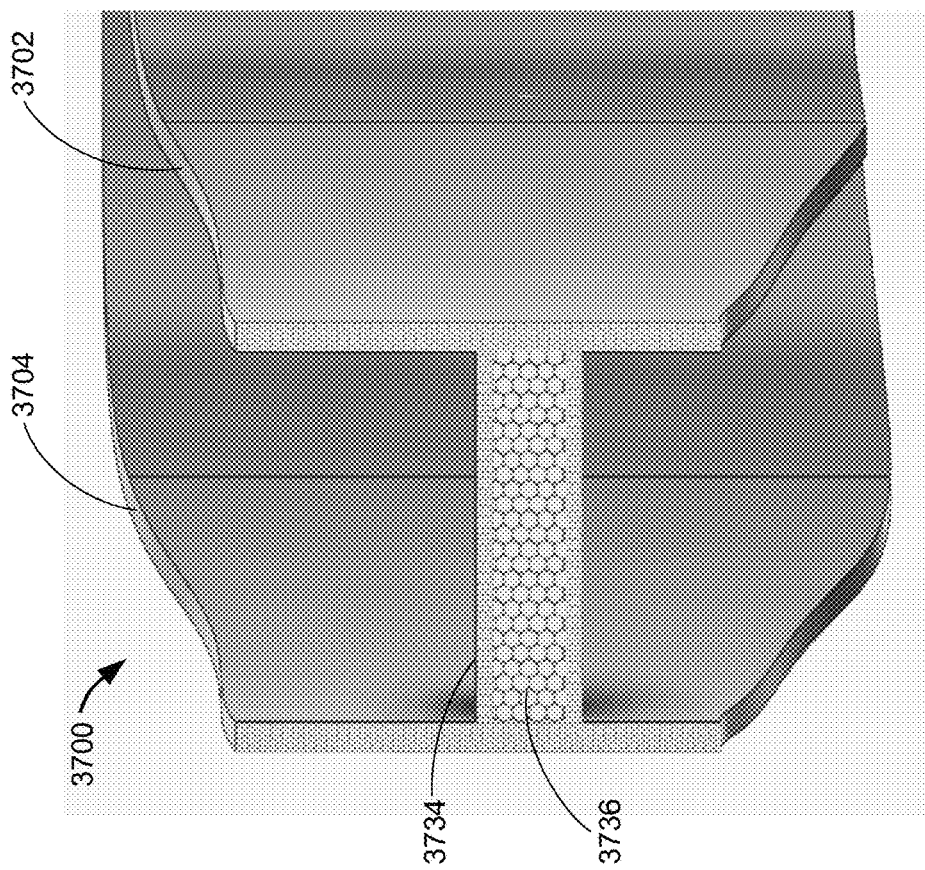

FIG. 37I shows customizations for an occlusal surface 3734 (e.g., a "bottom" surface for the upper cleaning tray 3728, or a "bottom" surface for the lower cleaning tray 3730) of the mouthpiece 3700. A density distribution of the material separating the occlusal surface 3734 may be customized, as shown by a customized density distribution 3736. FIG. 37J shows similar customizations, but with a customized lattice structure 3738 in place of the customized distribution density 3736 of FIG. 37I. Although shown as separate figures, in some embodiments, the customized density distribution 3736 and the customized lattice structure 3738 are optionally combined. In some embodiments, one or more other surfaces (e.g., the inner boundary wall 3702 and/or the outer boundary wall 3704) are similarly customized with customized distribution densities and/or lattice structures. In some embodiments, the customized density distribution 3736 and/or the customized lattice structure 3738 are localized to particular regions of the mouthpiece (e.g., particular areas of the occlusal surface 3734). These localized regions can be used to form bite points (e.g., bite points as discussed previously with reference to FIG. 28B) located at specific locations on the occlusal surface 3734. Such bite points allow the particular user to obtain a proper bite on the mouthpiece 3700 for optimal positioning of the particular user's teeth within the mouthpiece 3700 (e.g., so that cleaning tips of the representative teeth cleaning device are properly positioned with respect to the tooth surfaces). In some embodiments, the bite points have a lower density than the surrounding regions (e.g., to allow the user's teeth to partially sink into the occlusal surface 3734 at the correct locations). In some embodiments, the bite points comprise a lattice structure, while the surrounding regions are of solid construction (e.g., without any gaps in the internal structure).

Customizing one or more surfaces of the mouthpiece 3700 with customized density distributions and/or lattice structures allows the mouthpiece 3700 to be customized for comfort (e.g., customizing the occlusal surface 3734 to be less dense, to provide added comfort when the particular user bites down on the occlusal surface 3734) and/or performance characteristics (e.g., customizing the density distribution 3736 in order to achieve desired vibrational motion when the mouthpiece 3700 is coupled to an external drive mechanism). Customized density distributions and/or lattice structures also allows for reduced usage of materials during manufacturing (e.g., to reduce the cost of manufacturing).

Figure 37L:
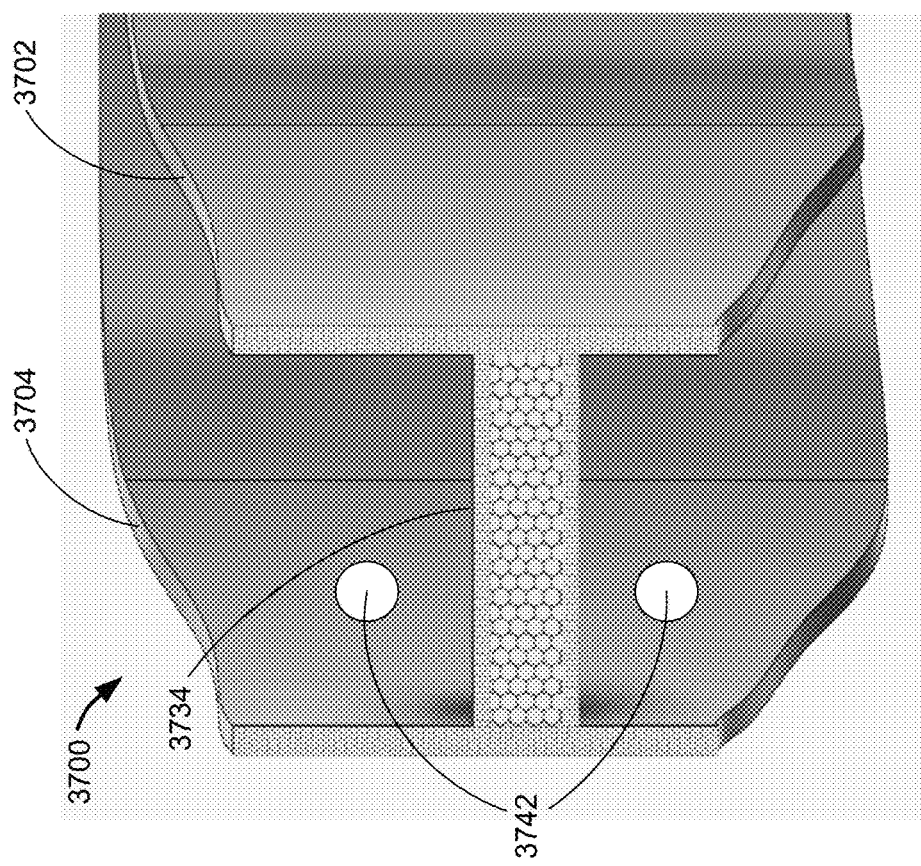
FIGS. 37K and 37L show exemplary customizations for therapeutic and/or diagnostic purposes.
Figure 37K:
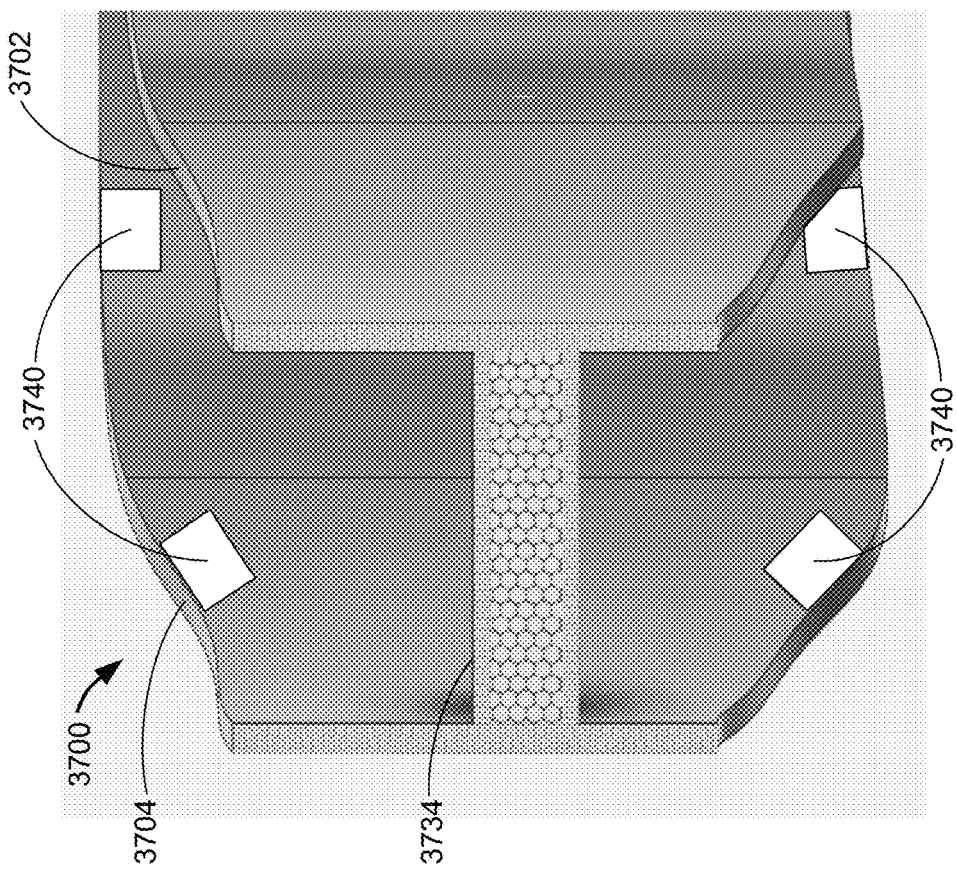

FIGS. 37K and 37L show exemplary customizations for therapeutic and/or diagnostic purposes. FIG. 37K shows dispensers 3740 located on or in the outer boundary wall 3704. In some embodiments, the dispensers are alternatively, or additionally, located on or in the inner boundary wall 3702. In some embodiments, the dispensers 3740 dispense an oral care agent (e.g., toothpaste), and are positioned at a location on or in the inner boundary wall 3702 and/or the outer boundary wall 3704 based on the specific needs of the user. For example, in some embodiments, the oral care agent is a gum care agent that addresses the specific gum issues of the particular user. In such embodiments, the dispensers 3740 are positioned at the particular locations of the gum issues for the particular user. In some embodiments, the oral care agent is a cleaning agent (e.g., toothpaste), and the dispensers 3740 are positioned to provide optimal coverage of the particular user's teeth.

FIG. 37L shows sensors 3742 located on or in the outer boundary wall 3704. In some embodiments, the sensors 3742 are alternatively, or additionally, located on or in the inner boundary wall 3702. In some embodiments, the sensors 3742 are configured to detect microorganisms within the oral cavity of the particular user (e.g., microorganisms indicative of certain tooth or gum diseases, microorganisms indicative of tooth decay, etc.). The sensors 3742 allow for preventative medicine and early detection of oral health issues. In some embodiments, the sensors 3742 are positioned at particular locations where they are most likely to detect the microorganisms in question. In some embodiments the sensors 3742 are positioned at particular locations based on the particular risk factors for the particular user (e.g., sensitive areas of the particular user's mouth which may receive less brushing or lighter brushing, genetic susceptibility to gum disease, etc.).

FIGS. 38A-38H show possible customizations to a set of cleaning elements of the mouthpiece 3700 for a personalized toothbrush device. For ease of explanation, individual customizations are described below, but in some embodiments, multiple different customizations are combined.

In some embodiments, the possible customizations for the set of cleaning elements of the mouthpiece 3700 are based at least in part on a second physical characteristic of a particular user's mouth. Some examples of the second physical characteristic of the particular user's mouth include: the shape, size, position, and spacing of tooth surfaces of the teeth of the particular user's mouth; an interproximal distance (i.e., distance between the particular user's teeth) of the particular user's mouth; one or more missing teeth in the particular user's mouth; a gum condition of the particular user's mouth; an enamel condition of one or more teeth of the particular user's mouth; the presence of dental correctors in the particular user's mouth; the presence of one or more third molars in the particular user's mouth, the presence of dental hardware (e.g., inlays, onlays, crowns, veneers, bridges, implants, etc.) in the particular user's mouth; a width of the particular user's teeth; and a gum health state of the particular user's mouth. In some embodiments, the second physical characteristic is a combination of physical characteristics of the particular user's mouth (e.g., size and position of tooth surfaces of the teeth of the particular user's mouth) and planned customizations (e.g., a size of the upper and/or lower cleaning trays). For example, the set of cleaning elements may be customized to account for a distance from the outer boundary wall for the top or bottom customized cleaning tray to the surface of a tooth of the particular user's mouth and/or a distance from the inner boundary wall for the top or bottom customized cleaning tray to the surface of a tooth of the particular user's mouth.

In some embodiments, the possible customizations for the set of cleaning elements of the mouthpiece 3700, based at least in part on the second physical characteristic of the particular user's mouth, include: customizing a length of the cleaning elements of the set of cleaning elements (e.g., to ensure the cleaning elements reach the surface of the particular user's teeth, and/or to include an "interference distance" by which the length of the cleaning elements extend beyond the surface of the particular user's teeth), customizing a spacing between cleaning elements of the set of cleaning elements, customizing a diameter of each cleaning element of the set of cleaning elements, customizing a taper of each cleaning element of the set of cleaning elements, customizing an angle of each cleaning element of the set of cleaning elements, relative to a surface of the top and bottom customized cleaning trays and/or the particular user's teeth, customizing a density of each cleaning element of the set of cleaning elements, customizing a surface texture (or pattern) of each cleaning element of the set of cleaning elements (e.g., as discussed with reference to FIGS. 34-36C), customizing a cross-section of each cleaning element of the set of cleaning elements, customizing the spatial distribution of the set of customized cleaning elements, and/or customizing a material composition of the set of customized cleaning elements.

In some embodiments, each cleaning element of the set of cleaning elements is individually customized based on the particular user's mouth (e.g., one or more of the second physical characteristics described above). In some embodiments, each cleaning element of the set of cleaning elements is individually customized by selecting a value for a physical characteristic of the cleaning element. In some embodiments, this individual customization includes selecting a respective value for a physical characteristic for each respective cleaning element of the set of cleaning elements, such that a respective cleaning element of the set of cleaning elements contacts a respective tooth of the particular user's mouth with a predetermined amount of contact force (e.g., 0-12 Newtons). In some embodiments, the predetermined amount of contact force is selected based on efficacy (e.g., to ensure the set of cleaning elements can clean the user's teeth effectively), comfort (e.g., similar to soft and firm toothbrushes), and/or the particular user's needs and requirements. In some embodiments, this individual customization includes selecting a respective value for a physical characteristic for each respective cleaning element of the set of cleaning elements, such that a respective cleaning element of the set of cleaning elements contacts a respective tooth of the particular user's mouth with a predetermined amount of overlap with a surface of the particular user's mouth. In some embodiments, the predetermined amount of contact force and/or the predetermined amount of overlap are achieved by customizing an amount of interference distance. In some embodiments, each cleaning element has the same interference distance. In some embodiments, the interference distances are customized per cleaning element, or subset of cleaning elements (e.g., cleaning elements corresponding to sensitive regions of the particular user's mouth may have smaller interference distances than cleaning elements corresponding to other regions of the particular user's mouth).

In some embodiments, the physical characteristic is an amount of taper of a respective cleaning element, a diameter of the respective cleaning element, an angle of the respective cleaning element relative to a surface of the top and bottom customized cleaning trays, or a cross-section of the respective cleaning element. In some embodiments, multiple physical characteristics are customized for each cleaning element of the set of cleaning elements.

For example, if the particular user has sensitive or receding gums, a lower predetermined amount of contact force may be desired, so as not to hurt or damage the particular user's gums. To achieve this goal, the customization for the set of cleaning elements corresponding to sensitive regions of the particular user's gums could feature a mix of shorter cleaning elements (e.g., cleaning elements with lower interference distances) and/or cleaning elements with smaller diameters, resulting in a low predetermined amount of contact force. Alternatively, if the particular user has high levels of plaque buildup on particular teeth in the particular user's mouth, firmer brushing for those particular teeth may be desired. To achieve this goal, the customizations for the set of cleaning elements corresponding to the region with high levels of plaque buildup feature longer cleaning elements (e.g., cleaning elements with larger interference distances) and/or cleaning elements with larger diameters, resulting in a higher predetermined amount of contact force. Other possible customizations to achieve this goal include using different materials (e.g., materials with different densities) or 3-D printing the cleaning elements with different densities (e.g., but from the same material).

Figure 38A:
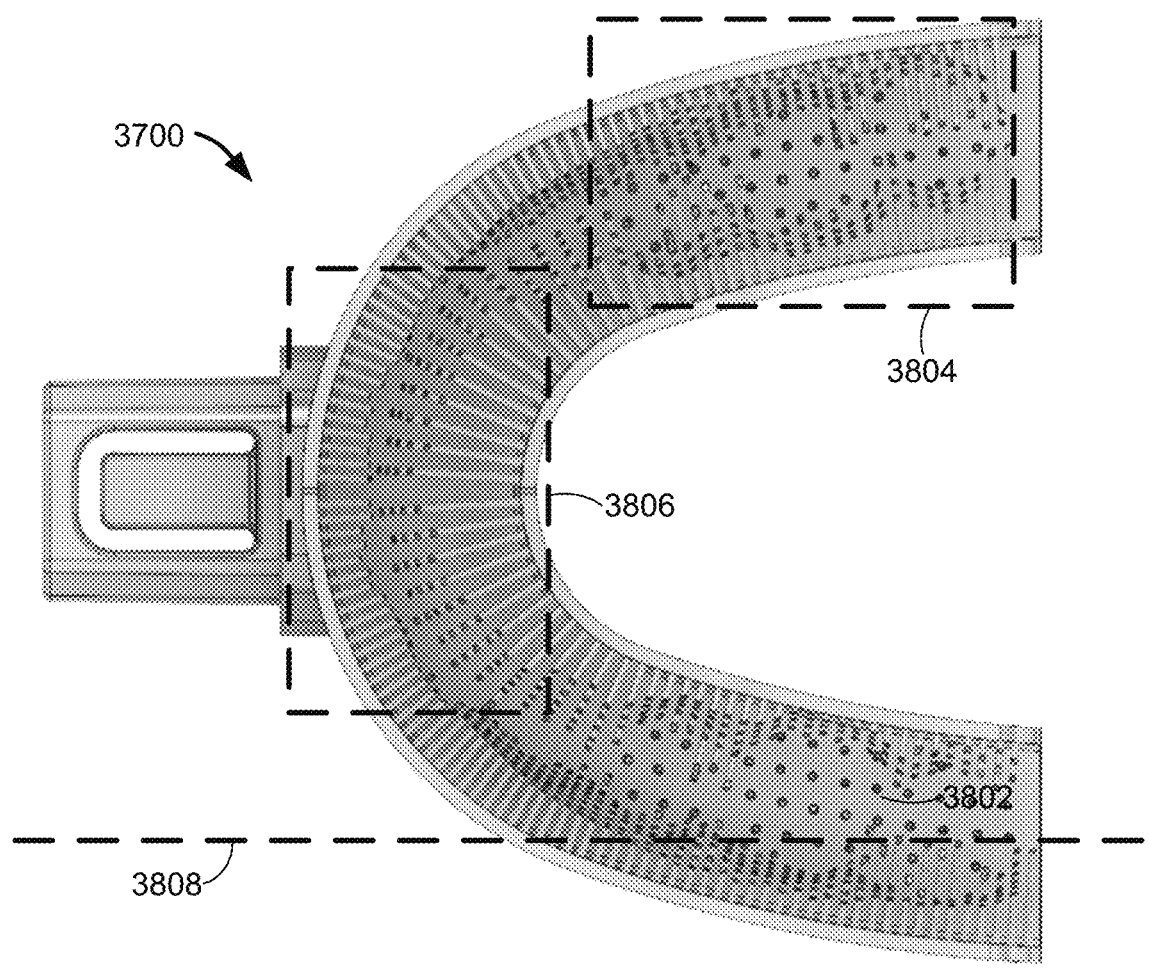
FIGS. 38A-38H show exemplary customizations for cleaning elements of a personalized toothbrush device.

FIG. 38A shows a top-down view of a mouthpiece of the personalized toothbrush device, including a set of customized cleaning elements, including a respective cleaning element 3802. The set of customized cleaning elements includes cleaning elements in a molar region 3804 and cleaning elements in an incisor region 3806. As described above, each cleaning element (or a subset of cleaning elements) of the set of cleaning elements can be individually customized. For example, each cleaning element in the molar region 3804 has a customized length and angle (relative to one of the surfaces of the mouthpiece 3700 and/or the particular user's teeth), and the distribution density of the cleaning elements is customized (e.g., to fit the shape of the particular user's molars). In some embodiments, the customization includes the presence (or absence) of cleaning elements. For example, in the molar region 3804, one or more cleaning elements are present on the occlusal surface 3734 of the cleaning tray of the mouthpiece 3700 (e.g., because molars are wide, have large occlusal surfaces with multiple cusps). In contrast, cleaning elements may be absent on the occlusal surface of the cleaning tray in the incisor region 3806 (e.g., because incisors are narrow). In some embodiments, the presence or absence of cleaning elements may be based on missing teeth (e.g., due to accident, injury, age, etc.) and/or additional teeth (e.g., third molars/wisdom teeth).

Figure 38B:
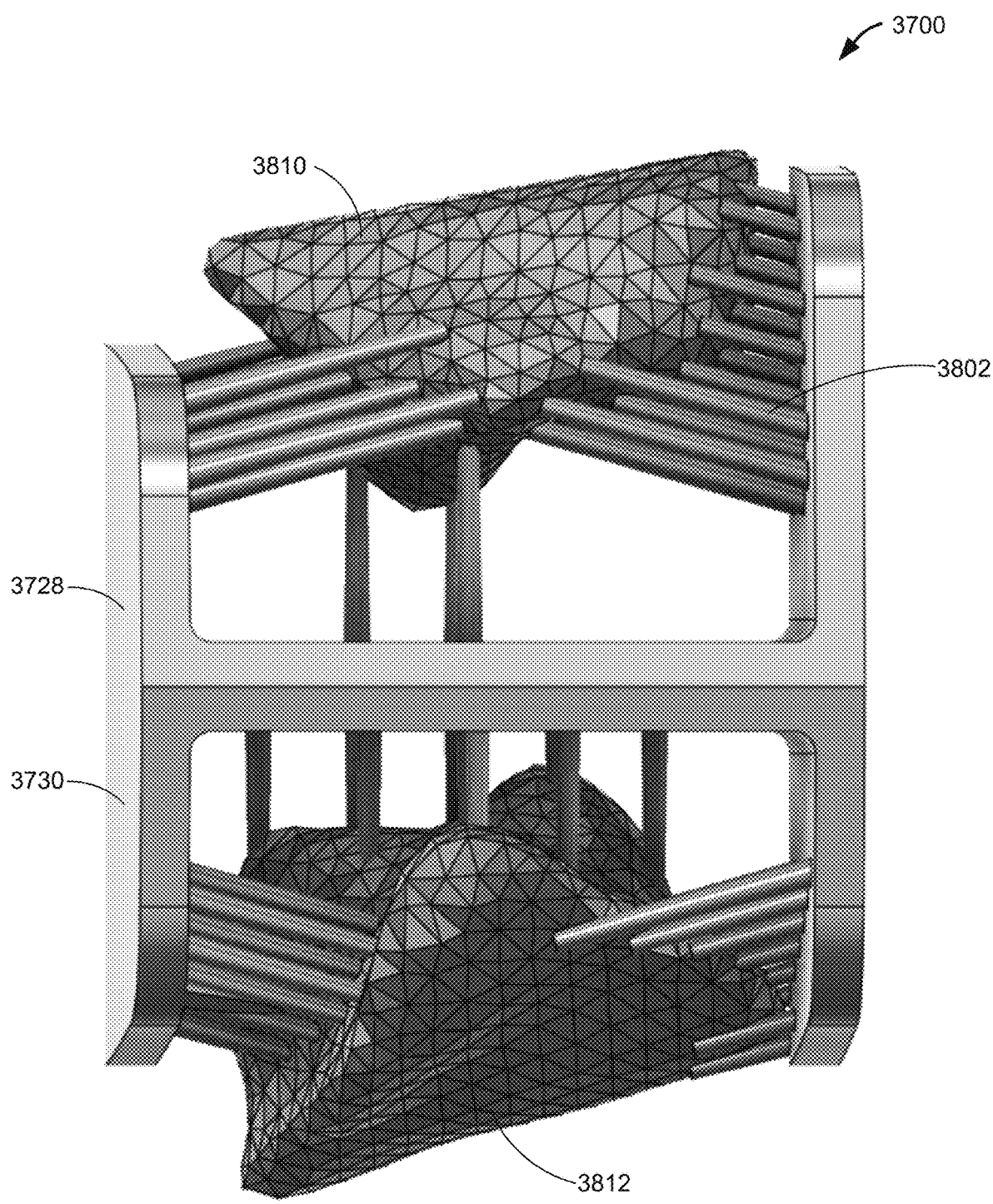

FIG. 38B shows a view of the set of customized cleaning elements, as viewed along an axis 3808 (as shown in FIG. 38A). Also shown are portions of an upper tooth 3810 and a lower tooth 3812. Multiple cleaning elements for the upper cleaning tray 3728 have each been customized (e.g., with respect to length, position, and distribution density) based on the upper tooth 3810. Multiple cleaning element for the lower cleaning tray 3730 have been customized based on the lower tooth 3812, and as such, do not mirror the cleaning elements for the upper cleaning tray 3728.

Figure 38C:
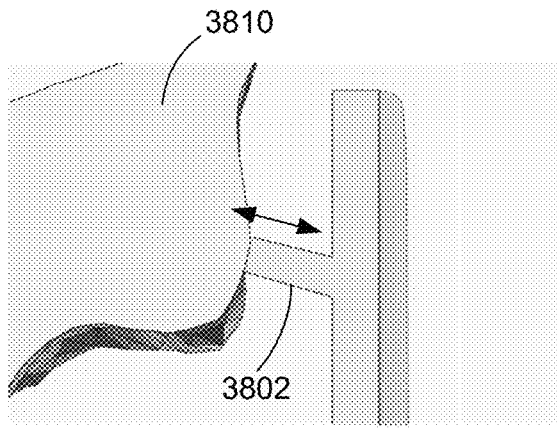
Figure 38D:
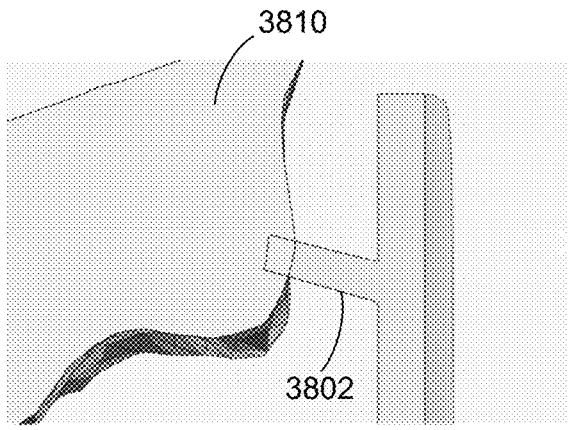

FIG. 38C shows potential customizations for a length of the respective cleaning element 3802, where the length of the respective cleaning element 3802 can be adjusted to be longer or shorter (e.g., as indicated by the double arrow in FIG. 38C). FIG. 38D shows the respective cleaning element 3802 after the length has been customized.

Figure 38E:
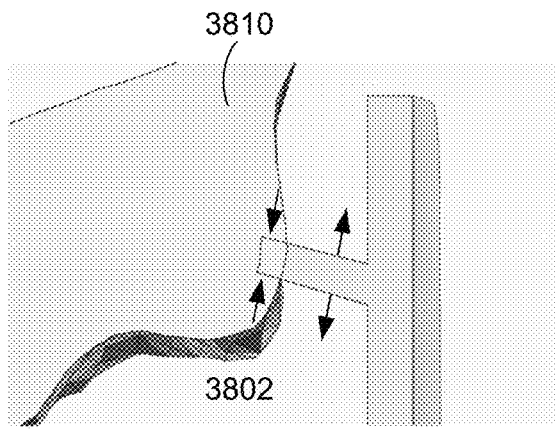
Figure 38F:
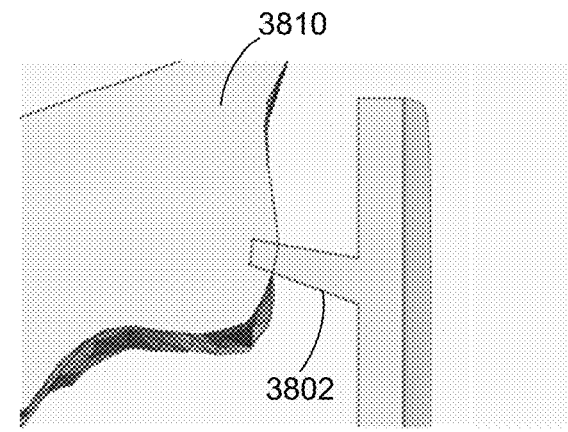

FIG. 38E shows potential customizations for an amount of taper for the respective cleaning element 3802, where the amount of taper can be increased or decreased (e.g., as indicated by the two sets of arrows in FIG. 38E). FIG. 38F shows the respective cleaning element 3802 after the amount of taper has been customized.

Figure 38G:
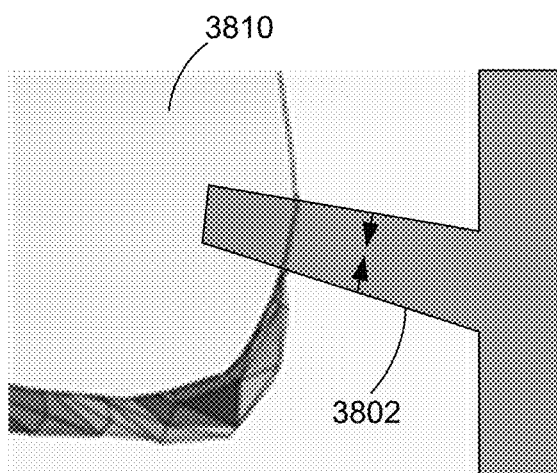
Figure 38H:
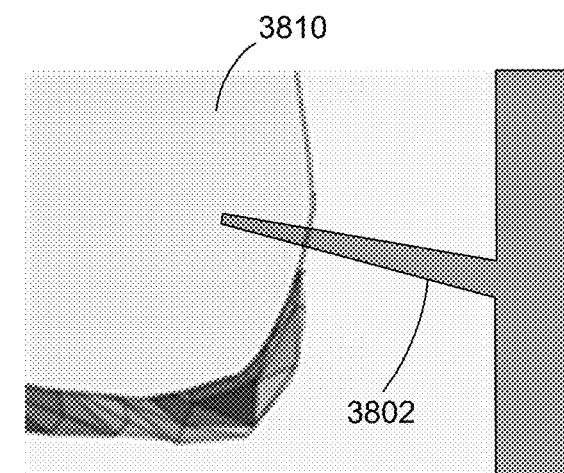

FIG. 38G shows potential customizations for the diameter of the respective cleaning element 3802, where the diameter of the cleaning element can be increased or decreased (e.g., as indicated by the set of arrows in FIG. 38F). In contrast to customizing the amount of taper, in some embodiments, customizing the diameter of the respective cleaning element includes customizing the diameter by the same amount along the entire length of the respective cleaning element 3802. FIG. 38H shows the respective cleaning element 3802 after the diameter has been customized. In some embodiments, the customized diameter for the respective cleaning element changes in a non-linear fashion along the length of the respective cleaning element (e.g., in contrast to a linear change in diameter to achieve a taper of the respective cleaning element).

In some embodiments, customizing each cleaning element of the set of cleaning elements includes customizing one or more seeding elements. The seeding elements are cleaning elements that determine the configuration (e.g., spatial distribution, customizations, etc.) for the remaining cleaning elements of the set (or a subset) of cleaning elements. In some embodiments, the spatial distribution and/or customizations (e.g., length, density, diameter, taper, angle relative to a surface of the top or bottom customized cleaning tray, and/or shape) of the seeding elements are configured manually (e.g., by a dental professional), and the configuration for the remainder of the cleaning elements of the personalized toothbrush device is determined automatically (e.g., such that the dental professional need not manually select the spatial arrangement and/or physical characteristics for each of hundreds of thousands of cleaning elements). In some embodiments, automatically determining the configuration for the remainder of the cleaning elements includes automatically determining customizations for the remainder of the cleaning elements (e.g., the spatial arrangement for the remainder of the cleaning elements is a preset pattern, and each cleaning element of the remainder of the cleaning elements is automatically customized with an appropriate length to ensure each cleaning element contacts the user's teeth with the desired contact force and/or amount of overlap). In some embodiments, automatically determining customizations for the remainder of cleaning elements includes automatically determining customizations for the remainder of the cleaning elements based at least in part on the customizations of one or more seeding elements (e.g., if the one or more seeding elements are customized to have a particular length, including a particular interference distance, the remaining cleaning elements can be automatically customized to have the same interference distance, for example, by automatically customizing a combination of length, angle, and position of the remaining cleaning elements). In some embodiments, automatically determining customizations for the remainder of cleaning elements includes automatically determining customizations for a respective cleaning elements of the remainder of the cleaning elements based at least in part on customizations for neighboring cleaning elements (e.g., the respective cleaning element of the remainder of cleaning elements may automatically be customized to have an angle similar to the angle of neighboring cleaning elements in order to prevent the cleaning elements from physically interfering with the motion of nearby cleaning elements, and the length, diameter, taper, and/or density of the respective cleaning element is automatically customized in order to ensure the respective cleaning element contacts a respective tooth of the particular user's mouth with the desired contact force and/or overlap).

In some embodiments, the configuration for the remainder of the cleaning elements of the personalized toothbrush device is determined through interpolation. In some embodiments, the configuration the configuration for the remainder of the cleaning elements of the personalized toothbrush device is determined at least in part based on previously generated configurations for sets of cleaning elements (e.g., the configuration for the remainder of cleaning elements is determined in part based on machine learning (e.g., based on a data set of previously generated configurations for sets of cleaning elements)). In some embodiments, the interpolation and/or machine learning prioritizes cleaning efficiency (e.g., by minimizing the number of cleaning elements to fully clean the particular user's teeth), coverage (e.g., by creating the densest groupings of cleaning elements possible), and/or manufacturability (e.g., by maximizing efficiency and/or coverage to the fullest extent allowed by manufacturing limitations).

Figure 39A:
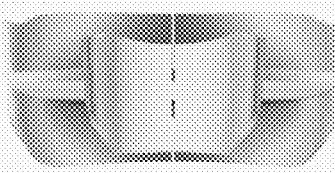
FIGS. 39A-39B show exemplary vibrational modes for a personalized toothbrush device.
Figure 39A:
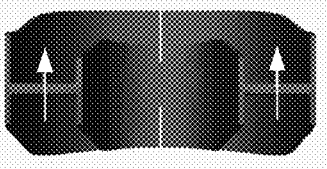
Figure 39A:
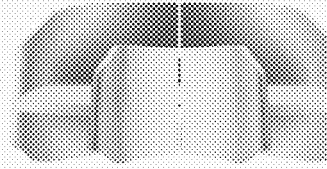
Figure 39A:
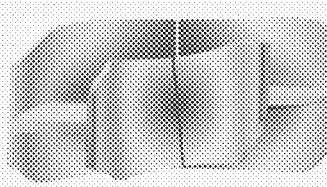
Figure 39A:
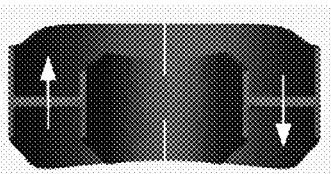
Figure 39A:
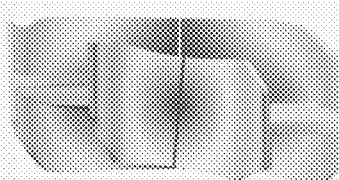
Figure 39A:
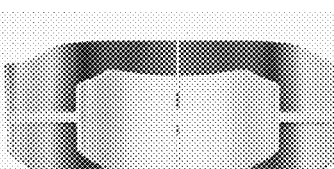
Figure 39A:
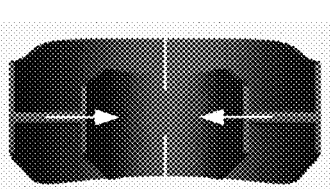
Figure 39A:
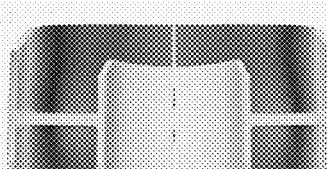
Figure 39A:
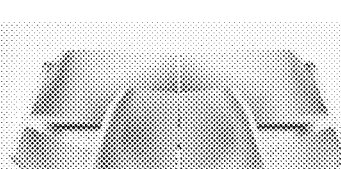
Figure 39A:
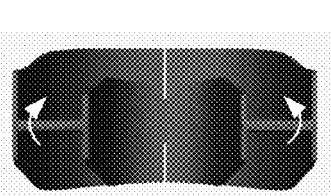
Figure 39A:
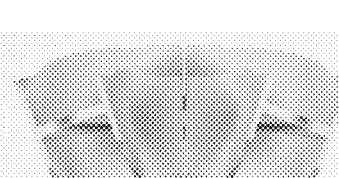
Figure 39A:
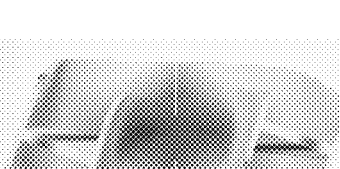
Figure 39A:
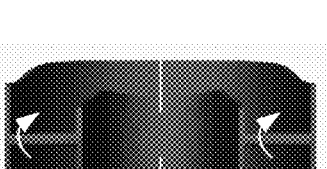
Figure 39A:
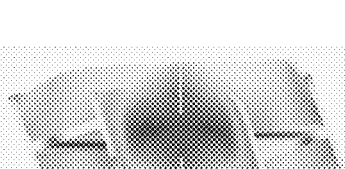
Figure 39B:
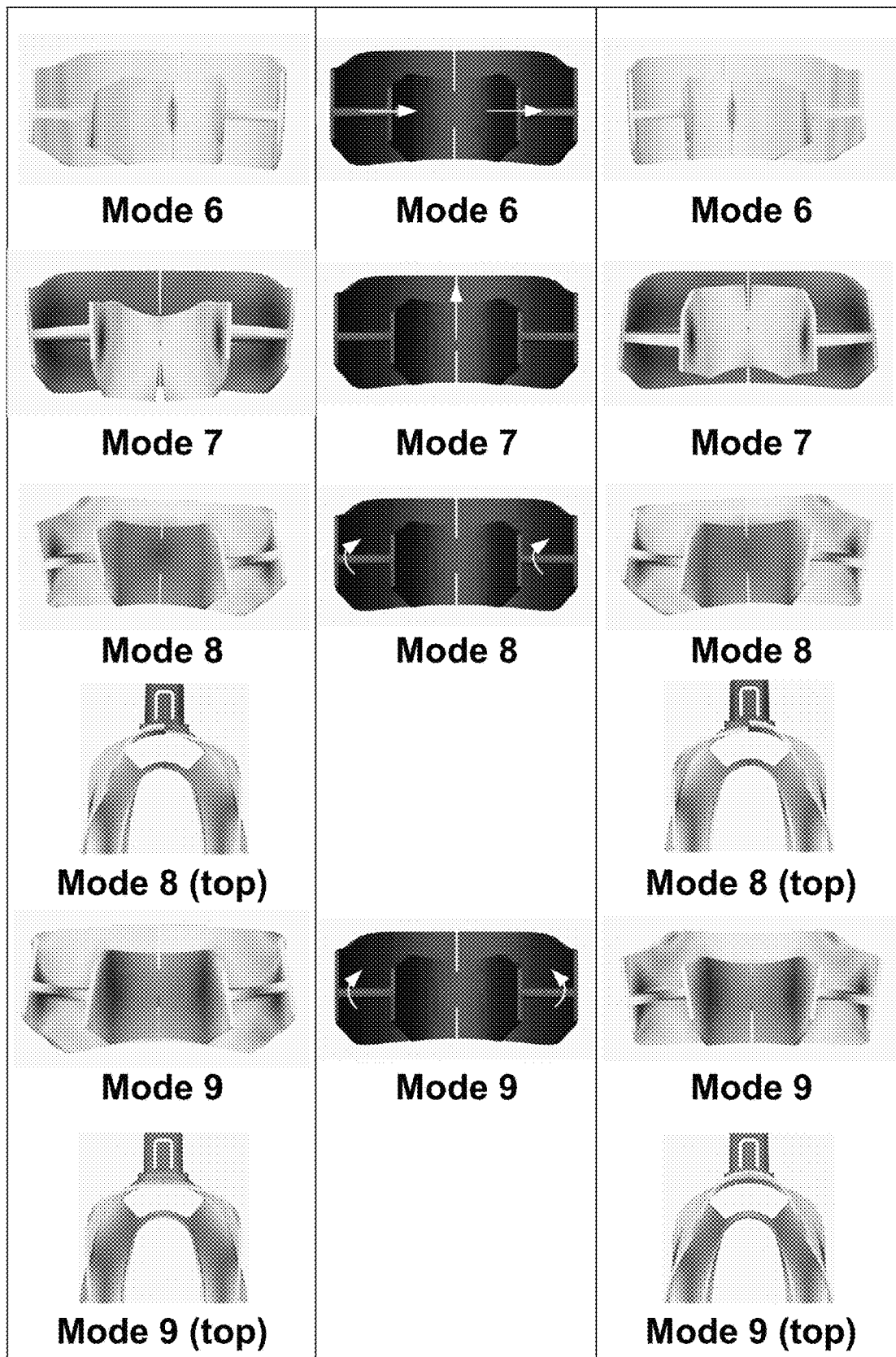

FIGS. 39A-39B show a table of exemplary vibrational modes for the mouthpiece 3700 of the personalized toothbrush device when being used, as viewed from behind (e.g., along the axis 3808 in FIG. 38A). The "Direction" column shows the direction of movement of the relevant portions of the mouthpiece 3700. The "Extreme 1" and "Extreme 2" columns show the mouthpiece 3700 at two opposite extremes during the movement of the relevant portions of the mouthpiece 3700. For ease of explanation, the directions "up," "down," "left," "right," "front," and "rear" are used with reference to the particular user (e.g., "up" means towards the roof of the particular user's mouth, "down" means towards the floor of the user's mouth, "left" means towards the particular user's left side, "right" means towards the particular user's right side, "front" means towards to front of the user's mouth, and "rear" means towards the back of the user's mouth).

The mouthpiece 3700 can be configured to vibrate at a variety of frequencies (e.g., by being coupled to an external drive mechanism that is driven at different speeds) that result in different types of motion. Although the types of motion shown in the various vibrational modes of FIG. 39 may be the same across multiple users, the frequencies at which the modes of motion are achieved, and the specific desired vibrational mode, will differ depending on the mouthpiece of the particular user. For example, different users will have mouthpieces with different customizations (e.g., length, width, height, shape, density, etc.) that affect the motion of the mouthpiece, and the particular dental needs of the particular user (e.g., a user with a history of high plaque build up may require more vigorous movement of the mouthpiece 3700 over all of, or portions of, the mouth piece 3700, while a user with sensitive teeth or gums may require less vigorous movement of the mouthpiece 3700) are different for each particular user. In some embodiments, customized vibration profiles are created for each particular user, and programmed into the personalized toothbrush device (e.g., as described previously with reference to dental care device 100), thus providing further unique customization of the oral care for the particular user of the personalized toothbrush device.

As shown in FIG. 39A, Mode 1 includes an up and down movement of the rear ends of the mouthpiece (e.g., the portions of the mouthpiece corresponding to the particular user's rearmost teeth). In Mode 1, the rear ends of the mouthpiece move in tandem (e.g., both ends move up together, and move down together). As the rear ends of the mouthpiece move up and down, the front end of the mouthpiece (e.g., the portion of the mouthpiece corresponding to the particular user's front teeth) remains predominately stationary.

Mode 2 includes the same up and down movement as Mode 1, but the rear ends of the mouthpiece move in an alternating fashion (e.g., as one end moves up, the other end moves down).

Mode 3 includes movement along the midplane of the mouthpiece. Mode 3 includes alternating between movement of the rear ends towards one another (e.g., the left end of the mouthpiece moves to the right, while the right end of the mouthpiece moves to the left), and movement of the rear ends away from one another. (e.g., the left end of the mouthpiece moves to the left, while the right end of the mouthpiece moves to the right).

Mode 4 includes rotational movement where the rear ends twist along a center line of the mouthpiece (e.g., a line running from the back of the particular user's mouth towards the front of the particular user's mouth). Mode 4 includes alternating the direction of rotation (e.g., first clockwise, then counterclockwise, relative to the center line of the mouthpiece), and each end of the mouthpiece rotates in a direction opposite the other end (e.g., when the left end rotates clockwise, the right end rotates counterclockwise).

Mode 5 includes rotational movement similar to Mode 4, but the rear ends of the mouthpiece rotate in tandem (e.g., both rotate clockwise together, then rotate counterclockwise together).

With reference to FIG. 39B, Mode 6 includes movement along the midplane of the mouthpiece similar to Mode 3, but the rear ends of the mouthpiece move in tandem (e.g., both ends move to the right, then both ends move to the left).

Mode 7 includes movement of a lingual center portion of the mouthpiece (e.g., the portion of the mouthpiece 3700 comprising the inner boundary wall 3702). The lingual center portion of the mouthpiece moves up and down (e.g., while the other portions of the mouthpiece, such as the outer boundary walls, remain predominately stationary).

Mode 8 includes rotational movement similar to Mode 5, but the vibrational mode includes a second harmonic. The Mode 8 labels show the rotational movement as viewed from the back of the mouthpiece, while the Mode 8 (top) labels show two top-down views of the mouthpiece. Notably, the outer boundary wall has two peaks in Mode 8 (as shown by the top-down views with the Mode 8 (top) labels) rather than just one peak (e.g., as in Mode 5). Similarly, Mode 9 includes rotational movement similar to Mode 4, but the vibrational mode includes a second harmonic.

Figure 39C:
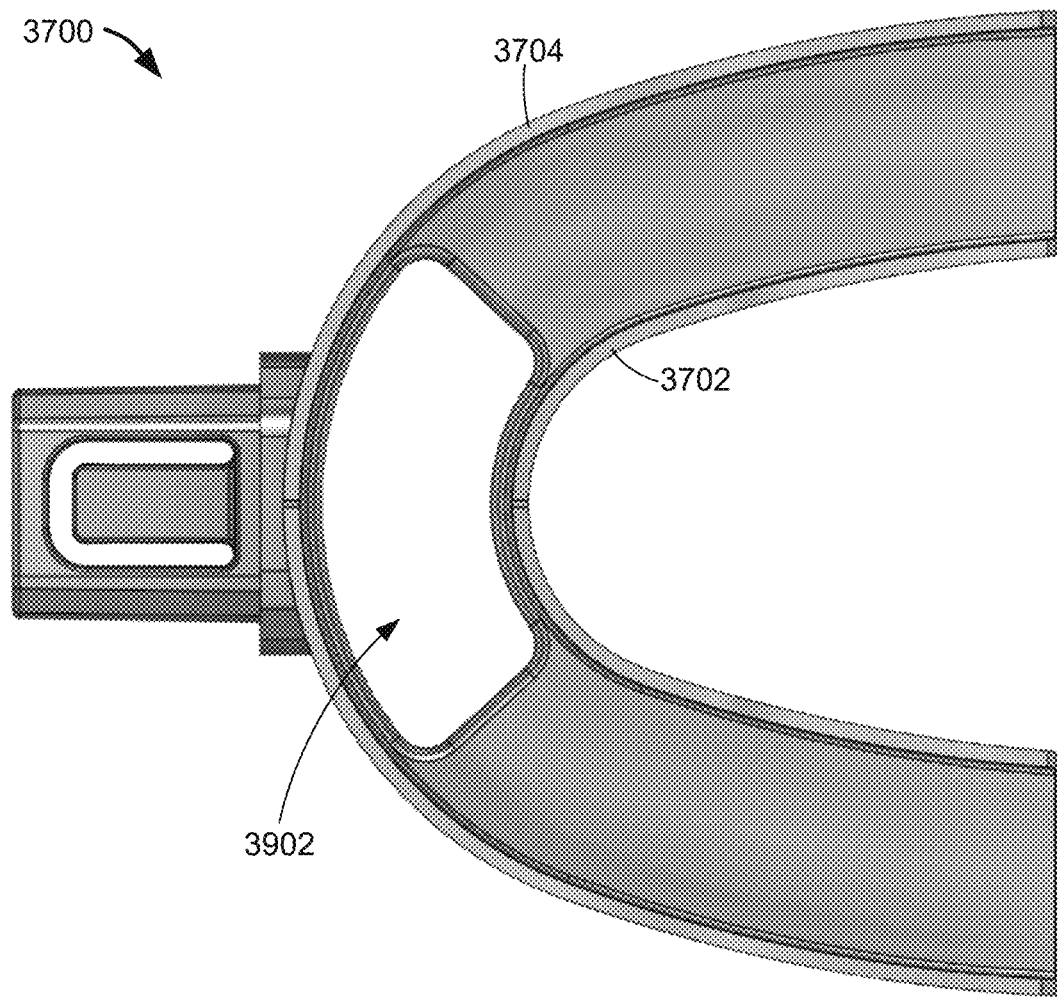
FIG. 39C shows exemplary customizations to a mouthpiece of a personalized toothbrush device to facilitate a desired vibrational mode.

FIG. 39C shows the mouthpiece 3700, with a customized cutout 3902 in a surface of the mouthpiece 3700. In some embodiments, the customized cutout 3902 is used in order to achieve the desired vibrational mode (e.g., as shown in Modes 8 and 9 in FIG. 39B). While FIG. 39C shows a specific customized cutout 3902, in other embodiments, the physical structure of the mouthpiece 3700 can be further customized in order to achieve the desired vibrational mode (e.g., through additional cutouts, by varying the size and/or shape of one or more cutouts, by other structural elements such as notches, etc.).

Figure 40:
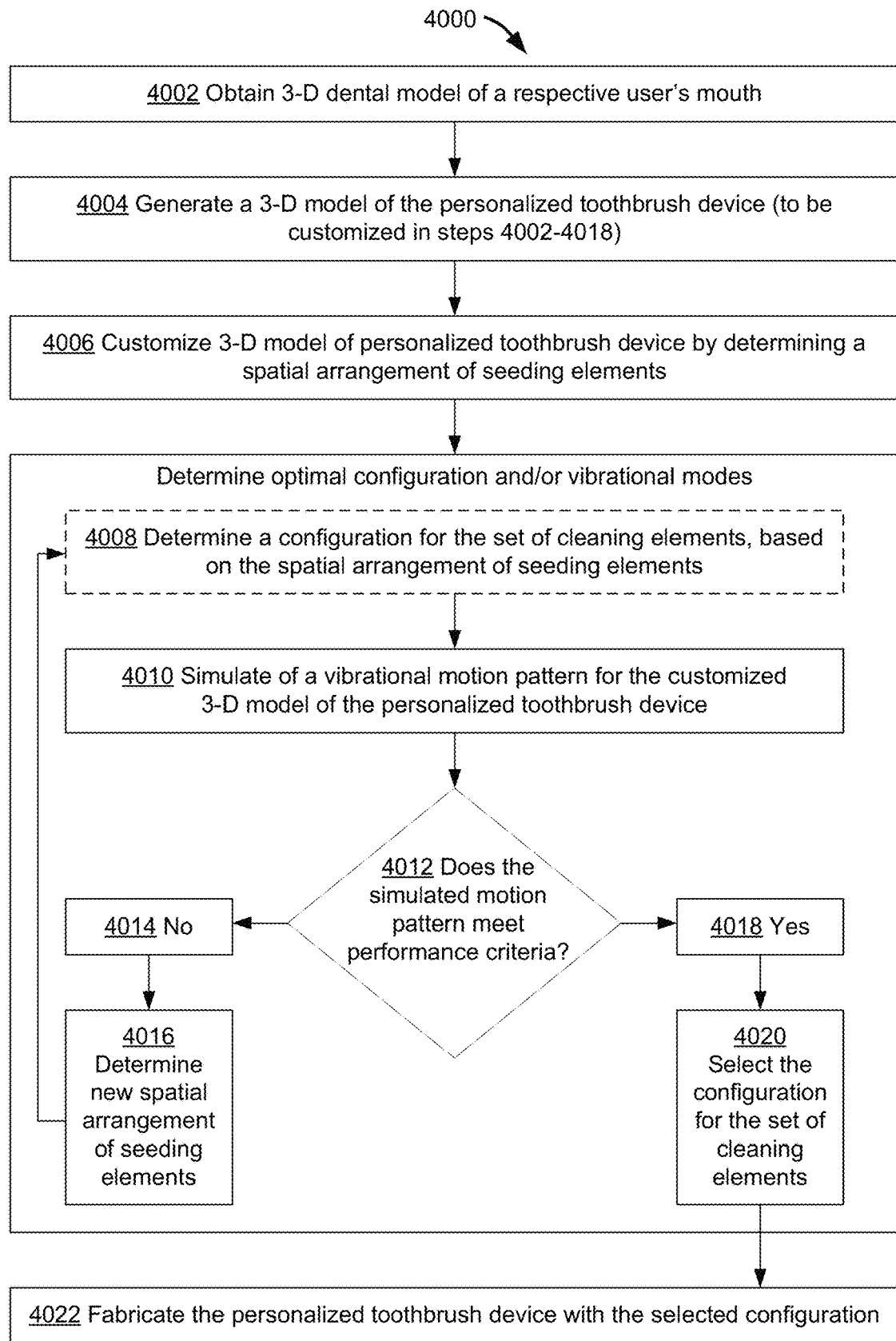
FIG. 40 is a flowchart for a method of selecting a configuration for a set of cleaning elements that result in a desired vibrational motion pattern.

FIG. 40 is a flowchart describing a method 4000 of making a customized or personalized toothbrush device 3700. While this description is for a single user or patient, the same method is applied for each of a plurality of users or patients. The method starts by obtaining (4002), for a respective user of the plurality of users, an electronic 3-D dental model of the respective user's mouth. For example, the dental model may be obtained by a digital scan of the user's mouth while at their dentist's offices.

A 3-D model of the personalized toothbrush device is then generated (4004), as discussed in detail above. Also as discussed in detail above, the personalized toothbrush device is specific to the teeth and mouth of a particular user and provides the ideal amount of pressure, coverage, and overall cleaning for a user's teeth and gums. This is especially important for tray-type toothbrush devices, which generally cannot be adjusted during use, as is the case for traditional toothbrushes where users can move the toothbrush head to a certain location and hold it there for a certain location for a certain amount of time, or adjust the head to be closer or further from a surface of a tooth to adjust the cleaning pressure. This in-use adjustment, while beneficial for diligent and knowledgeable users who are paying attention while brushing their teeth, is also a traditional toothbrush's biggest downfall, as it typically leads to improper brushing that does not last long enough and address all teeth and gums.

In some embodiments, the 3-D model of the personalized toothbrush device is customized by optionally determining (4006) a spatial arrangement of a set of seeding elements (e.g., less than all) that are personalized for the user based on the electronic 3-D dental model of the particular user's mouth. Thereafter, the system optionally automatically determining (4008), based on the spatial arrangement of the set of seeding elements, a configuration for a set of cleaning elements of the personalized toothbrush device (e.g., as described above with reference to FIG. 38G). For example, a technician may generate one or more cleaning elements in the 3-D model of the personalized toothbrush device, and the computer system will auto-generate the remainder of the cleaning elements in the 3-D model of the personalized toothbrush device, as described above.

In some embodiments, the method further includes simulating (4010) a vibrational pattern for the customized 3-D model of the personalized toothbrush device (e.g., including the configuration for the set of cleaning elements). In some embodiments, the method further includes determining (4012), based on the simulation of the vibrational pattern, whether the toothbrush cleaning device meets certain performance criteria when being used. For example, when being used, the toothbrush cleaning device should be in a minimum or acceptable threshold for cleaning all of the desired areas within the user's mouth. In some embodiments, the performance criteria or minimum threshold is met when each area of the user's teeth, gums, and/or any interstitial spaces between the teeth and/or gums are exposed to at least one rubbing or cleaning motion of at least one cleaning element. In other embodiments, the performance criteria or minimum threshold is that each area of the user's teeth, gums, and/or any interstitial spaces between the teeth and/or gums are exposed to a predetermined number of rubbing or cleaning motions (e.g., 5) of a predetermined number of cleaning elements (e.g., 2).

In some embodiments, in accordance with a determination (4014) that the vibrational pattern does not meet the performance criteria, the method repeats (4016) steps 4008-4012 with different configurations of the personalized toothbrush device (e.g., by changing the number, location, lengths, etc. of the cleaning elements) and/or with a different vibrational pattern, until the simulated vibrational motion pattern meets the performance criteria. In accordance with a determination (4018) that the vibrational motion pattern meets the performance criteria, the method selects (4020) the last configuration of the personalized toothbrush device and/or the last vibrational pattern.

In some embodiments, the simulated vibrational pattern is compared against a target vibrational pattern (e.g., one of the vibrational modes discussed with references to FIGS. 39A-39B). Achieving the target vibrational motion pattern is important to ensure that the set of cleaning elements contacts the particular user's teeth frequently enough to achieve an optimal cleaning experience. For example, although some combinations of physical characteristics for the set of cleaning elements may achieve the desired contact force and/or amount of overlap, those customizations may result in the set of cleaning elements making infrequent contact with the user's teeth when the personalized toothbrush device is in use (e.g., because the cleaning elements are customized with a higher density to achieve the desired contact force, and the higher density causes the cleaning elements to move slowly due to the stiffness of the cleaning elements). Thus, different variations of the possible customizations are simulated in order to find an optimal configuration that results in the optimal cleaning experience for the particular user. In some embodiments, in accordance with a determination that the simulated vibrational mode does not meet the performance criteria (e.g., the simulated vibrational mode does not substantially match the target vibrational motion pattern), the virtual model of the mouthpiece 3700 and/or vibrational modes is/are further customized. For example, some combination of physical characteristics of the upper and lower cleaning trays (e.g., the inner boundary wall 3702, the outer boundary wall 3704, and/or the occlusal surface 3734, as discussed above with reference to FIGS. 37A-37H), and/or the set of cleaning elements (e.g., the length, density, diameter, taper, angle relative to a surface of the top or bottom customized cleaning tray, or shape of one or more cleaning elements) are modified. Alternately, or additionally, an output frequency of a powered driving mechanism of the personalized toothbrush device is modified. In some embodiments, the powered driving mechanism is configured to cycle through multiple output frequencies. After the 3-D model of the mouthpiece 3700 is modified, the computer uses the updated 3-D model of the mouthpiece 3700 to simulate a new vibrational motion pattern. This method can be repeated until the requirements are met (e.g., all surface or teeth and/or gums sufficiently cleaned and/or stimulated).

In some embodiments, the method includes fabricating (4022) the personalized toothbrush device (e.g., by a 3-D printing process described above) with the selected configuration (that will use the selected vibrational pattern in use). In some embodiments, multiple different vibrational patterns may be selected for the same personalized toothbrush device. In some embodiments, the selected configuration of the 3D model of the personalized toothbrush device is sent to a third party for fabrication. In some embodiments, the selected vibrational pattern (or patterns) is loaded onto the powered driving mechanism of the personalized toothbrush device (e.g., locally in the factory, transmitted to a user's device in their home, etc.).

The method concludes by performing (4024) post-processing steps to further customize the personalized toothbrush device. For example, in some embodiments, the post-processing steps include applying a biocompatible silicone (or other biocompatible agent) coating the external surfaces of the personalized toothbrush device (e.g., for comfort). In some embodiments, the post-processing steps include optimizing the personalized toothbrush device for specific use cases, such as for ultrasonic cleaning. In other embodiments, the post-processing removes some small amount of material in order to smooth or refine the toothbrush device. For example, Acetone smoothing may be used. In these embodiments, the toothbrush device is printed slightly larger to accommodate for the removal of some material.

Figure 41:
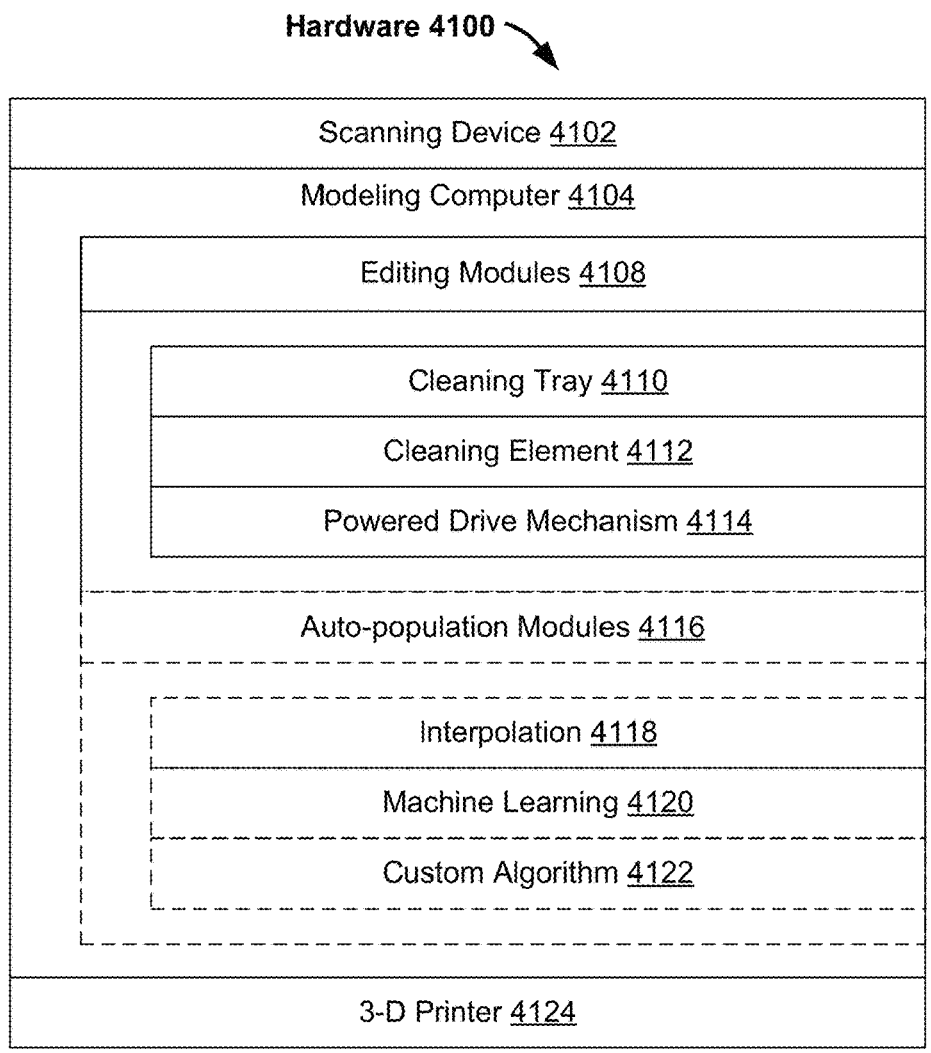
FIG. 41 shows exemplary hardware for customizing and fabricating a personalized toothbrush device.

FIG. 41 shows the hardware 4100 for performing the method 4000 described above. The hardware 4100 includes a scanning device 4102, which is used to obtain the electronic 3-D dental model of the respective user's mouth. The scanning device 4012 transmits the 3-D dental model of the respective user's mouth to a modeling computer 4104. The modeling computer 4104 includes editing modules 4108, and the editing modules 4108 include a cleaning tray module 4110 (e.g., for customizing an upper and/or lower cleaning tray, as described previously with reference to FIGS. 37A-37I), a cleaning element module 4112 (e.g., for manually editing one or more seeding elements with various customizations, such as those described above with reference to FIGS. 38A-38H), and a powered drive mechanism module 4114 (e.g., for configuring output frequencies of a powered drive mechanism to be coupled with the mouthpiece of the personalized toothbrush device). In some embodiments, the modeling computer 4104 also includes auto-population modules 4116 (e.g., for automatically determining a configuration for a remainder of cleaning elements, based off a set of seeding elements, as described previously). In some embodiments, the auto-population modules 4116 include an interpolation module 4118, a machine learning module 4120, and/or a custom algorithm module 4122. The various auto-population modules 4116 provide a variety of options for automatically configuring the set of cleaning elements. For example, while the interpolation module 4118 and the machine learning module 4120 may be useful for maximizing cleaning efficient of the cleaning elements, the custom algorithm 4122 module can be useful for preference-based automation (e.g., simulating a "soft" or "firm" toothbrush, via various customizations of the set of cleaning elements). The hardware 4100 also includes a 3-D printer 4124. In some embodiments, the scanning device 4102, modeling computer 4104 and 3-D printer 4124 are connected locally. In other embodiments, one or more elements of the hardware 4100 are connected to the other hardware elements remotely. For example, the scanning device 4102 may be in a dentist's office, the scanning device 4102 and modeling computer 4014 can be in a dentist's office, such that the dentist can scan a particular user's mouth and customize the design and configuration for a mouthpiece of a personalized toothbrush device at the dentist's office. The modeling computer 4014 can transmit the customized design and configuration for the mouthpiece (e.g., as 3-D printing instructions) to an off-site 3-D printer (e.g., to a 3-D printer in a factory or other manufacturing facility) for 3-D printing.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

It will also be understood that, although the terms first, second, etc. are, in some instances, used herein to describe various elements, these elements should not be limited by these terms. These terms are only used to distinguish one element from another. For example, a first current could be termed a second current, and, similarly, a second current could be termed a first current, without departing from the scope of the various described embodiments. The first current and the second current are both currents, but they are not the same condition unless explicitly stated as such.

The terminology used in the description of the various described embodiments herein is for the purpose of describing particular embodiments only and is not intended to be limiting. As used in the description of the various described embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. A method of making personalized toothbrush devices for a plurality of users, the method comprising:
    for each of a plurality of users:
        obtaining, for a respective user of the plurality of users, an electronic 3-D dental model of the respective user's mouth;
        determining, based on the electronic 3-D dental model of the respective user's mouth, a configuration for a mouthpiece of a personalized toothbrush device;
        3-D printing the mouthpiece of the personalized toothbrush device, the mouthpiece of the personalized toothbrush device including a top cleaning tray, a bottom cleaning tray, and a set of cleaning elements, wherein each of the top cleaning tray, the bottom cleaning tray, and the set of cleaning elements are each customized based at least in part on the electronic 3-D dental model of the respective user's mouth; and
    wherein each personalized toothbrush device 3-D printed for each respective user of the plurality of users is different from every other user's personalized toothbrush device, and
wherein the mouthpiece of the personalized toothbrush device is 3-D printed as a single, integral unit.

2. The method of claim 1, wherein at least some of the 3-D printed cleaning elements of the set of cleaning elements have diameters of no more than 0.2 mm.

3. The method of claim 1, wherein the top cleaning tray, the bottom cleaning tray, and the set of cleaning elements are 3-D printed together, and from the same material.

4. The method of claim 1, including 3-D printing the mouthpiece of the personalized toothbrush device using a powder bed fusion process.

5. The method of claim 4, wherein the powder bed fusion process is a multi jet fusion printing process.

6. The method of claim 1, further comprising:
    after 3-D printing the mouthpiece of the personalized toothbrush device, applying a biocompatible silicone coating to the 3-D printed mouthpiece of the personalized toothbrush.

7. The method of claim 1, wherein the top cleaning tray and the bottom cleaning tray each comprise an outer boundary wall and an inner boundary wall, and the method includes customizing the top cleaning tray and the bottom cleaning tray based at least in part on a first physical characteristic of the particular user's mouth.

8. The method of claim 7, wherein the first physical characteristic is:
    a length of the dental arch of the particular user's mouth,
    a width of the dental arch of the particular user's mouth,
    an occlusion classification of the particular user's mouth,
    a tooth alignment of the particular user's mouth, the presence of dental correctors in the particular user's mouth,
the presence of one or more third molars in the particular user's mouth,
a width of the particular user's teeth, or
a gum line of the particular user's teeth.

9. The method of claim 7, wherein customizing the top cleaning tray and the bottom cleaning tray includes:
customizing a length of the top cleaning tray or bottom cleaning tray,
customizing a width of the top cleaning tray or bottom cleaning tray,
customizing a distance between the outer boundary wall and the inner boundary wall for the top cleaning tray or bottom cleaning tray,
customizing an offset between the top cleaning tray and bottom cleaning tray,
customizing a thickness of the outer boundary wall or the inner boundary wall for the top cleaning tray or bottom cleaning tray,
customizing a density of the outer boundary wall or the inner boundary wall for the top cleaning tray or bottom cleaning tray;
customizing an internal structure of the top cleaning tray or bottom cleaning tray,
adding one or more bite points to the top cleaning tray or bottom cleaning tray;
adding one or more oral care agent dispensers to the outer boundary wall or the inner boundary wall for the top cleaning tray or bottom cleaning tray; or
adding one or more sensors to the outer boundary wall or the inner boundary wall for the top cleaning tray or bottom cleaning tray.

10. The method of claim 1, including customizing the set of cleaning elements based at least in part on a second physical characteristic of the particular user's mouth.

11. The method of claim 10, where the second physical characteristic is:
a distance from the outer boundary wall for the top or bottom customized cleaning tray to the surface of a tooth of the particular user's mouth,
a distance from the inner boundary wall for the top or bottom customized cleaning tray to the surface of a tooth of the particular user's mouth,
the tooth surfaces of the teeth of the particular user's mouth,
an interproximal distance of the particular user's mouth,
one or more missing teeth in the particular user's mouth,
a gum condition of the particular user's mouth,
an enamel condition of one or more teeth of the particular user's mouth,
the presence of one or more third molars in the particular user's mouth,
the presence of dental hardware in the particular user's mouth,
a width of the particular user's teeth, or
a gum health state of the particular user's mouth.

12. The method of claim 10, wherein customizing the set of cleaning elements includes:
customizing a length of the cleaning elements of the set of cleaning elements,
customizing a spacing between cleaning elements of the set of cleaning elements,
customizing a diameter of the cleaning elements of the set of cleaning elements,
customizing a taper of the cleaning elements of the set of cleaning elements,
customizing an angle of the cleaning elements of the set of cleaning elements, relative to a surface of the top and bottom customized cleaning trays,
customizing a density of the cleaning elements of the set of cleaning elements,
customizing a surface texture of the cleaning elements of the set of cleaning elements,
customizing a cross-section of the cleaning elements of the set of cleaning elements, or
customizing the spatial distribution of the set of customized cleaning elements.

13. The method of claim 1, including selecting a respective value for a physical characteristic for each respective cleaning element of the set of cleaning elements, such that a respective cleaning element of the set of cleaning elements contacts a respective tooth of the particular user's mouth with a predetermined amount of contact force.

14. The method of claim 1, including selecting a respective value for a physical characteristic for each respective cleaning element of the set of cleaning elements, such that a respective cleaning element of the set of cleaning elements contacts a respective tooth of the particular user's mouth with a predetermined amount of overlap with a surface of a respective tooth of the particular user's mouth.

15. The method of claim 14, wherein the physical characteristic is a length of the respective cleaning element.

16. The method of claim 14, wherein the physical characteristic is a density of the respective cleaning element.

17. The method of claim 14, wherein the physical characteristic is an amount of taper of the respective cleaning element.

18. The method of claim 14, wherein the physical characteristic is a diameter of the respective cleaning element.

19. The method of claim 14, wherein the physical characteristic is an angle of the respective cleaning element relative to a surface of the top and bottom customized cleaning trays.

20. The method of claim 14, wherein the physical characteristic is a cross-section of the respective cleaning element.

21. The method of claim 1, further comprising:
importing the 3-D dental model of the particular user's mouth into a computer system;
determining a spatial arrangement of a set of seeding elements personalized for the particular user based on the electronic 3-D dental model of the particular user's mouth;
automatically determining, at the computer system and without human intervention, a configuration for the remainder of the cleaning elements for the toothbrush device, based on the spatial arrangement of the set of seeding elements.

22. The method of claim 21, wherein automatically determining the configuration for the remainder of the cleaning elements of the personalized toothbrush device includes determining the configuration for the remainder of the cleaning elements through interpolation.

23. The method of claim 21, wherein automatically determining the configuration for the remainder of the cleaning elements of the personalized toothbrush device includes determining the configuration for the remainder of the cleaning elements based at least in part on previously generated configurations for sets of cleaning elements.

24. The method of claim 1, further comprising:
(i) generating a 3-D model of the personalized toothbrush device (ii) customizing the 3-D model of the personalized toothbrush device by:
  (iii) determining a spatial arrangement of a set of seeding elements, personalized for the particular user based on the electronic 3-D dental model of the particular user's mouth, and
  (iv) automatically determining, based on the spatial arrangement of the set of seeding elements, a configuration for a set of cleaning elements of the personalized toothbrush device;
(v) simulating, based on the customized 3-D model of the personalized toothbrush device, a vibrational pattern of the personalized toothbrush device;
(vi) determining, based on the simulation of the vibrational pattern, whether the vibrational pattern meets performance criteria for cleaning all of the desired areas within the user's mouth;
in accordance with a determination that the vibrational pattern does not meet the performance criteria, determining a new spatial arrangement of the set of seeding elements and repeating steps (ii)-(vi) with the new spatial arrangement of the set of seeding elements; and
in accordance with a determination that the vibrational pattern meets the performance criteria, selecting the configuration for the set of cleaning elements of the personalized toothbrush device.

25. The method of claim 24, further comprising:
determining a first value for a first physical characteristic for one or more cleaning elements of the set of cleaning elements, wherein the first physical characteristic includes one or more of length, density, diameter, taper, angle relative to a surface of the top or bottom customized cleaning tray, or shape; and
in accordance with a determination that the vibrational motion pattern does not meet the performance criteria, determining a new value for the first physical characteristic for the one or more cleaning elements of the set of cleaning elements.

26. The method of claim 24, further comprising:
determining a density distribution for the top and bottom customized cleaning trays; and
in accordance with a determination that the vibrational motion pattern does not meet the performance criteria, determining a new density distribution for the top and bottom customized cleaning trays.

27. The method of claim 24, further comprising:
determining an output frequency for a powered driving mechanism of the personalized toothbrush device; and
in accordance with a determination that the vibrational motion pattern does not meet the performance criteria, determining a new output frequency for a powered driving mechanism of the personalized toothbrush device.

* * * * *